(12) United States Patent
Ariyama et al.

(10) Patent No.: US 11,485,779 B2
(45) Date of Patent: Nov. 1, 2022

(54) ANTI-BMP10 MONOCLONAL ANTIBODY OR FRAGMENT THEREOF

(71) Applicant: Kyowa Kirin Co., Ltd., Tokyo (JP)

(72) Inventors: Hiroyuki Ariyama, Tokyo (JP); Shinya Ogawa, Tokyo (JP); Tetsuya Kitayama, Tokyo (JP); Takenao Yamada, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 16/771,828

(22) PCT Filed: Dec. 12, 2018

(86) PCT No.: PCT/JP2018/045739
§ 371 (c)(1),
(2) Date: Jun. 11, 2020

(87) PCT Pub. No.: WO2019/117208
PCT Pub. Date: Jun. 20, 2019

(65) Prior Publication Data
US 2021/0122813 A1 Apr. 29, 2021

(30) Foreign Application Priority Data
Dec. 12, 2017 (JP) .............. JP2017-238106

(51) Int. Cl.
| | | |
|---|---|---|
| *C07K 16/22* | (2006.01) | |
| *A61P 9/12* | (2006.01) | |
| *A61K 39/395* | (2006.01) | |
| *A61K 45/06* | (2006.01) | |
| *A61K 39/00* | (2006.01) | |

(52) U.S. Cl.
CPC .......... *C07K 16/22* (2013.01); *A61K 39/3955* (2013.01); *A61K 45/06* (2013.01); *A61P 9/12* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,287,868 | B2 | 10/2012 | Seehra et al. |
| 2012/0183543 | A1 | 7/2012 | Buckler et al. |
| 2017/0137503 | A1 | 5/2017 | Seehra et al. |

FOREIGN PATENT DOCUMENTS

| | | |
|---|---|---|
| JP | 2010-529041 | 8/2010 |
| JP | 2012-526087 | 10/2012 |
| WO | 2008/151078 | 12/2008 |
| WO | 2010/126169 | 11/2010 |
| WO | 2010/128158 | 11/2010 |

OTHER PUBLICATIONS (Paul, Fundamental Immunology, 3rd Edition, 1993, pp. 292-295, under the heading "Fv Structure and Diversity in Three Dimensions").*
Rudikoff et al. (PNAS 79: 1979-1983, 1982).*
MacCallum, et al. (J. Mol. Biol. 262: 732-745, 1996).*
De Pacalis et al. (J. Immunol. 169: 3076-3084, 2002).*
Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
Amit et al. (Science 233: 747-753, 1986).*
Vajdos et al. (J. Mol. Biol 320: 415-428, 2002).*
International Search Report, dated Mar. 5, 2019 in corresponding International Patent Application No. PCT/JP2018/045739.
Mueller, T.D et al., "Promiscuity and specificity in BMP receptor activation", FEBS Letters, 2012, vol. 586, pp. 1846-1859.
Susan-Resiga, D. et al., "Protein Synthesis and Degradation: Furin Is the Major Processing Enzyme of the Cardiac-specific Growth Factor Bone Morphogenetic Protein 10" J. Biol. Chem., 2011, vol. 286, No. 26, pp. 22785-22794.
Neuhaus, H. et al., "Heart specific expression of mouse BMP-10 a novel member of the TGF-β superfamily", Mech. Dev., 1999, vol. 80, No. 2, pp. 181-184.
Teichmann, U. et al., "Highly restricted BMP10 expression in the trabeculating myocardium of the chick embryo", Dev. Genes Evol., 2004, vol. 214, No. 2, pp. 96-98.
Ricard, N. et al., "BMP9 and BMP10 are critical for postnatal retinal vascular remodeling", Blood, 2012, vol. 119, No. 25, pp. 6162-6171.
Chen, H. et al., "Context-dependent signaling defines roles of BMP9 and BMP10 in embryonic and postnatal development", Proc. Natl. Acad. Sci., 2013, vol. 110, No. 29, pp. 11887-11892.
Chen, H. et al., "BMP10 is essential for maintaining cardiac growth during murine cardiogenesis" Development, 2004,vol. 131, No. 9, pp. 2219-2231.
Levet, S. et al., "BMP9 and BMP10 are necessary for proper closure of the ductus arteriosus" Proc. Natl. Acad. Sci., 2015, vol. 112, No. 25, pp. E3207-E3215.

(Continued)

*Primary Examiner* — Christine J Saoud
(74) *Attorney, Agent, or Firm* — Wenderoth, Lind & Ponack, L.L.P.

(57) ABSTRACT

An object of the present invention is to provide an anti-BMP10 antibody, and a therapeutic agent for hypertension and a hypertensive disease, containing the antibody as an active ingredient. The present invention relates to an anti-BMP10 monoclonal antibody or an antibody fragment thereof that binds to human BMP10 (bone morphogenetic protein 10). Further, the present invention relates to a therapeutic agent for hypertension and a hypertensive disease containing an antagonist for at least one of BMP10 and a BMP9/BMP10 heterodimer, a diagnostic agent or a pharmaceutical composition for a disease associated with human BMP10, an immunological detection method or a measurement method for human BMP10 using the antagonist, and use of the antagonist for producing a pharmaceutical composition for treating hypertension and a hypertensive disease.

7 Claims, 22 Drawing Sheets

Specification includes a Sequence Listing.

(56) References Cited

OTHER PUBLICATIONS

Huy Do, T. et al., "Vaccines in the management of hypertension" Expert Opinion Biological Therapy, 2010, vol. 10, No. 7, pp. 1077-1087.
Kawarazaki, W. et al. "Forefront of research in salt and hypertension", Experimental Medicine, 2015, vol. 33, No. 7, pp. 1078-1084, with concise explanation in English.
Liu, M. et al., "Cardiovascular disease and its relationship with chronic kidney disease", Eur. Rev. Med. Pharmacol. Sci., 2014, vol. 18, No. 19, pp. 2918-2926.
Nakano, N. et al., "Interaction of BMP10 with Leap may modulate the course of hypertensive cardiac hypertrophy" Am. J. Physiol. Heart Circ. Physiol., 2007, vol. 293, No. 6, pp. H3396-H3403.
International Preliminary Report on Patentability dated Jun. 16, 2020 in corresponding International (PCT) Application No. PCT/JP2018/045739, with English Translation.

* cited by examiner

FIG. 7
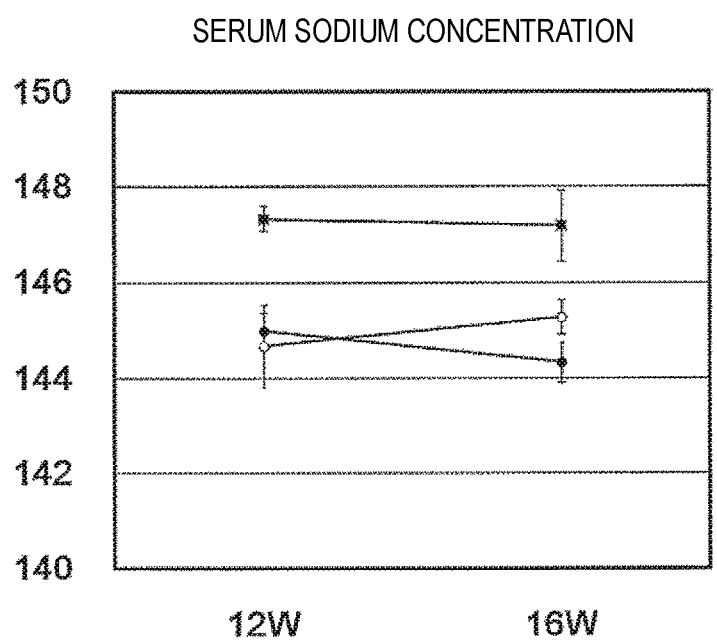
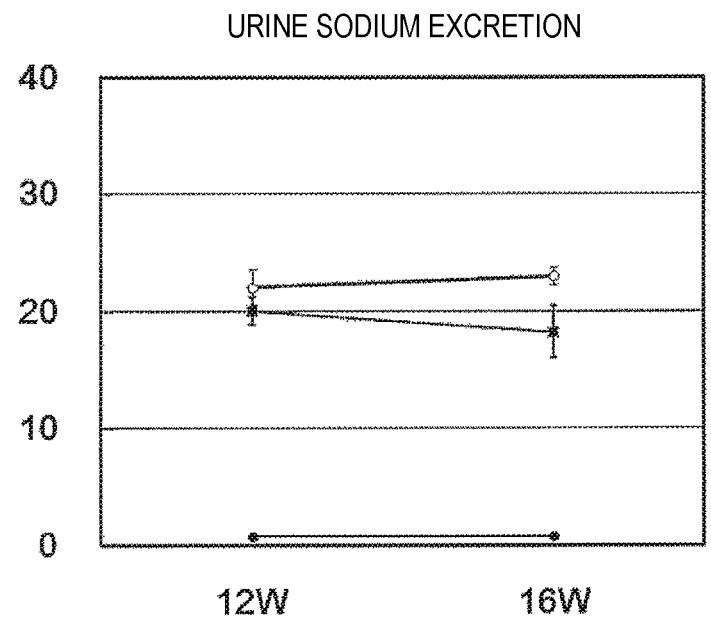

FIG. 11
A
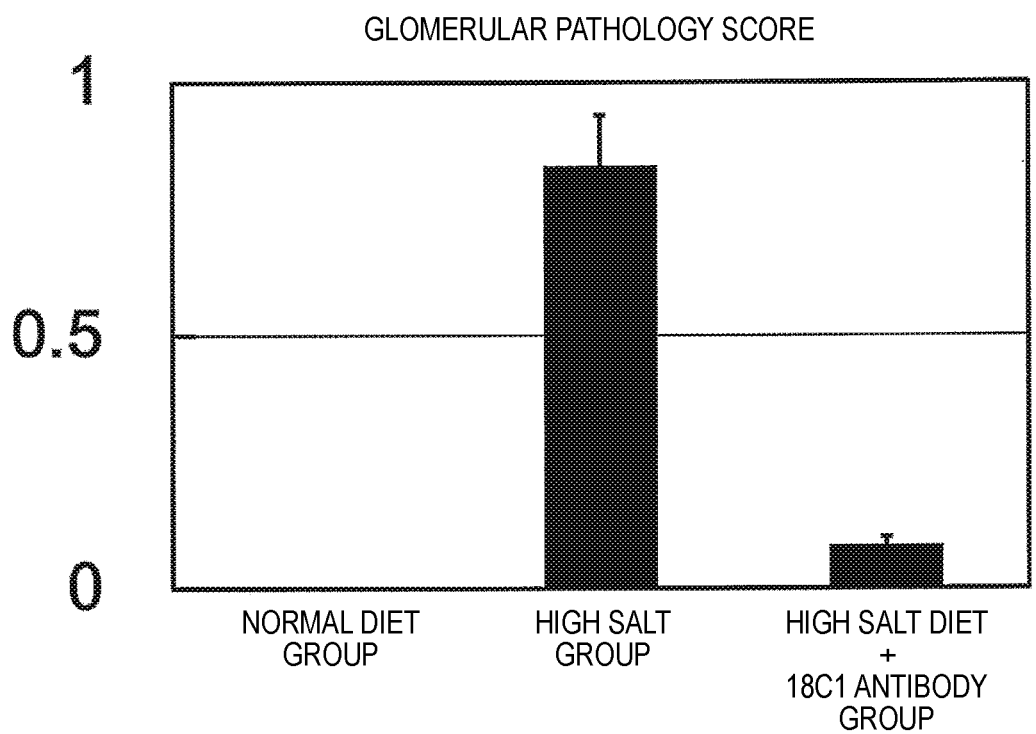
B
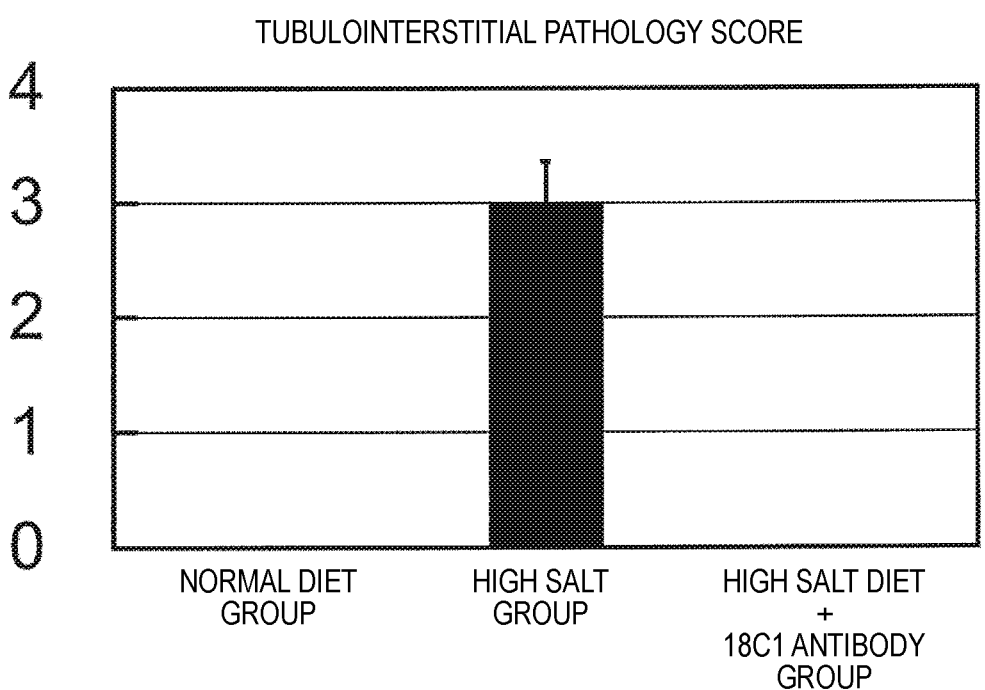

FIG. 12
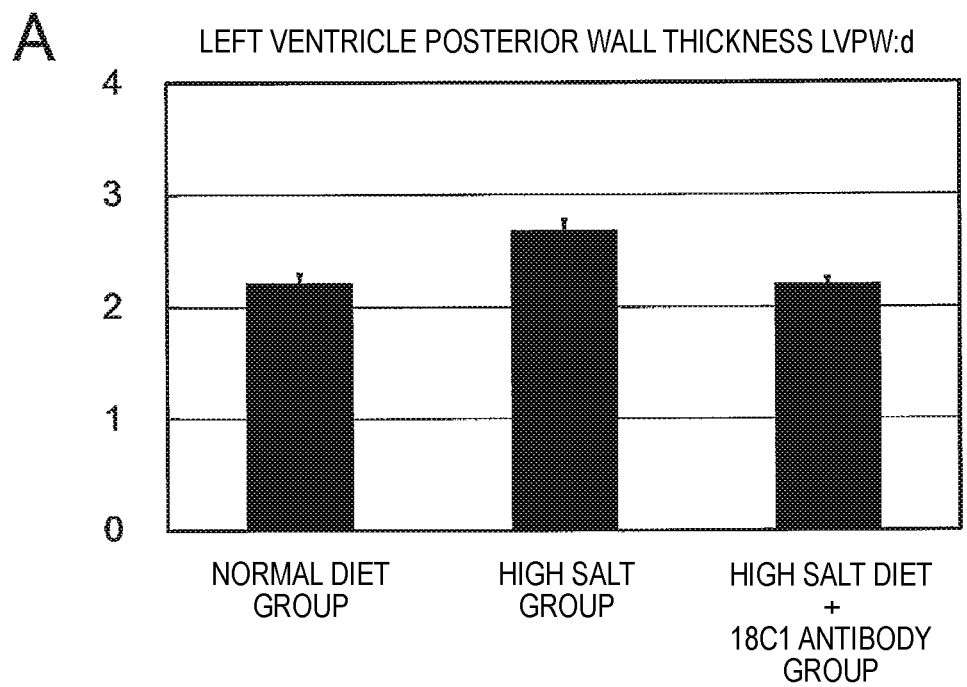
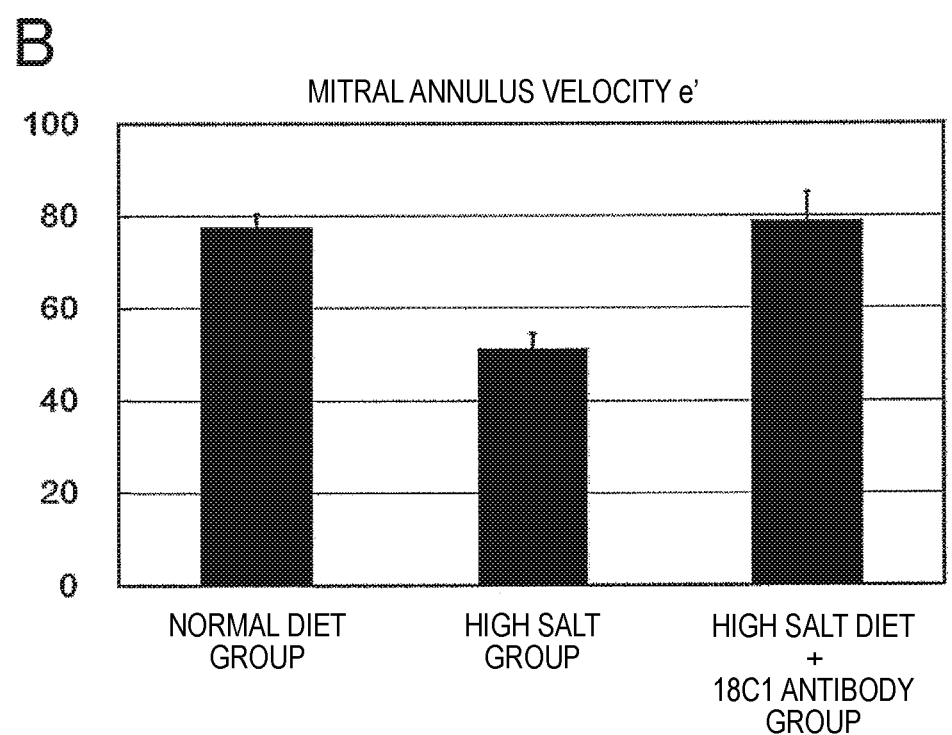

FIG. 16

```
            1234567890123456789012345678  12345  6789012345678  012345678901234  67890123456789012345678  8901234  56789012345
18C1 VH     QVQLKETGPDLVQLTQTLSITCTVSGFSLT TYNVH  WVRQPPGKGLEWMG TMWNGGGIDYNSAFKS RLSISRDTSKSQVFLKMNSLQTDDTAKYFCAR LGYYYDY WGHGLMVTVSS
HV0         QVQLQESGPGLVKPSQTLSLTCTVSGGSVS        WIRQPPGKGLEWIG                  RVTISVDTSKNQFSLKLSSVTAADTAVYYCAR         WGQGTLVTVSS
HV2         QVQLQESGPGLVKPSQTLSLTCTVSGGSVS        WIRQPPGKGLEWIG                  RVTISRDTSKNQFSLKLSSVTAADTAVYYCAR         WGQGTLVTVSS
HV3         QVQLQESGPGLVKPSQTLSLTCTVSGFSVS        WIRQPPGKGLEWIG                  RVTISRDTSKNQFSLKLSSVTAADTAKYYCAR         WGQGTLVTVSS
HV4a        QVQLQESGPGLVKPSQTLSLTCTVSGFSVS        WIRQPPGKGLEWIG                  RVTISRDTSKNQVSLKLSSVTAADTAKYYCAR         WGQGTLVTVSS
HV4b        QVQLQESGPGLVKPSQTLSLTCTVSGFSVS        WIRQPPGKGLEWIG                  RLTISVDTSKNQFSLKLSSVTAADTAKYYCAR         WGQGTLVTVSS
HV4c        QVQLQESGPGLVKPSQTLSLTCTVSGFSVS        WIRQPPGKGLEWMG                  RVTISRDTSKNQFSLKLSSVTAADTAKYYCAR         WGQGTLVTVSS
HV5         QVQLQESGPGLVKPSQTLSLTCTVSGFSVS        WIRQPPGKGLEWIG                  RVTISRDTSKNQVSLKLSSVTAADTAKYYCAR         WGQGTLVTVSS
HV6         QVQLQESGPGLVKPSQTLSLTCTVSGFSVS        WIRQPPGKGLEWMG                  RLTISRDTSKNQFSLKLSSVTAADTAKYYCAR         WGQGTLVTVSS
HV7         QVQLQESGPGLVKPSQTLSLTCTVSGFSVT        WIRQPPGKGLEWMG                  RVTISRDTSKNQVSLKMSSVTAADTAKYYCAR         WGQGTLVTVSS
HV8         QVQLQESGPGLVKPSQTLSITCTVSGFSVT        WIRQPPGKGLEWMG                  RLTISRDTSKNQFSLKLSSVTAADTAKYFCAR         WGQGTLVTVSS
HV10        QVQLQESGPGLVKPSQTLSITCTVSGFSVT        WVRQPPGKGLEWMG                  RLTISRDTSKNQVSLKMSSVTAADTAVYFCAR         WGQGTLVTVSS
HV13        QVQLQESGPGLVKLSQTLSITCTVSGFSLT        WIRQPPGKGLEWMG                  RLTISRDTSKSQVSLKMSSLTAADTAKYFCAR         WGQGILVTVSS
HV16        QVQLQESGPGLVKLSQTLSITCTVSGFSLT        WVRQPPGKGLEWMG                  RLTISRDTSKSQVSLKMSSLTAADTAKYFCAR         WGQGILVTVSS 12345678901234567890           12345  6789012345678  012345678901234  67890123456789012345678  8901234  56789012345
HV0'        QVQLQESGPGLVKPSQTLSLTCTVSGGSVS TYNVH  WIRQPPGKGLEWIG TMWNGGGIDYNSAFKD RVTISVDTSKNQFSLKLSSVTAADTAVYYCAR LGYYYDY WGQGTLVTVSS
HV2'        QVQLQESGPGLVKPSQTLSLTCTVSGGSVS        WIRQPPGKGLEWIG                  RVTISRDTSKNQFSLKLSSVTAADTAVYYCAR         WGQGTLVTVSS
HV3'        QVQLQESGPGLVKPSQTLSLTCTVSGFSVS        WIRQPPGKGLEWIG                  RVTISRDTSKNQFSLKLSSVTAADTAKYYCAR         WGQGTLVTVSS
HV4a'       QVQLQESGPGLVKPSQTLSLTCTVSGFSVS        WIRQPPGKGLEWIG                  RVTISRDTSKNQVSLKLSSVTAADTAKYYCAR         WGQGTLVTVSS
HV4b'       QVQLQESGPGLVKPSQTLSLTCTVSGFSVS        WIRQPPGKGLEWIG                  RLTISVDTSKNQFSLKLSSVTAADTAKYYCAR         WGQGTLVTVSS
HV4c'       QVQLQESGPGLVKPSQTLSLTCTVSGFSVS        WIRQPPGKGLEWMG                  RVTISRDTSKNQFSLKLSSVTAADTAKYYCAR         WGQGTLVTVSS
HV5'        QVQLQESGPGLVKPSQTLSLTCTVSGFSVS        WIRQPPGKGLEWIG                  RVTISRDTSKNQVSLKLSSVTAADTAKYYCAR         WGQGTLVTVSS
HV6'        QVQLQESGPGLVKPSQTLSLTCTVSGFSVS        WIRQPPGKGLEWMG                  RLTISRDTSKNQFSLKLSSVTAADTAKYYCAR         WGQGTLVTVSS
HV7'        QVQLQESGPGLVKPSQTLSITCTVSGFSVT        WIRQPPGKGLEWMG                  RVTISRDTSKNQVSLKMSSVTAADTAKYYCAR         WGQGTLVTVSS
HV8'        QVQLQESGPGLVKPSQTLSITCTVSGFSVT        WIRQPPGKGLEWMG                  RLTISRDTSKNQFSLKLSSVTAADTAKYFCAR         WGQGTLVTVSS
HV10'       QVQLQESGPGLVKPSQTLSITCTVSGFSLT        WIRQPPGKGLEWMG                  RLTISRDTSKNQVSLKMSSVTAADTAVYFCAR         WGQGTLVTVSS
HV13'       QVQLQESGPGLVKLSQTLSITCTVSGFSLT        WIRQPPGKGLEWMG                  RLTISRDTSKSQVSLKMSSLTAADTAKYFCAR         WGQGILVTVSS
HV16'       QVQLQESGPGLVKLSQTLSITCTVSGFSLT        WVRQPPGKGLEWMG                  RLTISRDTSKSQVSLKMSSLTAADTAKYFCAR         WGQGILVTVSS 12345678901234567890           12345  6789012345678  012345678901234  67890123456789012345678  8901234  56789012345
HV0"        QVQLQESGPGLVKPSQTLSLTCTVSGGSVS TYNAH  WIRQPPGKGLEWIG TMWNGGGIDYNSAFKD RVTISVDTSKNQFSLKLSSVTAADTAVYYCAR LGYYYDY WGQGTLVTVSS
HV2"        QVQLQESGPGLVKPSQTLSLTCTVSGGSVS        WIRQPPGKGLEWIG                  RVTISRDTSKNQFSLKLSSVTAADTAVYYCAR         WGQGTLVTVSS
HV3"        QVQLQESGPGLVKPSQTLSLTCTVSGFSVS        WIRQPPGKGLEWIG                  RVTISRDTSKNQFSLKLSSVTAADTAKYYCAR         WGQGTLVTVSS
HV4a"       QVQLQESGPGLVKPSQTLSLTCTVSGFSVS        WIRQPPGKGLEWIG                  RVTISRDTSKNQVSLKLSSVTAADTAKYYCAR         WGQGTLVTVSS
HV4b"       QVQLQESGPGLVKPSQTLSLTCTVSGFSVS        WIRQPPGKGLEWIG                  RLTISVDTSKNQFSLKLSSVTAADTAKYYCAR         WGQGTLVTVSS
HV4c"       QVQLQESGPGLVKPSQTLSLTCTVSGFSVS        WIRQPPGKGLEWMG                  RVTISRDTSKNQFSLKLSSVTAADTAKYYCAR         WGQGTLVTVSS
HV5"        QVQLQESGPGLVKPSQTLSLTCTVSGFSVS        WIRQPPGKGLEWIG                  RVTISRDTSKNQVSLKLSSVTAADTAKYYCAR         WGQGTLVTVSS
HV6"        QVQLQESGPGLVKPSQTLSLTCTVSGFSVS        WIRQPPGKGLEWMG                  RLTISRDTSKNQFSLKLSSVTAADTAKYYCAR         WGQGTLVTVSS
HV7"        QVQLQESGPGLVKPSQTLSLTCTVSGFSVT        WIRQPPGKGLEWMG                  RVTISRDTSKNQVSLKMSSVTAADTAKYYCAR         WGQGTLVTVSS
HV8"        QVQLQESGPGLVKPSQTLSITCTVSGFSVS        WIRQPPGKGLEWMG                  RLTISRDTSKNQFSLKLSSVTAADTAKYFCAR         WGQGTLVTVSS
HV10"       QVQLQESGPGLVKPSQTLSITCTVSGFSVT        WIRQPPGKGLEWMG                  RLTISRDTSKNQVSLKMSSVTAADTAVYFCAR         WGQGTLVTVSS
HV13"       QVQLQESGPGLVKLSQTLSITCTVSGFSLT        WVRQPPGKGLEWMG                  RLTISRDTSKSQVSLKMSSLTAADTAVYFCAR         WGQGILVTVSS
HV16"       QVQLQESGPGLVKLSQTLSITCTVSGFSLT        WVRQPPGKGLEWMG                  RLTISRDTSKSQVSLKMSSLTAADTAKYFCAR         WGQGILVTVSS
```

FIG. 17

| | 1234567890123456789012345678 90 | 12345 | 678901234 56789 | 012345678 9012345 | 678901234567890123456789012345 67 | 8901234 | 56789012345 |
|---|---|---|---|---|---|---|---|
| 18C1 VH | QVQLKETGPDLVQLFQTLSITCTVSGFSLT | TYNVH | WVRQPPGKGLEWMG | TMWNGGGIDYNSAFKS | RLSISRDTSKSQVFLKMNSLQTDDTAKYFCAR | LGYYVDY | WGHGIMVTVSS |
| VHres01 | QVQLKETGPDAVQLTQTLDITCTVSGASLT | | WVRQPPGKGLEWMG | | RLAISKDTSKSEVFLKMDSDQTDDTAKYFCAR | | WGQGIMVTVSS |
| VHres02 | QVQLKETGPDLVQPTQTLDITCTVSGASLT | | WVRQPPGKGLEWMG | | RLAISKDTSKSEVFLKMDSDQTDDTAKYFCAR | | WGQGIMVTVSS |
| VHres03 | QVQLKETGPDLVQLTQTLDITCTVSGFSLT | | WVRQPPGKGLEWMG | | RLAISKDTSKSEVFLKMDSDQTDDTAKYFCAR | | WGQGIMVTVSS |
| VHres04 | QVQLKETGPDLVQPTQTLDITCTVSGFSLT | | WVRQPPGKGLEWMG | | RLAISKDTSKSEVFLKMDSDQTDDTAKYFCAR | | WGQGIMVTVSS |
| VHres05 | QVQLKETGPDAVQLFQTLDITCTVSGASLT | | WVRQPPGKGLEWMG | | RLSISKDTSKSQVALKMDSDQTDDTAKYFCAR | | WGQGIMVTVSS |
| VHres06 | QVQLKETGPDLVQPTQTLDITCTVSGFSLT | | WVRQPPGKGLEWMG | | RLSISKDTSKSQVALKMDSDQTDDTAKYFCAR | | WGQGIMVTVSS |
| VHres07 | QVQLKETGPDAVQLTQTLDITCTVSGFSLT | | WVRQPPGKGLEWMG | | RLSISKDTSKSQVALKMDSDQTDDTAKYFCAR | | WGQGIMVTVSS |
| VHres08 | QVQLKETGPDLVQPTQTLDITCTVSGFSLT | | WVRQPPGKGLEWMG | | RLSISKDTSKSQVALKMDSDQTDDTAKYFCAR | | WGQGIMVTVSS |
| VHres09 | QVQLKETGPDLVQPTQTLDITCTVSGFSLT | | WVRQPPGKGLEWMG | | RLSISKDTSKSEVFLKMDSDQTDDTAKYFCAR | | WGQGIMVTVSS |
| VHres10 | QVQLKETGPDAVQLTQTLDITCTVSGASLT | | WVRQPPGKGLEWMG | | RLAISKDTSKSEVFLKMDSDQTDDTAKYFCAR | | WGQGIMVTVSS |
| VHres11 | QVQLKETGPDLVQPTQTLDITCTVSGASLT | | WVRQPPGKGLEWMG | | RLAISKDTSKSEVFLKMDSDQTDDTAKYFCAR | | WGQGIMVTVSS |
| VHres12 | QVQLKETGPDAVQLFQTLDITCTVSGASLT | | WVRQPPGKGLEWMG | | RLAISKDTSKSEVFLKMDSLQTDDTAKYFCAR | | WGQGIMVTVSS |
| VHres13 | QVQLKETGPDLVQPTQTLDITCTVSGFSLT | | WVRQPPGKGLEWMG | | RLAISKDTSKSEVFLKMDSLQTDDTAKYFCAR | | WGQGIMVTVSS |
| VHres14 | QVQLKETGPDAVQLTQTLDITCTVSGFSLT | | WVRQPPGKGLEWMG | | RLAISKDTSKSEVFLKMDSLQTDDTAKYFCAR | | WGQGIMVTVSS |
| VHres15 | QVQLKETGPDAVQLTQTLDITCTVSGFSLT | | WVRQPPGKGLEWMG | | RLAISKDTSKSEVFLKMDSLQTDDTAKYFCAR | | WGQGIMVTVSS |
| VHres16 | QVQLKETGPDLVQPTQTLDITCTVSGFSLT | | WVRQPPGKGLEWMG | | RLAISKDTSKSEVFLKMDSLQTDDTAKYFCAR | | WGQGIMVTVSS |
| | 1234567890123456789012345678 90 | 12345 | 678901234 56789 | 012345678 9012345 | 678901234567890123456789012345 67 | 8901234 | 56789012345 |
| VHres17 | QVQLKETGPDAVQLTQTLDITCTVSGASLT | TYNAH | WVRQPPGKGLEWMG | TMWNGGGIDYNSAFKD | RLAISKDTSKSEVFLKMDSDQTDDTAKYFCAR | LGYYVDY | WGQGIMVTVSS |
| VHres18 | QVQLKETGPDLVQPTQTLDITCTVSGASLT | | WVRQPPGKGLEWMG | | RLAISKDTSKSEVFLKMDSDQTDDTAKYFCAR | | WGQGIMVTVSS |
| VHres19 | QVQLKETGPDLVQLTQTLDITCTVSGFSLT | | WVRQPPGKGLEWMG | | RLAISKDTSKSEVFLKMDSDQTDDTAKYFCAR | | WGQGIMVTVSS |
| VHres20 | QVQLKETGPDLVQPTQTLDITCTVSGFSLT | | WVRQPPGKGLEWMG | | RLAISKDTSKSEVFLKMDSDQTDDTAKYFCAR | | WGQGIMVTVSS |
| VHres21 | QVQLKETGPDAVQLFQTLDITCTVSGASLT | | WVRQPPGKGLEWMG | | RLSISKDTSKSQVALKMDSDQTDDTAKYFCAR | | WGQGIMVTVSS |
| VHres22 | QVQLKETGPDLVQPTQTLDITCTVSGFSLT | | WVRQPPGKGLEWMG | | RLSISKDTSKSQVALKMDSDQTDDTAKYFCAR | | WGQGIMVTVSS |
| VHres23 | QVQLKETGPDAVQLTQTLDITCTVSGFSLT | | WVRQPPGKGLEWMG | | RLSISKDTSKSQVALKMDSDQTDDTAKYFCAR | | WGQGIMVTVSS |
| VHres24 | QVQLKETGPDLVQPTQTLDITCTVSGFSLT | | WVRQPPGKGLEWMG | | RLSISKDTSKSQVALKMDSDQTDDTAKYFCAR | | WGQGIMVTVSS |
| VHres25 | QVQLKETGPDAVQLTQTLDITCTVSGASLT | | WVRQPPGKGLEWMG | | RLAISKDTSKSEVFLKMDSDQTDDTAKYFCAR | | WGQGIMVTVSS |
| VHres26 | QVQLKETGPDLVQPTQTLDITCTVSGASLT | | WVRQPPGKGLEWMG | | RLAISKDTSKSEVFLKMDSDQTDDTAKYFCAR | | WGQGIMVTVSS |
| VHres27 | QVQLKETGPDAVQLTQTLDITCTVSGFSLT | | WVRQPPGKGLEWMG | | RLAISKDTSKSEVFLKMDSDQTDDTAKYFCAR | | WGQGIMVTVSS |
| VHres28 | QVQLKETGPDLVQPTQTLDITCTVSGFSLT | | WVRQPPGKGLEWMG | | RLAISKDTSKSEVFLKMDSDQTDDTAKYFCAR | | WGQGIMVTVSS |
| VHres29 | QVQLKETGPDAVQLFQTLDITCTVSGASLT | | WVRQPPGKGLEWMG | | RLAISKDTSKSEVFLKMDSLQTDDTAKYFCAR | | WGQGIMVTVSS |
| VHres30 | QVQLKETGPDLVQPTQTLDITCTVSGFSLT | | WVRQPPGKGLEWMG | | RLAISKDTSKSEVFLKMDSLQTDDTAKYFCAR | | WGQGIMVTVSS |
| VHres31 | QVQLKETGPDAVQLTQTLDITCTVSGFSLT | | WVRQPPGKGLEWMG | | RLAISKDTSKSEVFLKMDSLQTDDTAKYFCAR | | WGQGIMVTVSS |
| VHres32 | QVQLKETGPDLVQPTQTLDITCTVSGFSLT | | WVRQPPGKGLEWMG | | RLAISKDTSKSEVFLKMDSLQTDDTAKYFCAR | | WGQGIMVTVSS |

|  | 123456789012 | 345678901234 5 | 678901234567890 | 1234567 | 8901234567890123456789 01 | 2345678901 | 2345678901 |
|---|---|---|---|---|---|---|---|
| 18C1 VL | QFVLIQSNSMSTSLGSTVKLSC | KRSTGNIGSSYVY | WYQQHEGRSPTTMIY | DGDKRPD | GVPDRFSGSIDSSSNSAFLTINNVQIEDEAIYFC | QSFSSGIKFI | FGGGTKLTVL |
| LV0 | NFMLTQPHSVSESPGKTVTISC |  | WYQQREGSSPTTMIY |  | GVPDRFSGSIDSSSNSASLTISGLKTEDEADYYC |  | FGGGTKLTVL |
| LV3 | NFMLTQPHSVSESPGKTVTISC |  | WYQQREGSSPTTVIY |  | GVPDRFSGSIDSSSNSASLTISGLKTEDEAIYYC |  | FGGGTKLTVL |
| LV4a | NFMLTQPHSVSESPGKTVTISC |  | WYQQREGSSPTTMIY |  | GVPDRFSGSIDSSSNSASLTISGLKTEDEAIYYC |  | FGGGTKLTVL |
| LV4b | NFMLTQPHSVSESPGKTVKISC |  | WYQQREGSSPTTMIY |  | GVPDRFSGSIDSSSNSASLTISGLKTEDEAIYYC |  | FGGGTKLTVL |
| LV5a | NFMLTQPHSVSTSLGKTVTISC |  | WYQQREGSSPTTVIY |  | GVPDRFSGSIDSSSNSAFLTISGLKTEDEAIYYC |  | FGGGTKLTVL |
| LV5b | NFMLTQPHSVSTSPGSTVKISC |  | WYQQREGSSPTTVIY |  | GVPDRFSGSIDSSSNSASLTISGLQTEDEAIYYC |  | FGGGTKLTVL |
| LV6a | NFMLTQPHSVSTSPGSTVLSC |  | WYQQREGSSPTTMIY |  | GVPDRFSGSIDSSSNSASLTISGLKTEBEAIYYC |  | FGGGTKLTVL |
| LV6b | NFMLTQPHSVSESPGSTVTLSC |  | WYQQREGSSPTTMIY |  | GVPDRFSGSIDSSSNSASLTISGLKTEDEAIYYC |  | FGGGTKLTVL |
| LV6c | NFMLTQPHSVSESLGKTVTLSC |  | WYQQREGSSPTTMIY |  | GVPDRFSGSIDSSSNSASLTISGVKTEDEAIYYC |  | FGGGTKLTVL |
| LV6d | NFMLTQPHSVSTSLGKTVTLSC |  | WYQQREGSSPTTMIY |  | GVPDRFSGSIDSSSNSASLTISGLQTEDEADYYC |  | FGGGTKLTVL |
| LV7 | NFMLTQPHSVSTSPGKTVTISC |  | WYQQREGSSPTTMIY |  | GVPDRFSGSIDSSSNSAFLTISGLKTEDEAIYYC |  | FGGGTKLTVL |
| LV8 | NFMLTQSHSVSTSLGSTVKISC |  | WYQQREGSSPTTMIY |  | GVPDRFSGSIDSSSNSAFLTISGVKTEDEAIYYC |  | FGGGTKLTVL |
| LV9 | NFMLTQSHSVSTSPGKTVTISC |  | WYQQREGSSPTTMIY |  | GVPDRFSGSIDSSSNSAFLTISGLKTEDEAIYYC |  | FGGGTKLTVL |
| LV10 | NFMLTQSHSMSTSLGKTVKLSC |  | WYQQREGSSPTTMIY |  | GVPDRFSGSIDSSSNSAFLTISGLKTEDEAIYYC |  | FGGGTKLTVL |
| LV14 | NFMLTQSHSMSTSLGSTVKLSC |  | WYQQREGSSPTTMIY |  | GVPDRFSGSIDSSSNSAFLTISGVQTEDEAIYYC |  | FGGGTKLTVL |

B

|  | 123456789012345678 9012 | 345678901234 5 | 678901234567890 | 1234567 | 8901234567890123456789 01 | 2345678901 | 2345678901 |
|---|---|---|---|---|---|---|---|
| 18C1 VL | QFVLIQSNSMSTSLGSTVKLSC | KRSTGNIGSSYVY | WYQQHEGRSPTTMIY | DGDKRPD | GVPDRFSGSIDSSSNSAFLTINNVQIEDEAIYFC | QSFSSGIKFI | FGGGTKLTVL |
| VLres01 | QFALIQSDSMSTSAGSTVKLSC |  | WYQQHEGRSPTTMIY |  | GVPDRFSGSIDSSSNSASLTINDVQIEDEAVYFC |  | FGGGTKLTVL |
| VLres02 | QFVLIQSDSMSTSAGSTVKLSC |  | WYQQHEGRSPTTMIY |  | GVPDRFSGSIDSSSNSASLTINDVQIEDEAVYFC |  | FGGGTKLTVL |
| VLres03 | QFALIQSDSMSTSAGSTVLSC |  | WYQQHEGRSPTTMIY |  | GVPDRFSGSIDSSSNSASLTINDVQIEDEAVYFC |  | FGGGTKLTVL |
| VLres04 | QFALIQSDSMSTSAGSTVKLSC |  | WYQQHEGRSPTTMIY |  | GVPDRFSGSIDSSSNSASLTIINDVQIEDEAVYFC |  | FGGGTKLTVL |
| VLres05 | QFALIQSDSMSTSAGSTVKLSC |  | WYQQHEGRSPTTMIY |  | GVPDRFSGSIDSSSNSASLTINDVQVEDEAIYFC |  | FGGGTKLTVL |
| VLres06 | QFVLIQSDSMSTSAGSTVKLSC |  | WYQQHEGRSPTTMIY |  | GVPDRFSGSIDSSSNSASLTINDVQVEDEAIYFC |  | FGGGTKLTVL |
| VLres07 | QFALIQSDSMSTSAGSTVKLSC |  | WYQQHEGRSPTTMIY |  | GVPDRFSGSIDSSSNSASLTINDVQVEDEAIYFC |  | FGGGTKLTVL |
| VLres08 | QFALIQSDSMSTSAGSTVKLSC |  | WYQQHEGRSPTTMIY |  | GVPDRFSGSIDSSSNSASLTINDVQVEDEAIYFC |  | FGGGTKLTVL |
| VLres09 | QFALIQSDSMSTSAGSTVLSC |  | WYQQHEGRSPTTMIY |  | GVPDRFSGSIDSSSNSASLTINNVQIEDEAVYFC |  | FGGGTKLTVL |
| VLres10 | QFALIQSDSMSTSAGSTVLSC |  | WYQQHEGRSPTTMIY |  | GVPDRFSGSIDSSSNSASLTINNVQIEDEAVYFC |  | FGGGTKLTVL |
| VLres11 | QFVLIQSDSMSTSLGSTVKLSC |  | WYQQHEGRSPTTMIY |  | GVPDRFSGSIDSSSNSASLTINNVQIEDEAVYFC |  | FGGGTKLTVL |
| VLres12 | QFALIQSDSMSTSAGSTVKLSC |  | WYQQHEGRSPTTMIY |  | GVPDRFSGSIDSSSNSASLTINNVQIEDEAVYFC |  | FGGGTKLTVL |
| VLres13 | QFALIQSDSMSTSAGSTVLSC |  | WYQQHEGRSPTTMIY |  | GVPDRFSGSIDSSSNSAFLTINNVQIEDEAVYFC |  | FGGGTKLTVL |
| VLres14 | QFVLIQSDSMSTSLGSTVKLSC |  | WYQQHEGRSPTTMIY |  | GVPDRFSGSIDSSSNSAFLTINDVQIEDEAVYFC |  | FGGGTKLTVL |
| VLres15 | QFALIQSDSMSTSAGSTVLSC |  | WYQQHEGRSPTTMIY |  | GVPDRFSGSIDSSSNSAFLTINDVQIEDEAVYFC |  | FGGGTKLTVL |
| VLres16 | QFALIQSDSMSTSAGSTVKLSC |  | WYQQHEGRSPTTMIY |  | GVPDRFSGSIDSSSNSAFLTINDVQIEDEAVYFC |  | FGGGTKLTVL |

FIG. 19

| | 1234567890123456789 0 | 12345 | 67890123456789 | 012345678901 2345 | 67890123456789012345678901234567 | 8901234 | 56789012345 |
|---|---|---|---|---|---|---|---|
| HVmut01 | QVQLQESGPDLVQPSQTLDITCTVSGFSLT | TYNVH | WVRQPPGKGLEWMG | TMWNGGGIDYNSAFKS | RLAISRDTSKNQVSLKMDSLQTDDTAVYFCAR | LGYYVDY | WGQGILVTVSS |
| HVmut02 | QVQLQESGPDLVKPSQTLDITCTVSGFSLT | | WVRQPPGKGLEWMG | | RLTISRDTSKNQVFLKMDSLQTDDTAVYFCAR | | WGQGTLVTVSS |
| HVmut03 | QVQLQESGPGLVKPSQTLDITCTVSGFSLT | | WVRQPPGKGLEWMG | | RLAISRDTSKNEVFLKMDSLITAADTAVYFCAR | | WGQGTLVTVSS |
| HVmut04 | QVQLQESGPDLVQPSQTLDITCTVSGFSLT | | WVRQPPGKGLEWMG | | RLAISRDTSKNEVFLKMDSLQTDDTAKYFCAR | | WGQGILVTVSS |
| HVmut05 | QVQLQESGPGLVKPSQTLDITCTVSGFSLT | | WVRQPPGKGLEWMG | | RLAISRDTSKNEVFLKMSSLTAADTAVYFCAR | | WGQGTLVTVSS |
| HVmut06 | QVQLQESGPDLVKPSQTLDITCTVSGFSLT | | WVRQPPGKGLEWMG | TMWNGGGIDYNSAFKD | RLTISRDTSKNEVFLKMSSLTAADTAVYFCAR | | WGQGILVTVSS |
| HVmut07 | QVQLQESGPDLVQPSQTLDITCTVSGFSLT | | WVRQPPGKGLEWMG | | RLAISRDTSKNQVSLKMDSLQTDDTAKYFCAR | | WGQGILVTVSS |
| HVmut08 | QVQLQESGPGLVQPSQTLDITCTVSGFSLT | | WVRQPPGKGLEWMG | | RLTISRDTSKNQVFLKMDSLQTDDTAVYFCAR | | WGQGTLVTVSS |
| HVmut09 | QVQLQESGPDLVKPSQTLDITCTVSGFSLT | | WVRQPPGKGLEWMG | | RLAISRDTSKNEVFLKMDSLITAADTAKYFCAR | | WGQGTLVTVSS |
| HVmut10 | QVQLQESGPDLVQPSQTLDITCTVSGFSLT | | WVRQPPGKGLEWMG | | RLAISRDTSKNEVFLKMDSLQTDDTAVYFCAR | | WGQGILVTVSS |

FIG. 27
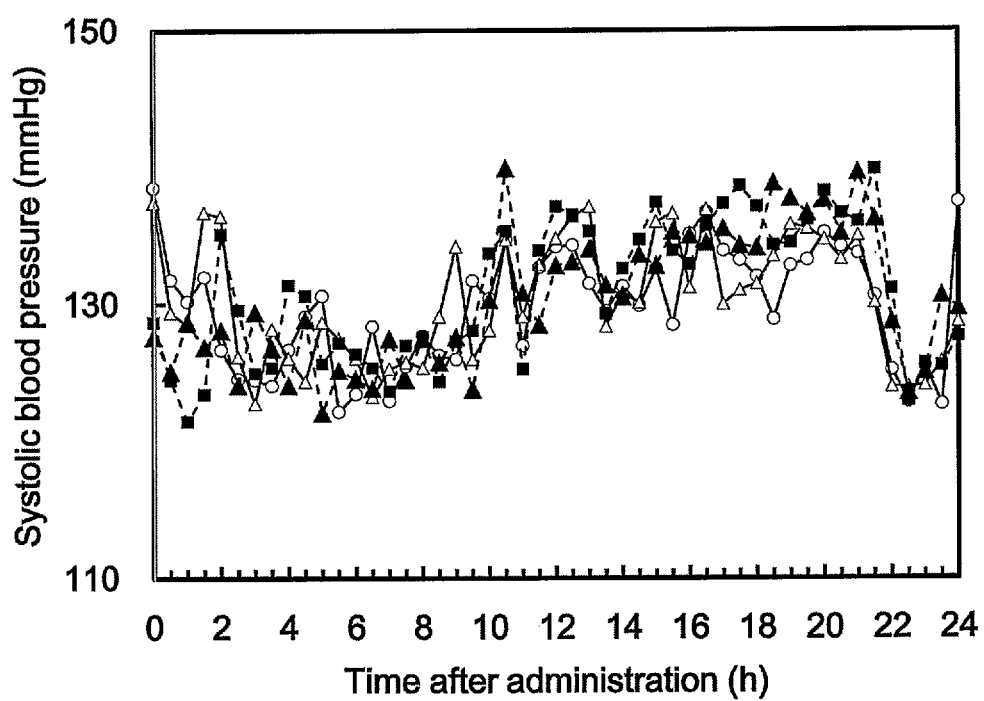
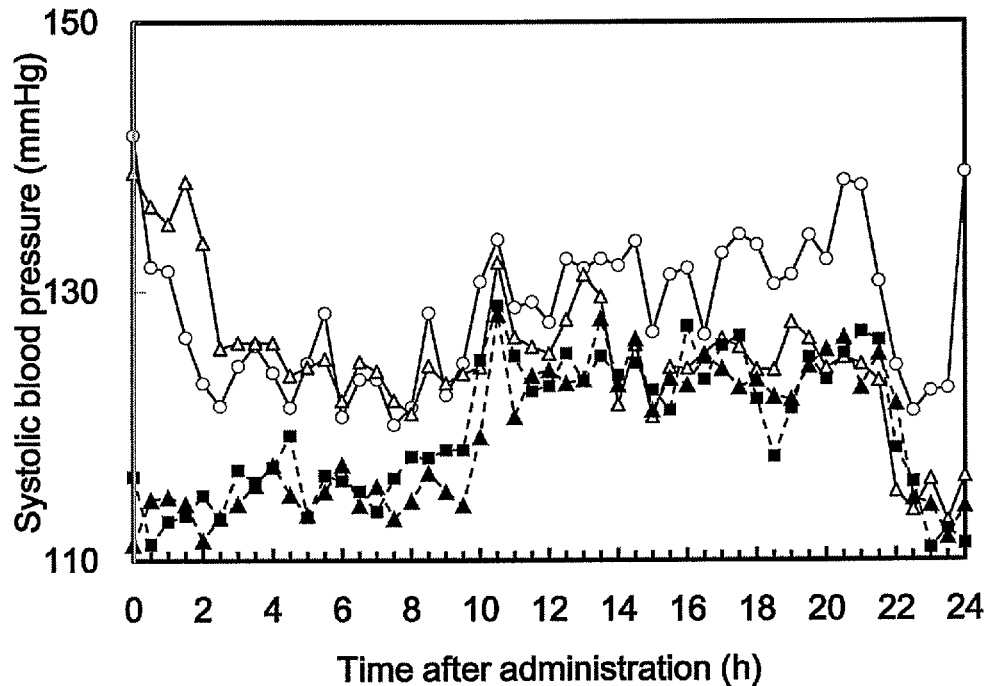

SEQUENCE LISTING

```
<160> NUMBER OF SEQ ID NOS: 182

<210> SEQ ID NO 1
<211> LENGTH: 25
<212> TYPE: DNA
<213> ORGANISM: Artificial
<220> FEATURE:
<223> OTHER INFORMATION: Description of the artificial sequence: RV1
      primer for rat IgG1

<400> SEQUENCE: 1
tagagyccag actgcaggac agctg                                              25

<210> SEQ ID NO 2
<211> LENGTH: 19
<212> TYPE: DNA
<213> ORGANISM: Artificial
<220> FEATURE:
<223> OTHER INFORMATION: Description of the artificial sequence: RV1
      primer for rat IgG2a

<400> SEQUENCE: 2
ggatagacag akggggctg                                                     19

<210> SEQ ID NO 3
<211> LENGTH: 22
<212> TYPE: DNA
<213> ORGANISM: Artificial
<220> FEATURE:
<223> OTHER INFORMATION: description of the artificial sequence: RV1
      primer for rat Ig kappa

<400> SEQUENCE: 3
```

```
cttggtcaac gagagggtgc tg                                              22

<210> SEQ ID NO 4
<211> LENGTH: 20
<212> TYPE: DNA
<213> ORGANISM: Artificial
<220> FEATURE:
<223> OTHER INFORMATION: description of the artificial sequence: RV1
      primer for rat Ig rambda

<400> SEQUENCE: 4
gagctcytca gwkgaaggtg                                                 20

<210> SEQ ID NO 5
<211> LENGTH: 402
<212> TYPE: DNA
<213> ORGANISM: Rattus norvegicus

<400> SEQUENCE: 5
atggctgtgc tggtgctgct cctctgcctg gtgacatttc caaactctgt cttgacccag     60
gtacaactga aggagacagg acctgaccta gtgcaactga cacagaccct gtccatcaca    120
tgcactgtct ctgggttctc attaaccacc tataatgtgc actgggtccg tcagcctcca    180
ggaaaaggtc tggagtggat gggaacaatg tggaatggtg gaggcataga ttataattca    240
gcattcaaat cccgactgag tatcagcagg acacctcca  agagccaagt gttcttgaaa    300
atgaacagtc tgcaaactga tgacacagcc aagtacttct gtgccagact gggctactac    360
gttgattact ggggccacgg aatcatggtc acagtctcct ca                       402

<210> SEQ ID NO 6
<211> LENGTH: 402
<212> TYPE: DNA
<213> ORGANISM: Rattus norvegicus

<400> SEQUENCE: 6
atggctgtgc ttgtgctgct cctctgcctg gtgacatttc caaactctgt cttgacccag     60
gtacaactga aggagacagg acctgaccta gtgcaactga cacagaccct gtccatcaca    120
tgcactgtct ctgggttctc attaagcacc tataatgttc attgggtccg tcagcctcca    180
ggaaagggtc tggagtggat gggagcaatg tggaatggtg gaggtataaa ttataattca    240
gcatttaaat cccgactgag tatcagtagg acacctcca  agagccaagt tttcttaaaa    300
atgaacagtt tgcaaactga tgacacagcc aagtacttct gtgccagatt cggctatggg    360
tttgattact ggggccaagg agtcatggtc acagtctcct ca                       402

<210> SEQ ID NO 7
<211> LENGTH: 402
<212> TYPE: DNA
<213> ORGANISM: Rattus norvegicus

<400> SEQUENCE: 7
atggctgtgc tggtgctgct cctctgcctg gtgacatttc caaactctgt cttgacccag     60
gtacaactga aggagacagg acctgaccta gtgcaactga cacagaccct gtccatcaca    120
tgcactgtct ctgggttctc attaaccacc tataatgttc actgggtccg tcagcctcca    180
ggaaagggtc tggagtggat gggagcaatg tggaatggtg gaggcacaga ttataattca    240
gcatttaaat cccgactgag tatcagcagg acacctcca  agagccaagt tttcttaaaa    300
atgaacagtt tgcaaactga tgacacagcc aagtacttct gtgccaggct agctgaggga    360
```
tttgattact ggggccaagg agtcatggtc acagtctcct ca                            402

<210> SEQ ID NO 8
<211> LENGTH: 134
<212> TYPE: PRT
<213> ORGANISM: Rattus norvegicus

<400> SEQUENCE: 8

Met Ala Val Leu Val Leu Leu Leu Cys Leu Val Thr Phe Pro Asn Ser
1               5                   10                  15

Val Leu Thr Gln Val Gln Leu Lys Glu Thr Gly Pro Asp Leu Val Gln
            20                  25                  30

Leu Thr Gln Thr Leu Ser Ile Thr Cys Thr Val Ser Gly Phe Ser Leu
        35                  40                  45

Thr Thr Tyr Asn Val His Trp Val Arg Gln Pro Pro Gly Lys Gly Leu
    50                  55                  60

Glu Trp Met Gly Thr Met Trp Asn Gly Gly Gly Ile Asp Tyr Asn Ser
65                  70                  75                  80

Ala Phe Lys Ser Arg Leu Ser Ile Ser Arg Asp Thr Ser Lys Ser Gln
                85                  90                  95

Val Phe Leu Lys Met Asn Ser Leu Gln Thr Asp Asp Thr Ala Lys Tyr
            100                 105                 110

Phe Cys Ala Arg Leu Gly Tyr Tyr Val Asp Tyr Trp Gly His Gly Ile
        115                 120                 125

Met Val Thr Val Ser Ser
    130

<210> SEQ ID NO 9
<211> LENGTH: 134
<212> TYPE: PRT
<213> ORGANISM: Rattus norvegicus

<400> SEQUENCE: 9

Met Ala Val Leu Val Leu Leu Leu Cys Leu Val Thr Phe Pro Asn Ser
1               5                   10                  15

Val Leu Thr Gln Val Gln Leu Lys Glu Thr Gly Pro Asp Leu Val Gln
            20                  25                  30

Leu Thr Gln Thr Leu Ser Ile Thr Cys Thr Val Ser Gly Phe Ser Leu
        35                  40                  45

Ser Thr Tyr Asn Val His Trp Val Arg Gln Pro Pro Gly Lys Gly Leu
    50                  55                  60

Glu Trp Met Gly Ala Met Trp Asn Gly Gly Gly Ile Asn Tyr Asn Ser
65                  70                  75                  80

Ala Phe Lys Ser Arg Leu Ser Ile Ser Arg Asp Thr Ser Lys Ser Gln
                85                  90                  95

Val Phe Leu Lys Met Asn Ser Leu Gln Thr Asp Asp Thr Ala Lys Tyr
            100                 105                 110

Phe Cys Ala Arg Phe Gly Tyr Gly Phe Asp Tyr Trp Gly Gln Gly Val
        115                 120                 125

Met Val Thr Val Ser Ser
    130

<210> SEQ ID NO 10
<211> LENGTH: 134
<212> TYPE: PRT
<213> ORGANISM: Rattus norvegicus

<400> SEQUENCE: 10

```
Met Ala Val Leu Val Leu Leu Cys Leu Val Thr Phe Pro Asn Ser
1               5                   10                  15

Val Leu Thr Gln Val Gln Leu Lys Glu Thr Gly Pro Asp Leu Val Gln
            20                  25                  30

Leu Thr Gln Thr Leu Ser Ile Thr Cys Thr Val Ser Gly Phe Ser Leu
            35                  40                  45

Ser Thr Tyr Asn Val His Trp Val Arg Gln Pro Pro Gly Lys Gly Leu
    50                  55                  60

Glu Trp Met Gly Ala Met Trp Asn Gly Gly Ile Asn Tyr Asn Ser
65              70                  75                  80

Ala Phe Lys Ser Arg Leu Ser Ile Ser Arg Asp Thr Ser Lys Ser Gln
                85                  90                  95

Val Phe Leu Lys Met Asn Ser Leu Gln Thr Asp Asp Thr Ala Lys Tyr
                100                 105                 110

Phe Cys Ala Arg Phe Gly Tyr Gly Phe Asp Tyr Trp Gly Gln Gly Val
            115                 120                 125

Met Val Thr Val Ser Ser
    130
```

<210> SEQ ID NO 11
<211> LENGTH: 390
<212> TYPE: DNA
<213> ORGANISM: Rattus norvegicus

<400> SEQUENCE: 11

```
atgacatgga ctctactatt ccttgctgtt cttcatcact taacagggtc atgtgcccag    60
tttgtgctta ttcagtcaaa ctctatgtct acgtctctag aagcacagt caaactgtct   120
tgcaagcgca gcactggtaa cattggaagc agctatgtgt actggtacca gcagcatgag   180
ggaagatctc ccaccactat gatttatgat ggtgataaga ccagatgg agttcctgat   240
aggttctctg gctccattga cagctcttcc aactcagcct tcctgacaat caataatgtg   300
cagattgaag atgaagctat ctacttctgt cagtctttca gtagtggtat taagtttatt   360
ttcggcggtg gaaccaagct cactgtccta                                    390
```

<210> SEQ ID NO 12
<211> LENGTH: 393
<212> TYPE: DNA
<213> ORGANISM: Rattus norvegicus

<400> SEQUENCE: 12

```
atgggcatca ggatggagtc acatactagg gtcttcatat tcctgctgct ctggttgtct    60
ggtggtgatg gggaaactgt gatgacccag tctcccacat ccatgtccac atcaatagga   120
gagagggtca ccctgaactg caaggccagt cagagtgtgg cattaatgt agactggtac   180
caacggacac cagggcagtc tcctaaactg ctgatacatg ggcatccaa tcggcacact   240
ggggtccctg atcgcttcac aggcagtgga tttggagaga tttcactct caccatcagc   300
aacgtggagg ctgaagacct gactattat tattgtctgc agtatggctc cattcctctc   360
acgtttggag ctgggaccaa gctggaactg ata                                393
```

<210> SEQ ID NO 13
<211> LENGTH: 381
<212> TYPE: DNA
<213> ORGANISM: Rattus norvegicus

<400> SEQUENCE: 13

```
atggaatcac atactcaggt cttcatattc ctgctgctct ggttgtctgg tgcagatggg    60
gacactgtga tgacccagtc tcccgcatcc atgtccacgt cagtgggaga gagggtcacc   120
gtgaactgca aggccagtca gagtgtgggt actgttgttg cctggttcca acagaaacca   180 ggcagtctc ctaaacgact gatctacttg caaccaatc ggcacactgg ggtccctgat    240
cgcttcacag gcagtggatt tgggagagat ttcactctta ccatcagcaa tgtggaggct   300
gaagacctgg ctgtttatta ctgtctgcag tatggctcca ttccattcac gttcggctca   360
gggacgaagt tggaaataaa a                                             381
```

```
<210> SEQ ID NO 14
<211> LENGTH: 130
<212> TYPE: PRT
<213> ORGANISM: Rattus norvegicus

<400> SEQUENCE: 14
```

Met Thr Trp Thr Leu Leu Phe Leu Ala Val Leu His His Leu Thr Gly
1               5                   10                  15

Ser Cys Ala Gln Phe Val Leu Ile Gln Ser Asn Ser Met Ser Thr Ser
            20                  25                  30

Leu Gly Ser Thr Val Lys Leu Ser Cys Lys Arg Ser Thr Gly Asn Ile
        35                  40                  45

Gly Ser Ser Tyr Val Tyr Trp Tyr Gln Gln His Glu Gly Arg Ser Pro
    50                  55                  60

Thr Thr Met Ile Tyr Asp Gly Asp Lys Arg Pro Asp Gly Val Pro Asp
65                  70                  75                  80

Arg Phe Ser Gly Ser Ile Asp Ser Ser Asn Ser Ala Phe Leu Thr
                85                  90                  95

Ile Asn Asn Val Gln Ile Glu Asp Glu Ala Ile Tyr Phe Cys Gln Ser
            100                 105                 110

Phe Ser Ser Gly Ile Lys Phe Ile Phe Gly Gly Gly Thr Lys Leu Thr
        115                 120                 125

Val Leu
    130

```
<210> SEQ ID NO 15
<211> LENGTH: 131
<212> TYPE: PRT
<213> ORGANISM: Rattus norvegicus

<400> SEQUENCE: 15
```

Met Gly Ile Arg Met Glu Ser His Thr Arg Val Phe Ile Phe Leu Leu
1               5                   10                  15

Leu Trp Leu Ser Gly Gly Asp Gly Glu Thr Val Met Thr Gln Ser Pro
            20                  25                  30

Thr Ser Met Ser Thr Ser Ile Gly Glu Arg Val Thr Leu Asn Cys Lys
        35                  40                  45

Ala Ser Gln Ser Val Gly Ile Asn Val Asp Trp Tyr Gln Arg Thr Pro
    50                  55                  60

Gly Gln Ser Pro Lys Leu Leu Ile His Gly Ala Ser Asn Arg His Thr
65                  70                  75                  80

Gly Val Pro Asp Arg Phe Thr Gly Ser Gly Phe Gly Arg Asp Phe Thr
                85                  90                  95

Leu Thr Ile Ser Asn Val Glu Ala Glu Asp Leu Thr Ile Tyr Tyr Cys
            100                 105                 110

```
Leu Gln Tyr Gly Ser Ile Pro Leu Thr Phe Gly Ala Gly Thr Lys Leu
            115                 120                 125
Glu Leu Ile
    130
```

```
<210> SEQ ID NO 16
<211> LENGTH: 127
<212> TYPE: PRT
<213> ORGANISM: Rattus norvegicus

<400> SEQUENCE: 16

Met Glu Ser His Thr Gln Val Phe Ile Phe Leu Leu Leu Trp Leu Ser
1               5                   10                  15

Gly Ala Asp Gly Asp Thr Val Met Thr Gln Ser Pro Ala Ser Met Ser
            20                  25                  30

Thr Ser Val Gly Glu Arg Val Thr Val Asn Cys Lys Ala Ser Gln Ser
        35                  40                  45

Val Gly Thr Val Val Ala Trp Phe Gln Gln Lys Pro Gly Gln Ser Pro
    50                  55                  60

Lys Arg Leu Ile Tyr Leu Ala Thr Asn Arg His Thr Gly Val Pro Asp
65                  70                  75                  80

Arg Phe Thr Gly Ser Gly Phe Gly Arg Asp Phe Thr Leu Thr Ile Ser
                85                  90                  95

Asn Val Glu Ala Glu Asp Leu Ala Val Tyr Tyr Cys Leu Gln Tyr Gly
            100                 105                 110

Ser Ile Pro Phe Thr Phe Gly Ser Gly Thr Lys Leu Glu Ile Lys
        115                 120                 125
```

```
<210> SEQ ID NO 17
<211> LENGTH: 345
<212> TYPE: DNA
<213> ORGANISM: Rattus norvegicus

<400> SEQUENCE: 17
caggtacaac tgaaggagac aggacctgac ctagtgcaac tgacacagac cctgtccatc      60
acatgcactg tctctgggtt ctcattaacc acctataatg tgcactgggt ccgtcagcct     120
ccaggaaaag gtctggagtg gatgggaaca atgtggaatg gtggaggcat agattataat     180
tcagcattca atcccgact gagtatcagc agggacacct ccaagagcca agtgttcttg     240
aaaatgaaca gtctgcaaac tgatgacaca gccaagtact tctgtgccag actgggctac     300
tacgttgatt actggggcca cggaatcatg gtcacagtct cctca                     345
```

```
<210> SEQ ID NO 18
<211> LENGTH: 345
<212> TYPE: DNA
<213> ORGANISM: Rattus norvegicus

<400> SEQUENCE: 18
caggtacaac tgaaggagac aggacctgac ctagtgcaac tgacacagac cctgtccatc      60
acatgcactg tctctgggtt ctcattaagc acctataatg ttcattgggt ccgtcagcct     120
ccaggaaagg gtctggagtg gatgggagca atgtggaatg tggaggtat aaattataat      180 tcagcattta atcccgact gagtatcagt agggacacct ccaagagcca agttttctta     240
aaaatgaaca gtctgcaaac tgatgacaca gccaagtact tctgtgccag attcggctat     300
gggtttgatt actggggcca aggagtcatg gtcacagtct cctca                     345
```

```
<210> SEQ ID NO 19
<211> LENGTH: 345
<212> TYPE: DNA
<213> ORGANISM: Rattus norvegicus

<400> SEQUENCE: 19
caggtacaac tgaaggagac aggacctgac ctagtgcaac tgacacagac cctgtccatc    60
acatgcactg tctctggtt ctcattaacc acctataatg ttcactgggt ccgtcagcct   120
ccaggaaagg gtctggagtg gatgggagca atgtggaatg gtggaggcac agattataat   180
tcagcattta atcccgact gagtatcagc aggacacct ccaagagcca agttttctta    240
aaaatgaaca gtttgcaaac tgatgacaca gccaagtact tctgtgccag gctagctgag   300
ggatttgatt actggggcca aggagtcatg gtcacagtct cctca              345

<210> SEQ ID NO 20
<211> LENGTH: 333
<212> TYPE: DNA
<213> ORGANISM: Rattus norvegicus

<400> SEQUENCE: 20
cagtttgtgc ttattcagtc aaactctatg tctacgtctc taggaagcac agtcaaactg    60
tcttgcaagc gcagcactgg taacattgga agcagctatg tgtactggta ccagcagcat   120
gagggaagat ctcccaccac tatgatttat gatggtgata agagaccaga tggagttcct   180
gataggttct ctggctccat tgacagctct tccaactcag ccttcctgac aatcaataat   240
gtgcagattg aagatgaagc tatctacttc tgtcagtctt tcagtagtgg tattaagttt   300
attttcggcg gtggaaccaa gctcactgtc cta                         333

<210> SEQ ID NO 21
<211> LENGTH: 321
<212> TYPE: DNA
<213> ORGANISM: Rattus norvegicus

<400> SEQUENCE: 21
gaaactgtga tgacccagtc tcccacatcc atgtccacat caataggaga gagggtcacc    60
ctgaactgca aggccagtca gagtgtgggc attaatgtag actggtacca acggacacca   120
gggcagtctc ctaaactgct gatacatggg gcatccaatc ggcacactgg ggtccctgat   180
cgcttcacag gcagtggatt tgggagagat ttcactctca ccatcagcaa cgtggaggct   240
gaagacctga ctatttatta ttgtctgcag tatggctcca ttcctctcac gtttggagct   300
gggaccaagc tggaactgat a                                      321

<210> SEQ ID NO 22
<211> LENGTH: 321
<212> TYPE: DNA
<213> ORGANISM: Rattus norvegicus

<400> SEQUENCE: 22
gacactgtga tgacccagtc tcccgcatcc atgtccacgt cagtgggaga gagggtcacc    60
gtgaactgca aggccagtca gagtgtgggt actgttgttg cctggttcca acagaaacca   120
gggcagtctc ctaaacgact gatctacttg gcaaccaatc ggcacactgg ggtccctgat   180
cgcttcacag gcagtggatt tgggagagat ttcactctta ccatcagcaa tgtggaggct   240
gaagacctgg ctgtttatta ctgtctgcag tatggctcca ttccattcac gttcggctca   300
gggacgaagt tggaaataaa a                                      321
```

<210> SEQ ID NO 23
<211> LENGTH: 115
<212> TYPE: PRT
<213> ORGANISM: Rattus norvegicus

<400> SEQUENCE: 23

Gln Val Gln Leu Lys Glu Thr Gly Pro Asp Leu Val Gln Leu Thr Gln
1               5                   10                  15

Thr Leu Ser Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Asp Asp Thr Ala Lys Tyr Phe Cys Ala
                85                  90                  95

Arg Leu Gly Tyr Tyr Val Asp Tyr Trp Gly His Gly Ile Met Val Thr
            100                 105                 110

Val Ser Ser
        115

<210> SEQ ID NO 24
<211> LENGTH: 115
<212> TYPE: PRT
<213> ORGANISM: Rattus norvegicus

<400> SEQUENCE: 24

Gln Val Gln Leu Lys Glu Thr Gly Pro Asp Leu Val Gln Leu Thr Gln
1               5                   10                  15

Thr Leu Ser Ile Thr Cys Thr Val Ser Gly Phe Ser Leu Ser Thr Tyr
            20                  25                  30

Asn Val His Trp Val Arg Gln Pro Pro Gly Lys Gly Leu Glu Trp Met
        35                  40                  45

Gly Ala Met Trp Asn Gly Gly Ile Asn Tyr Asn Ser Ala Phe Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Asp Asp Thr Ala Lys Tyr Phe Cys Ala
                85                  90                  95

Arg Phe Gly Tyr Gly Phe Asp Tyr Trp Gly Gln Gly Val Met Val Thr
            100                 105                 110

Val Ser Ser
        115

<210> SEQ ID NO 25
<211> LENGTH: 115
<212> TYPE: PRT
<213> ORGANISM: Rattus norvegicus

<400> SEQUENCE: 25

Gln Val Gln Leu Lys Glu Thr Gly Pro Asp Leu Val Gln Leu Thr Gln
1               5                   10                  15

Thr Leu Ser Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met

```
            35                  40                  45
Gly Ala Met Trp Asn Gly Gly Thr Asp Tyr Asn Ser Ala Phe Lys
        50                  55                  60

Ser Arg Leu Ser Ile Ser Arg Asp Thr Ser Lys Ser Gln Val Phe Leu
65                  70                  75                  80

Lys Met Asn Ser Leu Gln Thr Asp Asp Thr Ala Lys Tyr Phe Cys Ala
                85                  90                  95

Arg Leu Ala Glu Gly Phe Asp Tyr Trp Gly Gln Gly Val Met Val Thr
            100                 105                 110

Val Ser Ser
        115

<210> SEQ ID NO 26
<211> LENGTH: 111
<212> TYPE: PRT
<213> ORGANISM: Rattus norvegicus

<400> SEQUENCE: 26

Gln Phe Val Leu Ile Gln Ser Asn Ser Met Ser Thr Ser Leu Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Phe Leu Thr Ile Asn Asn
65                  70                  75                  80

Val Gln Ile Glu Asp Glu Ala Ile Tyr Phe Cys Gln Ser Phe Ser Ser
                85                  90                  95

Gly Ile Lys Phe Ile Phe Gly Gly Thr Lys Leu Thr Val Leu
            100                 105                 110

<210> SEQ ID NO 27
<211> LENGTH: 107
<212> TYPE: PRT
<213> ORGANISM: Rattus norvegicus

<400> SEQUENCE: 27

Glu Thr Val Met Thr Gln Ser Pro Thr Ser Met Ser Thr Ser Ile Gly
1               5                   10                  15

Glu Arg Val Thr Leu Asn Cys Lys Ala Ser Gln Ser Val Gly Ile Asn
            20                  25                  30

Val Asp Trp Tyr Gln Arg Thr Pro Gly Gln Ser Pro Lys Leu Leu Ile
        35                  40                  45

His Gly Ala Ser Asn Arg His Thr Gly Val Pro Asp Arg Phe Thr Gly
    50                  55                  60

Ser Gly Phe Gly Arg Asp Phe Thr Leu Thr Ile Ser Asn Val Glu Ala
65                  70                  75                  80

Glu Asp Leu Thr Ile Tyr Tyr Cys Leu Gln Tyr Gly Ser Ile Pro Leu
                85                  90                  95

Thr Phe Gly Ala Gly Thr Lys Leu Glu Leu Ile
            100                 105

<210> SEQ ID NO 28
<211> LENGTH: 107
<212> TYPE: PRT
```

<213> ORGANISM: Rattus norvegicus

<400> SEQUENCE: 28

Asp Thr Val Met Thr Gln Ser Pro Ala Ser Met Ser Thr Ser Val Gly
1               5                   10                  15

Glu Arg Val Thr Val Asn Cys Lys Ala Ser Gln Ser Val Gly Thr Val
            20                  25                  30

Val Ala Trp Phe Gln Gln Lys Pro Gly Gln Ser Pro Lys Arg Leu Ile
        35                  40                  45

Tyr Leu Ala Thr Asn Arg His Thr Gly Val Pro Asp Arg Phe Thr Gly
    50                  55                  60

Ser Gly Phe Gly Arg Asp Phe Thr Leu Thr Ile Ser Asn Val Glu Ala
65                  70                  75                  80

Glu Asp Leu Ala Val Tyr Tyr Cys Leu Gln Tyr Gly Ser Ile Pro Phe
                85                  90                  95

Thr Phe Gly Ser Gly Thr Lys Leu Glu Ile Lys
            100                 105

<210> SEQ ID NO 29
<211> LENGTH: 5
<212> TYPE: PRT
<213> ORGANISM: Rattus norvegicus

<400> SEQUENCE: 29

Thr Tyr Asn Val His
1               5

<210> SEQ ID NO 30
<211> LENGTH: 16
<212> TYPE: PRT
<213> ORGANISM: Rattus norvegicus

<400> SEQUENCE: 30

Thr Met Trp Asn Gly Gly Gly Ile Asp Tyr Asn Ser Ala Phe Lys Ser
1               5                   10                  15

<210> SEQ ID NO 31
<211> LENGTH: 7
<212> TYPE: PRT
<213> ORGANISM: Rattus norvegicus

<400> SEQUENCE: 31

Leu Gly Tyr Tyr Val Asp Tyr
1               5

<210> SEQ ID NO 32
<211> LENGTH: 13
<212> TYPE: PRT
<213> ORGANISM: Rattus norvegicus

<400> SEQUENCE: 32

Lys Arg Ser Thr Gly Asn Ile Gly Ser Ser Tyr Val Tyr
1               5                   10

<210> SEQ ID NO 33
<211> LENGTH: 7
<212> TYPE: PRT
<213> ORGANISM: Rattus norvegicus

<400> SEQUENCE: 33

Asp Gly Asp Lys Arg Pro Asp
1               5

<210> SEQ ID NO 34
<211> LENGTH: 10
<212> TYPE: PRT
<213> ORGANISM: Rattus norvegicus

<400> SEQUENCE: 34

Gln Ser Phe Ser Ser Gly Ile Lys Phe Ile
1               5                   10

<210> SEQ ID NO 35
<211> LENGTH: 5
<212> TYPE: PRT
<213> ORGANISM: Rattus norvegicus

<400> SEQUENCE: 35

Thr Tyr Asn Val His
1               5

<210> SEQ ID NO 36
<211> LENGTH: 16
<212> TYPE: PRT
<213> ORGANISM: Rattus norvegicus

<400> SEQUENCE: 36

Ala Met Trp Asn Gly Gly Gly Ile Asn Tyr Asn Ser Ala Phe Lys Ser
1               5                   10                  15

<210> SEQ ID NO 37
<211> LENGTH: 7
<212> TYPE: PRT
<213> ORGANISM: Rattus norvegicus

<400> SEQUENCE: 37

Phe Gly Tyr Gly Phe Asp Tyr
1               5

<210> SEQ ID NO 38
<211> LENGTH: 11
<212> TYPE: PRT
<213> ORGANISM: Rattus norvegicus

<400> SEQUENCE: 38

Lys Ala Ser Gln Ser Val Gly Ile Asn Val Asp
1               5                   10

<210> SEQ ID NO 39
<211> LENGTH: 7
<212> TYPE: PRT
<213> ORGANISM: Rattus norvegicus

<400> SEQUENCE: 39

Gly Ala Ser Asn Arg His Thr
1               5

<210> SEQ ID NO 40
<211> LENGTH: 9
<212> TYPE: PRT
<213> ORGANISM: Rattus norvegicus

<400> SEQUENCE: 40

Leu Gln Tyr Gly Ser Ile Pro Leu Thr
1               5

```
<210> SEQ ID NO 41
<211> LENGTH: 5
<212> TYPE: PRT
<213> ORGANISM: Rattus norvegicus

<400> SEQUENCE: 41

Thr Tyr Asn Val His
1               5

<210> SEQ ID NO 42
<211> LENGTH: 16
<212> TYPE: PRT
<213> ORGANISM: Rattus norvegicus

<400> SEQUENCE: 42

Ala Met Trp Asn Gly Gly Gly Thr Asp Tyr Asn Ser Ala Phe Lys Ser
1               5                   10                  15

<210> SEQ ID NO 43
<211> LENGTH: 7
<212> TYPE: PRT
<213> ORGANISM: Rattus norvegicus

<400> SEQUENCE: 43

Leu Ala Glu Gly Phe Asp Tyr
1               5

<210> SEQ ID NO 44
<211> LENGTH: 11
<212> TYPE: PRT
<213> ORGANISM: Rattus norvegicus

<400> SEQUENCE: 44

Lys Ala Ser Gln Ser Val Gly Thr Val Val Ala
1               5                   10

<210> SEQ ID NO 45
<211> LENGTH: 7
<212> TYPE: PRT
<213> ORGANISM: Rattus norvegicus

<400> SEQUENCE: 45

Leu Ala Thr Asn Arg His Thr
1               5

<210> SEQ ID NO 46
<211> LENGTH: 9
<212> TYPE: PRT
<213> ORGANISM: Rattus norvegicus

<400> SEQUENCE: 46

Leu Gln Tyr Gly Ser Ile Pro Phe Thr
1               5

<210> SEQ ID NO 47
<211> LENGTH: 424
<212> TYPE: PRT
<213> ORGANISM: Homo sapiens

<400> SEQUENCE: 47

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
                20                  25                  30
```

-continued

Glu Glu Asp Met Ser Leu Phe Gly Asp Val Phe Ser Glu Gln Asp Gly
 35                  40                  45

Val Asp Phe Asn Thr Leu Leu Gln Ser Met Lys Asp Glu Phe Leu Lys
 50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
                 85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
        115                 120                 125

Leu Phe Asn Val Ser Ile Pro His His Glu Glu Val Ile Met Ala Glu
    130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
        275                 280                 285

Ser Phe Ser Ser Gly Pro Gly Glu Glu Ala Leu Leu Gln Met Arg Ser
    290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
        355                 360                 365

His Ala Ile Ile Gln Ala Leu Val His Leu Lys Asn Ser Gln Lys Ala
    370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420

<210> SEQ ID NO 48
<211> LENGTH: 108
<212> TYPE: PRT

<213> ORGANISM: Homo sapiens

<400> SEQUENCE: 48

| Asn | Ala | Lys | Gly | Asn | Tyr | Cys | Lys | Arg | Thr | Pro | Leu | Tyr | Ile | Asp | Phe |
| 1 | | | | 5 | | | | | 10 | | | | | 15 | |

| Lys | Glu | Ile | Gly | Trp | Asp | Ser | Trp | Ile | Ile | Ala | Pro | Pro | Gly | Tyr | Glu |
| | | | 20 | | | | | 25 | | | | | 30 | | |

| Ala | Tyr | Glu | Cys | Arg | Gly | Val | Cys | Asn | Tyr | Pro | Leu | Ala | Glu | His | Leu |
| | | | 35 | | | | | 40 | | | | | 45 | | |

| Thr | Pro | Thr | Lys | His | Ala | Ile | Ile | Gln | Ala | Leu | Val | His | Leu | Lys | Asn |
| | | | 50 | | | | | 55 | | | | | 60 | | |

| Ser | Gln | Lys | Ala | Ser | Lys | Ala | Cys | Cys | Val | Pro | Thr | Lys | Leu | Glu | Pro |
| 65 | | | | | 70 | | | | | 75 | | | | | 80 |

| Ile | Ser | Ile | Leu | Tyr | Leu | Asp | Lys | Gly | Val | Val | Thr | Tyr | Lys | Phe | Lys |
| | | | | 85 | | | | | 90 | | | | | 95 | |

| Tyr | Glu | Gly | Met | Ala | Val | Ser | Glu | Cys | Gly | Cys | Arg |
| | | | 100 | | | | | 105 | | | |

<210> SEQ ID NO 49
<211> LENGTH: 1275
<212> TYPE: DNA
<213> ORGANISM: Homo sapiens

<400> SEQUENCE: 49

| atgggctctc tggtcctgac actgtgcgct cttttctgcc tggcagctta cttggtttct | 60 |
| ggcagcccca tcatgaacct agagcagtct cctctggaag aagatatgtc cctctttggt | 120 |
| gatgttttct cagagcaaga cggtgtcgac tttaacacac tgctccagag catgaaggat | 180 |
| gagtttctta agacactaaa cctctctgac atccccacgc aggattcagc caaggtggac | 240 |
| ccaccagagt acatgttgga actctacaac aaatttgcaa cagatcggac ctccatgccc | 300 |
| tctgccaaca tcattaggag tttcaagaat gaagatctgt tttcccagcc ggtcagtttt | 360 |
| aatgggctcc gaaataccc cctcctcttc aatgtgtcca ttcctcacca tgaagaggtc | 420 |
| atcatggctg aacttaggct atacacactg gtgcaaaggg atcgtatgat atacgatgga | 480 |
| gtagaccgga aaattaccat ttttgaagtg ctggagagca aggggataa tgagggagaa | 540 |
| agaaacatgc tggtcttggt gtctggggag atatatggaa ccaacagtga gtgggagact | 600 |
| tttgatgtca cagatgccat cagacgttgg caaaagtcag gctcatccac ccaccagctg | 660 |
| gaggtccaca ttgagagcaa acacgatgaa gctgaggatg ccagcagtgg acggctagaa | 720 |
| atagatacca gtgcccagaa taagcataac cctttgctca tcgtgttttc tgatgaccaa | 780 |
| agcagtgaca aggagaggaa ggaggaactg aatgaaatga tttcccatga gcaacttcca | 840 |
| gagctggaca acttgggcct ggatagcttt tccagtggac ctgggaaga ggctttgttg | 900 |
| cagatgagat caaacatcat ctatgactcc actgcccgaa tcagaaggaa cgccaaagga | 960 |
| aactactgta gaggaccccc gctctacatc gacttcaagg agattgggtg ggactcctgg | 1020 |
| atcatcgctc cgcctggata cgaagcctat gaatgccgtg gtgtttgtaa ctacccctg | 1080 |
| gcagagcatc tcacacccac aaagcatgca attatccagg ccttggtcca cctcaagaat | 1140 |
| tcccagaaag cttccaaagc ctgctgtgtg cccacaaagc tagagcccat ctccatcctc | 1200 |
| tatttagaca aaggcgtcgt cacctacaag tttaaatacg aaggcatggc cgtctccgaa | 1260 |
| tgtggctgta gatag | 1275 |

<210> SEQ ID NO 50

```
<211> LENGTH: 327
<212> TYPE: DNA
<213> ORGANISM: Homo sapiens

<400> SEQUENCE: 50
aacgccaaag gaaactactg taagaggacc ccgctctaca tcgacttcaa ggagattggg      60
tgggactcct ggatcatcgc tccgcctgga tacgaagcct atgaatgccg tggtgtttgt     120 aactacccccc tggcagagca tctcacaccc acaaagcatg caattatcca ggccttggtc    180
cacctcaaga attcccagaa agcttccaaa gcctgctgtg tgcccacaaa gctagagccc     240
atctccatcc tctatttaga caaaggcgtc gtcacctaca gtttaaaata cgaaggcatg     300
gccgtctccg aatgtggctg tagatag                                         327

<210> SEQ ID NO 51
<211> LENGTH: 1038
<212> TYPE: PRT
<213> ORGANISM: Homo sapiens

<400> SEQUENCE: 51
```

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

```
Lys Tyr Leu Ser Leu His Thr Ser Asp Trp Val Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                    325                 330                 335

Arg Asn Val Leu Val Lys Asn Asp Gly Thr Cys Val Ile Ser Asp Phe
                340                 345                 350

Gly Leu Ser Met Arg Leu Thr Gly Asn Arg Leu Val Arg Pro Gly Glu
            355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Asp Glu Asn Leu Met Glu His
        675                 680                 685

Ser Leu Lys Gln Phe Ser Gly Pro Asp Pro Leu Ser Ser Thr Ser Ser
    690                 695                 700
```

```
Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
                820                 825                 830

Gly Gln Thr Thr Asn Ile Val Thr His Arg Ala Gln Glu Met Leu Gln
            835                 840                 845

Asn Gln Phe Ile Gly Glu Asp Thr Arg Leu Asn Ile Asn Ser Ser Pro
850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925

Pro Ser Lys Pro Arg Arg Ala Gln Arg Pro Asn Ser Leu Asp Leu Ser
930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly
    1010                1015                1020

Thr Ala Thr Thr Met Val Ser Lys Asp Ile Gly Met Asn Cys Leu
    1025                1030                1035

<210> SEQ ID NO 52
<211> LENGTH: 503
<212> TYPE: PRT
<213> ORGANISM: Homo sapiens

<400> SEQUENCE: 52

Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
            20                  25                  30

Thr Cys Thr Cys Glu Ser Pro His Cys Lys Gly Pro Thr Cys Arg Gly
        35                  40                  45
```

-continued

```
Ala Trp Cys Thr Val Val Leu Val Arg Glu Glu Gly Arg His Pro Gln
     50                  55                  60

Glu His Arg Gly Cys Gly Asn Leu His Arg Glu Leu Cys Arg Gly Arg
 65                  70                  75                  80

Pro Thr Glu Phe Val Asn His Tyr Cys Cys Asp Ser His Leu Cys Asn
                 85                  90                  95

His Asn Val Ser Leu Val Leu Glu Ala Thr Gln Pro Pro Ser Glu Gln
                100                 105                 110

Pro Gly Thr Asp Gly Gln Leu Ala Leu Ile Leu Gly Pro Val Leu Ala
            115                 120                 125

Leu Leu Ala Leu Val Ala Leu Gly Val Leu Gly Leu Trp His Val Arg
        130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Ser Met Leu Gly Asp
                165                 170                 175

Leu Leu Asp Ser Asp Cys Thr Thr Gly Ser Gly Ser Gly Leu Pro Phe
            180                 185                 190

Leu Val Gln Arg Thr Val Ala Arg Gln Val Ala Leu Val Glu Cys Val
        195                 200                 205

Gly Lys Gly Arg Tyr Gly Glu Val Trp Arg Gly Leu Trp His Gly Glu
210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
            260                 265                 270

Leu Trp Leu Ile Thr His Tyr His Glu His Gly Ser Leu Tyr Asp Phe
        275                 280                 285

Leu Gln Arg Gln Thr Leu Glu Pro His Leu Ala Leu Arg Leu Ala Val
        290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                325                 330                 335

Leu Val Lys Ser Asn Leu Gln Cys Cys Ile Ala Asp Leu Gly Leu Ala
            340                 345                 350

Val Met His Ser Gln Gly Ser Asp Tyr Leu Asp Ile Gly Asn Asn Pro
        355                 360                 365

Arg Val Gly Thr Lys Arg Tyr Met Ala Pro Glu Val Leu Asp Glu Gln
        370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415

Ile Val Glu Asp Tyr Arg Pro Pro Phe Tyr Asp Val Val Pro Asn Asp
            420                 425                 430

Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
    450                 455                 460
```

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
            485                 490                 495

Glu Lys Pro Lys Val Ile Gln
            500

<210> SEQ ID NO 53
<211> LENGTH: 44
<212> TYPE: DNA
<213> ORGANISM: Artificial
<220> FEATURE:
<223> OTHER INFORMATION: discription of the artificial sequence: forward
      primer for 18C1 light chain

<400> SEQUENCE: 53
attgtgccgg aagctgggct cagtttgtgc ttattcagtc aaac                44

<210> SEQ ID NO 54
<211> LENGTH: 40
<212> TYPE: DNA
<213> ORGANISM: Artificial
<220> FEATURE:
<223> OTHER INFORMATION: description of the artificial sequence: primer
      R for 18C1 light chain

<400> SEQUENCE: 54
gcggccttgg gctgacctag gacagtgagc ttggttccac                    40

<210> SEQ ID NO 55
<211> LENGTH: 40
<212> TYPE: DNA
<213> ORGANISM: Artificial
<220> FEATURE:
<223> OTHER INFORMATION: description of the artificial sequence: primer
      F for 18C1 heavy chain

<400> SEQUENCE: 55
aagggcgtgc agtgccaggt acaactgaag gagacaggac                    40

<210> SEQ ID NO 56
<211> LENGTH: 44
<212> TYPE: DNA
<213> ORGANISM: Artificial
<220> FEATURE:
<223> OTHER INFORMATION: description of the artificial sequence: primer
      R for 18C1 heavy chain

<400> SEQUENCE: 56
gccccttggt gctagctgag gagactgtga ccatgattcc gtgg                44

<210> SEQ ID NO 57
<211> LENGTH: 38
<212> TYPE: DNA
<213> ORGANISM: Artificial
<220> FEATURE:
<223> OTHER INFORMATION: description of the artificial sequence: primer
      F for 12H3 light chain

<400> SEQUENCE: 57
tcccgcgtcc tctagtgaaa ctgtgatgac ccagtctc                      38

<210> SEQ ID NO 58
<211> LENGTH: 42
<212> TYPE: DNA
<213> ORGANISM: Artificial

<220> FEATURE:
<223> OTHER INFORMATION: description of the artificial sequence: primer
      R for 12H3 light chain

<400> SEQUENCE: 58
gtgcagccac cgtacgtatc agttccagct tggtcccagc tc                 42

<210> SEQ ID NO 59
<211> LENGTH: 40
<212> TYPE: DNA
<213> ORGANISM: Artificial
<220> FEATURE:
<223> OTHER INFORMATION: description of the artificail sequence: primer
      F for 12H3 heavy chain

<400> SEQUENCE: 59
aagggcgtgc agtgccaggt acaactgaag gagacaggac                    40

<210> SEQ ID NO 60
<211> LENGTH: 39
<212> TYPE: DNA
<213> ORGANISM: Artificial
<220> FEATURE:
<223> OTHER INFORMATION: description of the artificial sequence: primer
      R for 12H3 heavy chain

<400> SEQUENCE: 60
gccccttggt gctagctgag gagactgtga ccatgactc                     39

<210> SEQ ID NO 61
<211> LENGTH: 40
<212> TYPE: DNA
<213> ORGANISM: Artificial
<220> FEATURE:
<223> OTHER INFORMATION: description of the artificial sequence: primer
      F for 11H10 light chain

<400> SEQUENCE: 61
cccgcgtcct ctagtgacac tgtgatgacc cagtctcccg                    40

<210> SEQ ID NO 62
<211> LENGTH: 40
<212> TYPE: DNA
<213> ORGANISM: Artificial
<220> FEATURE:
<223> OTHER INFORMATION: description of the artificial sequence: primer
      R for 11H10 light chain

<400> SEQUENCE: 62
gtgcagccac cgtacgtttt atttccaact tcgtccctga                    40

<210> SEQ ID NO 63
<211> LENGTH: 40
<212> TYPE: DNA
<213> ORGANISM: Artificial
<220> FEATURE:
<223> OTHER INFORMATION: description of the artificial sequence: primer
      F for 11H10 heavy chain

<400> SEQUENCE: 63
aagggcgtgc agtgccaggt acaactgaag gagacaggac                    40

<210> SEQ ID NO 64
<211> LENGTH: 40
<212> TYPE: DNA
<213> ORGANISM: Artificial
<220> FEATURE:

<223> OTHER INFORMATION: description of the artificial sequence: primer
      R for 11H10 heavy chain

<400> SEQUENCE: 64
gccccttggt gctagctgag gagactgtga ccatgactcc                              40

<210> SEQ ID NO 65
<211> LENGTH: 110
<212> TYPE: PRT
<213> ORGANISM: Homo sapiens

<400> SEQUENCE: 65

```
Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
        35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110
```

<210> SEQ ID NO 66
<211> LENGTH: 429
<212> TYPE: PRT
<213> ORGANISM: Homo sapiens

<400> SEQUENCE: 66

```
Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
        115                 120                 125

Gln Lys His Ile Leu Leu Phe Asn Ile Ser Ile Pro Arg His Glu Gln
    130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190
```

Val Ser Gln Asp Ile Gln Asp Glu Gly Trp Glu Thr Leu Glu Val Ser
    195                 200                 205

Ser Ala Val Lys Arg Trp Val Arg Ser Asp Ser Thr Lys Ser Lys Asn
    210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
    290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
        355                 360                 365

Thr Pro Thr Lys His Ala Ile Val Gln Thr Leu Val His Leu Lys Phe
    370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
            420                 425

<210> SEQ ID NO 67
<211> LENGTH: 1290
<212> TYPE: DNA
<213> ORGANISM: Homo sapiens

<400> SEQUENCE: 67
atgtgtcctg gggcactgtg gtggccctg ccctgctgt ccctgctggc tggctccta      60 cagggaagc cactgcagag ctggggacga gggtctgctg ggggaaacgc ccacagccca    120 ctggggtgc ctggaggtgg gctgcctgag cacaccttca acctgaagat gtttctggag    180
aacgtgaagg tggatttcct gcgcagcctt aacctgagtg gggtcccttc gcaggacaaa   240
accagggtgg agccgccgca gtacatgatt gacctgtaca caggtacac gtccgataag    300 tcgactacgc cagcgtccaa cattgtgcgg agcttcagca tggaagatgc catctccata   360
actgccacag aggacttccc cttccagaag cacatcttgc tcttcaacat ctccattcct   420
aggcatgagc agatcaccag agctgagctc cgactctatg tctcctgtca aaatcacgtg   480
gacccctctc atgacctgaa aggaagcgtg gtcatttatg atgttctgga tgaacagat    540 gcctgggata gtgctacaga gaccaagacc ttcctggtgt cccaggacat tcaggatgag   600
ggctgggaga ccttggaagt gtccagcgcg gtgaagcgct gggtccggtc gactccacc    660 aagagcaaaa ataagctgga agtgactgtg gagagccaca ggaagggctg cgacacgctg   720
gacatcagtg tccccccagg ttccagaaac ctgcccttct tgttgtctt ctccaatgac   780

-continued

```
cacagcagtg ggaccaagga gaccaggctg gagctgaggg agatgatcag ccatgaacaa      840
gagagcgtgc tcaagaagct gtccaaggac ggctccacag aggcaggtga gagcagtcac      900
gaggaggaca cggatggcca cgtggctgcg gggtcgactt tagccaggcg gaaaaggagc      960
gccggggctg gcagccactg tcaaaagacc tccctgcggg taaacttcga ggacatcggc     1020
tgggacagct ggatcattgc acccaaggag tatgaagcct acgagtgtaa gggcggctgc     1080
ttcttcccct ggctgacga tgtgacgccg acgaaacacg ctatcgtgca gaccctggtg      1140
catctcaagt tccccacaaa ggtgggcaag gcctgctgtg tgcccaccaa actgagcccc     1200
atctccgtcc tctacaagga tgacatgggg gtgcccaccc tcaagtacca ttacgagggc     1260
atgagcgtgg cagagtgtgg gtgcaggtag                                      1290
```

<210> SEQ ID NO 68
<211> LENGTH: 333
<212> TYPE: DNA
<213> ORGANISM: Homo sapiens

<400> SEQUENCE: 68

```
agcgccgggg ctggcagcca ctgtcaaaag acctccctgc gggtaaactt cgaggacatc       60
ggctgggaca gctggatcat tgcacccaag gagtatgaag cctacgagtg taagggcggc      120
tgcttcttcc ccttggctga cgatgtgacg ccgacgaaac acgctatcgt gcagaccctg      180
gtgcatctca agttccccac aaaggtgggc aaggcctgct gtgtgcccac caaactgagc      240
cccatctccg tcctctacaa ggatgacatg ggggtgccca ccctcaagta ccattacgag      300
ggcatgagcg tggcagagtg tgggtgcagg tag                                   333
```

<210> SEQ ID NO 69
<211> LENGTH: 658
<212> TYPE: PRT
<213> ORGANISM: Homo sapiens

<400> SEQUENCE: 69

```
Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
                20                  25                  30

Gln Pro Val Gly Pro Glu Arg Gly Glu Val Thr Tyr Thr Thr Ser Gln
            35                  40                  45

Val Ser Lys Gly Cys Val Ala Gln Ala Pro Asn Ala Ile Leu Glu Val
        50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
                100                 105                 110

Gly Ile Pro Leu His Leu Ala Tyr Asn Ser Ser Leu Val Thr Phe Gln
            115                 120                 125

Glu Pro Pro Gly Val Asn Thr Thr Glu Leu Pro Ser Phe Pro Lys Thr
        130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175
```

```
Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
            195                 200                 205

Leu Glu Gly Val Ala Gly His Lys Glu Ala His Ile Leu Arg Val Leu
            210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
            275                 280                 285

Gly Phe Lys Leu Pro Asp Thr Pro Gln Gly Leu Leu Gly Glu Ala Arg
            290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
            355                 360                 365

Thr Leu Val Leu Lys Lys Glu Leu Val Ala His Leu Lys Cys Thr Ile
            370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430

Ser Ser Pro Gln Arg Lys Lys Val His Cys Leu Asn Met Asp Ser Leu
            435                 440                 445

Ser Phe Gln Leu Gly Leu Tyr Leu Ser Pro His Phe Leu Gln Ala Ser
450                 455                 460

Asn Thr Ile Glu Pro Gly Gln Gln Ser Phe Gln Val Arg Val Ser
465                 470                 475                 480

Pro Ser Val Ser Glu Phe Leu Leu Gln Leu Asp Ser Cys His Leu Asp
                485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
            515                 520                 525

Arg Phe Ser Phe Leu Leu His Phe Tyr Thr Val Pro Ile Pro Lys Thr
530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590
```

-continued

```
Leu Gly Ile Thr Phe Gly Ala Phe Leu Ile Gly Ala Leu Thr Ala
            595                 600                 605

Ala Leu Trp Tyr Ile Tyr Ser His Thr Arg Ser Pro Ser Lys Arg Glu
        610                 615                 620

Pro Val Ala Val Ala Ala Pro Ala Ser Ser Glu Ser Ser Ser Thr
625                 630                 635                 640

Asn His Ser Ile Gly Ser Thr Gln Ser Thr Pro Cys Ser Thr Ser Ser
                    645                 650                 655

Met Ala

<210> SEQ ID NO 70
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HV0

<400> SEQUENCE: 70

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 71
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 LV0

<400> SEQUENCE: 71

Asn Phe Met Leu Thr Gln Pro His Ser Val Ser Glu Ser Pro Gly Lys
1               5                   10                  15

Thr Val Thr Ile Ser Cys Lys Arg Ser Thr Gly Asn Ile Gly Ser Ser
            20                  25                  30

Tyr Val Tyr Trp Tyr Gln Gln Arg Pro Gly Ser Ser Pro Thr Thr Val
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Ser Ser
                85                  90                  95

Gly Ile Lys Phe Ile Phe Gly Gly Gly Thr Lys Leu Thr Val Leu
```

<210> SEQ ID NO 72
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres01

<400> SEQUENCE: 72

Gln Phe Ala Leu Ile Gln Ser Asp Ser Met Ser Thr Ser Ala Gly Ser
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asp
65                  70                  75                  80

Val Gln Ile Glu Asp Glu Ala Val Tyr Phe Cys Gln Ser Phe Ser Ser
                85                  90                  95

Gly Ile Lys Phe Ile Phe Gly Gly Thr Lys Leu Thr Val Leu
            100                 105                 110

<210> SEQ ID NO 73
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres02

<400> SEQUENCE: 73

Gln Phe Val Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asp
65                  70                  75                  80

Val Gln Ile Glu Asp Glu Ala Val Tyr Phe Cys Gln Ser Phe Ser Ser
                85                  90                  95

Gly Ile Lys Phe Ile Phe Gly Gly Thr Lys Leu Thr Val Leu
            100                 105                 110

<210> SEQ ID NO 74
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres03

<400> SEQUENCE: 74

Gln Phe Ala Leu Ile Gln Ser Asp Ser Met Ser Thr Ser Leu Gly Ser
1               5                   10                  15

```
Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asp
65                  70                  75                  80

Val Gln Ile Glu Asp Glu Ala Val Tyr Phe Cys Gln Ser Phe Ser Ser
                85                  90                  95

Gly Ile Lys Phe Ile Phe Gly Gly Thr Lys Leu Thr Val Leu
                100                 105                 110

<210> SEQ ID NO 75
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres04

<400> SEQUENCE: 75

Gln Phe Ala Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asp
65                  70                  75                  80

Val Gln Ile Glu Asp Glu Ala Val Tyr Phe Cys Gln Ser Phe Ser Ser
                85                  90                  95

Gly Ile Lys Phe Ile Phe Gly Gly Thr Lys Leu Thr Val Leu
                100                 105                 110

<210> SEQ ID NO 76
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres05

<400> SEQUENCE: 76

Gln Phe Ala Leu Ile Gln Ser Asp Ser Met Ser Thr Ser Ala Gly Ser
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asp
65                  70                  75                  80

Val Gln Val Glu Asp Glu Ala Ile Tyr Phe Cys Gln Ser Phe Ser Ser
                85                  90                  95
```

```
Gly Ile Lys Phe Ile Phe Gly Gly Thr Lys Leu Thr Val Leu
            100                 105                 110

<210> SEQ ID NO 77
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres06

<400> SEQUENCE: 77

Gln Phe Val Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Ser Leu Thr Ile Asn Asp
65                  70                  75                  80

Val Gln Val Glu Asp Glu Ala Ile Tyr Phe Cys Gln Ser Phe Ser Ser
                85                  90                  95

Gly Ile Lys Phe Ile Phe Gly Gly Thr Lys Leu Thr Val Leu
            100                 105                 110

<210> SEQ ID NO 78
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres07

<400> SEQUENCE: 78

Gln Phe Ala Leu Ile Gln Ser Asp Ser Met Ser Thr Ser Leu Gly Ser
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Ser Leu Thr Ile Asn Asp
65                  70                  75                  80

Val Gln Val Glu Asp Glu Ala Ile Tyr Phe Cys Gln Ser Phe Ser Ser
                85                  90                  95

Gly Ile Lys Phe Ile Phe Gly Gly Thr Lys Leu Thr Val Leu
            100                 105                 110

<210> SEQ ID NO 79
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres08

<400> SEQUENCE: 79
```

```
Gln Phe Ala Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asp
65                  70                  75                  80

Val Gln Val Glu Asp Glu Ala Ile Tyr Phe Cys Gln Ser Phe Ser Ser
                85                  90                  95

Gly Ile Lys Phe Ile Phe Gly Gly Gly Thr Lys Leu Thr Val Leu
            100                 105                 110
```

<210> SEQ ID NO 80
<211> LENGTH: 111
<212> TYPE: PRT
<213> ORGANISM: Artificial
<220> FEATURE:
<223> OTHER INFORMATION: description of the artificial sequence: the amino acid sequence of humanized 18C1 VLres09

<400> SEQUENCE: 80

```
Gln Phe Ala Leu Ile Gln Ser Asp Ser Met Ser Thr Ser Ala Gly Ser
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asn
65                  70                  75                  80

Val Gln Ile Glu Asp Glu Ala Val Tyr Phe Cys Gln Ser Phe Ser Ser
                85                  90                  95

Gly Ile Lys Phe Ile Phe Gly Gly Gly Thr Lys Leu Thr Val Leu
            100                 105                 110
```

<210> SEQ ID NO 81
<211> LENGTH: 111
<212> TYPE: PRT
<213> ORGANISM: Artificial
<220> FEATURE:
<223> OTHER INFORMATION: description of the artificial sequence: the amino acid sequence of humanized 18C1 VLres10

<400> SEQUENCE: 81

```
Gln Phe Val Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asn
65                  70                  75                  80
```

Val Gln Ile Glu Asp Glu Ala Val Tyr Phe Cys Gln Ser Phe Ser Ser
            85                  90                  95

Gly Ile Lys Phe Ile Phe Gly Gly Gly Thr Lys Leu Thr Val Leu
            100                 105                 110

<210> SEQ ID NO 82
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres11

<400> SEQUENCE: 82

Gln Phe Ala Leu Ile Gln Ser Asp Ser Met Ser Thr Ser Leu Gly Ser
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asn
65                  70                  75                  80

Val Gln Ile Glu Asp Glu Ala Val Tyr Phe Cys Gln Ser Phe Ser Ser
            85                  90                  95

Gly Ile Lys Phe Ile Phe Gly Gly Gly Thr Lys Leu Thr Val Leu
            100                 105                 110

<210> SEQ ID NO 83
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres12

<400> SEQUENCE: 83

Gln Phe Ala Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Asn Asn
65                  70                  75                  80

Val Gln Ile Glu Asp Glu Ala Val Tyr Phe Cys Gln Ser Phe Ser Ser
            85                  90                  95

Gly Ile Lys Phe Ile Phe Gly Gly Gly Thr Lys Leu Thr Val Leu
            100                 105                 110

<210> SEQ ID NO 84
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres13

-continued

```
<400> SEQUENCE: 84

Gln Phe Ala Leu Ile Gln Ser Asp Ser Met Ser Thr Ser Ala Gly Ser
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Phe Leu Thr Ile Asn Asp
65                  70                  75                  80

Val Gln Ile Glu Asp Glu Ala Val Tyr Phe Cys Gln Ser Phe Ser Ser
                85                  90                  95

Gly Ile Lys Phe Ile Phe Gly Gly Gly Thr Lys Leu Thr Val Leu
            100                 105                 110

<210> SEQ ID NO 85
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres14

<400> SEQUENCE: 85

Gln Phe Val Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Phe Leu Thr Ile Asn Asp
65                  70                  75                  80

Val Gln Ile Glu Asp Glu Ala Val Tyr Phe Cys Gln Ser Phe Ser Ser
                85                  90                  95

Gly Ile Lys Phe Ile Phe Gly Gly Gly Thr Lys Leu Thr Val Leu
            100                 105                 110

<210> SEQ ID NO 86
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres15

<400> SEQUENCE: 86

Gln Phe Ala Leu Ile Gln Ser Asp Ser Met Ser Thr Ser Leu Gly Ser
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln His Glu Gly Arg Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Phe Leu Thr Ile Asn Asp
```

```
                65                  70                  75                  80
Val Gln Ile Glu Asp Glu Ala Val Tyr Phe Cys Gln Ser Phe Ser Ser
                    85                  90                  95

Gly Ile Lys Phe Ile Phe Gly Gly Gly Thr Lys Leu Thr Val Leu
                100                 105                 110

<210> SEQ ID NO 87
<211> LENGTH: 111
<212> TYPE: PRT
<213> ORGANISM: Artificial
<220> FEATURE:
<223> OTHER INFORMATION: description of the artificial sequence: the
      amino acid sequence of humanized 18C1 VLres16

<400> SEQUENCE: 87

Gln Phe Ala Leu Ile Gln Ser Asp Ser Met Ser Thr Ser Ala Gly Ser
1               5                   10                  15

Thr Val Lys Leu Ser Cys Lys Arg Ser Thr Gly Asn Ile Gly Ser Ser
                20                  25                  30

Tyr Val Tyr Trp Tyr Gln Gln His Glu Gly Arg Ser Pro Thr Thr Met
            35                  40                  45

Ile Tyr Asp Gly Asp Lys Arg Pro Asp Gly Val Pro Asp Arg Phe Ser
50                  55                  60

Gly Ser Ile Asp Ser Ser Asn Ser Ala Phe Leu Thr Ile Asn Asp
65                  70                  75                  80

Val Gln Ile Glu Asp Glu Ala Val Tyr Phe Cys Gln Ser Phe Ser Ser
                    85                  90                  95

Gly Ile Lys Phe Ile Phe Gly Gly Gly Thr Lys Leu Thr Val Leu
                100                 105                 110

<210> SEQ ID NO 88
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut01

<400> SEQUENCE: 88

Gln Val Gln Leu Gln Glu Ser Gly Pro Asp Leu Val Gln Pro Ser Gln
1               5                   10                  15

Thr Leu Asp Ile Thr Cys Thr Val Ser Gly Phe Ser Leu Thr Thr Tyr
                20                  25                  30

Asn Val His Trp Val Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Ser Arg Leu Ala Ile Ser Arg Asp Thr Ser Lys Asn Gln Val Ser Leu
65                  70                  75                  80

Lys Met Asp Ser Leu Gln Thr Asp Thr Ala Val Tyr Phe Cys Ala
                85                  90                  95

Arg Leu Gly Tyr Tyr Val Asp Tyr Trp Gly Gln Gly Ile Leu Val Thr
                100                 105                 110

Val Ser Ser
        115

<210> SEQ ID NO 89
<211> LENGTH: 115
<212> TYPE: PRT
```

<213> ORGANISM: Artificial
<220> FEATURE:
<223> OTHER INFORMATION: description of the artificial sequence: the
      amino acid sequence of humanized 18C1 HVmut02

<400> SEQUENCE: 89

Gln Val Gln Leu Gln Glu Ser Gly Pro Asp Leu Val Lys Pro Ser Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Thr Ile Ser Arg Asp Thr Ser Lys Asn Gln Val Phe Leu
65                  70                  75                  80

Lys Met Asp Ser Leu Gln Thr Asp Asp Thr Ala Lys Tyr Phe Cys Ala
                85                  90                  95

Arg Leu Gly Tyr Tyr Val Asp Tyr Trp Gly Gln Gly Ile Leu Val Thr
            100                 105                 110

Val Ser Ser
        115

<210> SEQ ID NO 90
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut03

<400> SEQUENCE: 90

Gln Val Gln Leu Gln Glu Ser Gly Pro Gly Leu Val Gln Pro Ser Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ala Ile Ser Arg Asp Thr Ser Lys Asn Glu Val Phe Leu
65                  70                  75                  80

Lys Met Asp Ser Leu Thr Ala Ala Asp Thr Ala Val Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 91
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut04

<400> SEQUENCE: 91

Gln Val Gln Leu Gln Glu Ser Gly Pro Asp Leu Val Gln Pro Ser Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
 50                  55                  60

Ser Arg Leu Ala Ile Ser Arg Asp Thr Ser Lys Asn Glu Val Phe Leu
 65                  70                  75                  80

Lys Met Asp Ser Leu Gln Thr Asp Asp Thr Ala Lys Tyr Phe Cys Ala
                85                  90                  95

Arg Leu Gly Tyr Tyr Val Asp Tyr Trp Gly Gln Gly Ile Leu Val Thr
            100                 105                 110

Val Ser Ser
        115

<210> SEQ ID NO 92
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut05

<400> SEQUENCE: 92

Gln Val Gln Leu Gln Glu Ser Gly Pro Gly Leu Val Lys Pro Ser Gln
 1               5                  10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
 50                  55                  60

Asp Arg Leu Ala Ile Ser Arg Asp Thr Ser Lys Asn Glu Val Phe Leu
 65                  70                  75                  80

Lys Met Ser Ser Leu Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 93
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut06

<400> SEQUENCE: 93

Gln Val Gln Leu Gln Glu Ser Gly Pro Gly Leu Val Lys Pro Ser Gln
 1               5                  10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
 50                  55                  60

Asp Arg Leu Thr Ile Ser Arg Asp Thr Ser Lys Asn Glu Val Phe Leu
65                  70                  75                  80

Lys Met Ser Ser Leu Thr Ala Ala Asp Thr Ala Val Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 94
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut07

<400> SEQUENCE: 94

Gln Val Gln Leu Gln Glu Ser Gly Pro Asp Leu Val Gln Pro Ser Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ala Ile Ser Arg Asp Thr Ser Lys Asn Gln Val Ser Leu
65                  70                  75                  80

Lys Met Asp Ser Leu Gln Thr Asp Asp Thr Ala Lys Tyr Phe Cys Ala
                85                  90                  95

Arg Leu Gly Tyr Tyr Val Asp Tyr Trp Gly Gln Gly Ile Leu Val Thr
            100                 105                 110

Val Ser Ser
        115

<210> SEQ ID NO 95
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut08

<400> SEQUENCE: 95

Gln Val Gln Leu Gln Glu Ser Gly Pro Asp Leu Val Lys Pro Ser Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Arg Asp Thr Ser Lys Asn Val Phe Leu
65                  70                  75                  80

Lys Met Asp Ser Leu Gln Thr Asp Asp Thr Ala Val Tyr Phe Cys Ala
                85                  90                  95

Arg Leu Gly Tyr Tyr Val Asp Tyr Trp Gly Gln Gly Ile Leu Val Thr
            100                 105                 110

```
Val Ser Ser
        115

<210> SEQ ID NO 96
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut09

<400> SEQUENCE: 96

Gln Val Gln Leu Gln Glu Ser Gly Pro Gly Leu Val Gln Pro Ser Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ala Ile Ser Arg Asp Thr Ser Lys Asn Glu Val Phe Leu
65                  70                  75                  80

Lys Met Asp Ser Leu Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 97
<211> LENGTH: 115
<212> TYPE: PRT
<213> ORGANISM: Artificial
<220> FEATURE:
<223> OTHER INFORMATION: description of the artificial sequence: the
      amino acid sequence of humanized 18C1 HVmut10

<400> SEQUENCE: 97

Gln Val Gln Leu Gln Glu Ser Gly Pro Asp Leu Val Gln Pro Ser Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ala Ile Ser Arg Asp Thr Ser Lys Asn Glu Val Phe Leu
65                  70                  75                  80

Lys Met Asp Ser Leu Gln Thr Asp Asp Thr Ala Val Tyr Phe Cys Ala
                85                  90                  95

Arg Leu Gly Tyr Tyr Val Asp Tyr Trp Gly Gln Gly Ile Leu Val Thr
            100                 105                 110

Val Ser Ser
        115

<210> SEQ ID NO 98
<211> LENGTH: 115
<212> TYPE: PRT
<213> ORGANISM: Artificial
```

```
<220> FEATURE:
<223> OTHER INFORMATION: description of the artificial sequence: the
      amino acid sequence of humanized 18C1 VHres16

<400> SEQUENCE: 98

Gln Val Gln Leu Lys Glu Thr Gly Pro Asp Leu Val Gln Pro Thr Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
50                      55                  60

Ser Arg Leu Ala Ile Ser Arg Asp Thr Ser Lys Ser Glu Val Phe Leu
65                  70                  75                  80

Lys Met Asp Ser Leu Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 99
<211> LENGTH: 16
<212> TYPE: PRT
<213> ORGANISM: Artificial
<220> FEATURE:
<223> OTHER INFORMATION: description of the artificial sequence: the
      amino acid sequence of CDR2 of humanized 18C1 HVmut05-10

<400> SEQUENCE: 99

Thr Met Trp Asn Gly Gly Ile Asp Tyr Asn Ser Ala Phe Lys Asp
1               5                   10                  15

<210> SEQ ID NO 100
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized 18C1 HV2

<400> SEQUENCE: 100

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
50                      55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115
```

```
<210> SEQ ID NO 101
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV3

<400> SEQUENCE: 101

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 102
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4a

<400> SEQUENCE: 102

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 103
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4b
```

<400> SEQUENCE: 103

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Thr Ile Ser Val Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 104
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4c

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 105
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV5

<400> SEQUENCE: 105

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Val His Trp Ile Arg Gln Pro Pro Gly Lys Gly Leu Glu Trp Met

```
                    35                  40                  45
Gly Thr Met Trp Asn Gly Gly Ile Asp Tyr Asn Ser Ala Phe Lys
            50                  55                  60
Ser Arg Leu Thr Ile Ser Arg Asp Thr Ser Lys Asn Gln Val Ser Leu
65                  70                  75                  80
Lys Leu Ser Ser Val Thr Ala Ala Asp Thr Ala Lys Tyr Tyr Cys Ala
                85                  90                  95
Arg Leu Gly Tyr Tyr Val Asp Tyr Trp Gly Gln Gly Thr Leu Val Thr
                100                 105                 110
Val Ser Ser
        115

<210> SEQ ID NO 106
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV6

<400> SEQUENCE: 106

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Thr Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
            50                  55                  60

Ser Arg Leu Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 107
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV7

<400> SEQUENCE: 107

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Val Ser Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
            50                  55                  60

Ser Arg Val Thr Ile Ser Arg Asp Thr Ser Lys Asn Gln Val Ser Leu
65                  70                  75                  80

Lys Met Ser Ser Val Thr Ala Ala Asp Thr Ala Lys Tyr Tyr Cys Ala
```

```
                    85                  90                  95
Arg Leu Gly Tyr Tyr Val Asp Tyr Trp Gly Gln Gly Thr Leu Val Thr
                100                 105                 110

Val Ser Ser
        115

<210> SEQ ID NO 108
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV8

<400> SEQUENCE: 108

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Thr Tyr
                20                  25                  30

Asn Val His Trp Ile Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Ser Arg Leu Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 109
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV10

<400> SEQUENCE: 109

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Val Thr Thr Tyr
                20                  25                  30

Asn Val His Trp Ile Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Ser Arg Leu Thr Ile Ser Arg Asp Thr Ser Lys Asn Gln Val Ser Leu
65                  70                  75                  80

Lys Met Ser Ser Val Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
                100                 105                 110

Val Ser Ser
        115
```

```
<210> SEQ ID NO 110
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV13

<400> SEQUENCE: 110

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Thr Ile Ser Arg Asp Thr Ser Lys Asn Gln Val Ser Leu
65                  70                  75                  80

Lys Met Ser Ser Leu Thr Ala Ala Asp Thr Ala Val Tyr Phe Cys Ala
                85                  90                  95

Arg Leu Gly Tyr Tyr Val Asp Tyr Trp Gly Gln Gly Ile Leu Val Thr
            100                 105                 110

Val Ser Ser
        115

<210> SEQ ID NO 111
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV16

<400> SEQUENCE: 111

Gln Val Gln Leu Gln Glu Ser Gly Pro Gly Leu Val Lys Leu Ser Gln
1               5                   10                  15

Thr Leu Ser Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Thr Ile Ser Arg Asp Thr Ser Lys Ser Gln Val Ser Leu
65                  70                  75                  80

Lys Met Ser Ser Leu Thr Ala Ala Asp Thr Ala Lys Tyr Phe Cys Ala
                85                  90                  95

Arg Leu Gly Tyr Tyr Val Asp Tyr Trp Gly Gln Gly Ile Leu Val Thr
            100                 105                 110

Val Ser Ser
        115

<210> SEQ ID NO 112
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV0'

<400> SEQUENCE: 112
```

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Asp Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
    115

<210> SEQ ID NO 113
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV2'

<400> SEQUENCE: 113

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Asp Arg Val Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
    115

<210> SEQ ID NO 114
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV3'

<400> SEQUENCE: 114

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Val His Trp Ile Arg Gln Pro Pro Gly Lys Gly Leu Glu Trp Ile
        35                  40                  45
```

```
Gly Thr Met Trp Asn Gly Gly Ile Asp Tyr Asn Ser Ala Phe Lys
        50                  55                  60

Asp Arg Val Thr Ile Ser Arg Asp Thr Ser Lys Asn Gln Phe Ser Leu
 65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 115
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4a'

<400> SEQUENCE: 115

Gln Val Gln Leu Gln Glu Ser Gly Pro Gly Leu Val Lys Pro Ser Gln
 1               5                  10                  15

Thr Leu Ser Leu Thr Cys Thr Val Ser Gly Phe Ser Val Ser Thr Tyr
                20                  25                  30

Asn Val His Trp Ile Arg Gln Pro Pro Gly Lys Gly Leu Glu Trp Ile
            35                  40                  45

Gly Thr Met Trp Asn Gly Gly Ile Asp Tyr Asn Ser Ala Phe Lys
        50                  55                  60

Asp Arg Val Thr Ile Ser Arg Asp Thr Ser Lys Asn Gln Val Ser Leu
 65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 116
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4b'

<400> SEQUENCE: 116

Gln Val Gln Leu Gln Glu Ser Gly Pro Gly Leu Val Lys Pro Ser Gln
 1               5                  10                  15

Thr Leu Ser Leu Thr Cys Thr Val Ser Gly Phe Ser Val Ser Thr Tyr
                20                  25                  30

Asn Val His Trp Ile Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Asp Arg Leu Thr Ile Ser Val Asp Thr Ser Lys Asn Gln Phe Ser Leu
 65                  70                  75                  80

Lys Leu Ser Ser Val Thr Ala Ala Asp Thr Ala Lys Tyr Tyr Cys Ala
                85                  90                  95
```

```
Arg Leu Gly Tyr Tyr Val Asp Tyr Trp Gly Gln Gly Thr Leu Val Thr
            100                 105                 110

Val Ser Ser
        115

<210> SEQ ID NO 117
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4c'

<400> SEQUENCE: 117

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Val His Trp Ile Arg Gln Pro Pro Gly Lys Gly Leu Glu Trp Ile
        35                  40                  45

Gly Thr Met Trp Asn Gly Gly Gly Ile Asp Tyr Asn Ser Ala Phe Lys
    50                  55                  60

Asp Arg Val Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 118
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV5'

<400> SEQUENCE: 118

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Gly Ile Asp Tyr Asn Ser Ala Phe Lys
    50                  55                  60

Asp Arg Leu Thr Ile Ser Arg Asp Thr Ser Lys Asn Gln Val Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 119
```

```
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV6'

<400> SEQUENCE: 119
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Thr Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

```
<210> SEQ ID NO 120
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV7'

<400> SEQUENCE: 120
```

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Val Ser Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Val Thr Ile Ser Arg Asp Thr Ser Lys Asn Gln Val Ser Leu
65                  70                  75                  80

Lys Met Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

```
<210> SEQ ID NO 121
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV8'

<400> SEQUENCE: 121
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Phe Cys Ala
            85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 122
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV10'

<400> SEQUENCE: 122

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Val Thr Thr Tyr
            20                  25                  30

Asn Val His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Arg Asp Thr Ser Lys Asn Gln Val Ser Leu
65                  70                  75                  80

Lys Met Ser Ser Val Thr Ala Ala Asp Thr Ala Lys Tyr Phe Cys Ala
            85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 123
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV13'

<400> SEQUENCE: 123

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Gly Ile Asp Tyr Asn Ser Ala Phe Lys
            50                  55                  60

Asp Arg Leu Thr Ile Ser Arg Asp Thr Ser Lys Asn Gln Val Ser Leu
65                  70                  75                  80

Lys Met Ser Ser Leu Thr Ala Ala Asp Thr Ala Val Tyr Phe Cys Ala
                    85                  90                  95

Arg Leu Gly Tyr Tyr Val Asp Tyr Trp Gly Gln Gly Ile Leu Val Thr
                100                 105                 110

Val Ser Ser
        115

<210> SEQ ID NO 124
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV16'

<400> SEQUENCE: 124

Gln Val Gln Leu Gln Glu Ser Gly Pro Gly Leu Val Lys Leu Ser Gln
1               5                   10                  15

Thr Leu Ser Ile Thr Cys Thr Val Ser Gly Phe Ser Leu Thr Thr Tyr
                20                  25                  30

Asn Val His Trp Val Arg Gln Pro Pro Gly Lys Gly Leu Glu Trp Met
            35                  40                  45

Gly Thr Met Trp Asn Gly Gly Gly Ile Asp Tyr Asn Ser Ala Phe Lys
        50                  55                  60

Asp Arg Leu Thr Ile Ser Arg Asp Thr Ser Lys Ser Gln Val Ser Leu
65                  70                  75                  80

Lys Met Ser Ser Leu Thr Ala Ala Asp Thr Ala Lys Tyr Phe Cys Ala
                85                  90                  95

Arg Leu Gly Tyr Tyr Val Asp Tyr Trp Gly Gln Gly Ile Leu Val Thr
                100                 105                 110

Val Ser Ser
        115

<210> SEQ ID NO 125
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres01

<400> SEQUENCE: 125

Gln Val Gln Leu Lys Glu Thr Gly Pro Asp Ala Val Gln Leu Thr Gln
1               5                   10                  15

Thr Leu Asp Ile Thr Cys Thr Val Ser Gly Ala Ser Leu Thr Thr Tyr
                20                  25                  30

Asn Val His Trp Val Arg Gln Pro Pro Gly Lys Gly Leu Glu Trp Met
            35                  40                  45

Gly Thr Met Trp Asn Gly Gly Gly Ile Asp Tyr Asn Ser Ala Phe Lys
        50                  55                  60

Ser Arg Leu Ala Ile Ser Lys Asp Thr Ser Lys Ser Glu Val Phe Leu
65                  70                  75                  80

Lys Met Asp Ser Asp Gln Thr Asp Asp Thr Ala Lys Tyr Phe Cys Ala
                85                  90                  95

-continued

```
Arg Leu Gly Tyr Tyr Val Asp Tyr Trp Gly Gln Gly Ile Met Val Thr
            100                 105                 110

Val Ser Ser
        115

<210> SEQ ID NO 126
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres02

<400> SEQUENCE: 126

Gln Val Gln Leu Lys Glu Thr Gly Pro Asp Leu Val Gln Pro Thr Gln
1               5                   10                  15

Thr Leu Asp Ile Thr Cys Thr Val Ser Gly Ala Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ala Ile Ser Lys Asp Thr Ser Lys Ser Glu Val Phe Leu
65                  70                  75                  80

Lys Met Asp Ser Asp Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 127
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres03

<400> SEQUENCE: 127

Gln Val Gln Leu Lys Glu Thr Gly Pro Asp Ala Val Gln Leu Thr Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ala Ile Ser Lys Asp Thr Ser Lys Ser Glu Val Phe Leu
65                  70                  75                  80

Lys Met Asp Ser Asp Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 128
<211> LENGTH: 115
```

<212> TYPE: PRT
<213> ORGANISM: Artificial Sequence
<220> FEATURE:
<223> OTHER INFORMATION: description of the artificial sequence: the
      amino acid sequence of humanized VHres04

<400> SEQUENCE: 128

Gln Val Gln Leu Lys Glu Thr Gly Pro Asp Leu Val Gln Pro Thr Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ala Ile Ser Lys Asp Thr Ser Lys Ser Glu Val Phe Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 129
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres05

<400> SEQUENCE: 129

Gln Val Gln Leu Lys Glu Thr Gly Pro Asp Ala Val Gln Leu Thr Gln
1               5                   10                  15

Thr Leu Asp Ile Thr Cys Thr Val Ser Gly Ala Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ser Ile Ser Lys Asp Thr Ser Lys Ser Gln Val Ala Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 130
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres06

<400> SEQUENCE: 130

Gln Val Gln Leu Lys Glu Thr Gly Pro Asp Leu Val Gln Pro Thr Gln

```
1               5                   10                  15
Thr Leu Asp Ile Thr Cys Thr Val Ser Gly Ala Ser Leu Thr Thr Tyr
                20                  25                  30

Asn Val His Trp Val Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Ser Arg Leu Ser Ile Ser Lys Asp Thr Ser Lys Ser Gln Val Ala Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
                100                 105                 110

Val Ser Ser
        115

<210> SEQ ID NO 131
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres07

<400> SEQUENCE: 131

Gln Val Gln Leu Lys Glu Thr Gly Pro Asp Ala Val Gln Leu Thr Gln
1               5                   10                  15

Thr Leu Asp Ile Thr Cys Thr Val Ser Gly Phe Ser Leu Thr Thr Tyr
                20                  25                  30

Asn Val His Trp Val Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Ser Arg Leu Ser Ile Ser Lys Asp Thr Ser Lys Ser Gln Val Ala Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
                100                 105                 110

Val Ser Ser
        115

<210> SEQ ID NO 132
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres08

<400> SEQUENCE: 132

Gln Val Gln Leu Lys Glu Thr Gly Pro Asp Leu Val Gln Pro Thr Gln
1               5                   10                  15

Thr Leu Asp Ile Thr Cys Thr Val Ser Gly Phe Ser Leu Thr Thr Tyr
                20                  25                  30

Asn Val His Trp Val Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60
```

```
                50                  55                  60

Ser Arg Leu Ser Ile Ser Lys Asp Thr Ser Lys Ser Gln Val Ala Leu
 65                  70                  75                  80

Lys Met Asp Ser Asp Gln Thr Asp Thr Ala Lys Tyr Phe Cys Ala
                 85                  90                  95

Arg Leu Gly Tyr Tyr Val Asp Tyr Trp Gly Gln Gly Ile Met Val Thr
                100                 105                 110

Val Ser Ser
        115

<210> SEQ ID NO 133
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres09

<400> SEQUENCE: 133

Gln Val Gln Leu Lys Glu Thr Gly Pro Asp Ala Val Gln Leu Thr Gln
  1               5                  10                  15

Thr Leu Asp Ile Thr Cys Thr Val Ser Gly Ala Ser Leu Thr Thr Tyr
                 20                  25                  30

Asn Val His Trp Val Arg Gln Pro Pro Gly Lys Gly Leu Glu Trp Met
                 35                  40                  45

Gly Thr Met Trp Asn Gly Gly Ile Asp Tyr Asn Ser Ala Phe Lys
 50                  55                  60

Ser Arg Leu Ala Ile Ser Arg Asp Thr Ser Lys Ser Glu Val Phe Leu
 65                  70                  75                  80

Lys Met Asp Ser Asp Gln Thr Asp Thr Ala Lys Tyr Phe Cys Ala
                 85                  90                  95

Arg Leu Gly Tyr Tyr Val Asp Tyr Trp Gly Gln Gly Ile Met Val Thr
                100                 105                 110

Val Ser Ser
        115

<210> SEQ ID NO 134
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres10

<400> SEQUENCE: 134

Gln Val Gln Leu Lys Glu Thr Gly Pro Asp Leu Val Gln Pro Thr Gln
  1               5                  10                  15

Thr Leu Asp Ile Thr Cys Thr Val Ser Gly Ala Ser Leu Thr Thr Tyr
                 20                  25                  30

Asn Val His Trp Val Arg Gln Pro Pro Gly Lys Gly Leu Glu Trp Met
                 35                  40                  45

Gly Thr Met Trp Asn Gly Gly Ile Asp Tyr Asn Ser Ala Phe Lys
 50                  55                  60

Ser Arg Leu Ala Ile Ser Arg Asp Thr Ser Lys Ser Glu Val Phe Leu
 65                  70                  75                  80

Lys Met Asp Ser Asp Gln Thr Asp Thr Ala Lys Tyr Phe Cys Ala
                 85                  90                  95

Arg Leu Gly Tyr Tyr Val Asp Tyr Trp Gly Gln Gly Ile Met Val Thr
```

Val Ser Ser
    115

<210> SEQ ID NO 135
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres11

<400> SEQUENCE: 135

Gln Val Gln Leu Lys Glu Thr Gly Pro Asp Ala Val Gln Leu Thr Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ala Ile Ser Arg Asp Thr Ser Lys Ser Glu Val Phe Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
    115

<210> SEQ ID NO 136
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres12

<400> SEQUENCE: 136

Gln Val Gln Leu Lys Glu Thr Gly Pro Asp Leu Val Gln Pro Thr Gln
1               5                   10                  15

Thr Leu Asp Ile Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Ser Arg Leu Ala Ile Ser Arg Asp Thr Ser Lys Ser Glu Val Phe Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
    115

<210> SEQ ID NO 137
<211> LENGTH: 115
<212> TYPE: PRT

<213> ORGANISM: Artificial Sequence
<220> FEATURE:
<223> OTHER INFORMATION: description of the artificial sequence: the
      amino acid sequence of humanized VHres13

<400> SEQUENCE: 137

Gln Val Gln Leu Lys Glu Thr Gly Pro Asp Ala Val Gln Leu Thr Gln
1               5                   10                  15

Thr Leu Asp Ile Thr Cys Thr Val Ser Gly Ala Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
50                  55                  60

Ser Arg Leu Ala Ile Ser Arg Asp Thr Ser Lys Ser Glu Val Phe Leu
65                  70                  75                  80

Lys Met Asp Ser Leu Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 138
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres14

<400> SEQUENCE: 138

Gln Val Gln Leu Lys Glu Thr Gly Pro Asp Leu Val Gln Pro Thr Gln
1               5                   10                  15

Thr Leu Asp Ile Thr Cys Thr Val Ser Gly Ala Ser Leu Thr Thr Tyr
            20                  25                  30

Asn Val His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
50                  55                  60

Ser Arg Leu Ala Ile Ser Arg Asp Thr Ser Lys Ser Glu Val Phe Leu
65                  70                  75                  80

Lys Met Asp Ser Leu Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 139
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres15

<400> SEQUENCE: 139

Gln Val Gln Leu Lys Glu Thr Gly Pro Asp Ala Val Gln Leu Thr Gln
1               5                   10                  15

```
Thr Leu Asp Ile Thr Cys Thr Val Ser Gly Phe Ser Leu Thr Thr Tyr
         20                  25                  30

Asn Val His Trp Val Arg Gln Pro Gly Lys Gly Leu Glu Trp Met
         35                  40                  45

Gly Thr Met Trp Asn Gly Gly Ile Asp Tyr Asn Ser Ala Phe Lys
 50                  55                  60

Ser Arg Leu Ala Ile Ser Arg Asp Thr Ser Lys Ser Glu Val Phe Leu
 65                  70                  75                  80

Lys Met Asp Ser Leu Gln Thr Asp Asp Thr Ala Lys Tyr Phe Cys Ala
                 85                  90                  95

Arg Leu Gly Tyr Tyr Val Asp Tyr Trp Gly Gln Gly Ile Met Val Thr
                100                 105                 110

Val Ser Ser
        115

<210> SEQ ID NO 140
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres17

<400> SEQUENCE: 140

Gln Val Gln Leu Lys Glu Thr Gly Pro Asp Ala Val Gln Leu Thr Gln
1               5                  10                  15

Thr Leu Asp Ile Thr Cys Thr Val Ser Gly Ala Ser Leu Thr Thr Tyr
         20                  25                  30

Asn Ala His Trp Val Arg Gln Pro Pro Gly Lys Gly Leu Glu Trp Met
         35                  40                  45

Gly Thr Met Trp Asn Gly Gly Ile Asp Tyr Asn Ser Ala Phe Lys
 50                  55                  60

Asp Arg Leu Ala Ile Ser Lys Asp Thr Ser Lys Ser Glu Val Phe Leu
 65                  70                  75                  80

Lys Met Asp Ser Asp Gln Thr Asp Asp Thr Ala Lys Tyr Phe Cys Ala
                 85                  90                  95

Arg Leu Gly Tyr Tyr Val Asp Tyr Trp Gly Gln Gly Ile Met Val Thr
                100                 105                 110

Val Ser Ser
        115

<210> SEQ ID NO 141
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres18

<400> SEQUENCE: 141

Gln Val Gln Leu Lys Glu Thr Gly Pro Asp Leu Val Gln Pro Thr Gln
1               5                  10                  15

Thr Leu Asp Ile Thr Cys Thr Val Ser Gly Ala Ser Leu Thr Thr Tyr
         20                  25                  30

Asn Ala His Trp Val Arg Gln Pro Pro Gly Lys Gly Leu Glu Trp Met
         35                  40                  45

Gly Thr Met Trp Asn Gly Gly Ile Asp Tyr Asn Ser Ala Phe Lys
 50                  55                  60
```

```
Asp Arg Leu Ala Ile Ser Lys Asp Thr Ser Lys Ser Glu Val Phe Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 142
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres19

<400> SEQUENCE: 142

Gln Val Gln Leu Lys Glu Thr Gly Pro Asp Ala Val Gln Leu Thr Gln
1               5                   10                  15

Thr Leu Asp Ile Thr Cys Thr Val Ser Gly Phe Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ala Ile Ser Lys Asp Thr Ser Lys Ser Glu Val Phe Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 143
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres20

<400> SEQUENCE: 143

Gln Val Gln Leu Lys Glu Thr Gly Pro Asp Leu Val Gln Pro Thr Gln
1               5                   10                  15

Thr Leu Asp Ile Thr Cys Thr Val Ser Gly Phe Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ala Ile Ser Lys Asp Thr Ser Lys Ser Glu Val Phe Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110
```

Val Ser Ser
        115

<210> SEQ ID NO 144
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres21

<400> SEQUENCE: 144

Gln Val Gln Leu Lys Glu Thr Gly Pro Asp Ala Val Gln Leu Thr Gln
1               5                   10                  15

Thr Leu Asp Ile Thr Cys Thr Val Ser Gly Ala Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ser Ile Ser Lys Asp Thr Ser Lys Ser Gln Val Ala Leu
65                  70                  75                  80

Lys Met Asp Ser Asp Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 145
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres22

<400> SEQUENCE: 145

Gln Val Gln Leu Lys Glu Thr Gly Pro Asp Leu Val Gln Pro Thr Gln
1               5                   10                  15

Thr Leu Asp Ile Thr Cys Thr Val Ser Gly Ala Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ser Ile Ser Lys Asp Thr Ser Lys Ser Gln Val Ala Leu
65                  70                  75                  80

Lys Met Asp Ser Asp Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 146
<211> LENGTH: 115
<212> TYPE: PRT
<213> ORGANISM: Artificial Sequence

```
<220> FEATURE:
<223> OTHER INFORMATION: description of the artificial sequence: the
      amino acid sequence of humanized VHres23

<400> SEQUENCE: 146

Gln Val Gln Leu Lys Glu Thr Gly Pro Asp Ala Val Gln Leu Thr Gln
1               5                   10                  15

Thr Leu Asp Ile Thr Cys Thr Val Ser Gly Phe Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Gly Ile Asp Tyr Asn Ser Ala Phe Lys
    50                  55                  60

Asp Arg Leu Ser Ile Ser Lys Asp Thr Ser Lys Ser Gln Val Ala Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 147
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres24

<400> SEQUENCE: 147

Gln Val Gln Leu Lys Glu Thr Gly Pro Asp Leu Val Gln Pro Thr Gln
1               5                   10                  15

Thr Leu Asp Ile Thr Cys Thr Val Ser Gly Phe Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Gly Ile Asp Tyr Asn Ser Ala Phe Lys
    50                  55                  60

Asp Arg Leu Ser Ile Ser Lys Asp Thr Ser Lys Ser Gln Val Ala Leu
65                  70                  75                  80

Lys Met Asp Ser Asp Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 148
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres25

<400> SEQUENCE: 148

Gln Val Gln Leu Lys Glu Thr Gly Pro Asp Ala Val Gln Leu Thr Gln
1               5                   10                  15
```

```
Thr Leu Asp Ile Thr Cys Thr Val Ser Gly Ala Ser Leu Thr Thr Tyr
        20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
50                  55                  60

Asp Arg Leu Ala Ile Ser Arg Asp Thr Ser Lys Ser Glu Val Phe Leu
65                  70                  75                  80

Lys Met Asp Ser Asp Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115
```

<210> SEQ ID NO 149
<211> LENGTH: 115
<212> TYPE: PRT
<213> ORGANISM: Artificial Sequence
<220> FEATURE:
<223> OTHER INFORMATION: description of the artificial sequence: the amino acid sequence of humanized VHres26

<400> SEQUENCE: 149

```
Gln Val Gln Leu Lys Glu Thr Gly Pro Asp Leu Val Gln Pro Thr Gln
1               5                   10                  15

Thr Leu Asp Ile Thr Cys Thr Val Ser Gly Ala Ser Leu Thr Thr Tyr
        20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
50                  55                  60

Asp Arg Leu Ala Ile Ser Arg Asp Thr Ser Lys Ser Glu Val Phe Leu
65                  70                  75                  80

Lys Met Asp Ser Asp Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115
```

<210> SEQ ID NO 150
<211> LENGTH: 115
<212> TYPE: PRT
<213> ORGANISM: Artificial Sequence
<220> FEATURE:
<223> OTHER INFORMATION: description of the artificial sequence: the amino acid sequence of humanized VHres27

<400> SEQUENCE: 150

```
Gln Val Gln Leu Lys Glu Thr Gly Pro Asp Ala Val Gln Leu Thr Gln
1               5                   10                  15

Thr Leu Asp Ile Thr Cys Thr Val Ser Gly Phe Ser Leu Thr Thr Tyr
        20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
50                  55                  60
```

```
Asp Arg Leu Ala Ile Ser Arg Asp Thr Ser Lys Ser Glu Val Phe Leu
 65                  70                  75                  80

Lys Met Asp Ser Asp Gln Thr Asp Thr Ala Lys Tyr Phe Cys Ala
                 85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 151
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres28

<400> SEQUENCE: 151

Gln Val Gln Leu Lys Glu Thr Gly Pro Asp Leu Val Gln Pro Thr Gln
 1               5                  10                  15

Thr Leu Asp Ile Thr Cys Thr Val Ser Gly Phe Ser Leu Thr Thr Tyr
                 20                  25                  30

Asn Ala His Trp Val Arg Gln Pro Pro Gly Lys Gly Leu Glu Trp Met
             35                  40                  45

Gly Thr Met Trp Asn Gly Gly Ile Asp Tyr Asn Ser Ala Phe Lys
         50                  55                  60

Asp Arg Leu Ala Ile Ser Arg Asp Thr Ser Lys Ser Glu Val Phe Leu
 65                  70                  75                  80

Lys Met Asp Ser Asp Gln Thr Asp Thr Ala Lys Tyr Phe Cys Ala
                 85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 152
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres29

<400> SEQUENCE: 152

Gln Val Gln Leu Lys Glu Thr Gly Pro Asp Ala Val Leu Thr Gln
 1               5                  10                  15

Thr Leu Asp Ile Thr Cys Thr Val Ser Gly Ala Ser Leu Thr Thr Tyr
                 20                  25                  30

Asn Ala His Trp Val Arg Gln Pro Pro Gly Lys Gly Leu Glu Trp Met
             35                  40                  45

Gly Thr Met Trp Asn Gly Gly Gly Ile Asp Tyr Asn Ser Ala Phe Lys
         50                  55                  60

Asp Arg Leu Ala Ile Ser Arg Asp Thr Ser Lys Ser Glu Val Phe Leu
 65                  70                  75                  80

Lys Met Asp Ser Leu Gln Thr Asp Thr Ala Lys Tyr Phe Cys Ala
                 85                  90                  95

Arg Leu Gly Tyr Tyr Val Asp Tyr Trp Gly Gln Gly Ile Met Val Thr
            100                 105                 110
```

Val Ser Ser
        115

<210> SEQ ID NO 153
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres30

<400> SEQUENCE: 153

Gln Val Gln Leu Lys Glu Thr Gly Pro Asp Leu Val Gln Pro Thr Gln
1               5                   10                  15

Thr Leu Asp Ile Thr Cys Thr Val Ser Gly Ala Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Ala Ile Ser Arg Asp Thr Ser Lys Ser Glu Val Phe Leu
65                  70                  75                  80

Lys Met Asp Ser Leu Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 154
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized VHres31

<400> SEQUENCE: 154

Gln Val Gln Leu Lys Glu Thr Gly Pro Asp Ala Val Gln Leu Thr Gln
1               5                   10                  15

Thr Leu Asp Ile Thr Cys Thr Val Ser Gly Phe Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Gly Ile Asp Tyr Asn Ser Ala Phe Lys
    50                  55                  60

Asp Arg Leu Ala Ile Ser Arg Asp Thr Ser Lys Ser Glu Val Phe Leu
65                  70                  75                  80

Lys Met Asp Ser Leu Gln Thr Asp Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 155
<211> LENGTH: 115
<212> TYPE: PRT
<213> ORGANISM: Artificial Sequence
<220> FEATURE:

<223> OTHER INFORMATION: description of the artificial sequence: the
     amino acid sequence of humanized VHres32

<400> SEQUENCE: 155

Gln Val Gln Leu Lys Glu Thr Gly Pro Asp Leu Val Gln Pro Thr Gln
1               5                   10                  15

Thr Leu Asp Ile Thr Cys Thr Val Ser Gly Phe Ser Leu Thr Thr Tyr
            20                  25                  30

Asn Ala His Trp Val Arg Gln Pro Pro Gly Lys Gly Leu Glu Trp Met
        35                  40                  45

Gly Thr Met Trp Asn Gly Gly Ile Asp Tyr Asn Ser Ala Phe Lys
50                  55                  60

Asp Arg Leu Ala Ile Ser Arg Asp Thr Ser Lys Ser Glu Val Phe Leu
65                  70                  75                  80

Lys Met Asp Ser Leu Gln Thr Asp Thr Ala Lys Tyr Phe Cys Ala
                85                  90                  95

Arg Leu Gly Tyr Tyr Val Asp Tyr Trp Gly Gln Gly Ile Met Val Thr
            100                 105                 110

Val Ser Ser
        115

<210> SEQ ID NO 156
<211> LENGTH: 111
<212> TYPE: PRT
<213> ORGANISM: Artificial Sequence
<220> FEATURE:
<223> OTHER INFORMATION: description of the artificial sequence: the
     amino acid sequence of humanized LV3

<400> SEQUENCE: 156

Asn Phe Met Leu Thr Gln Pro His Ser Val Ser Glu Ser Pro Gly Lys
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln Arg Pro Gly Ser Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Ile Tyr Tyr Cys Gln Ser Phe Ser Ser
                85                  90                  95

Gly Ile Lys Phe Ile Phe Gly Gly Gly Thr Lys Leu Thr Val Leu
            100                 105                 110

<210> SEQ ID NO 157
<211> LENGTH: 111
<212> TYPE: PRT
<213> ORGANISM: Artificial Sequence
<220> FEATURE:
<223> OTHER INFORMATION: description of the artificial sequence: the
     amino acid sequence of humanized LV4a

<400> SEQUENCE: 157

Asn Phe Met Leu Thr Gln Pro His Ser Val Ser Glu Ser Pro Gly Lys
1               5                   10                  15

Thr Val Thr Ile Ser Cys Lys Arg Ser Thr Gly Asn Ile Gly Ser Ser
            20                  25                  30

Tyr Val Tyr Trp Tyr Gln Gln Arg Glu Gly Ser Ser Pro Thr Thr Val

```
                35                  40                  45
Ile Tyr Asp Gly Asp Lys Arg Pro Asp Gly Val Pro Asp Arg Phe Ser
 50                  55                  60
Gly Ser Ile Asp Ser Ser Asn Ser Ala Phe Leu Thr Ile Ser Gly
 65                  70                  75                  80
Leu Lys Thr Glu Asp Glu Ala Ile Tyr Phe Cys Gln Ser Phe Ser Ser
                 85                  90                  95
Gly Ile Lys Phe Ile Phe Gly Gly Gly Thr Lys Leu Thr Val Leu
                100                 105                 110

<210> SEQ ID NO 158
<211> LENGTH: 111
<212> TYPE: PRT
<213> ORGANISM: Artificial Sequence
<220> FEATURE:
<223> OTHER INFORMATION: description of the artificial sequence: the
      amino acid sequence of humanized LV4b

<400> SEQUENCE: 158

Asn Phe Met Leu Thr Gln Pro His Ser Val Ser Glu Ser Pro Gly Lys
  1               5                  10                  15
Thr Val Lys Ile Ser Cys Lys Arg Ser Thr Gly Asn Ile Gly Ser Ser
                 20                  25                  30
Tyr Val Tyr Trp Tyr Gln Gln Arg Glu Gly Ser Ser Pro Thr Thr Met
                 35                  40                  45
Ile Tyr Asp Gly Asp Lys Arg Pro Asp Gly Val Pro Asp Arg Phe Ser
 50                  55                  60
Gly Ser Ile Asp Ser Ser Asn Ser Ala Leu Thr Ile Ser Gly
 65                  70                  75                  80
Leu Lys Thr Glu Asp Glu Ala Ile Tyr Tyr Cys Gln Ser Phe Ser Ser
                 85                  90                  95
Gly Ile Lys Phe Ile Phe Gly Gly Gly Thr Lys Leu Thr Val Leu
                100                 105                 110

<210> SEQ ID NO 159
<211> LENGTH: 111
<212> TYPE: PRT
<213> ORGANISM: Artificial Sequence
<220> FEATURE:
<223> OTHER INFORMATION: description of the artificial sequence: the
      amino acid sequence of humanized LV5a

<400> SEQUENCE: 159

Asn Phe Met Leu Thr Gln Pro His Ser Val Ser Glu Ser Pro Gly Lys
  1               5                  10                  15
Thr Val Lys Ile Ser Cys Lys Arg Ser Thr Gly Asn Ile Gly Ser Ser
                 20                  25                  30
Tyr Val Tyr Trp Tyr Gln Gln Arg Glu Gly Ser Ser Pro Thr Thr Met
                 35                  40                  45
Ile Tyr Asp Gly Asp Lys Arg Pro Asp Gly Val Pro Asp Arg Phe Ser
 50                  55                  60
Gly Ser Ile Asp Ser Ser Asn Ser Ala Leu Thr Ile Ser Gly
 65                  70                  75                  80
Leu Lys Thr Glu Asp Glu Ala Ile Tyr Phe Cys Gln Ser Phe Ser Ser
                 85                  90                  95
Gly Ile Lys Phe Ile Phe Gly Gly Gly Thr Lys Leu Thr Val Leu
                100                 105                 110
```

```
<210> SEQ ID NO 160
<211> LENGTH: 111
<212> TYPE: PRT
<213> ORGANISM: Artificial Sequence
<220> FEATURE:
<223> OTHER INFORMATION: description of the artificial sequence: the
      amino acid sequence of humanized LV5b

<400> SEQUENCE: 160

Asn Phe Met Leu Thr Gln Pro His Ser Val Ser Thr Ser Leu Gly Lys
1               5                   10                  15

Thr Val Thr Ile Ser Cys Lys Arg Ser Thr Gly Asn Ile Gly Ser Ser
                20                  25                  30

Tyr Val Tyr Trp Tyr Gln Gln Arg Glu Gly Ser Ser Pro Thr Thr Val
            35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Phe Leu Thr Ile Ser Gly
65                  70                  75                  80

Leu Lys Thr Glu Asp Glu Ala Ile Tyr Tyr Cys Gln Ser Phe Ser Ser
                85                  90                  95

Gly Ile Lys Phe Ile Phe Gly Gly Gly Thr Lys Leu Thr Val Leu
            100                 105                 110

<210> SEQ ID NO 161
<211> LENGTH: 111
<212> TYPE: PRT
<213> ORGANISM: Artificial Sequence
<220> FEATURE:
<223> OTHER INFORMATION: description of the artificial sequence: the
      amino acid sequence of humanized LV6a

<400> SEQUENCE: 161

Asn Phe Met Leu Thr Gln Pro His Ser Val Ser Thr Ser Pro Gly Ser
1               5                   10                  15

Thr Val Lys Ile Ser Cys Lys Arg Ser Thr Gly Asn Ile Gly Ser Ser
                20                  25                  30

Tyr Val Tyr Trp Tyr Gln Gln Arg Glu Gly Ser Ser Pro Thr Thr Val
            35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Gln Thr Glu Asp Glu Ala Ile Tyr Tyr Cys Gln Ser Phe Ser Ser
                85                  90                  95

Gly Ile Lys Phe Ile Phe Gly Gly Gly Thr Lys Leu Thr Val Leu
            100                 105                 110

<210> SEQ ID NO 162
<211> LENGTH: 111
<212> TYPE: PRT
<213> ORGANISM: Artificial Sequence
<220> FEATURE:
<223> OTHER INFORMATION: description of the artificial sequence: the
      amino acid sequence of humanized LV6b

<400> SEQUENCE: 162

Asn Phe Met Leu Thr Gln Pro His Ser Val Ser Glu Ser Pro Gly Ser
1               5                   10                  15

Thr Val Thr Leu Ser Cys Lys Arg Ser Thr Gly Asn Ile Gly Ser Ser
                20                  25                  30
```

```
Tyr Val Tyr Trp Tyr Gln Gln Arg Glu Gly Ser Ser Pro Thr Thr Met
            35                  40                  45

Ile Tyr Asp Gly Asp Lys Arg Pro Asp Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Ile Tyr Phe Cys Gln Ser Phe Ser Ser
                85                  90                  95

Gly Ile Lys Phe Ile Phe Gly Gly Gly Thr Lys Leu Thr Val Leu
                100                 105                 110

<210> SEQ ID NO 163
<211> LENGTH: 111
<212> TYPE: PRT
<213> ORGANISM: Artificial Sequence
<220> FEATURE:
<223> OTHER INFORMATION: description of the artificial sequence: the
      amino acid sequence of humanized LV6c

<400> SEQUENCE: 163

Asn Phe Met Leu Thr Gln Pro His Ser Val Ser Glu Ser Leu Gly Lys
 1               5                  10                  15

Thr Val Thr Leu Ser Cys Lys Arg Ser Thr Gly Asn Ile Gly Ser Ser
                20                  25                  30

Tyr Val Tyr Trp Tyr Gln Gln Arg Gly Ser Ser Pro Thr Thr Met
            35                  40                  45

Ile Tyr Asp Gly Asp Lys Arg Pro Asp Gly Val Pro Asp Arg Phe Ser
 50                  55                  60

Gly Ser Ile Asp Ser Ser Ser Asn Ser Ala Phe Leu Thr Ile Ser Gly
 65                  70                  75                  80

Val Lys Thr Glu Asp Glu Ala Ile Tyr Tyr Cys Gln Ser Phe Ser Ser
                85                  90                  95

Gly Ile Lys Phe Ile Phe Gly Gly Gly Thr Lys Leu Thr Val Leu
                100                 105                 110

<210> SEQ ID NO 164
<211> LENGTH: 111
<212> TYPE: PRT
<213> ORGANISM: Artificial Sequence
<220> FEATURE:
<223> OTHER INFORMATION: description of the artificial sequence: the
      amino acid sequence of humanized LV6d

<400> SEQUENCE: 164

Asn Phe Met Leu Thr Gln Pro His Ser Val Ser Thr Ser Leu Gly Lys
 1               5                  10                  15

Thr Val Thr Leu Ser Cys Lys Arg Ser Thr Gly Asn Ile Gly Ser Ser
                20                  25                  30

Tyr Val Tyr Trp Tyr Gln Gln Arg Arg Gly Ser Ser Pro Thr Thr Met
            35                  40                  45

Ile Tyr Asp Gly Asp Lys Arg Pro Asp Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Gln Thr Glu Asp Glu Ala Asp Tyr Phe Cys Gln Ser Phe Ser Ser
                85                  90                  95

Gly Ile Lys Phe Ile Phe Gly Gly Gly Thr Lys Leu Thr Val Leu
                100                 105                 110
```

<210> SEQ ID NO 165
<211> LENGTH: 111
<212> TYPE: PRT
<213> ORGANISM: Artificial Sequence
<220> FEATURE:
<223> OTHER INFORMATION: description of the artificial sequence: the amino acid sequence of humanized LV7

<400> SEQUENCE: 165

Asn Phe Met Leu Thr Gln Pro His Ser Val Ser Thr Ser Pro Gly Lys
1               5                   10                  15

Thr Val Thr Leu Ser Cys Lys Arg Ser Thr Gly Asn Ile Gly Ser Ser
            20                  25                  30

Tyr Val Tyr Trp Tyr Gln Gln Arg Glu Gly Ser Ser Pro Thr Thr Met
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Phe Leu Thr Ile Ser Gly
65                  70                  75                  80

Leu Lys Thr Glu Asp Glu Ala Ile Tyr Phe Cys Gln Ser Phe Ser Ser
                85                  90                  95

Gly Ile Lys Phe Ile Phe Gly Gly Gly Thr Lys Leu Thr Val Leu
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: description of the artificial sequence: the amino acid sequence of humanized LV8

<400> SEQUENCE: 166

Asn Phe Met Leu Thr Gln Ser His Ser Val Ser Thr Ser Leu Gly Ser
1               5                   10                  15

Thr Val Lys Ile Ser Cys Lys Arg Ser Thr Gly Asn Ile Gly Ser Ser
            20                  25                  30

Tyr Val Tyr Trp Tyr Gln Gln Arg Glu Gly Ser Ser Pro Thr Thr Val
        35                  40                  45

Ile Tyr Asp Gly Asp Lys Arg Pro Asp Gly Val Pro Asp Arg Phe Ser
    50                  55                  60

Gly Ser Ile Asp Ser Ser Ser Asn Ser Ala Phe Leu Thr Ile Ser Gly
65                  70                  75                  80

Leu Lys Thr Glu Asp Glu Ala Ile Tyr Tyr Cys Gln Ser Phe Ser Ser
                85                  90                  95

Gly Ile Lys Phe Ile Phe Gly Gly Gly Thr Lys Leu Thr Val Leu
            100                 105                 110

<210> SEQ ID NO 167
<211> LENGTH: 111
<212> TYPE: PRT
<213> ORGANISM: Artificial Sequence
<220> FEATURE:
<223> OTHER INFORMATION: description of the artificial sequence: the amino acid sequence of humanized LV9

<400> SEQUENCE: 167

Asn Phe Met Leu Thr Gln Ser His Ser Val Ser Thr Ser Pro Gly Lys
1               5                   10                  15

```
Thr Val Lys Leu Ser Cys Lys Arg Ser Thr Gly Asn Ile Gly Ser Ser
            20                  25                  30

Tyr Val Tyr Trp Tyr Gln Gln Arg Arg Gly Ser Ser Pro Thr Thr Met
        35                  40                  45

Ile Tyr Asp Gly Asp Lys Arg Pro Asp Gly Val Pro Asp Arg Phe Ser
 50                  55                  60

Gly Ser Ile Asp Ser Ser Ser Asn Ser Ala Phe Leu Thr Ile Ser Gly
 65                  70                  75                  80

Val Lys Thr Glu Asp Glu Ala Ile Tyr Phe Cys Gln Ser Phe Ser Ser
            85                  90                  95

Gly Ile Lys Phe Ile Phe Gly Gly Gly Thr Lys Leu Thr Val Leu
            100                 105                 110
```

<210> SEQ ID NO 168
<211> LENGTH: 111
<212> TYPE: PRT
<213> ORGANISM: Artificial Sequence
<220> FEATURE:
<223> OTHER INFORMATION: description of the artificial sequence: the amino acid sequence of humanized LV10

<400> SEQUENCE: 168

```
Asn Phe Met Leu Thr Gln Ser His Ser Met Ser Thr Ser Leu Gly Lys
 1               5                  10                  15

Thr Val Lys Leu Ser Cys Lys Arg Ser Thr Gly Asn Ile Gly Ser Ser
            20                  25                  30

Tyr Val Tyr Trp Tyr Gln Gln Arg Glu Gly Ser Ser Pro Thr Thr Met
        35                  40                  45

Ile Tyr Asp Gly Asp Lys Arg Pro Asp Gly Val Pro Asp Arg Phe Ser
 50                  55                  60

Gly Ser Ile Asp Ser Ser Ser Asn Ser Ala Phe Leu Thr Ile Ser Gly
 65                  70                  75                  80

Leu Lys Thr Glu Asp Glu Ala Ile Tyr Tyr Cys Gln Ser Phe Ser Ser
            85                  90                  95

Gly Ile Lys Phe Ile Phe Gly Gly Gly Thr Lys Leu Thr Val Leu
            100                 105                 110
```

<210> SEQ ID NO 169
<211> LENGTH: 111
<212> TYPE: PRT
<213> ORGANISM: Artificial Sequence
<220> FEATURE:
<223> OTHER INFORMATION: description of the artificial sequence: the amino acid sequence of humanized LV14

<400> SEQUENCE: 169

```
Asn Phe Met Leu Thr Gln Ser His Ser Met Ser Thr Ser Leu Gly Ser
 1               5                  10                  15

Thr Val Lys Leu Ser Cys Lys Arg Ser Thr Gly Asn Ile Gly Ser Ser
            20                  25                  30

Tyr Val Tyr Trp Tyr Gln Gln Arg Glu Gly Ser Ser Pro Thr Thr Met
        35                  40                  45

Ile Tyr Asp Gly Asp Lys Arg Pro Asp Gly Val Pro Asp Arg Phe Ser
 50                  55                  60

Gly Ser Ile Asp Ser Ser Ser Asn Ser Ala Phe Leu Thr Ile Ser Gly
 65                  70                  75                  80

Val Gln Thr Glu Asp Glu Ala Ile Tyr Phe Cys Gln Ser Phe Ser Ser
            85                  90                  95
```

```
Gly Ile Lys Phe Ile Phe Gly Gly Gly Thr Lys Leu Thr Val Leu
            100                 105                 110
```

<210> SEQ ID NO 170
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV0"

<400> SEQUENCE: 170

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Ala His Trp Ile Arg Gln Pro Pro Gly Lys Gly Leu Glu Trp Ile
            35                  40                  45

Gly Thr Met Trp Asn Gly Gly Gly Ile Asp Tyr Asn Ser Ala Phe Lys
    50                  55                  60

Asp Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115
```

<210> SEQ ID NO 171
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV2"

<400> SEQUENCE: 171

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Ala His Trp Ile Arg Gln Pro Pro Gly Lys Gly Leu Glu Trp Ile
            35                  40                  45

Gly Thr Met Trp Asn Gly Gly Gly Ile Asp Tyr Asn Ser Ala Phe Lys
    50                  55                  60

Asp Arg Val Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115
```

<210> SEQ ID NO 172
<211> LENGTH: 115
<212> TYPE: PRT
<213> ORGANISM: Artificial Sequence
<220> FEATURE:

<223> OTHER INFORMATION: description of the artificial sequence: the
      amino acid sequence of humanized HV3"

<400> SEQUENCE: 172

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Ala His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Asp Arg Val Thr Ile Ser Arg Asp Thr Ser Lys Asn Gln Phe Ser Leu
65              70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 173
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4a"

<400> SEQUENCE: 173

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Ala His Trp Ile Arg Gln Pro Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Asp Arg Val Thr Ile Ser Arg Asp Thr Ser Lys Asn Gln Val Ser Leu
65              70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 174
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4b"

<400> SEQUENCE: 174

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr

```
            20                  25                  30
Asn Ala His Trp Ile Arg Gln Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Val Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 175
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV4c"

<400> SEQUENCE: 175

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Ser Thr Tyr
            20                  25                  30

Asn Ala His Trp Ile Arg Gln Pro Gly Lys Gly Leu Glu Trp Ile
        35                  40                  45

Gly Thr Met Trp Asn Gly Gly Ile Asp Tyr Asn Ser Ala Phe Lys
    50                  55                  60

Asp Arg Val Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 176
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV5"

<400> SEQUENCE: 176

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Thr Tyr
            20                  25                  30

Asn Ala His Trp Ile Arg Gln Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Arg Asp Thr Ser Lys Asn Gln Val Ser Leu
```

```
                65                  70                  75                  80
Lys Leu Ser Ser Val Thr Ala Ala Asp Thr Ala Lys Tyr Tyr Cys Ala
                    85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 177
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV6"

<400> SEQUENCE: 177

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Val Thr Thr Tyr
                20                  25                  30

Asn Ala His Trp Ile Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Asp Arg Leu Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Tyr Cys Ala
                    85                  90                  95

Arg Leu Gly Tyr Tyr Val Asp Tyr Trp Gly Gln Gly Thr Leu Val Thr
                100                 105                 110

Val Ser Ser
        115

<210> SEQ ID NO 178
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV7"

<400> SEQUENCE: 178

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Val Ser Thr Tyr
                20                  25                  30

Asn Ala His Trp Ile Arg Gln Pro Pro Gly Lys Gly Leu Glu Trp Met
            35                  40                  45

Gly Thr Met Trp Asn Gly Gly Ile Asp Tyr Asn Ser Ala Phe Lys
        50                  55                  60

Asp Arg Val Thr Ile Ser Arg Asp Thr Ser Lys Asn Gln Val Ser Leu
65                  70                  75                  80

Lys Met Ser Ser Val Thr Ala Ala Asp Thr Ala Lys Tyr Tyr Cys Ala
                    85                  90                  95

Arg Leu Gly Tyr Tyr Val Asp Tyr Trp Gly Gln Gly Thr Leu Val Thr
                100                 105                 110

Val Ser Ser
```

-continued

```
              115

<210> SEQ ID NO 179
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV8"

<400> SEQUENCE: 179

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Thr Tyr
            20                  25                  30

Asn Ala His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Arg Asp Thr Ser Lys Asn Gln Phe Ser Leu
65                  70                  75                  80

Lys Leu Ser Ser Val Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 180
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV10"

<400> SEQUENCE: 180

Gln Val Gln Leu Gln Glu Ser Gly Pro Gly Leu Val Lys Pro Ser Gln
1               5                   10                  15

Thr Leu Ser Ile Thr Cys Thr Val Ser Gly Phe Ser Val Thr Thr Tyr
            20                  25                  30

Asn Ala His Trp Ile Arg Gln Pro Pro Gly Lys Gly Leu Glu Trp Met
        35                  40                  45

Gly Thr Met Trp Asn Gly Gly Ile Asp Tyr Asn Ser Ala Phe Lys
    50                  55                  60

Asp Arg Leu Thr Ile Ser Arg Asp Thr Ser Lys Asn Gln Val Ser Leu
65                  70                  75                  80

Lys Met Ser Ser Val Thr Ala Ala Asp Thr Ala Lys Tyr Phe Cys Ala
                85                  90                  95

Arg Leu Gly Tyr Tyr Val Asp Tyr Trp Gly Gln Gly Thr Leu Val Thr
            100                 105                 110

Val Ser Ser
        115

<210> SEQ ID NO 181
<211> LENGTH: 115
<212> TYPE: PRT
<213> ORGANISM: Artificial Sequence
<220> FEATURE:
<223> OTHER INFORMATION: description of the artificial sequence: the
``` amino acid sequence of humanized HV13"

<400> SEQUENCE: 181

```
Gln Val Gln Leu Gln Glu Ser Gly Pro Gly Leu Val Lys Pro Ser Gln
1               5                   10                  15
Thr Leu Ser Ile Thr Cys Thr Val Ser Gly Phe Ser Leu Thr Thr Tyr
            20                  25                  30
Asn Ala His Trp Val Arg Gln Pro Pro Gly Lys Gly Leu Glu Trp Met
        35                  40                  45
Gly Thr Met Trp Asn Gly Gly Gly Ile Asp Tyr Asn Ser Ala Phe Lys
    50                  55                  60
Asp Arg Leu Thr Ile Ser Arg Asp Thr Ser Lys Asn Gln Val Ser Leu
65                  70                  75                  80
Lys Met Ser Ser Leu Thr Ala Ala Asp Thr Ala Val Tyr Phe Cys Ala
                85                  90                  95
Arg Leu Gly Tyr Tyr Val Asp Tyr Trp Gly Gln Gly Ile Leu Val Thr
            100                 105                 110
Val Ser Ser
        115
```

<210> SEQ ID NO 182
<211> LENGTH: 115
<212> TYPE: PRT
<213> ORGANISM: Artificial Sequence
<220> FEATURE:
<223> OTHER INFORMATION: description of the artificial sequence: the
      amino acid sequence of humanized HV16"

<400> SEQUENCE: 182

```
Gln Val Gln Leu Gln Glu Ser Gly Pro Gly Leu Val Lys Leu Ser Gln
1               5                   10                  15
Thr Leu Ser Ile Thr Cys Thr Val Ser Gly Phe Ser Leu Thr Thr Tyr
            20                  25                  30
Asn Ala His Trp Val Arg Gln Pro Pro Gly Lys Gly Leu Glu Trp Met
        35                  40                  45
Gly Thr Met Trp Asn Gly Gly Gly Ile Asp Tyr Asn Ser Ala Phe Lys
    50                  55                  60
Asp Arg Leu Thr Ile Ser Arg Asp Thr Ser Lys Ser Gln Val Ser Leu
65                  70                  75                  80
Lys Met Ser Ser Leu Thr Ala Ala Asp Thr Ala Lys Tyr Phe Cys Ala
                85                  90                  95
Arg Leu Gly Tyr Tyr Val Asp Tyr Trp Gly Gln Gly Ile Leu Val Thr
            100                 105                 110
Val Ser Ser
        115
```

ANTI-BMP10 MONOCLONAL ANTIBODY OR FRAGMENT THEREOF

A sequence listing in electronic (ASCII text file) format is filed with this application and incorporated herein by reference. The name of the ASCII text file is "2020_1657A_ST25.txt"; the file was created on Feb. 11, 2022; the size of the file is 190592 bytes.

TECHNICAL FIELD

The present invention relates to an anti-BMP10 monoclonal antibody or an antibody fragment thereof that binds to human BMP10 (bone morphogenetic protein 10), a DNA encoding the antibody or the antibody fragment thereof, a recombinant vector comprising the DNA, a transformant obtained by introducing the recombinant vector into a host cell, and a method for producing the antibody or the antibody fragment thereof using the transformant.

Further, the present invention relates to a therapeutic agent for hypertension and a hypertensive disease containing an antagonist for at least one of BMP10 and a BMP9/BMP10 heterodimer, a diagnostic agent or a pharmaceutical composition for a disease associated with human BMP10, an immunological detection method or a measurement method for human BMP10 using the antagonist, and use of the antagonist for producing a pharmaceutical composition for treating hypertension and a hypertensive disease.

BACKGROUND ART

BMP10 is an abbreviation of bone morphogenetic protein 10. BMP10 belongs to BMP (bone morphogenetic protein) family molecules composed of about 20 types, and human BMP10 is a secretory protein composed of 424 amino acids (Non-Patent Literatures 1 and 2). BMP10 binds to two receptors of type I and type TT so as to activate the receptors, followed by phosphorylation of Smad1/5/8, and further the Smad1/5/8 activated by phosphorylation form a complex with Smad4, and thereafter, the complex translocates into the nucleus and functions as a transcription factor.

It is known that BMP10 is mainly expressed in a heart (Non-Patent Literatures 2, 3, and 4), and that human BMP10 is a blood circulation factor present in blood at a concentration of about 10 ng/mL (Non-Patent Literature 5).

With respect to the in vivo role of BMP10, based on an analysis using BMP10-deficient mice, it has been reported that BMP10 is an important factor for heart development and angiogenesis in the embryonic stage so far (Non-Patent Literatures 6 and 7). However, the BMP10-deficient mice are embryonic lethal, and therefore, there have been no reports on the effect of BMP10 in the adult stage. In addition, there have been no reports based on the administration of an anti-BMP10 antibody to an animal in the adult stage.

Further, it has been reported that there is a gene mutation in BMP10 in a patient with HT-DCM that is dilated cardiomyopathy accompanied by hypertension, and the gene mutation causes hypersecretion of BMP10 (Non-Patent Literature 12). In Non-Patent Literature 12, it is indicated that when hypertensive rats are given high salt to cause cardiac hypertrophy, the expression of BMP10 mRNA is increased. However, Non-Patent Literature 12 does not describe neutralization and deletion of BMP10, and it is very difficult to predict the antihypertensive effect by neutralization of BMP10.

Therefore, it was extremely difficult to predict that an anti-BMP10 antibody has an antihypertensive effect, a renal protective effect, and a cardioprotective effect in vivo.

As an anti-BMP10 monoclonal antibody that specifically neutralizes BMP10, MAB2926 (clone No. 462732) sold by R & D Systems, Inc., and one antibody (clone No. 13C11) reported in the literature are known. Further, it is indicated that MAB2926 has a stronger BMP10 neutralizing activity than 13C11 (Non-Patent Literature 8). There were no other known specific neutralizing antibodies against BMP10.

Hypertension is a lifestyle disease, and the number of patients with hypertension is the largest among the lifestyle diseases. There exist many drugs such as a Ca antagonist, a diuretic agent, an ACE inhibitor, and an ARB, however, it has been reported that the blood pressure could be appropriately controlled only in 35% of the patients in the USA (Non-Patent Literature 9). As one of the causes why hypertension cannot be controlled, a decrease in adherence due to long administration period is exemplified. Therefore, a novel antihypertensive drug capable of persistently and stably controlling the blood pressure has been awaited.

One of the forms of hypertension that is difficult to control by an existing antihypertensive drug is salt-sensitive hypertension. Healthy individuals excrete sodium from the kidney according to salt intake and maintain homeostasis, but in salt-sensitive hypertensive patients, an abnormality occurs in the mechanism of sodium excretion in the kidney. In a pathological condition in which enhancement of salt sensitivity occurs, in order to excrete the same amount of sodium as healthy individuals, a higher blood pressure is needed, and therefore, hypertension is exhibited according to the salt intake. As a symptomatic treatment, sodium reduction therapy is carried out, however, there are not many patients who can achieve reduction in blood pressure by sodium reduction therapy due to a decrease in QOL by a low-sodium diet (Non-Patent Literature 10). Therefore, an antihypertensive drug with a new mechanism which targets a novel molecule and is capable of treating salt-sensitive hypertension has been demanded.

Poorly controlled hypertension is associated with the risk of developing a cardiovascular disease such as stroke, heart attack, heart failure, or a kidney disease. Progression of renal failure leads to blood sodium retention, body fluid retention, activation of a blood pressure regulator, accumulation of a uremic substance, or the like, and further increases blood pressure. In addition, heart failure due to body fluid retention causes an abnormality in a sympathetic nerve or a body fluid regulator as a result of a decrease in cardiac output so as to make the blood pressure control difficult. In such a manner, a vicious circle of cardiorenal syndrome is caused in which renal failure and heart failure exacerbate hemodynamic failure such as hypertension, and hemodynamic failure exacerbate the pathological conditions of renal failure and heart failure (Non-Patent Literature 11).

CITATION LIST

Patent Literature

Patent Literature 1: U.S. Pat. No. 8,287,868
Patent Literature 2: US Patent Application Publication No. 2017/0137503

Non-Patent Literature

Non-Patent Literature 1: FEBS Letters 586 1846-1859 (2012)
Non-Patent Literature 2: J Biol Chem. 2011 Jul. 1; 286(26): 22785-94

Non-Patent Literature 3: Mech Dev. 1999 February; 80(2): 181-4

Non-Patent Literature 4: Dev Genes Evol. 2004 February; 214(2): 96-8

Non-Patent Literature 5: Blood. 2012 Jun. 21; 119(25): 6162-6171

Non-Patent Literature 6: Proc Natl Acad Sci USA, 2013 Jul. 16; 110(29): 11887-92

Non-Patent Literature 7: Development. 2004 May; 131(9): 2219-2231

Non-Patent Literature 8: Proc Natl Acad Sci USA, 2015 Jun. 23; 112(25): E3207-15

Non-Patent Literature 9: Expert Opin Biol Ther. 2010 July; 10(7): 1077-87

Non-Patent Literature 10: Jikken Igaku (Experimental Medicine) 33(7): 1078-1084, 2015

Non-Patent Literature 11: Eur Rev Med Pharmacol Sci. 2014 October; 18(19): 2918-26

Non-Patent Literature 12: Am J Physiol Heart Circ Physiol 2007 Dec.; 293(6): H3396-403

SUMMARY OF INVENTION

Technical Problem

Therefore, as a novel therapeutic agent for hypertension, a therapeutic agent capable of achieving both renal protective effect and cardioprotective effect has been awaited. In addition, as described above, it has been demanded that a novel therapeutic agent for hypertension has three characteristics of persistent and stable control of blood pressure, an antihypertensive effect through a novel target, and a protective effect on kidney and heart.

An object of the present invention is to provide an anti-BMP10 antibody and a therapeutic agent for hypertension and a hypertensive disease containing the antibody as an active ingredient.

Solution to Problem

The present inventors attempted to obtain an anti-BMP10 antibody using rats for the purpose of clarifying the in vivo effect of an anti-BMP10 antibody, and successfully obtained an anti-BMP10 antibody having a remarkably improved neutralizing activity and binding activity against BMP10 as compared with existing antibodies. In addition, they clarified that while existing antibodies do not have a neutralizing activity against ALK1 highly expressing cells, the obtained anti-BMP10 antibody has a strong neutralizing activity.

Further, they found that while the existing antibodies compete with ALK1, the obtained anti-BMP10 antibody has a novel mode of inhibition of antagonizing BMPRII and endoglin. In addition, they revealed that by using the obtained anti-BMP10 antibody, a heterodimer composed of BMP9 and BMP10 is present in blood. Further, they revealed that the obtained anti-BMP10 antibody has a strong neutralizing activity against the heterodimer composed of BMP9 and BMP10 in ALK1 highly expressing cells.

Further, by using the obtained antibody, they examined the in vivo effect of the anti-BMP10 antibody. As a result, they found that the anti-BMP10 antibody of the present invention has a sustained antihypertensive effect, and further remarkably improves hypertension and a sodium excretion disorder in salt-sensitive pathological conditions, and has a therapeutic effect on a glomerular disorder, a renal tubular disorder, and heart diastolic dysfunction accompanying hypertension.

Based on these findings, the present inventors considered that a therapeutic agent for hypertension and a hypertensive disease containing an anti-BMP10 antibody as an active ingredient can be provided, and thus completed the present invention.

That is, the present invention relates to the following (1) to (18).

(1) A monoclonal antibody comprising: a heavy chain comprising complementarity determining regions (hereinafter abbreviated as CDRs) 1 and 3 comprising amino acid sequences represented by SEQ ID NOs: 29 and 31, respectively, and CDR2 comprising an amino acid sequence represented by SEQ ID NO: 30 or an amino acid sequence in which serine at position 16 of the amino acid sequence represented by SEQ ID NO: 30 is substituted with aspartic acid; and a light chain comprising CDRs 1 to 3 comprising amino acid sequences represented by SEQ ID NOs: 32 to 34, respectively, or an antibody fragment thereof.

(2) The monoclonal antibody or the antibody fragment thereof according to (1), comprising a light chain variable region (hereinafter abbreviated as VL) comprising any one amino acid sequence selected from SEQ ID NOs: 71 to 87 and/or a heavy chain variable region (hereinafter abbreviated as VH) comprising any one amino acid sequence selected from SEQ ID NOs: 70 and 88 to 98.

(3) The monoclonal antibody or the antibody fragment thereof according to (1) or (2) selected from the following (a) to (w):

(a) a monoclonal antibody comprising VH comprising an amino acid sequence represented by SEQ ID NO: 94 and VL comprising an amino acid sequence represented by SEQ ID NO: 73, or an antibody fragment thereof;

(b) a monoclonal antibody comprising VH comprising an amino acid sequence represented by SEQ ID NO: 95 and VL comprising an amino acid sequence represented by SEQ ID NO: 73, or an antibody fragment thereof, (c) a monoclonal antibody comprising VH comprising an amino acid sequence represented by SEQ ID NO: 91 and VL comprising an amino acid sequence represented by SEQ ID NO: 75, or an antibody fragment thereof, (d) a monoclonal antibody comprising VH comprising an amino acid sequence represented by SEQ ID NO: 98 and VL comprising an amino acid sequence represented by SEQ ID NO: 75, or an antibody fragment thereof;

(e) a monoclonal antibody comprising VH comprising an amino acid sequence represented by SEQ ID NO: 89 and VL comprising an amino acid sequence represented by SEQ ID NO: 77, or an antibody fragment thereof, (f) a monoclonal antibody comprising VH comprising an amino acid sequence represented by SEQ ID NO: 97 and VL comprising an amino acid sequence represented by SEQ ID NO: 77, or an antibody fragment thereof, (g) a monoclonal antibody comprising VH comprising an amino acid sequence represented by SEQ ID NO: 97 and VL comprising an amino acid sequence represented by SEQ ID NO: 78, or an antibody fragment thereof, (h) a monoclonal antibody comprising VH comprising an amino acid sequence represented by SEQ ID NO: 98 and VL comprising an amino acid sequence represented by SEQ ID NO: 78, or an antibody fragment thereof;

(i) a monoclonal antibody comprising VH comprising an amino acid sequence represented by SEQ ID NO: 91 and VL comprising an amino acid sequence represented by SEQ ID NO: 79, or an antibody fragment thereof;

(j) a monoclonal antibody comprising VH comprising an amino acid sequence represented by SEQ ID NO: 95 and VL comprising an amino acid sequence represented by SEQ ID NO: 79, or an antibody fragment thereof;

(k) a monoclonal antibody comprising VH comprising an amino acid sequence represented by SEQ ID NO: 98 and VL comprising an amino acid sequence represented by SEQ ID NO: 79, or an antibody fragment thereof;

(l) a monoclonal antibody comprising VH comprising an amino acid sequence represented by SEQ ID NO: 89 and VL comprising an amino acid sequence represented by SEQ ID NO: 81, or an antibody fragment thereof;

(m) a monoclonal antibody comprising VH comprising an amino acid sequence represented by SEQ ID NO: 91 and VL comprising an amino acid sequence represented by SEQ ID NO: 81, or an antibody fragment thereof;

(n) a monoclonal antibody comprising VH comprising an amino acid sequence represented by SEQ ID NO: 95 and VL comprising an amino acid sequence represented by SEQ ID NO: 81, or an antibody fragment thereof;

(o) a monoclonal antibody comprising VH comprising an amino acid sequence represented by SEQ ID NO: 97 and VL comprising an amino acid sequence represented by SEQ ID NO: 81, or an antibody fragment thereof;

(p) a monoclonal antibody comprising VH comprising an amino acid sequence represented by SEQ ID NO: 98 and VL comprising an amino acid sequence represented by SEQ ID NO: 81, or an antibody fragment thereof;

(q) a monoclonal antibody comprising VH comprising an amino acid sequence represented by SEQ ID NO: 94 and VL comprising an amino acid sequence represented by SEQ ID NO: 85, or an antibody fragment thereof;

(r) a monoclonal antibody comprising VH comprising an amino acid sequence represented by SEQ ID NO: 95 and VL comprising an amino acid sequence represented by SEQ ID NO: 85, or an antibody fragment thereof;

(s) a monoclonal antibody comprising VH comprising an amino acid sequence represented by SEQ ID NO: 97 and VL comprising an amino acid sequence represented by SEQ ID NO: 85, or an antibody fragment thereof;

(t) a monoclonal antibody comprising VH comprising an amino acid sequence represented by SEQ ID NO: 98 and VL comprising an amino acid sequence represented by SEQ ID NO: 85, or an antibody fragment thereof;

(u) a monoclonal antibody comprising VH comprising an amino acid sequence represented by SEQ ID NO: 94 and VL comprising an amino acid sequence represented by SEQ ID NO: 87, or an antibody fragment thereof;

(v) a monoclonal antibody comprising VH comprising an amino acid sequence represented by SEQ ID NO: 97 and VL comprising an amino acid sequence represented by SEQ ID NO: 87, or an antibody fragment thereof; and (w) a monoclonal antibody comprising VH comprising an amino acid sequence represented by SEQ ID NO: 98 and VL comprising an amino acid sequence represented by SEQ ID NO: 87, or an antibody fragment thereof.

(4) The monoclonal antibody or the antibody fragment thereof according to any one of (1) to (3), having a neutralizing activity against BMP10.

(5) The monoclonal antibody or the antibody fragment thereof according to any one of (1) to (4), having a neutralizing activity against a BMP9/BMP10 heterodimer.

(6) The monoclonal antibody or the antibody fragment thereof according to any one of (1) to (5), which is a genetically recombinant antibody.

(7) The antibody fragment according to any one of (1) to (6), which is an antibody fragment selected from a Fab, a Fab', a (Fab')$_2$, a single chain antibody (scFv), a dimerized V region (diabody), a disulfide stabilized V region (dsFv), and a peptide comprising a CDR.

(8) A DNA, encoding the monoclonal antibody or the antibody fragment thereof according to any one of (1) to (7).

(9) A recombinant vector, comprising the DNA according to (8).

(10) A transformant, obtained by introducing the recombinant vector according to (9) into a host cell.

(11) A method for producing the monoclonal antibody or the antibody fragment thereof according to any one of (1) to (7), comprising: culturing the transformant according to (10) in a culture medium, and collecting the antibody or the antibody fragment from the culture.

(12) A therapeutic agent for hypertension and/or a hypertensive disease, comprising an antagonist for at least one of BMP10 and a BMP9/BMP10 heterodimer.

(13) The therapeutic agent according to (12), which is administered concurrently or sequentially with a BMP9 antagonist.

(14) A therapeutic agent for hypertension and/or a hypertensive disease, the therapeutic agent comprising a BMP9 antagonist, characterized by being administered concurrently or sequentially with an antagonist for at least one of BMP10 and a BMP9/BMP10 heterodimer.

(15) A diagnostic agent for a disease associated with human BMP10, comprising an antagonist for at least one of BMP10 and a BMP9/BMP10 heterodimer.

(16) An immunological detection method or a measurement method for human BMP10, using an antagonist for at least one of BMP10 and a BMP9/BMP10 heterodimer.

(17) A pharmaceutical composition, comprising an antagonist for at least one of BMP10 and a BMP9/BMP10 heterodimer and a pharmacologically acceptable carrier.

(18) Use of an antagonist for at least one of BMP10 and a BMP9/BMP10 heterodimer for producing a pharmaceutical composition for treating hypertension and a hypertensive disease.

Advantageous Effects of Invention

The antibody of the present invention is an anti-BMP10 antibody in which at least one of the neutralizing activity against BMP10 and the binding activity thereto is remarkably improved as compared with existing antibodies. Further, the antibody of the present invention has a neutralizing activity against BMP10 in ALK1 highly expressing cells. Further, the antibody of the present invention inhibits binding of human BMP10 to human BMPRII and human endoglin.

In addition, by the antibody of the present invention, it was demonstrated that a heterodimer composed of human BMP9 and human BMP10 is present in human blood. Further, the antibody of the present invention has a neutralizing activity against a heterodimer composed of human BMP9 and human BMP10 in ALK1 highly expressing cells.

In addition, the antibody of the present invention has an effect of persistently lowering blood pressure in hypertensive pathology. Further, the antibody of the present invention remarkably improves high blood pressure and a sodium excretion disorder in salt-sensitive hypertension. In addition, the antibody of the present invention has an improving effect against a renal tubulointerstitial disorder, a renal glomerular disorder, and heart diastolic dysfunction accompanying hypertension.

The antibody of the present invention is an antibody having one or more or all of the characteristics described above. A DNA encoding the antibody having such a characteristic, a vector comprising the DNA, a transformant obtained by introducing the vector, a method for producing the antibody or the antibody fragment thereof using the transformant, and a therapeutic agent for hypertension and a hypertensive disease can be provided by using the antibody or the antibody fragment thereof as an active ingredient.

BRIEF DESCRIPTION OF DRAWINGS

FIG. 7A and FIG. 7B are figures showing the effect of 18C1 antibody that is an obtained anti-BMP10 antibody on sodium excretion in Dahl salt-sensitive hypertensive rats. FIG. 7A shows a change in blood sodium concentration. The horizontal axis of the graph represents the weeks of age (w) of the rats, and the vertical axis represents the serum sodium concentration (mEq). FIG. 7B shows a change in urine sodium excretion per day. The horizontal axis of the graph represents the weeks of age (w) of the rats, and the vertical axis represents the urine sodium excretion per day (mEq/day). Black circles indicate a normal diet group (n=6), black squares indicate a high salt group (n=12), and white circles indicate a high salt diet+18C1 antibody group (n=12). Error bars in the figures indicate the standard error (SE).

FIG. 9 shows a change in urine protein excretion per day. The horizontal axis of the graph represents the weeks of age (w) of the rats, and the vertical axis represents the urine protein excretion per day (mg/day). Black circles indicate a normal diet group (n=6), black squares indicate a high salt group (n=12), and white circles indicate a high salt diet+18C1 antibody group (n=12). Error bars in the figure indicate the standard error (SE).

FIG. 10A is a figure showing renal glomerular pathology in a normal diet group in Dahl salt-sensitive hypertensive rats. FIG. 10B is a figure showing renal glomerular pathology in a high salt diet group in Dahl salt-sensitive hypertensive rats. FIG. 10C is a figure showing renal glomerular pathology in a group in which a high salt diet was given and 18C1 antibody was administered to Dahl salt-sensitive hypertensive rats (high salt diet+18C1). FIG. 10D is a photograph of renal tubulointerstitial pathology in a normal diet group in Dahl salt-sensitive hypertensive rats. FIG. 10E is a photograph of renal tubulointerstitial pathology in a high salt diet group in Dahl salt sensitive hypertensive rats. FIG. 10F is a photograph of renal tubulointerstitial pathology in a group in which a high salt diet was given and 18C1 antibody was administered to Dahl salt-sensitive hypertensive rats (high salt diet+18C1).

FIG. 11A and FIG. 11B are figures showing the effect of 18C1 antibody that is an obtained anti-BMP10 antibody on a renal function in Dahl salt-sensitive hypertensive rats. FIG. 11A is a graph showing the glomerular pathology scores of Dahl salt-sensitive hypertensive rats. The vertical axis represents the pathology score. FIG. 11B is a graph showing the tubulointerstitial pathology score of Dahl salt-sensitive hypertensive rats. The vertical axis represents the pathology score.

FIG. 12A and FIG. 12B are figures showing the effect of 18C1 antibody that is an obtained anti-BMP10 antibody on a cardiac function in Dahl salt-sensitive hypertensive rats. FIG. 12A shows a left ventricle posterior wall thickness measured by echocardiography at 16 weeks of age. The horizontal axis of the graph represents the type of feed and the agent administered, and the vertical axis represents the left ventricle posterior wall thickness. FIG. 12B shows a mitral annulus velocity e' measured by echocardiography at 16 weeks of age. The horizontal axis of the graph represents the type of feed and the agent administered, and the vertical axis represents the e'. The tested groups are as follows: a normal diet group (n=6), a high salt group (n=12), and a high salt diet+18C1 antibody group (n=12). Error bars in the figures indicate the standard error (SE).

FIG. 13 shows a value obtained by correcting the weight of the lung dissected and collected at 16 weeks of age by the body weight. The vertical axis of the graph represents the lung weight to body weight ratio (lung weight (mg)/body weight (g)). The tested groups are as follows: a normal diet group (n=6), a high salt group (n=12), and a high salt diet+18C1 antibody group (n=12). Error bars in the figure indicate the standard error (SE).

FIG. 14 shows the neutralizing activity of an anti-BMP9 antibody and an anti-BMP10 antibody on BMP in blood in ALK1/Id1-Luc/CHO cells. The horizontal axis represents the added concentration of the antibodies (μg/mL), and the vertical axis represents the neutralizing activity (%). White circles indicate a control antibody, black circles indicate the 18C1 antibody, black squares indicate 12H3 antibody, black triangles indicate an 11H10 antibody, black diamonds indicate 10D5 antibody that is an anti-BMP9 antibody, white squares indicate a mixture of the 12H3 antibody and the 10D5 antibody, and white triangles indicate a mixture of the 11H10 antibody and the 10D5 antibody. The white squares and the white triangles are indicated by broken lines.

FIG. 15 shows the results of sandwich ELISA in which an anti-BMP10 antibody or an anti-BMP9 antibody was immobilized, human serum was reacted therewith, and detection was carried out with an antibody obtained by biotinylating 12H3 antibody that is an anti-BMP10 antibody. The vertical axis represents the absorbance (OD 450/570) in ELISA, and the horizontal axis represents the final concentration (%) of human serum. Black circles indicate 10D5 antibody that is an anti-BMP9 antibody and was immobilized, white squares indicate 11H10 antibody that was immobilized, and black triangles indicate a control antibody that was immobilized.

FIG. 16 shows amino acid sequences of heavy chain variable regions of humanized antibodies designed by alteration of 18C1 antibody and are designed by alteration from an amino acid sequence of SEQ ID NO: 70. Regions surrounded by a frame in the sequences indicate amino acid sequences of CDRs. FIG. 16 includes the following sequences:
18C1VH SEQ ID NO: 23; HV0 SEQ ID NO: 70;
HV2 SEQ ID NO: 100; HV3 SEQ ID NO: 101;
HV4a SEQ ID NO: 102; HV4b SEQ ID NO: 103;
HV4c SEQ ID NO: 104; HV5 SEQ ID NO: 105;
HV6 SEQ ID NO: 106; HV7 SEQ ID NO: 107;
HV8 SEQ ID NO: 108; HV10 SEQ ID NO: 109;
HV13 SEQ ID NO: 110; HV16 SEQ ID NO: 111;
HV0' SEQ ID NO: 112; HV2' SEQ ID NO: 113;
HV3' SEQ ID NO: 114; HV4a' SEQ ID NO: 115;
HV4b' SEQ ID NO: 116; HV4c' SEQ ID NO: 117;
HV5' SEQ ID NO: 118; HV6' SEQ ID NO: 119;
HV7' SEQ ID NO: 120; HV8' SEQ ID NO: 121;
HV10' SEQ ID NO: 122; HV13' SEQ ID NO: 123;
HV16' SEQ ID NO: 124; HV0" SEQ ID NO: 170;
HV2" SEQ ID NO: 171; HV3" SEQ ID NO: 172;
HV4a" SEQ ID NO: 173; HV4b" SEQ ID NO: 174;
HV4c" SEQ ID NO: 175; HV5" SEQ ID NO: 176;
HV6" SEQ ID NO: 177; HV7" SEQ ID NO: 178;
HV8" SEQ ID NO: 179; HV10" SEQ ID NO: 180;
HV13" SEQ ID NO: 181; and HV16" SEQ ID NO: 182.

FIG. 17 is a figure showing amino acid sequences of heavy chain variable regions of humanized antibodies designed by alteration of 18C1 antibody and shows amino acid sequences designed by alteration from an amino acid sequence of SEQ ID NO: 23. Regions surrounded by a frame in the sequences indicate amino acid sequences of CDRs. FIG. 17 includes the following sequences:
18C1 VH SEQ ID NO: 23; VHres01 SEQ ID NO: 125;
VHres02 SEQ ID NO: 126; VHres03 SEQ ID NO: 127;
VHres04 SEQ ID NO: 128; VHres05 SEQ ID NO: 129;
VHres06 SEQ ID NO: 130; VHres07 SEQ ID NO: 131;
VHres08 SEQ ID NO: 132; VHres09 SEQ ID NO: 133;
VHres10 SEQ ID NO: 134; VHres11 SEQ ID NO: 135;
VHres12 SEQ ID NO: 136; VHres13 SEQ ID NO: 137;
VHres14 SEQ ID NO: 138; VHres15 SEQ ID NO: 139;
VHres16 SEQ ID NO: 98; VHres17 SEQ ID NO: 140;
VHres18 SEQ ID NO: 141; VHres19 SEQ ID NO: 142;
VHres20 SEQ ID NO: 143; VHres21 SEQ ID NO: 144;
VHres22 SEQ ID NO: 145; VHres23 SEQ ID NO: 146;
VHres24 SEQ ID NO: 147; VHres25 SEQ ID NO: 148;
VHres26 SEQ ID NO: 149; VHres27 SEQ ID NO: 150;
VHres28 SEQ ID NO: 151; VHres29 SEQ ID NO: 152;
VHres30 SEQ ID NO: 153; VHres31 SEQ ID NO: 154; and
VHres32 SEQ ID NO: 155.

FIG. 18A and FIG. 18B are each a figure showing amino acid sequences of light chain variable regions of humanized antibodies designed by alteration of 18C1 antibody. Regions surrounded by a frame in each sequence indicate amino acid sequences of CDRs. FIG. 18A shows amino acid sequences designed by alteration from an amino acid sequence of SEQ ID NO: 71. FIG. 18B shows amino acid sequences designed by alteration from an amino acid sequence of SEQ ID NO: 26. FIG. 18A includes the following sequences:
18C1 VL SEQ ID NO: 26; LV0 SEQ ID NO: 71;
LV3 SEQ ID NO: 156; LV4a SEQ ID NO: 157;
LV4b SEQ ID NO: 158; LV5a SEQ ID NO: 159;
LV5b SEQ ID NO: 160; LV6a SEQ ID NO: 161;
LV6b SEQ ID NO: 162; LV6c SEQ ID NO: 163;
LV6d SEQ ID NO: 164; LV7 SEQ ID NO: 165;
LV8 SEQ ID NO: 166; LV9 SEQ ID NO: 167;
LV10 SEQ ID NO: 168; and LV14 SEQ ID NO: 169.
FIG. 18B includes the following sequences:
18C1 VL SEQ ID NO: 26; VLres01 SEQ ID NO: 72;
VLres02 SEQ ID NO: 73; VLres03 SEQ ID NO: 74;
VLres04 SEQ ID NO: 75; VLres05 SEQ ID NO: 76;
VLres06 SEQ ID NO: 77; VLres07 SEQ ID NO: 78;
VLres08 SEQ ID NO: 79; VLres09 SEQ ID NO: 80;
VLres10 SEQ ID NO: 81; VLres11 SEQ ID NO: 82;
VLres12 SEQ ID NO: 83; VLres13 SEQ ID NO: 84;
VLres14 SEQ ID NO: 85; VLres15 SEQ ID NO: 86; and
VLres16 SEQ ID NO: 87.

FIG. 19 is a figure showing amino acid sequences of heavy chain variable regions of humanized antibodies designed by alteration of 18C1 antibody and shows amino acid sequences designed by alteration from an amino acid sequence of SEQ ID NO: 70. Regions surrounded by a frame in the sequences indicate amino acid sequences of CDRs. FIG. 19 includes the following sequences:

HVmut01 SEQ ID NO: 88; HVmut02 SEQ ID NO: 89; HVmut03 SEQ ID NO: 90; HVmut04 SEQ ID NO: 91; HVmut05 SEQ ID NO: 92; HVmut06 SEQ ID NO: 93; HVmut07 SEQ ID NO: 94; HVmut08 SEQ ID NO: 95; HVmut09 SEQ ID NO: 96; and HVmut10 SEQ ID NO: 97.

Figure 20:
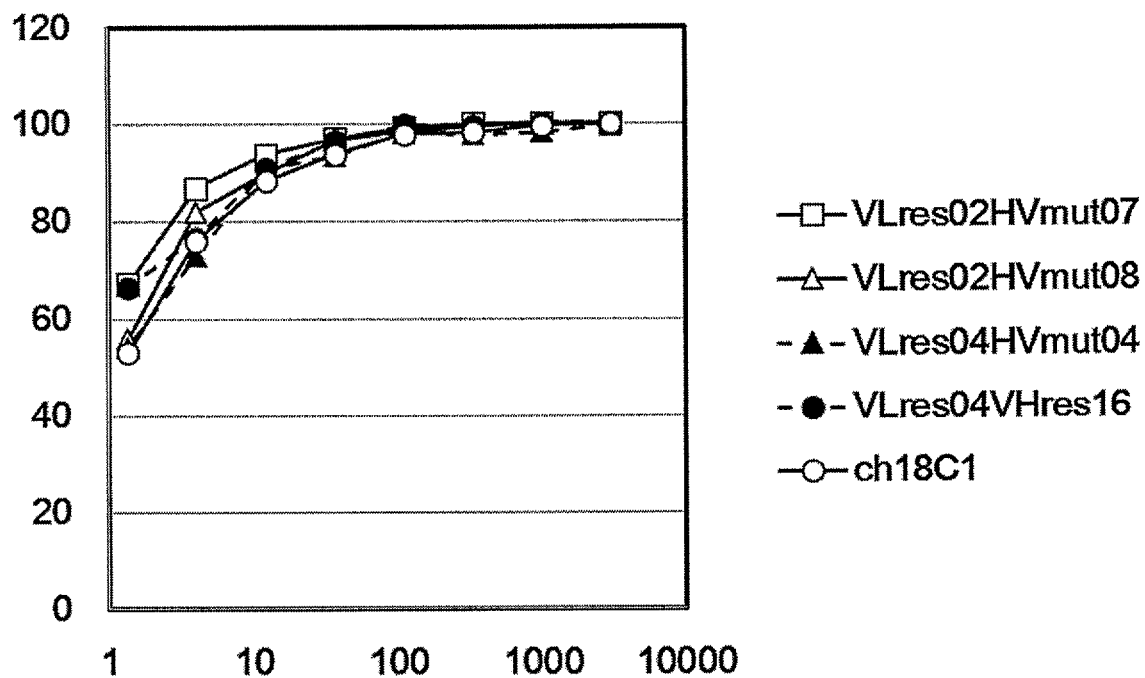

FIG. 20 is a graph comparing the BMP10 neutralizing activity of anti-BMP10 humanized antibodies with that of 18C1 chimeric antibody using ALK1/Id1-Luc/CHO cells. The horizontal axis represents the added concentration of the antibodies (ng/mL), and the vertical axis represents the neutralizing activity (%). White squares indicate VLres02HVmut07, white triangles indicate VLres02HVmut08, black triangles indicate a VLres04HVmut04 antibody, black circles indicate a VLres04VHres16 antibody, and white circles indicate ch18C1 antibody. The black circles and the black triangles are indicated by broken lines.

Figure 21:
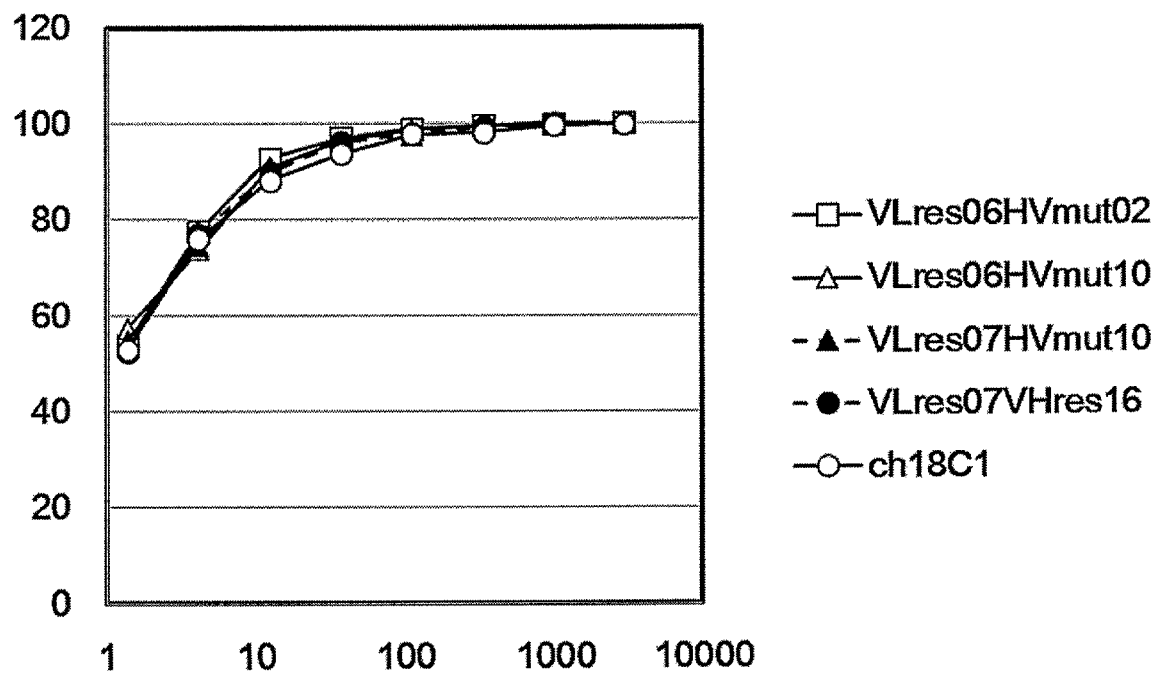

FIG. 21 is a graph comparing the BMP10 neutralizing activity of anti-BMP10 humanized antibodies with that of 18C1 chimeric antibody using ALK1/Id1-Luc/CHO cells. The horizontal axis represents the added concentration of the antibodies (ng/mL), and the vertical axis represents the neutralizing activity (%). White squares indicate VLres06HVmut02, white triangles indicate VLres06HVmut10, black triangles indicate a VLres07HVmut10 antibody, black circles indicate a VLres07VHres16 antibody, and white circles indicate ch18C1 antibody. The black circles and the black triangles are indicated by broken lines.

Figure 22:
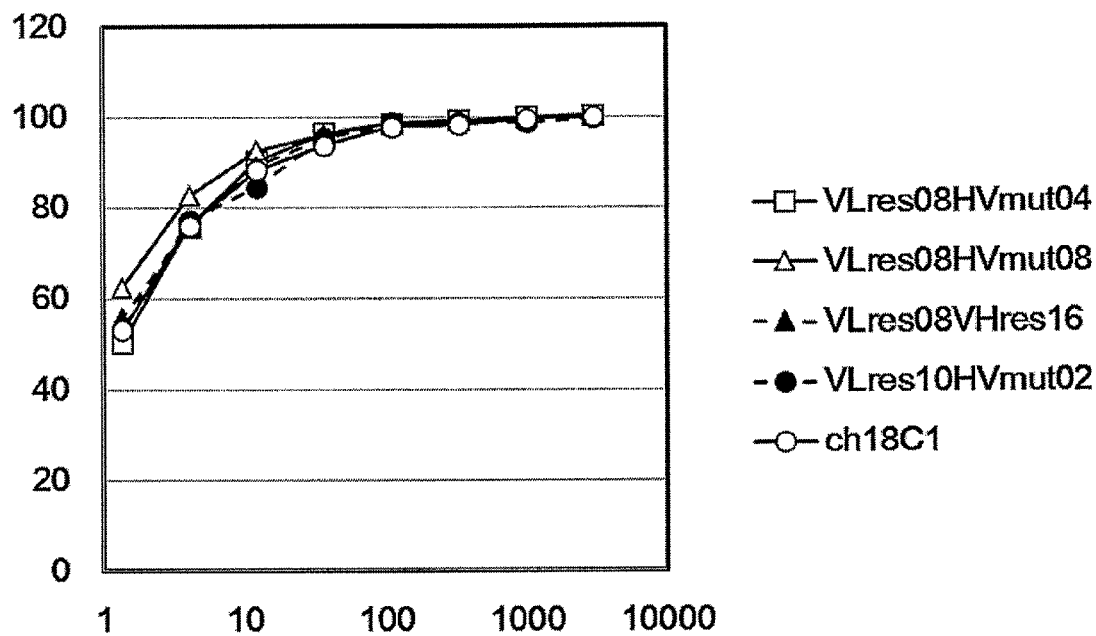

FIG. 22 is a graph comparing the BMP10 neutralizing activity of anti-BMP10 humanized antibodies with that of 18C1 chimeric antibody using ALK1/Id1-Luc/CHO cells. The horizontal axis represents the added concentration of the antibodies (ng/mL), and the vertical axis represents the neutralizing activity (%). White squares indicate VLres08HVmut04, white triangles indicate VLres08HVmut08, black triangles indicate a VLres08VHres16 antibody, black circles indicate a VLres10HVmut02 antibody, and white circles indicate ch18C1 antibody. The black circles and the black triangles are indicated by broken lines.

Figure 23:
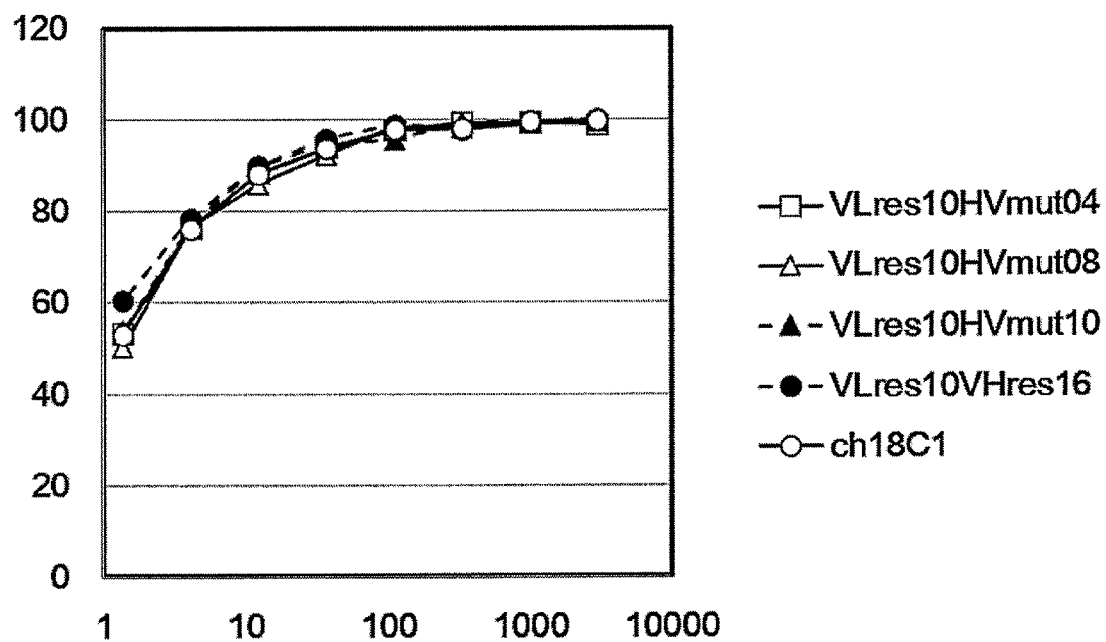

FIG. 23 is a graph comparing the BMP10 neutralizing activity of anti-BMP10 humanized antibodies with that of 18C1 chimeric antibody using ALK1/Id1-Luc/CHO cells. The horizontal axis represents the added concentration of the antibodies (ng/mL), and the vertical axis represents the neutralizing activity (%). White squares indicate VLres10HVmut04, white triangles indicate VLres10HVmut08, black triangles indicate a VLres10HVmut10 antibody, black circles indicate a VLres10VHres16 antibody, and white circles indicate ch18C1 antibody. The black circles and the black triangles are indicated by broken lines.

Figure 24:
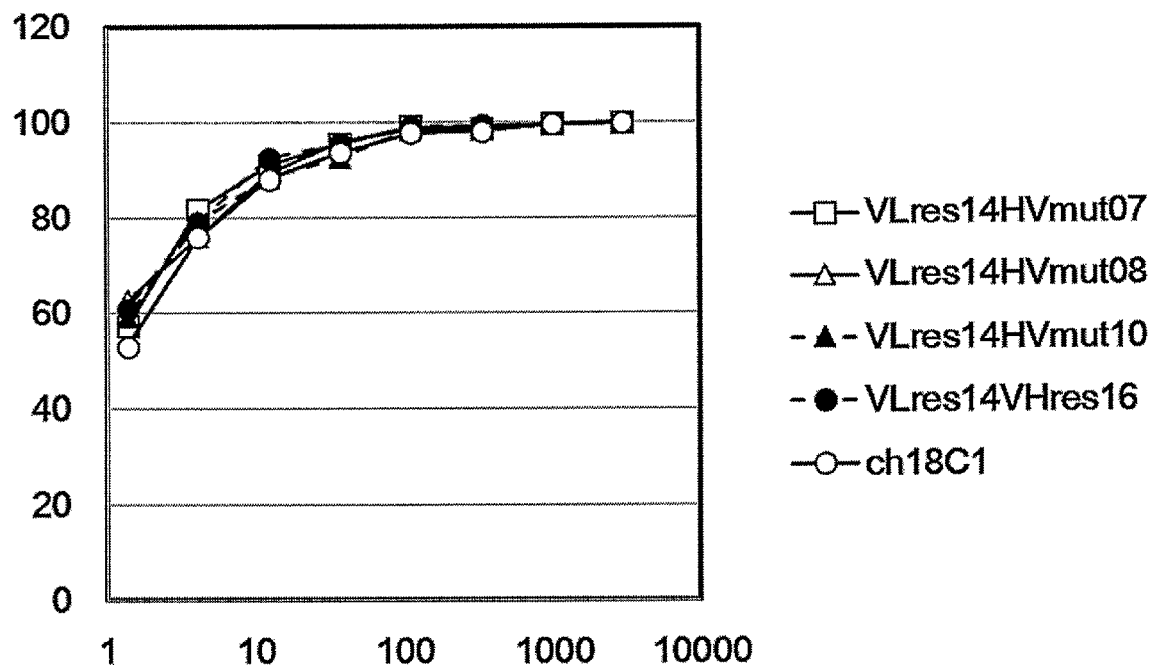

FIG. 24 is a graph comparing the BMP10 neutralizing activity of anti-BMP10 humanized antibodies with that of 18C1 chimeric antibody using ALK1/Id1-Luc/CHO cells. The horizontal axis represents the added concentration of the antibodies (ng/mL), and the vertical axis represents the neutralizing activity (%). White squares indicate VLres14HVmut07, white triangles indicate VLres14HVmut08, black triangles indicate a VLres14HVmut10 antibody, black circles indicate a VLres14VHres16 antibody, and white circles indicate ch18C1 antibody. The black circles and the black triangles are indicated by broken lines.

Figure 25:
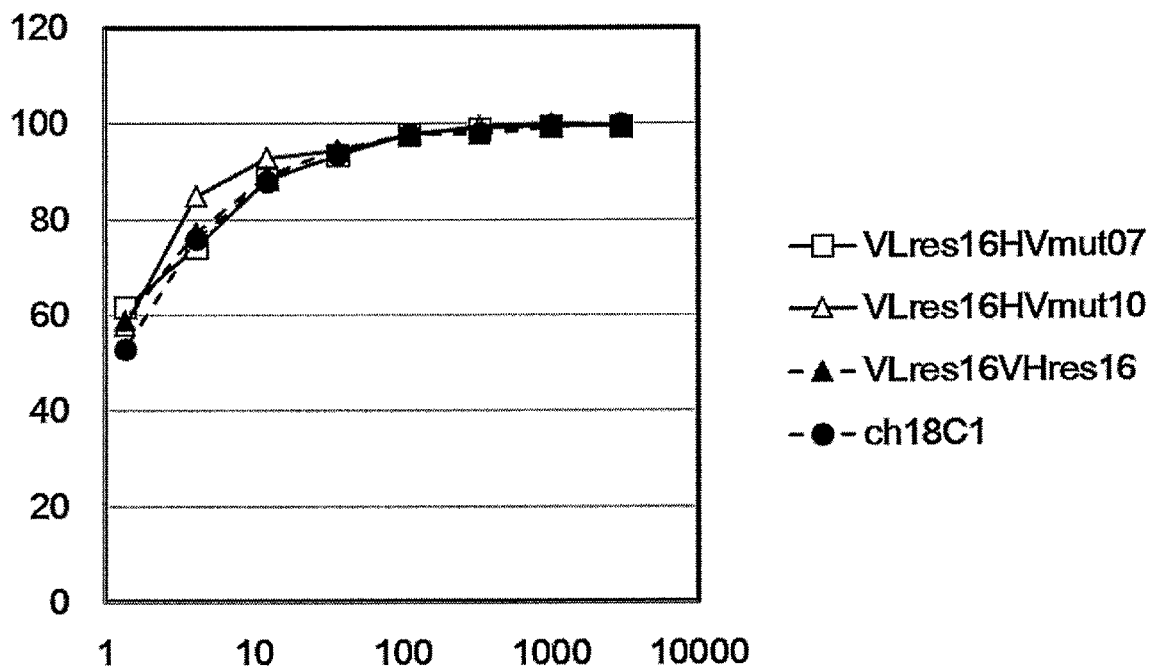

FIG. 25 is a graph comparing the BMP10 neutralizing activity of anti-BMP10 humanized antibodies with that of 18C1 chimeric antibody using ALK1/Id1-Luc/CHO cells. The horizontal axis represents the added concentration of the antibodies (ng/mL), and the vertical axis represents the neutralizing activity (%). White squares indicate VLres16HVmut07, white triangles indicate VLres16HVmut10, black triangles indicate a VLres16VHres16 antibody, and black circles indicate ch18C1 antibody. The black circles and the black triangles are indicated by broken lines.

Figure 26:
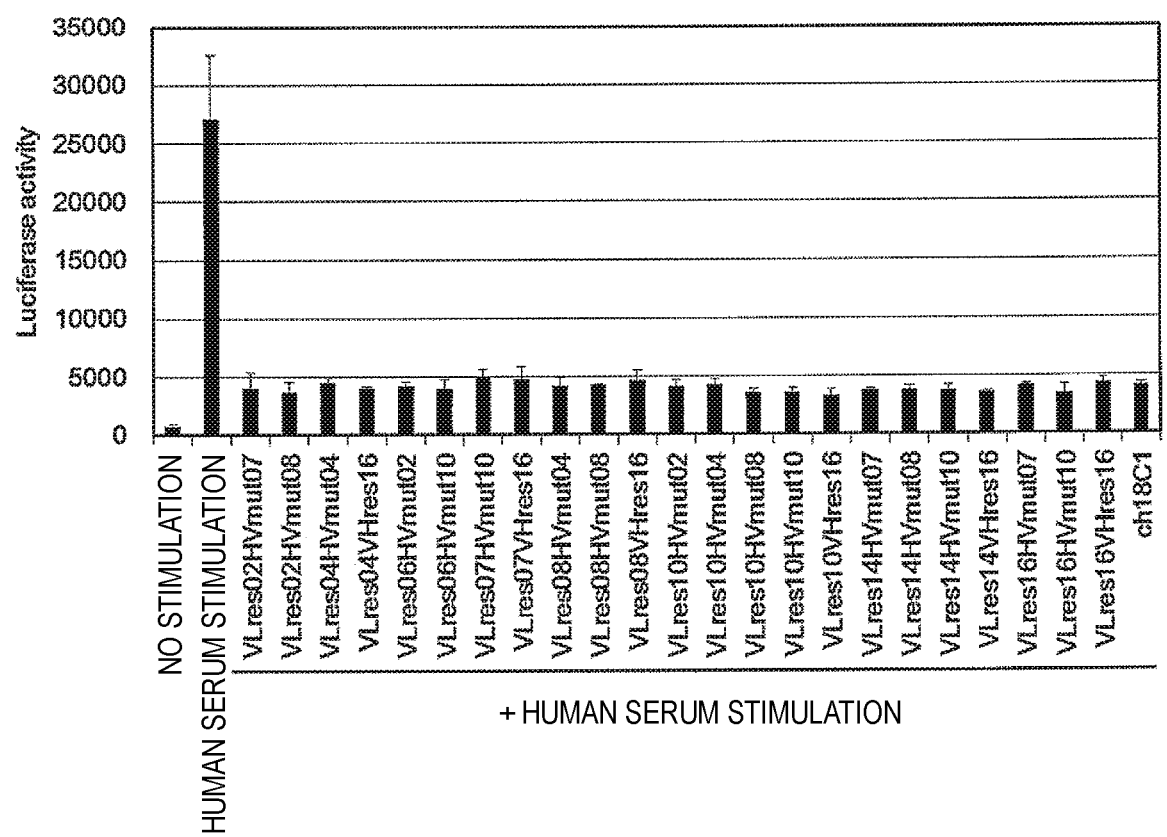

FIG. 26 is a graph comparing the neutralizing activity of anti-BMP10 humanized antibodies against a BMP9/BMP10 heterodimer in human blood with that of 18C1 chimeric antibody using ALK1/Id1-Luc/CHO cells. The vertical axis represents the luciferase activity.

FIG. 27A and FIG. 27B are each a figure showing an effect on the systemic blood pressure of normal rats by single administration of an anti-BMP9 antibody or a mixed solution of an anti-BMP9 antibody and an anti-BMP10 antibody. FIG. 27A shows a change in systolic blood pressure by single administration of 10D5 antibody. FIG. 27B shows a change in systolic blood pressure by single administration of a mixed solution of 10D5 antibody and 11H10 antibody. White circles indicate a change on the day of administration of a vehicle (PBS), white triangles indicate a change on the day of administration of the antibody, black squares indicate a change one day after administration of the antibody, and black triangles indicate a change two days after administration of the antibody. The black squares and the black triangles are indicated by broken lines. The horizontal axis of the graph represents the elapsed time when the time at which the drug solution was administered was set as 0 hour, and the vertical axis represents the systolic blood pressure (mmHg).

Figure 28:
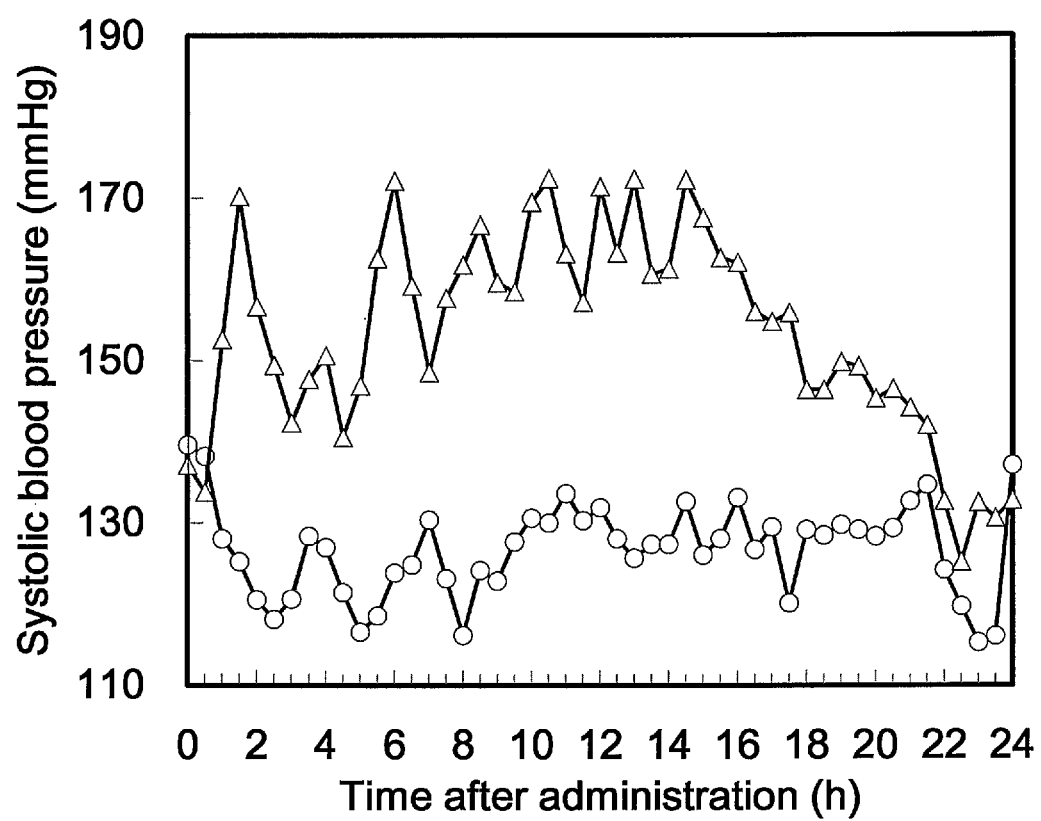

FIG. 28 is a figure showing the effect on the systemic blood pressure of normal rats by single administration of a human BMP10 recombinant protein. White circles indicate a change on the day of administration of a vehicle (PBS), white triangles indicate a change on the day of administration of the human BMP10 recombinant protein, the horizontal axis of the graph represents the elapsed time when the time at which the drug solution was administered was set as 0 hour, and the vertical axis represents the systolic blood pressure (mmHg).

DESCRIPTION OF EMBODIMENTS

The present invention relates to a monoclonal antibody that binds to human BMP10. Further, the present invention relates to a monoclonal antibody that binds to a BMP9/BMP10 heterodimer.

In the present invention, an antibody that binds to human BMP10 while competing with the monoclonal antibody of the present invention refers to an antibody that inhibits the binding of the monoclonal antibody of the present invention to human BMP10 in a desired binding assay system.

An antibody that binds to the same epitope as the epitope to which the monoclonal antibody of the present invention binds refers to an antibody that recognizes and binds to the same sequence as the amino acid sequence of human BMP10 that is recognized by the monoclonal antibody of the present invention.

The human BMP10 is synthesized as a single-chain precursor protein (Pre-Pro protein) having an amino acid sequence represented by SEQ ID NO: 47. This single-chain Pre-Pro protein forms a dimer (a Pro dimer or a full-length protein dimer) through a disulfide bond between cysteine residues present at position 388 after forming a full-length protein by cleaving off, from the amino acid sequence represented by SEQ ID NO: 2, a signal peptide region which is from position 1 to position 21 of it.

Thereafter, by a furin-like protease, cleavage occurs between amino acid residues at positions 316 and 317 of the amino acid sequence represented by SEQ ID NO: 47, and it is divided into a propeptide region of an N-terminal side fragment (a peptide comprising an amino acid sequence from an amino acid at position 22 to an amino acid at position 316 of the amino acid sequence represented by SEQ ID NO: 47, also referred to as an N-terminal propeptide protein) and a C-terminal side fragment (also referred to as a mature region or a mature protein) composed of an amino acid sequence represented by SEQ ID NO: 48.

The mature region forms a dimer (hereinafter referred to as a mature dimer) through a disulfide bond between cysteine residues remaining at position 72 of the amino acid sequence represented by SEQ ID NO: 48 even after cleavage of the propeptide region. Two molecules of the cleaved N-terminal side propeptide region form a complex with one molecule of this mature dimer through a non-covalent bond, and are secreted from a cell in the form of the complex. Both the mature dimer and the complex in which the N-terminal propeptide region is bound to the mature dimer have the function of BMP10.

Therefore, as the human BMP10 in the present invention, a polypeptide that comprises an amino acid sequence (SEQ ID NO: 48) which is from position 317 to position 424 of the amino acid sequence represented by SEQ ID NO: 47 or GenBank Accession No. NP_055297, corresponding to the mature region, and has the function of human BMP10 is mentioned.

Further, as the human BMP10 in the present invention, a polypeptide that comprises an amino acid sequence in which one or more amino acids are deleted, substituted, or added in the amino acid sequence represented by SEQ ID NO: 48 and has the function of human BMP10 is mentioned. In addition, as the human BMP10 in the present invention, a polypeptide that comprises an amino acid sequence having 60% or more, preferably 80% or more, more preferably 90% or more, and most preferably 95% or more homology with the amino acid sequence represented by SEQ ID NO: 48, and has the function of human BMP10 is mentioned. Further, as the human BMP10 in the present invention, the mature dimer and the complex in which the N-terminal propeptide region is bound to the mature dimer described above are also included.

The human BMP9 is synthesized as a single-chain precursor protein (Pre-Pro protein) having an amino acid sequence represented by SEQ ID NO: 66. This single-chain Pre-Pro protein forms a dimer (a Pro dimer) through a disulfide bond between cysteine residues present at position 392 after cleaving off, from the amino acid sequence represented by SEQ ID NO: 66, a signal peptide region which is from position 1 to position 22 of it.

Thereafter, by a furin-like protease, cleavage occurs between amino acid residues at positions 319 and 320 of the amino acid sequence represented by SEQ ID NO: 66, and it is divided into a propeptide region of an N-terminal side fragment (a peptide comprising an amino acid sequence from an amino acid at position 23 to an amino acid at position 319 of the amino acid sequence represented by SEQ ID NO: 66) and a C-terminal side fragment (a mature region) composed of an amino acid sequence represented by SEQ ID NO: 65.

The mature region forms a dimer (hereinafter referred to as a mature dimer) through a disulfide bond between cysteine residues remaining at position 73 of an amino acid sequence represented by SEQ ID NO: 65 even after cleavage of the propeptide region. Two molecules of the cleaved N-terminal side propeptide region form a complex with one molecule of this mature dimer through a non-covalent bond, and are secreted from a cell in the form of the complex [J. Biol. Chem., 280, 26, 25111 (2005)]. Both the mature dimer and the complex in which the N-terminal propeptide region is bound to the mature dimer have the function of BMP9.

Therefore, as the human BMP9 in the present invention, a polypeptide that contains an amino acid sequence (SEQ ID NO: 65) which is from position 320 to position 429 of the amino acid sequence represented by SEQ ID NO: 66 or GenBank Accession No. NP_057288, corresponding to the mature region, and has the function of human BMP9 is mentioned.

Further, as the human BMP9 in the present invention, a polypeptide that comprises an amino acid sequence in which one or more amino acids are deleted, substituted, or added in the amino acid sequence represented by SEQ ID NO: 65 and has the function of human BMP9 is mentioned.

In addition, as the human BMP9 in the present invention, a polypeptide that comprises an amino acid sequence having 60% or more, preferably 80% or more, more preferably 90% or more, and most preferably 95% or more homology with the amino acid sequence represented by SEQ ID NO: 65, and has the function of human BMP9 is mentioned. Further, as the human BMP9 in the present invention, the mature dimer and the complex in which the N-terminal propeptide region is bound to the mature dimer described above are also included.

The above-mentioned BMP forms not only a dimer of the same protein (hereinafter referred to as a homodimer), but also a dimer of different proteins belonging to the BMP family (hereinafter referred to as a heterodimer). The heterodimer composed of BMP9 and BMP10 (also referred to as a BMP9/BMP10 heterodimer) in the present invention comprises both the amino acid sequence corresponding to the BMP10 mature region represented by SEQ ID NO: 48 and the amino acid sequence corresponding to the BMP9 mature region represented by SEQ ID NO: 65.

Further, in the BMP9/BMP10 heterodimer in the present invention, a polypeptide that comprises an amino acid sequence in which one or more amino acids are deleted, substituted, or added in at least one of the amino acid sequence represented by SEQ ID NO: 48 and the amino acid sequence represented by SEQ ID NO: 65 and has the function of a human BMP9/BMP10 heterodimer is also included. In addition, in the BMP9/BMP10 heterodimer in the present invention, a polypeptide that comprises an amino acid sequence having 60% or more, preferably 80% or more, more preferably 90% or more, and most preferably 95% or more homology with at least one of the amino acid sequence represented by SEQ ID NO: 48 and the amino acid sequence represented by SEQ ID NO: 65, and has the function of the human BMP9/BMP10 heterodimer is also included. Further, as the BMP9/BMP10 heterodimer in the present invention, a complex in which an N-terminal propeptide region is bound to the human BMP9/BMP10 heterodimer is also included.

As the function of the above-mentioned BMP10, involvement of BMP10 in the intracellular signal transduction is mentioned. In the intracellular signal transduction, BMP10 binds to two receptors of type I and type II belonging to the TGFβ superfamily so as to activate the receptors, followed by Smad1/5/8 phosphorylation, and further, the Smad1/5/8 activated by phosphorylation forms a complex with Smad4, and thereafter, the complex translocates into the nucleus and functions as a transcription factor.

As the function of the above-mentioned BMP9, involvement of BMP9 in the intracellular signal transduction is mentioned. In the intracellular signal transduction, BMP9 binds to two receptors of type I and type II belonging to the TGFβ superfamily so as to activate the receptors, followed by Smad1/5/8 phosphorylation, and further, the Smad1/5/8 activated by phosphorylation forms a complex with Smad4, and thereafter, the complex translocates into the nucleus and functions as a transcription factor.

Examples of the type I receptor include ALK1, ALK2, ALK3, and ALK6. Further, examples of the type II receptor include a BMP type II receptor (BMPRII), an activin type IIa receptor (ActRIIa), and an activin type IIb receptor (ActRIIb). In addition, as a receptor other than type I and type II, endoglin is exemplified.

As a method for obtaining the polypeptide having an amino acid sequence in which one or more amino acids are deleted, substituted, or added in at least one of the amino acid sequence represented by SEQ ID NO: 48 and the amino acid sequence represented by SEQ ID NO: 65, for example, a method for introducing a site-specific mutation into a gene encoding the polypeptide having the amino acid sequence represented by SEQ ID NO: 48 or SEQ ID NO: 65 using a site-specific mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Proc. Natl. Acad. Sci. USA, 82, 488 (1985)], or the like is exemplified.

The number of amino acids to be deleted, substituted, or added is not particularly limited, but is preferably one to several tens, for example, 1 to 20, and more preferably one to several, for example, 1 to 5 amino acids.

As a gene encoding human BMP10, a base sequence represented by SEQ ID NO: 49 or GenBank Accession No. NM_014482 is exemplified. A gene that is composed of a nucleotide sequence in which one or more nucleotides are deleted, substituted, or added in a nucleotide sequence represented by SEQ ID NO: 50 corresponding to a mature region therein, and contains a DNA encoding a polypeptide having the function of human BMP10 is also included in the gene encoding human BMP10 of the present invention. Further, a gene that is composed of a nucleotide sequence having at least 60% or more, preferably 80% or more, and further more preferably 95% or more homology with the nucleotide sequence represented by SEQ ID NO: 50, and contains a DNA encoding a polypeptide having the function of human BMP10 is also included in the gene encoding human BMP10 of the present invention. In addition, a gene that is composed of a DNA which hybridizes with a DNA having the nucleotide sequence represented by SEQ ID NO: 50 under stringent conditions, and that contains a DNA encoding a polypeptide having the function of human BMP10, and the like are also included in the gene encoding human BMP10 of the present invention.

The DNA which hybridizes under stringent conditions means, for example, a hybridizable DNA that is obtained by a colony hybridization method, a plaque hybridization method, a southern blot hybridization method, a DNA microarray method, or the like using a DNA having the nucleotide sequence represented by SEQ ID NO: 50 as a probe.

Specifically, a DNA that can be identified by washing a filter or a microscope slide under the condition of 65° C. using an SSC solution having a concentration of 0.1 to 2 times (a composition of the SSC solution having a concentration of 1 time is composed of 150 mmol/L sodium chloride and 15 mmol/L sodium citrate), after performing hybridization [Molecular Cloning, A Laboratory Manual, Second Edition, Cold Spring Harbor Laboratory Press (1989), Current Protocols in Molecular Biology, John Wiley & Sons (1987-1997), DNA Cloning 1: Core Techniques, A Practical Approach, Second Edition, Oxford University (1995)] at 65° C. in the presence of 0.7 to 1.0 mol/L sodium chloride using a filter or a microscope slide on which a DNA derived from a hybridized colony or plaque, or a PCR product or an oligo DNA having the sequence is immobilized can be exemplified.

As the hybridizable DNA, a DNA having at least 60% or more homology, more preferably a DNA having 80% or more homology, and further more preferably a DNA having 95% or more homology with the nucleotide sequence represented by SEQ ID NO: 50 can be exemplified.

A gene polymorphism is often recognized in a nucleotide sequence of a gene encoding a protein of a eukaryote. A gene in which a small-scale mutation has occurred in a nucleotide sequence due to such a polymorphism in a gene used in the present invention is also included in the gene encoding the human BMP10 of the present invention.

The value of homology in the present invention may be a value calculated using a homology search program known to those skilled in the art unless otherwise particularly specified, however, with respect to a nucleotide sequence, a value calculated using a default parameter in BLAST [J. Mol. Biol., 215, 403 (1990)], and the like are exemplified, and with respect to an amino acid sequence, a value calculated using a default parameter in BLAST2 [Nucleic Acids Res., 25, 3389 (1997), Genome Res., 7, 649 (1997), http://www.ncbi.nlm.nih.gov/Education/BLASTinfo/information3.html], and the like are exemplified.

As for the default parameters, G (Cost to open gap) is 5 in the case of a nucleotide sequence and 11 in the case of an amino acid sequence, -E (Cost to extend gap) is 2 in the case of a nucleotide sequence and 1 in the case of an amino acid sequence, -q (Penalty for nucleotide mismatch) is -3, -r (reward for nucleotide match) is 1, -e (expect value) is 10, -W (wordsize) is 11 residues in the case of a nucleotide sequence and 3 residues in the case of an amino acid sequence, -y [Dropoff (X) for blast extensions in bits] is 20 in the case of blastn and 7 in the case of programs other than blastn, -X (X dropoff value for gapped alignment in bits) is 15, and Z (final X dropoff value for gapped alignment in bits) is 50 in the case of blastn and 25 in the case of programs other than blastn (http://www.ncbi.nlm.nih.gov/blast/html/blastcgihelp.html).

A polypeptide composed of a partial sequence of the amino acid sequence represented by SEQ ID NO: 47 or GenBank accession No. NP_055297 can be produced by a method known to those skilled in the art, and can be produced by, for example, deleting part of the DNA encoding the amino acid sequence represented by SEQ ID NO: 47 and culturing a transformant transfected with an expression vector comprising the resulting DNA.

In addition, a polypeptide having an amino acid sequence in which one or more amino acids are deleted, substituted, or added in the partial sequence of the amino acid sequence represented by SEQ ID NO: 47 or GenBank accession No. NP_055297 can be obtained by the same method as described above based on the polypeptide or the DNA produced by the above-mentioned method.

Further, a polypeptide composed of the partial sequence of the amino acid sequence represented by SEQ ID NO: 47 or GenBank accession No. NP_055297, or a polypeptide having an amino acid sequence in which one or more amino acids are deleted, substituted, or added in the partial sequence of the amino acid sequence represented by SEQ ID NO: 47 or GenBank accession No. NP_055297 can also be produced by a chemical synthesis method such as a fluorenylmethyloxycarbonyl (Fmoc) method or a t-butyloxycarbonyl (tBoc) method.

With respect also to the BMP9, a polypeptide having an amino acid sequence in which one or more amino acids are deleted, substituted, or added can be produced by the above-mentioned method or a known method such as a method described in JP-A-2017-25011.

The antagonist of the present invention refers to a substance that inhibits the activation of a receptor by inhibiting the binding of a ligand to its receptor protein.

The BMP10 antagonist of the present invention refers to a substance that inhibits the activation of its receptor by inhibiting the binding of at least one of BMP10 and a BMP9/BMP10 heterodimer to their receptor protein. Further, the BMP10 antagonist of the present invention refers to a substance that has a neutralizing activity against at least one of BMP10 and a BMP9/BMP10 heterodimer. The BMP10 antagonist of the present invention includes the anti-BMP10 monoclonal antibody or the antibody fragment thereof of the present invention.

The BMP9 antagonist of the present invention refers to a substance that inhibits the activation of its receptor by inhibiting the binding of BMP9 to its receptor protein. Further, the BMP9 antagonist of the present invention refers to a substance that has a neutralizing activity against BMP9. As the BMP9 antagonist of the invention, for example, an anti-BMP9 antibody is exemplified.

One aspect of the anti-BMP10 monoclonal antibody of the present invention (hereinafter also referred to as the antibody of the present invention or the monoclonal antibody of the present invention) or an antibody fragment thereof is an antibody or an antibody fragment thereof that recognizes and binds to the amino acid sequence of human BMP10 or a conformation thereof. One aspect of the antibody or the antibody fragment thereof of the present invention is an antibody or an antibody fragment thereof that binds to the amino acid sequence of human BMP10 or a conformation thereof, inhibits the binding of BMP10 to BMPRII, inhibits the binding of BMP10 to endoglin, and does not inhibit the binding of BMP10 to ALK1. Further, one aspect of the antibody or the antibody fragment thereof of the present invention is an antibody or an antibody fragment thereof that recognizes and binds to the amino acid sequence of a human BMP9/BMP10 heterodimer or a conformation thereof. One aspect of the antibody or the antibody fragment thereof of the present invention is an antibody or an antibody fragment thereof that has a neutralizing activity against BMP10. One aspect of the antibody or the antibody fragment thereof of the present invention is an antibody or an antibody fragment thereof that has a neutralizing activity against a BMP9/BMP10 heterodimer.

The antibody or the antibody fragment thereof of the present invention may be anything as long as it has one or more of the characteristics described above, but an antibody or an antibody fragment thereof that has all the characteristics that it binds to BMP10, inhibits the binding of BMP10 to BMPRII and the binding of BMP10 to endoglin, does not inhibit the binding of BMP10 to ALK1, has a neutralizing activity against BMP10, binds to a BMP9/BMP10 heterodimer, and has a neutralizing activity against a BMP9/BMP10 heterodimer is most preferred.

Further, as one aspect of the monoclonal antibody or the antibody fragment thereof of the present invention, an antibody or an antibody fragment thereof that binds to human BMP10 while competing with the monoclonal antibody of the present invention is also included. Preferably, an antibody or an antibody fragment thereof that binds to human BMP10 while competing with the monoclonal antibody or the antibody fragment thereof of the present invention, and has a neutralizing activity against at least one of BMP10 and a BMP9/BMP10 heterodimer is also included.

Further, as one aspect of the monoclonal antibody or the antibody fragment thereof of the present invention, an antibody or an antibody fragment thereof that binds to the same epitope as the epitope to which the monoclonal antibody or the antibody fragment thereof of the present invention binds is also included. Preferably, an antibody or an antibody fragment thereof that binds to the same epitope as the epitope to which the monoclonal antibody or the antibody fragment thereof of the present invention binds, and has a neutralizing activity against at least one of BMP10 and a BMP9/BMP10 heterodimer is also included.

Examples of the amino acid sequence of the human BMP10 in the present invention include an amino acid sequence that contains two amino acid sequences of a human BMP10 mature region represented by SEQ ID NO: 48, and forms a disulfide bond between cysteine residues at position 72.

The conformation of the human BMP10 in the present invention may be any conformation as long as it has an equivalent conformation to a conformation that the human BMP10 comprising the amino acid sequence represented by SEQ ID NO: 47, GenBank accession No. NP_055297, or SEQ ID NO: 48 can take in a natural state. The conformation that the human BMP10 can take in a natural state refers to a natural conformation of the human BMP10.

Examples of the amino acid sequence of the human BMP9 in the present invention include an amino acid sequence that contains two amino acid sequences of a human BMP9 mature region represented by SEQ ID NO: 65, and forms a disulfide bond between cysteine residues at position 73.

The conformation of the human BMP9 in the present invention may be any conformation as long as it has an equivalent conformation to a conformation that the human BMP9 comprising the amino acid sequence represented by SEQ ID NO: 66, GenBank accession No. NP_057288, or SEQ ID NO: 65 can take in a natural state. The conformation that the human BMP9 can take in a natural state refers to a natural conformation of the human BMP9.

Examples of the amino acid sequence of the human BMP9/BMP10 heterodimer in the present invention include an amino acid sequence that contains one amino acid sequence of a human BMP10 mature region represented by SEQ ID NO: 48 and one amino acid sequence of a human BMP9 mature region represented by SEQ ID NO: 65, and forms a disulfide bond between cysteine residues.

The conformation of the human BMP9/BMP10 heterodimer in the present invention may be any conformation as long as it has an equivalent conformation to a conformation that the human BMP9/BMP10 heterodimer comprising two amino acid sequences: the amino acid sequence represented by SEQ ID NO: 47, GenBank accession No. NP_055297, or SEQ ID NO: 48; and the amino acid sequence represented by SEQ ID NO: 66, GenBank accession No. NP_057288, or SEQ ID NO: 65 can take in a natural state. The conformation that the human BMP9/BMP10 heterodimer can take in a natural state refers to a natural conformation of the human BMP9/BMP10 heterodimer.

As the BMPRII in the present invention, a polypeptide comprising an amino acid sequence from position 27 to position 150 corresponding to an extracellular domain of an amino acid sequence represented by SEQ ID NO: 51 or GenBank Accession No. NP_001195 is exemplified.

As the ALK1 in the present invention, a polypeptide comprising an amino acid sequence from position 22 to position 118 corresponding to an extracellular domain of an amino acid sequence represented by SEQ ID NO: 52 or GenBank Accession No. NP_000011 is exemplified.

As the endoglin in the present invention, a polypeptide comprising an amino acid sequence from position 27 to position 586 corresponding to an extracellular domain of an amino acid sequence represented by SEQ ID NO: 69 or GenBank Accession No. NP_001108225 is exemplified.

The ALK1 highly expressing cell in the present invention refers to a cell that expresses ALK1 more than usual. The ALK1 highly expressing cell also includes a human ALK1 expressing reporter cell and an ALK1/Id1-Luc/CHO cell described in the below-mentioned Example 3, 3-1).

As the antibody in the present invention, specifically, a monoclonal antibody and an antibody fragment thereof specified in the following (A) or (B) are exemplified.

(A) A monoclonal antibody that includes: a heavy chain comprising complementarity determining regions (hereinafter abbreviated as CDRs) 1 to 3 comprising amino acid sequences represented by SEQ ID NOS: 29 to 31, respectively; and a light chain comprising CDRs 1 to 3 comprising amino acid sequences represented by SEQ ID NOS: 32 to 34, respectively, and an antibody fragment thereof (B) A monoclonal antibody that includes: a heavy chain comprising complementarity determining regions (hereinafter abbreviated as CDRs) 1 and 3 comprising amino acid sequences represented by SEQ ID NOS: 29 and 31, respectively, and CDR2 comprising an amino acid sequence (SEQ ID NO: 99) in which serine at position 16 of the amino acid sequence represented by SEQ ID NO: 30 is substituted with aspartic acid; and a light chain comprising CDRs 1 to 3 comprising amino acid sequences represented by SEQ ID NOS: 32 to 34, respectively, and an antibody fragment thereof Further, as the monoclonal antibody or the antibody fragment thereof of the present invention, an antibody or an antibody fragment thereof that binds to human BMP10 while competing with the monoclonal antibody or the antibody fragment thereof can be exemplified.

Further, as the monoclonal antibody or the antibody fragment thereof of the present invention, a monoclonal antibody and an antibody fragment thereof that binds to the same epitope as the epitope present in human BMP10 to which the monoclonal antibody or the antibody fragment thereof binds can be exemplified.

The binding activity refers to, for example, that the antibody or the antibody fragment thereof of the present invention has an activity of binding to the amino acid sequence of human BMP10 or the conformation thereof.

The binding activity of the antibody of the present invention can be confirmed by for example, a known immunological detection method for human BMP10 or a tissue expressing human BMP10 such as an enzyme-linked immunosorbent assay (ELISA) using a solid-phase antigen, a method capable of examining the binding affinity between a specific antigen and an antibody to the specific antigen, or the like. Other than these, a method such as surface plasmon resonance using a Biacore system (manufactured by GE Healthcare, Inc.) or the like, and isothermal titration calorimetry using ITC (manufactured by DKSH Holding AG).

The binding dissociation constant (Kd value) of an antibody for an antigen can be determined by any method of ELISA, surface plasmon resonance, and isothermal titration calorimetry by performing a Scatchard plot or an analysis according to the package insert of each apparatus. Specifically, the Kd value can be calculated by performing an analysis according to a single cycle kinetics calculation method (BIAevaluation Software ver. 3, manufactured by GE Healthcare, Inc.) from a sensorgram measured using a Biacore system (manufactured by GE Healthcare, Inc.).

The neutralizing activity against BMP10 of the present invention means, for example, that an antibody or an antibody fragment thereof bound to human BMP10 inhibits the binding of human BMP10 to a receptor so as to inhibit the activation of the receptor. The neutralizing activity can be measured by, for example, a method using human BMP10 receptor expressing cells, a method capable of examining the inhibition of an antibody for binding of human BMP10 to a receptor protein, or the like.

The neutralizing activity against a human BMP9/BMP10 heterodimer of the present invention means, for example, that an antibody or an antibody fragment thereof binding to a human BMP9/BMP10 heterodimer inhibits the binding of the human BMP9/BMP10 heterodimer to its receptor so as to inhibit the activation of the receptor.

As a method for neutralizing a human BMP9/BMP10 heterodimer, for example, a method in which an antibody or an antibody fragment thereof that binds to human BMP9 and an antibody or an antibody fragment thereof that binds to human BMP10 are mixed, and the binding of a human BMP9/BMP10 heterodimer to its receptor is inhibited so as to inhibit the activation of the receptor is exemplified. Further, a method in which by using an antibody that binds to human BMP10 and inhibits the binding of a human BMP9/BMP10 heterodimer to its receptor, the activation of the receptor is inhibited is also exemplified.

As a measurement method for the neutralizing activity, for example, it can be confirmed by a method using human BMP9/BMP10 heterodimer receptor expressing cells, a method capable of examining the inhibition of an antibody for the binding of the human BMP9/BMP10 heterodimer to a receptor protein, or the like.

As the measurement method for the neutralizing activity using human BMP10 receptor expressing cells or human BMP9/BMP10 heterodimer receptor expressing cells, for example, a method such as a reporter assay for detecting the activation of a transcription factor using an enzyme such as luciferase is exemplified.

As a method for examining the inhibition of an antibody for the binding of human BMP10 to a receptor protein or a human BMP9/BMP10 heterodimer to a receptor protein, for example, a method such as surface plasmon resonance using a Biacore system (manufactured by GE Healthcare, Inc.) or the like or an enzyme-linked immunosorbent assay (ELISA) is exemplified.

The binding of the antibody or the antibody fragment thereof of the present invention to the amino acid sequence of human BMP10 or the conformation thereof can be confirmed by a known immunological detection method for human BMP10 or a tissue expressing human BMP10 such as an enzyme-linked immunosorbent assay (ELISA) using a solid-phase antigen, a method capable of examining the binding affinity between a specific antigen and an antibody to the specific antigen, or the like.

Further, it can also be confirmed using known immunological detection methods [Monoclonal Antibodies-Principles and practice, Third edition, Academic Press (1996), Antibodies-A Laboratory Manual, Cold Spring Harbor Laboratory (1988), Monoclonal Antibody Experimental Manual, Kodansha Scientific books (1987)] and the like in combination.

The tissue expressing human BMP10 may be any tissue as long as it expresses the BMP10, and for example, blood, heart, liver, and the like are exemplified.

As the monoclonal antibody of the present invention, an antibody produced by a hybridoma or a genetically recombinant antibody produced by a transformant transformed with an expression vector comprising an antibody gene can be exemplified.

The monoclonal antibody is an antibody that is secreted by antibody-producing cells of a single clone, and has characteristics that it recognizes only one epitope (also referred to as an antigenic determinant), and amino acid sequences (primary structures) constituting the monoclonal antibodies are uniform.

As the epitope, for example, a single amino acid sequence, a conformation composed of an amino acid sequence, an amino acid sequence to which a sugar chain is bound, a conformation composed of an amino acid sequence to which a sugar chain is bound, and the like, each of which a monoclonal antibody recognizes and binds to, are exemplified.

The monoclonal antibody of the present invention binds to the amino acid sequence of human BMP10.

The epitope to which the monoclonal antibody of the present invention binds is included in the amino acid sequence of human BMP10 represented by SEQ ID NO: 47, and more preferably included in the amino acid sequence represented by SEQ ID NO: 48.

In the present invention, a bispecific antibody refers to an antibody having two types of antigen-binding domains with different specificities. Each of the antigen-binding domains of the bispecific antibody may bind to different epitopes of a single antigen or may bind to different antigens.

In a single molecule of a bispecific antibody, one or more antigen-binding domains bind to each of different epitopes of a single antigen or different antigens, that is, each binds in a monovalent or higher valent manner. For example, in the present invention, when a single molecule of a bispecific antibody has one antigen-binding domain that binds to BMP10 and one antigen-binding domain that binds to BMP9, such a bispecific antibody binds to each of BMP10 and BMP9 in a monovalent manner.

The antibody of the present invention also includes the bispecific antibody that binds to BMP9 and BMP10.

The hybridoma can be prepared by, for example, preparing the above-mentioned human BMP10 as an antigen, inducing antibody-producing cells having antigen specificity from an animal immunized with the antigen, and further fusing the antibody-producing cells with myeloma cells. The hybridoma is cultured, or the hybridoma cells are administered to an animal to induce an ascites tumor in the animal, and the culture solution or the ascites is separated and purified, whereby an anti-BMP10 monoclonal antibody can be obtained.

As the animal to be immunized with the antigen, any animal can be used as long as it can produce a hybridoma, however, a mouse, a rat, a hamster, a domestic fowl, a rabbit, or the like is preferably used. In addition, an antibody produced by a hybridoma prepared by obtaining cells having an antibody-producing ability from such an animal, subjecting the cells to in vitro immunization, and then fusing the cells with myeloma cells, and the like are also included in the antibody of the present invention.

The genetically recombinant antibody in the present invention includes antibodies produced by gene recombination such as a human chimeric antibody, a humanized antibody, a human antibody, or an antibody fragment are also included. In the genetically recombinant antibodies, an antibody having the characteristics of a monoclonal antibody, low antigenicity, and an extended blood half-life is preferred as a therapeutic agent. Examples of the genetically recombinant antibody include antibodies obtained by altering the above-mentioned monoclonal antibody of the present invention using a gene recombinant technique.

The human chimeric antibody refers to an antibody composed of a heavy chain variable region (also referred to as VH) and a light chain variable region (also referred to as VL) of an antibody of an animal other than a human, and a heavy chain constant region (also referred to as CH) and a light chain constant region (also referred to as CL) of a human antibody. The human chimeric antibody of the present invention can be produced by obtaining cDNAs encoding VH and VL from the above-mentioned hybridoma, inserting each of the cDNAs into an expression vector for an animal cell having genes encoding CH and CL of a human antibody, thereby constructing a human chimeric antibody expression vector, and then introducing the vector into an animal cell to cause expression.

The CH of the human chimeric antibody may be any as long as it belongs to a human immunoglobulin (hereinafter referred to as hIg), but preferably those of the hIgG class are used, and further, any one of the subclasses belonging to the hIgG class, such as hIgG1, hIgG2, hIgG3, or hIgG4, or a variant thereof can be used. As the variant, for example, a heavy chain constant region of an IgG4 mutant obtained by substituting a Ser residue at position 228 according to the EU-index in the heavy chain constant region of hIgG4 with Pro, a Leu residue at position 235 therein with Glu, and an Arg residue at position 409 therein with Lys (hereinafter referred to as IgG4PE R409K) can be used. Further, the CL of the human chimeric antibody may be any as long as it belongs to hIg, and those of κ class or λ class can be used.

As the human chimeric antibody of the present invention, specifically, a chimeric antibody that comprises VH of an antibody comprising an amino acid sequence represented by SEQ ID NO: 23 and comprises VL of an antibody comprising an amino acid sequence represented by SEQ ID NO: 26 is exemplified. Further, a chimeric antibody that comprises VH of an antibody comprising an amino acid sequence represented by SEQ ID NO: 24 and comprises VL of an antibody comprising an amino acid sequence represented by SEQ ID NO: 27 is exemplified. Further, a chimeric antibody that comprises VH of an antibody comprising an amino acid sequence represented by SEQ ID NO: 25 and comprises VL of an antibody comprising an amino acid sequence represented by SEQ ID NO: 28 is exemplified.

As the humanized antibody, a human CDR-grafted antibody or a humanized antibody by a surface reconstruction method is exemplified. Further, an antibody produced by a method in combination with a method for producing such a humanized antibody is also included in the humanized antibody of the present invention. Further, an antibody that has an amino acid sequence in which one or more amino acids are deleted, substituted, or added in an amino acid sequence of a humanized antibody designed by such a method, and specifically recognizes human BMP10 and/or a BMP9/BMP10 heterodimer is also included in the humanized antibody of the present invention.

The human CDR-grafted antibody refers to an antibody in which the amino acid sequences of CDRs of VH and VL of an antibody of an animal other than a human are grafted into appropriate positions of VH and VL of a human antibody. The human CDR-grafted antibody of the present invention can be produced as follows. That is, cDNAs encoding V regions, in which the amino acid sequences of CDRs of VH and VL of a monoclonal antibody of an animal other than a human that specifically recognizes human BMP10 and/or a BMP9/BMP10 heterodimer, and binds to the amino acid sequence of the human BMP10 and/or the BMP9/BMP10 heterodimer or the conformation thereof are grafted into the framework regions (hereinafter referred to as FRs) of VH and VL of an arbitrary human antibody are constructed. Subsequently, each of the cDNAs is inserted into an expression vector for an animal cell having genes encoding CH and CL of a human antibody, thereby constructing a human CDR-grafted antibody expression vector, and then introducing the vector into an animal cell to cause expression.

The humanized antibody by a surface reconstruction method refers to an antibody in which an amino acid residue of FR that is considered not to affect the binding activity of an antibody of an animal other than a human among the amino acids of the variable region of the antibody is substituted with an amino acid residue considered to lower the antigenicity by a surface reconstruction method (Proc. Natl. Acad. Sci. USA, 1994, 91(3): 969-73, and Protein Engineering, 1996, 10, 895-90). The humanized antibody by a surface reconstruction method of the present invention can be produced as follows. That is, cDNAs encoding V regions, in which an arbitrary amino acid residue of FRs of VH and VL of a monoclonal antibody of an animal other than a human that specifically recognizes human BMP10 and/or a BMP9/BMP10 heterodimer, and binds to the amino acid sequence of the human BMP10 and/or the BMP9/BMP10 heterodimer or the conformation thereof is substituted with another amino acid residue are constructed. Subsequently, each of the cDNAs is inserted into an expression vector for an animal cell having genes encoding CH and CL of a human antibody, thereby constructing an expression vector for a humanized antibody by a surface reconstruction method, and then introducing the vector into an animal cell to cause expression.

The CH of the humanized antibody may be any as long as it belongs to hIg, but preferably those of the hIgG class are used, and further, any one of the subclasses belonging to the hIgG class, such as hIgG1, hIgG2, hIgG3, or hIgG4, or a variant thereof can be used. As the variant, for example, CH of IgG4PE R409K can be used. Further, the CL of the humanized antibody may be any as long as it belongs to hIg, and those of a class or X class can be used.

As the humanized antibody of the present invention, specifically, a humanized antibody that comprises: a heavy chain comprising complementarity determining regions (hereinafter abbreviated as CDRs) 1 and 3 comprising amino acid sequences represented by SEQ ID NOS: 29 and 31, respectively, and CDR2 comprising an amino acid sequence represented by SEQ ID NO: 30 or an amino acid sequence in which serine at position 16 of the amino acid sequence represented by SEQ ID NO: 30 is substituted with aspartic acid; and a light chain comprising CDRs 1 to 3 comprising amino acid sequences represented by SEQ ID NOS: 32 to 34, respectively, is exemplified.

As the humanized antibody of the present invention, specifically, a humanized antibody that comprises at least one of the following (a) VH and (b) VL is exemplified.

(a) VH of an antibody comprising an amino acid sequence represented by SEQ ID NO: 70 or an amino acid sequence in which at least one amino acid residue selected from Pro at position 14, Leu at position 20, Gly at position 27, Val at position 29, Ser at position 30, Ile at position 37, Ile at position 48, Val at position 67, Val at position 71, Asn at position 76, Phe at position 78, Leu at position 82, Val at position 85, Val at position 92, Tyr at position 94, and Thr at position 109 in the amino acid sequence represented by SEQ ID NO: 70 is substituted with another amino acid residue (b) VL of an antibody comprising an amino acid sequence represented by SEQ ID NO: 71 or an amino acid sequence in which at least one amino acid residue selected from Pro at position 7, Val at position 10, Glu at position 12, Pro at position 14, Lys at position 16, Thr at position 19, Ile at position 20, Pro at position 41, Val at position 48, Ser at position 75, Leu at position 81, Lys at position 82, Asp at position 88, and Tyr at position 90 in the amino acid sequence represented by SEQ ID NO: 71 is substituted with another amino acid residue The humanized antibody of the present invention also includes an antibody in which the amino acid sequences of CDRs of VH are subjected to substitution as specified in the following (A).

(A) the amino acid sequences of CDRs in which CDR1 of VH comprises an amino acid sequence represented by SEQ ID NO: 29 or an amino acid sequence in which an alteration of substituting Val at position 4 in the amino acid sequence represented by SEQ ID NO: 29 with Ala is introduced, CDR2 of VH comprises an amino acid sequence represented by SEQ ID NO: 30 or an amino acid sequence in which an alteration of substituting Ser at position 16 in the amino acid sequence represented by SEQ ID NO: 30 with Asp is introduced, and CDR3 of VH comprises an amino acid sequence represented by SEQ ID NO: 31

Further, the VH comprised in the humanized antibody of the present invention is preferably the following (1) to (14).

(1) VH comprising an amino acid sequence in which Pro at position 14, Leu at position 20, Gly at position 27, Val at position 29, Ser at position 30, Ile at position 37, Ile at position 48, Val at position 67, Val at position 71, Asn at position 76, Phe at position 78, Leu at position 82, Val at position 85, Val at position 92, Tyr at position 94, and Thr at position 109 in the amino acid sequence represented by SEQ ID NO: 70 are each substituted with another amino acid residue (2) VH comprising an amino acid sequence in which Leu at position 20, Gly at position 27, Val at position 29, Ser at position 30, Ile at position 37, Ile at position 48, Val at position 67, Val at position 71, Phe at position 78, Leu at position 82, Val at position 85, Tyr at position 94, and Thr at position 109 in the amino acid sequence represented by SEQ ID NO: 70 are each substituted with another amino acid residue (3) VH comprising an amino acid sequence in which Leu at position 20, Gly at position 27, Ser at position 30, Ile at position 48, Val at position 67, Val at position 71, Phe at position 78, Leu at position 82, Val at position 92, and Tyr at position 94 in the amino acid sequence represented by SEQ ID NO: 70 are each substituted with another amino acid residue (4) VH comprising an amino acid sequence in which Gly at position 27, Val at position 29, Ser at position 30, Ile at position 48, Val at position 67, Val at position 71, Val at position 92, and Tyr at position 94 in the amino acid sequence represented by SEQ ID NO: 70 are each substituted with another amino acid residue (5) VH comprising an amino acid sequence in which Leu at position 20, Gly at position 27, Ile at position 48, Val at position 71, Phe at position 78, Leu at position 82, and Val at position 92 in the amino acid sequence represented by SEQ ID NO: 70 are each substituted with another amino acid residue (6) VH comprising an amino acid sequence in which Gly at position 27, Ser at position 30, Ile at position 48, Val at position 67, Val at position 71, and Val at position 92 in the amino acid sequence represented by SEQ ID NO: 70 are each substituted with another amino acid residue (7) VH comprising an amino acid sequence in which Ile at position 48, Val at position 67, Val at position 71, Phe at position 78, and Val at position 92 in the amino acid sequence represented by SEQ ID NO: 70 are each substituted with another amino acid residue (8) VH comprising an amino acid sequence in which Gly at position 27, Val at position 71, Phe at position 78, and Val at position 92 in the amino acid sequence represented by SEQ ID NO: 70 are each substituted with another amino acid residue (9) VH comprising an amino acid sequence in which Gly at position 27, Ile at position 48, Val at position 67, and Val at position 92 in the amino acid sequence represented by SEQ ID NO: 70 are each substituted with another amino acid residue

(10) VH comprising an amino acid sequence in which Gly at position 27, Val at position 71, Val at position 92, and Tyr at position 94 in the amino acid sequence represented by SEQ ID NO: 70 are each substituted with another amino acid residue

(11) VH comprising an amino acid sequence in which Gly at position 27, Val at position 71, and Val at position 92 in the amino acid sequence represented by SEQ ID NO: 70 are each substituted with another amino acid residue

(12) VH comprising an amino acid sequence in which Val at position 71 and Val at position 92 in the amino acid sequence represented by SEQ ID NO: 70 are each substituted with another amino acid residue

(13) VH comprising the amino acid sequence represented by SEQ ID NO: 70

(14) VH comprising an amino acid sequence in which with respect to VH specified in the above (1) to (13), the amino acid sequences of the CDRs thereof are substituted with the amino acid sequences of the CDRs specified in the above (A)

As the amino acid sequence of the VH, for example, an amino acid sequence in which at least one alteration selected from alterations of substituting Pro at position 14 with Leu, Leu at position 20 with Ile, Gly at position 27 with Phe, Val at position 29 with Leu, Ser at position 30 with Thr, Val at position 34 with Ala, Ile at position 37 with Val, Ile at position 48 with Met, Ser at position 65 with Asp, Val at position 67 with Leu, Val at position 71 with Arg, Asn at position 76 with Ser, Phe at position 78 with Val, Leu at position 82 with Met, Val at position 85 with Leu, Val at position 92 with Lys, Tyr at position 94 with Phe, and Thr at position 109 with Ile is introduced in the amino acid sequence represented by SEQ ID NO: 70 is exemplified.

Further, the VL comprised in the humanized antibody of the present invention is preferably the following (1) to (15).

(1) VL comprising an amino acid sequence in which Pro at position 7, Val at position 10, Glu at position 12, Pro at position 14, Lys at position 16, Thr at position 19, Ile at position 20, Pro at position 41, Val at position 48, Ser at position 75, Leu at position 81, Lys at position 82, Asp at position 88, and Tyr at position 90 in the amino acid sequence represented by SEQ ID NO: 71 are each substituted with another amino acid residue (2) VL comprising an amino acid sequence in which Pro at position 7, Val at position 10, Glu at position 12, Pro at position 14, Thr at position 19, Ile at position 20, Pro at position 41, Val at position 48, Ser at position 75, and Asp at position 88 in the amino acid sequence represented by SEQ ID NO: 71 are each substituted with another amino acid residue (3) VL comprising an amino acid sequence in which Pro at position 7, Glu at position 12, Thr at position 19, Ile at position 20, Val at position 48, Ser at position 75, Leu at position 81, Asp at position 88, and Tyr at position 90 in the amino acid sequence represented by SEQ ID NO: 71 are each substituted with another amino acid residue (4) VL comprising an amino acid sequence in which Pro at position 7, Glu at position 12, Pro at position 14, Lys at position 16, Thr at position 19, Pro at position 41, Ser at position 75, and Asp at position 88 in the amino acid sequence represented by SEQ ID NO: 71 are each substituted with another amino acid residue (5) VL comprising an amino acid sequence in which Glu at position 12, Ile at position 20, Pro at position 41, Val at position 48, Ser at position 75, Asp at position 88, and Tyr at position 90 in the amino acid sequence represented by SEQ ID NO: 71 are each substituted with another amino acid residue (6) VL comprising an amino acid sequence in which Glu at position 12, Lys at position 16, Thr at position 19, Pro at position 41, Lys at position 82, and Asp at position 88 in the amino acid sequence represented by SEQ ID NO: 71 are each substituted with another amino acid residue (7) VL comprising an amino acid sequence in which Lys at position 16, Ile at position 20, Pro at position 41, Val at position 48, Asp at position 88, and Tyr at position 90 in the amino acid sequence represented by SEQ ID NO: 71 are each substituted with another amino acid residue (8) VL comprising an amino acid sequence in which Pro at position 14, Ile at position 20, Val at position 48, Ser at position 75, Leu at position 81, and Asp at position 88 in the amino acid sequence represented by SEQ ID NO: 71 are each substituted with another amino acid residue (9) VL comprising an amino acid sequence in which Glu at position 12, Pro at position 14, Ile at position 20, Val at position 48, Lys at position 82, and Tyr at position 90 in the amino acid sequence represented by SEQ ID NO: 71 are each substituted with another amino acid residue

(10) VL comprising an amino acid sequence in which Thr at position 19, Pro at position 41, Val at position 48, Asp at position 88, and Tyr at position 90 in the amino acid sequence represented by SEQ ID NO: 71 are each substituted with another amino acid residue

(11) VL comprising an amino acid sequence in which Glu at position 12, Pro at position 14, Pro at position 41, Ser at position 75, and Asp at position 88 in the amino acid sequence represented by SEQ ID NO: 71 are each substituted with another amino acid residue

(12) VL comprising an amino acid sequence in which Pro at position 41, Ser at position 75, Asp at position 88, and Tyr at position 90 in the amino acid sequence represented by SEQ ID NO: 71 are each substituted with another amino acid residue

(13) VL comprising an amino acid sequence in which Thr at position 19, Pro at position 41, Val at position 48, and Asp at position 88 in the amino acid sequence represented by SEQ ID NO: 71 are each substituted with another amino acid residue

(14) VL comprising an amino acid sequence in which Ile at position 20, Val at position 48, and Asp at position 88 in the amino acid sequence represented by SEQ ID NO: 71 are each substituted with another amino acid residue

(15) VL comprising the amino acid sequence represented by SEQ ID NO: 71

As the amino acid sequence of the VL, an amino acid sequence in which at least one alteration selected from alterations of substituting Pro at position 7 with Ser, Val at position 10 with Met, Glu at position 12 with Thr, Pro at position 14 with Leu, Lys at position 16 with Ser, Thr at position 19 with Lys, Ile at position 20 with Leu, Pro at position 41 with Glu or Arg, Val at position 48 with Met, Ser at position 75 with Phe, Leu at position 81 with Val, Lys at position 82 with Gln, Asp at position 88 with Ile, and Tyr at position 90 with Phe is introduced in the amino acid sequence represented by SEQ ID NO: 71 is exemplified.

Further, as the humanized antibody of the present invention, specifically, a humanized antibody that comprises VH specified in the following (a) or (c) and/or VL specified in (b) is exemplified.

(a) VH of an antibody comprising an amino acid sequence in which at least one amino acid residue selected from Leu at position 11, Leu at position 14, Ser at position 19, Phe at position 27, Ser at position 68, Arg at position 71, Gln at position 77, Phe at position 79, Asn at position 83, Leu at position 85, and His at position 107 in the amino acid sequence represented by SEQ ID NO: 23 is substituted with another amino acid residue (b) VL of an antibody comprising an amino acid sequence in which at least one amino acid residue selected from Val at position 3, Asn at position 8, Leu at position 14, Lys at position 19, Phe at position 75, Asn at position 80, Ile at position 83, and Ile at position 88 in the amino acid sequence represented by SEQ ID NO: 26 is substituted with another amino acid residue (c) VH of an antibody comprising an amino acid sequence in which at least one amino acid residue selected from Gly at position 10, Lys at position 13, Ser at position 19, Leu at position 20, Gly at position 27, Val at position 29, Ser at position 30, Ile at position 37, Ile at position 48, Val at position 67, Thr at position 68, Val at position 71, Gln at position 77, Phe at position 78, Ser at position 79, Leu at position 82, Ser at position 83, Val at position 85, Thr at position 86, Ala at position 87, Ala at position 88, Val at position 92, Tyr at position 94, and Thr at position 109 in the amino acid sequence represented by SEQ ID NO: 70 is substituted with another amino acid residue The humanized antibody also includes an antibody in which amino acids of CDRs of VH are substituted as follows.

VH of an antibody in which CDR1 of VH comprises an amino acid sequence represented by SEQ ID NO: 29 or an amino acid sequence in which an alteration of substituting Val at position 4 in the amino acid sequence represented by SEQ ID NO: 29 with Ala is introduced, CDR2 of VH comprises an amino acid sequence represented by SEQ ID NO: 30 or an amino acid sequence in which an alteration of substituting Ser at position 16 in the amino acid sequence represented by SEQ ID NO: 30 with Asp is introduced, and CDR3 of VH comprises an amino acid sequence represented by SEQ ID NO: 31

As the amino acid sequence of the VH, for example, an amino acid sequence in which at least one alteration selected from alterations of substituting Leu at position 11 with Ala, Leu at position 14 with Pro, Ser at position 19 with Asp, Phe at position 27 with Ala, Val at position 34 with Ala, Ser at position 65 with Asp, Ser at position 68 with Ala, Arg at position 71 with Lys, Gln at position 77 with Glu, Phe at position 79 with Ala, Asn at position 83 with Asp, Leu at position 85 with Asp, and His at position 107 with Gln is introduced in the amino acid sequence represented by SEQ ID NO: 23 is exemplified. Further, an amino acid sequence in which at least one alteration selected from alterations of substituting Gly at position 10 with Asp, Lys at position 13 with Gln, Ser at position 19 with Asp, Leu at position with Ile, Gly at position 27 with Phe, Val at position 29 with Leu, Ser at position 30 with Thr, Ile at position 37 with Val, Ile at position 48 with Met, Ser at position 65 with Asp, Val at position 67 with Leu, Thr at position 68 with Ala, Val at position 71 with Arg, Asn at position 76 with Ser, Gln at position 77 with Glu, Phe at position 78 with Val, Ser at position 79 with Phe, Leu at position 82 with Met, Ser at position 83 with Asp, Val at position 85 with Leu, Thr at position 86 with Gln, Ala at position 87 with Thr, Ala at position 88 with Asp, Val at position 92 with Lys, Tyr at position 94 with Phe, Thr at position 109 with Ile, and Leu at position 110 with Met is introduced in the amino acid sequence represented by SEQ ID NO: 70 is exemplified.

As the amino acid sequence of the VL, for example, an amino acid sequence in which at least one alteration selected from alterations of substituting Val at position 3 with Ala, Asn at position 8 with Asp, Leu at position 14 with Ala, Lys at position 19 with Thr, Phe at position 75 with Ser, Asn at position 80 with Asp, Ile at position 83 with Val, and Ile at position 88 with Val is introduced in the amino acid sequence represented by SEQ ID NO: 26 is exemplified.

As a specific example of the humanized antibody of the present invention, a humanized antibody that includes at least one of VH comprising any one of the amino acid sequences shown in FIG. 16, FIG. 17, and FIG. 19, and VL comprising any one of the amino acid sequences shown in FIG. 18A and FIG. 18B is exemplified.

Further, as a specific example of the humanized antibody of the present invention, a humanized antibody that comprises VL comprising any one amino acid sequence selected from SEQ ID NOS: 71 to 87 and/or VH comprising any one amino acid sequence selected from SEQ ID NOS: 70 and 88 to 98.

Further, as specific examples of the humanized antibody of the present invention, the following humanized antibodies (a) to (w) are exemplified.

(a) a humanized antibody comprising VH comprising an amino acid sequence represented by SEQ ID NO: 94 and VL comprising an amino acid sequence represented by SEQ ID NO: 73

(b) a humanized antibody comprising VH comprising an amino acid sequence represented by SEQ ID NO: 95 and VL comprising an amino acid sequence represented by SEQ ID NO: 73

(c) a humanized antibody comprising VH comprising an amino acid sequence represented by SEQ ID NO: 91 and VL comprising an amino acid sequence represented by SEQ ID NO: 75

(d) a humanized antibody comprising VH comprising an amino acid sequence represented by SEQ ID NO: 98 and VL comprising an amino acid sequence represented by SEQ ID NO: 75

(e) a humanized antibody comprising VH comprising an amino acid sequence represented by SEQ ID NO: 89 and VL comprising an amino acid sequence represented by SEQ ID NO: 77

(f) a humanized antibody comprising VH comprising an amino acid sequence represented by SEQ ID NO: 97 and VL comprising an amino acid sequence represented by SEQ ID NO: 77

(g) a humanized antibody comprising VH comprising an amino acid sequence represented by SEQ ID NO: 97 and VL comprising an amino acid sequence represented by SEQ ID NO: 78

(h) a humanized antibody comprising VH comprising an amino acid sequence represented by SEQ ID NO: 98 and VL comprising an amino acid sequence represented by SEQ ID NO: 78

(i) a humanized antibody comprising VH comprising an amino acid sequence represented by SEQ ID NO: 91 and VL comprising an amino acid sequence represented by SEQ ID NO: 79

(j) a humanized antibody comprising VH comprising an amino acid sequence represented by SEQ ID NO: 95 and VL comprising an amino acid sequence represented by SEQ ID NO: 79

(k) a humanized antibody comprising VH comprising an amino acid sequence represented by SEQ ID NO: 98 and VL comprising an amino acid sequence represented by SEQ ID NO: 79

(l) a humanized antibody comprising VH comprising an amino acid sequence represented by SEQ ID NO: 89 and VL comprising an amino acid sequence represented by SEQ ID NO: 81

(m) a humanized antibody comprising VH comprising an amino acid sequence represented by SEQ ID NO: 91 and VL comprising an amino acid sequence represented by SEQ ID NO: 81

(n) a humanized antibody comprising VH comprising an amino acid sequence represented by SEQ ID NO: 95 and VL comprising an amino acid sequence represented by SEQ ID NO: 81

(o) a humanized antibody comprising VH comprising an amino acid sequence represented by SEQ ID NO: 97 and VL comprising an amino acid sequence represented by SEQ ID NO: 81

(p) a humanized antibody comprising VH comprising an amino acid sequence represented by SEQ ID NO: 98 and VL comprising an amino acid sequence represented by SEQ ID NO: 81

(q) a humanized antibody comprising VH comprising an amino acid sequence represented by SEQ ID NO: 94 and VL comprising an amino acid sequence represented by SEQ ID NO: 85

(r) a humanized antibody comprising VH comprising an amino acid sequence represented by SEQ ID NO: 95 and VL comprising an amino acid sequence represented by SEQ ID NO: 85

(s) a humanized antibody comprising VH comprising an amino acid sequence represented by SEQ ID NO: 97 and VL comprising an amino acid sequence represented by SEQ ID NO: 85

(t) a humanized antibody comprising VH comprising an amino acid sequence represented by SEQ ID NO: 98 and VL comprising an amino acid sequence represented by SEQ ID NO: 85

(u) a humanized antibody comprising VH comprising an amino acid sequence represented by SEQ ID NO: 94 and VL comprising an amino acid sequence represented by SEQ ID NO: 87

(v) a humanized antibody comprising VH comprising an amino acid sequence represented by SEQ ID NO: 97 and VL comprising an amino acid sequence represented by SEQ ID NO: 87

(w) a humanized antibody comprising VH comprising an amino acid sequence represented by SEQ ID NO: 98 and VL comprising an amino acid sequence represented by SEQ ID NO: 87

The human antibody essentially refers to an antibody that is naturally present in the human body, but also includes antibodies that are obtained from a human antibody phage library and a human antibody-producing transgenic animal, each of which is produced due to the recent advancement of genetic engineering, cellular engineering, or developmental engineering technology, and the like.

As for the antibody that is naturally present in the human body, for example, human peripheral blood lymphocytes are isolated and infected with an EB virus or the like so as to immortalize the lymphocytes, followed by cloning, whereby a lymphocyte that produces the antibody can be cultured, and then the antibody can be purified from the culture supernatant.

The human antibody phage library is a library in which an antibody fragment such as a Fab or an scFv is expressed on the surfaces of phages by inserting an antibody gene prepared from a human B cell into a phage gene. It is possible to collect a phage that expresses an antibody fragment having a desired antigen-binding activity on the surface thereof from the library using a binding activity to a substrate onto which an antigen is immobilized as an index. The antibody fragment can further also be converted into a human antibody molecule composed of two complete H chains and two complete L chains using a genetic engineering technique.

The human antibody-producing transgenic animal means an animal in which a human antibody gene is incorporated into a cell. Specifically, for example, a human antibody-producing transgenic mouse can be produced by introducing a human antibody gene into a mouse ES cell, implanting the ES cell to an early embryo of a mouse and then allowing the embryo to develop. A human antibody from a human antibody-producing transgenic animal can be produced by obtaining a human antibody-producing hybridoma using a usual hybridoma production method that is performed for an animal other than a human, and culturing the hybridoma, thereby producing and accumulating the human antibody in the culture supernatant.

A monoclonal antibody or an antibody fragment thereof, in which one or more amino acids are deleted, added, substituted, or inserted in the amino acid sequence constituting the antibody or the antibody fragment described above, and which has the same activity as the antibody or the antibody fragment thereof described above is also included in the monoclonal antibody or the antibody fragment thereof of the present invention.

The number of amino acids to be deleted, substituted, inserted, and/or added is one or more, and is not particularly limited, and is a number such that deletion, substitution, insertion or addition can be carried out using a well-known technique such as a site-specific mutagenesis method [Molecular Cloning, 2nd Edition, Cold Spring Harbor Laboratory Press (1989), Current Protocols in Molecular Biology, John Willy & Sons (1987-1997), Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci. USA, 82, 488 (1985)]. For example, it is preferably one to several tens, more preferably 1 to 20, further more preferably 1 to 10, and particularly preferably 1 to 5.

The above description that one or more amino acid residues in the amino acid sequence of the antibody are deleted, substituted, inserted, or added indicates as follows. That is, the description means that there is a deletion, substitution, insertion, or addition of one or a plurality of amino acid residues in arbitrary one amino acid sequence or a plurality of amino acid sequences in the same sequence. Further, such a deletion, substitution, insertion, or addition may sometimes occur simultaneously, and the amino acid residues to be substituted, inserted, or added may be either a natural type or an unnatural type.

Examples of the natural amino acid residue include L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine, and the like.

Hereinafter, preferred examples of mutually substitutable amino acid residues are shown. Amino acid residues included in the same group can be mutually substituted.

group A: leucine, isoleucine, norleucine, valine, norvaline, alanine, 2-aminobutanoic acid, methionine, O-methylserine, t-butyl glycine, t-butyl alanine, and cyclohexylalanine group B: aspartic acid, glutamic acid, isoaspartic acid, isoglutamic acid, 2-aminoadipic acid, and 2-aminosuberic acid group C: asparagine and glutamine group D: lysine, arginine, ornithine, 2,4-diaminobutanoic acid, and 2,3-diaminopropionic acid group E: proline, 3-hydroxyproline, and 4-hydroxyproline group F: serine, threonine, and homoserine group G: phenylalanine and tyrosine In the present invention, examples of the antibody fragment include a Fab, a F(ab')$_2$, a Fab', a single chain antibody (scFv), a dimerized V region (diabody), a disulfide stabilized V region (dsFv), a peptide comprising a CDR and the like.

The Fab is an antibody fragment, which has a molecular weight of about 50,000 and has an antigen-binding activity, and in which about a half of an H chain at the N-terminal side of the fragments obtained by treating IgG with papain that is a protease (cleaved at an amino acid residue at position 224 in the H chain) and the entire L chain are bound through a disulfide bond.

The Fab of the present invention can be obtained by treating the monoclonal antibody of the present invention with papain. Further, the Fab can also be produced by inserting a DNA encoding a Fab of the antibody into an expression vector for a prokaryote or an expression vector for a eukaryote, and then introducing the vector into a prokaryote or a eukaryote to cause expression.

The F(ab')$_2$ is a fragment, which is formed by binding two Fab regions obtained by degrading a lower part of a disulfide bond in a hinge region of IgG with pepsin that is a protease through a hinge portion, and has a molecular weight of about 100,000, and has an antigen-binding activity.

The F(ab')$_2$ of the present invention can be obtained by treating the monoclonal antibody of the present invention with pepsin. Further, the F(ab')$_2$ can also be produced by binding the following Fab' through a thioether bond or a disulfide bond.

The Fab' is an antibody fragment, which is obtained by cleaving a disulfide bond in a hinge region of the above-mentioned F(ab')$_2$, and has a molecular weight of about 50,000 and has an antigen-binding activity. The Fab' of the present invention can be obtained by treating the F(ab') of the present invention with a reducing agent such as dithiothreitol. Further, the Fab' can also be produced by inserting a DNA encoding a Fab' fragment of the antibody into an expression vector for a prokaryote or an expression vector for a eukaryote, and then introducing the vector into a prokaryote or a eukaryote to cause expression.

The scFv is a VH-P-VL or VL-P-VH polypeptide in which one VH and one VL are linked using an appropriate peptide linker (hereinafter referred to as P), and is an antibody fragment having an antigen-binding activity.

The scFv of the present invention can be produced by obtaining cDNAs encoding VH and VL of the monoclonal antibody of the present invention, constructing a DNA encoding the scFv, inserting the DNA into an expression vector for a prokaryote or an expression vector for a eukaryote, and then introducing the expression vector into a prokaryote or a eukaryote to cause expression.

The diabody is an antibody fragment in which an scFv is dimerized, and is an antibody fragment having a divalent antigen-binding activity. The divalent antigen-binding activity can be the same or one can be a different antigen binding activity.

The diabody of the present invention can be produced by obtaining cDNAs encoding VH and VL of the monoclonal antibody of the present invention, constructing a DNA encoding an scFv so that the length of the amino acid sequence of a peptide linker is 8 residues or less, inserting the DNA into an expression vector for a prokaryote or an expression vector for a eukaryote, and then introducing the expression vector into a prokaryote or a eukaryote to cause expression.

The dsFv refers to a fragment obtained by binding polypeptides, in which one amino acid residue in each of VH and VL is substituted with a cysteine residue, through a disulfide bond between the cysteine residues. The amino acid residue to be substituted with a cysteine residue can be selected based on prediction of the conformation of the antibody according to a known method [Protein Engineering, 7, 697 (1994)].

The dsFv of the present invention can be produced by obtaining cDNAs encoding VH and VL of the monoclonal antibody of the present invention, constructing a DNA encoding a dsFv, inserting the DNA into an expression vector for a prokaryote or an expression vector for a eukaryote, and then introducing the expression vector into a prokaryote or a eukaryote to cause expression.

The peptide comprising a CDR is configured to include at least one or more regions of CDRs of VH or VL. In a peptide comprising a plurality of CDRs, the CDRs can be bound directly or through an appropriate peptide linker.

The peptide comprising a CDR of the present invention can be produced by constructing DNAs encoding CDRs of VH and VL of the monoclonal antibody of the present invention, inserting the DNAs into an expression vector for a prokaryote or an expression vector for a eukaryote, and then introducing the expression vector into a prokaryote or a eukaryote to cause expression. In addition, the peptide comprising a CDR can also be produced by a chemical synthesis method such as an Fmoc method or a tBoc method.

As the monoclonal antibody or the antibody fragment thereof of the present invention, a derivative of the antibody or the antibody fragment thereof in which a radioisotope, a low-molecular weight agent, a high-molecular weight agent, a protein, or the like is bound to the monoclonal antibody or the antibody fragment thereof of the present invention chemically or in a genetic engineering manner is included. When the derivative of the antibody or the antibody fragment thereof is used for a detection method or a quantification method, as a reagent for detection or a reagent for quantification, examples of the agent that binds to the monoclonal antibody or the antibody fragment thereof of the present invention include a labeling substance to be used for a usual immunological detection or measurement method.

The derivative of the antibody or the antibody fragment thereof in the present invention can be produced by binding a radioisotope, a low-molecular weight agent, a high-molecular weight agent, a protein, or the like to the N-terminal side or the C-terminal side of an H chain or an L chain of the monoclonal antibody or the antibody fragment thereof of the present invention, an appropriate substituent or side chain in the antibody or the antibody fragment thereof, further, a sugar chain or the like in the monoclonal antibody or the antibody fragment thereof using a chemical method [Introduction to Antibody Engineering, Chijin Shokan Co. Ltd. (1994)].

Further, the derivative of the antibody or the antibody fragment thereof in the present invention can be produced by a genetic engineering technique in which a DNA encoding the monoclonal antibody or the antibody fragment thereof of the present invention is ligated to a DNA encoding a protein intended to be bound, the resultant is inserted into an expression vector, and the expression vector is introduced into an appropriate host cell to cause expression.

Examples of the radioisotope include $^{131}$I, $^{125}$I, $^{90}$Y, $^{64}$Cu, $^{99}$Tc, $^{77}$Lu, $^{211}$At, and the like. The radioisotope can be directly bound to the antibody by a chloramine T method or the like. In addition, a substance that chelates the radioisotope may be bound to the antibody. Examples of the chelating agent include 1-isothiocyanatobenzyl-3-methyldiethylenetriaminepentaacetic acid (MX-DTPA) and the like.

Examples of the low-molecular weight agent include a luminescent substance such as an acridinium ester or lophine, or a fluorescent substance such as fluorescein isothiocyanate (FITC) or tetramethylrhodamine isothiocyanate (RITC), and the like.

Examples of a method for binding a low-molecular weight agent to the antibody include a method for binding the agent to an amino group of the antibody through glutaraldehyde, a method for binding an amino group of the agent to a carboxyl group of the antibody through a water-soluble carbodiimide, and the like.

Examples of the high-molecular weight agent include polyethylene glycol (hereinafter referred to as PEG), albumin, dextran, polyoxyethylene, a styrene-maleic acid copolymer, polyvinylpyrrolidone, a pyran copolymer, hydroxypropyl methacrylamide, and the like. By binding such a high-molecular weight compound to the antibody or the antibody fragment, an effect such as (1) improvement of the stability against various chemical, physical or biological factors, (2) significant extension of the blood half-life, or (3) elimination of immunogenicity or suppression of antibody production is expected [Bioconjugate pharmaceutical product, Hirokawa-Shoten Ltd. (1993)]. Examples of a method for binding PEG to the antibody include a method for reacting with a PEGylation reagent, and the like [Bioconjugate pharmaceutical product, Hirokawa-Shoten Ltd. (1993)]. Examples of the PEGylation reagent include a modifying agent to an e-amino group of lysine (JP-A-S61-178926), a modifying agent to a carboxyl group of aspartic acid and glutamic acid (JP-A-S56-23587), a modifying agent to a guanidino group of arginine (JP-A-H2-117920), and the like.

Examples of the protein include enzymes such as alkaline phosphatase, peroxidase, or luciferase, and the like.

The present invention relates to a therapeutic agent for hypertension and a hypertensive disease comprising a BMP10 antagonist. Further, a therapeutic agent for hypertension and a hypertensive disease which contains a BMP10 antagonist and is characterized by being administered concurrently or sequentially with a BMP9 antagonist is also included in the present invention. In addition, a therapeutic agent for hypertension and a hypertensive disease which contains a BMP9 antagonist and is characterized by being administered concurrently or sequentially with a BMP10 antagonist is also included in the present invention.

The BMP10 antagonist of the present invention includes the anti-BMP10 monoclonal antibody and the antibody fragment thereof of the present invention as described above.

The hypertension includes all cases where the blood pressure exceeds the normal range, but particularly, salt-sensitive hypertension and the like are exemplified. Note that the normal range refers to a systolic blood pressure less than 140 mmHg and a diastolic blood pressure less than 90 mmHg.

The hypertensive disease includes hypertension itself and a complication resulting from persistent high blood pressure. The hypertension can be divided into essential hypertension whose cause cannot be specified and secondary hypertension due to a specific cause. There is particularly salt-sensitive hypertension as a disease considered as the cause of essential hypertension.

Examples of the secondary hypertension include renovascular hypertension, renal parenchymal hypertension, primary aldosteronism, sleep apnea syndrome, pheochromocytoma, Cushing's syndrome, drug-induced hypertension, pregnancy-induced hypertension, aortic coarctation, hypothyroidism, hyperthyroidism, hyperparathyroidism, brain stem vascular compression, and the like. In addition, additional examples of the hypertensive disease include a sodium excretion disorder, a renal tubulointerstitial disorder, a renal glomerular disorder, and heart diastolic dysfunction which accompany hypertension, and the like.

Examples of the complication resulting from persistent high blood pressure include cerebral infarction, cerebral hemorrhage, subarachnoid hemorrhage, arteriosclerosis, angina, myocardial infarction, congestive heart failure (for example, systolic heart failure, diastolic heart failure, etc.), cardiomyopathy (for example, dilated cardiomyopathy, hypertrophic cardiomyopathy, restrictive cardiomyopathy, etc.), right heart failure, a chronic kidney disease (for example, diabetic nephropathy, nephrosclerosis, a polycystic kidney disease, chronic glomerulonephritis, tubulointerstitial nephritis, etc.), acute renal dysfunction (for example, rapidly progressive glomerulonephritis, acute tubular necrosis, etc.), aortic dissection, aortic aneurysm, retinal hemorrhage, and the like.

The therapeutic agent of the present invention contains the monoclonal antibody or the antibody fragment thereof of the present invention described above as an active ingredient.

The pharmaceutical composition of the present invention contains the monoclonal antibody or the antibody fragment thereof of the present invention described above as an active ingredient.

The pharmaceutical composition of the present invention contains a physiologically acceptable diluent or carrier, and may be a mixture with another antibody or another agent such as an antibiotic. As a suitable carrier, for example, physiological saline, phosphate buffered saline, a phosphate buffered saline glucose solution, and buffered physiological saline are exemplified, but it is not limited thereto. Alternatively, the antibody is lyophilized (freeze-dried) and may be reconstructed and used when needed by adding an aqueous buffer solution as described above.

Examples of the route of administration include oral administration or parenteral administration such as intraoral, intra-airway, intrarectal, subcutaneous, intramuscular, and intravenous administration, and intravenous administration is preferred. As for the dosage form, it can be administered in any of various forms, and examples of the form include a spray, a capsule, a tablet, a granule, a syrup, an emulsion, a suppository, an injection, an ointment, a tape, and the like.

A liquid preparation such as an emulsion or a syrup can be produced using, for example, water, a saccharide such as sucrose, sorbitol, or fructose, a glycol such as polyethylene glycol or propylene glycol, an oil such as sesame oil, olive oil, or soybean oil, a preservative such as a p-hydroxybenzoic acid ester, a flavor such as strawberry flavor or peppermint, or the like, as an additive.

A capsule, a tablet, a powder, a granule, or the like can be produced using, for example, an excipient such as lactose, glucose, sucrose, or mannitol, a disintegrating agent such as starch or sodium alginate, a lubricant such as magnesium stearate or talc, a binder such as polyvinyl alcohol, hydroxypropyl cellulose, or gelatin, a surfactant such as a fatty acid ester, a plasticizer such as glycerin, or the like as an additive. In an injection, water, a saccharide such as sucrose, sorbitol, xylose, trehalose, or fructose, a sugar alcohol such as mannitol, xylitol, or sorbitol; a buffer solution such as a phosphate buffer solution, a citrate buffer solution, or a glutamate buffer solution; a surfactant such as a fatty acid ester, or the like can be used as an additive.

Examples of the pharmaceutical preparation suitable for parenteral administration include an injection, a suppository, a spray, and the like. In the case of an injection, it is generally provided in a state of a unit dose ampoule or a multiple dose container. It may be in the form of a powder to be redissolved in a suitable carrier, for example, sterile pyrogen-free water upon use. Such a dosage form usually contains an additive such as an emulsifying agent or a suspending agent that is generally used for formulation in such a composition.

Examples of an injection method include intravenous infusion, intravenous injection, intramuscular injection, intraperitoneal injection, subcutaneous injection, intradermal injection, and the like. In addition, the dose thereof varies depending on the age of an administration subject, the route of administration, and administration frequency, and can be changed in a wide range.

A suppository is prepared using a carrier such as cacao butter, a hydrogenated fat, or carboxylic acid. Further, a spray can also be prepared using the antibody of the present invention or a functional fragment of the antibody itself, or is prepared using a carrier which does not stimulate the buccal and airway mucous membranes of a recipient (patient) and disperses the antibody or the functional fragment of the antibody as fine particles so as to facilitate absorption thereof, or the like.

Specific examples of the carrier include lactose, glycerin, and the like. It can also be formulated into a preparation such as an aerosol or a dry powder according to the property of the antibody or the functional fragment of the antibody or the property of the carrier to be used. Further, a component exemplified as the additive for the oral preparation can also be added to such a parenteral preparation.

The dose thereof varies depending on the symptoms, age, body weight, or the like, however, in general, in the case of oral administration, it can be administered to an adult at a daily dose of about 0.01 mg to 1000 mg once or in divided doses. Further, in the case of parenteral administration, it can be administered at a dose of about 0.01 mg to 1000 mg through subcutaneous injection, intramuscular injection, or intravenous injection.

The therapeutic agent comprising the antibody or the antibody fragment thereof of the present invention or a derivative thereof may contain only the antibody or the antibody fragment thereof, or a derivative thereof as an active ingredient, however, in general, it is preferably provided as a pharmaceutical preparation produced by mixing it together with one or more pharmacologically acceptable carriers using an arbitrary method known in the technical field of pharmaceutics.

As the route of administration, it is preferred to use the most effective route in the treatment, and examples thereof include oral administration or parenteral administration such as intraoral, intra-airway, intrarectal, subcutaneous, intramuscular, or intravenous administration, and preferred examples thereof include intravenous administration or subcutaneous administration.

Examples of the dosage form include a spray, a capsule, a tablet, a powder, a granule, a syrup, an emulsion, a suppository, an injection, an ointment, a tape, and the like.

Further, the present invention relates to an immunological detection or measurement method for BMP10, including a monoclonal antibody or an antibody fragment thereof that specifically recognizes and binds to the amino acid sequence of BMP10 or the conformation thereof as an active ingredient.

Examples of a method for detecting or measuring the amount of BMP10 in the present invention include arbitrary known methods. For example, an immunological detection or measurement method and the like are exemplified.

The immunological detection or measurement method is a method for detecting or measuring the amount of an antibody or the amount of an antigen using a labeled antigen or antibody. Examples of the immunological detection or measurement method include a radioimmunoassay method (RIA), an enzyme immunoassay method (EIA or ELISA), a fluorescence immunoassay method (FIA), a luminescent immunoassay method, a Western blotting method, a physicochemical method, and the like.

Hereinafter, a method for producing the antibody of the present invention, a therapeutic method for a disease, and a diagnostic method for a disease will be specifically described.

1. Method for Producing Monoclonal Antibody
(1) Preparation of Antigen

BMP10 to serve as an antigen or a tissue expressing BMP10 can be obtained by introducing an expression vector containing a cDNA encoding the full length of BMP10 or a partial length thereof into *E. coli*, yeast, an insect cell, an animal cell, or the like. In addition, BMP10 can be obtained by purifying BMP10 from a human tissue in which BMP10 is expressed in a large amount. In addition, the tissue or the like can also be used as an antigen as it is. Further, a synthetic peptide having a partial sequence of BMP10 is prepared by a chemical synthesis method such as an Fmoc method or a tBoc method and can also be used as an antigen.

BMP10 used in the present invention can be produced using a method described in Molecular Cloning, A Laboratory Manual, Second Edition, Cold Spring Harbor Laboratory Press (1989), or Current Protocols In Molecular Biology, John Wiley & Sons (1987-1997), or the like, for example, by expressing a DNA encoding the BMP10 in a host cell using the following method.

First, a recombinant vector is produced by inserting a full-length cDNA containing a region encoding BMP10 downstream of a promoter in an appropriate expression vector. A DNA fragment that is prepared based on the full-length cDNA and has an appropriate length containing a region encoding a polypeptide may be used in place of the full-length cDNA. Subsequently, by introducing the obtained recombinant vector into a host cell suitable for the expression vector, a transformant that produces the polypeptide can be obtained.

As the expression vector, any vector can be used as long as it can autonomously replicate or can be integrated into a chromosome in a host cell to be used, and contains an appropriate promoter at a position capable of transcribing a DNA encoding the polypeptide.

As the host cell, any cell can be used as long as it can express a target gene such as a microorganism belonging to the genus *Escherichia* such as *E. coli*, yeast, an insect cell, or an animal cell.

When a prokaryote such as *E. coli* is used as the host cell, the recombinant vector is preferably a vector that can autonomously replicate in the prokaryote, and also contains a promoter, a ribosomal binding sequence, a DNA containing a region encoding BMP10, and a transcription termination sequence. In addition, the transcription termination sequence is not necessarily needed for the recombinant vector, however, it is preferred that the transcription termination sequence is located immediately downstream of a structural gene. Further, the recombinant vector may contain a gene that controls the promoter.

As the recombinant vector, it is preferred to use a plasmid in which a distance between a Shine-Dalgarno sequence (also referred to as SD sequence), which is a ribosomal binding sequence, and a start codon is adjusted to an appropriate distance (for example, 6 to 18 bases).

In addition, in the base sequence of the DNA encoding the BMP10, it is possible to substitute a nucleotide so that a codon becomes optimum for expression in a host, and as a result, the production rate of the target BMP10 can be improved.

As the expression vector, any vector can be used as long as it can exhibit its function in a host cell to be used, and examples thereof include pBTrp2, pBTac1, pBTac2 (all manufactured by Roche Diagnostics K.K.), pKK233-2 (manufactured by Pharmacia Corporation), pSE280 (manufactured by Invitrogen, Inc.), pGEMEX-1 (manufactured by Promega Corporation), pQE-8 (manufactured by QIAGEN, Inc.), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript 11 SK(−) (manufactured by Stratagene Corporation), pTrs30 [prepared from *E. coli* JM109/pTrS30 (FERM BP-5407)], pTrs32 [prepared from *E. coli* JM109/pTrS32 (FERM BP-5408)], pGHA2 [prepared from *E. coli* IGHA2 (FERM BP-400), JP-A-S60-221091], pGKA2 [prepared from *E. coli* IGKA2 (FERM BP-6798), JP-A-S60-221091], pTerm2 (U.S. Pat. Nos. 4,686,191, 4,939,094, 5,160,735), pSupex, pUB110, pTP5, pC194, pEG400 [J. Bacteriol., 172, 2392 (1990)], pGEX (manufactured by Pharmacia Corporation), pET System (manufactured by Novagen, Inc.), pME18SFL3, and the like.

As the promoter, any promoter may be used as long as it can exhibit its function in a host cell to be used. Examples thereof include promoters derived from *E. coli*, a phage, or the like such as a trp promoter (Ptrp), a lac promoter, a PL promoter, a PR promoter, or a T7 promoter. In addition, it is also possible to use an artificially designed and altered promoter such as a tandem promoter in which two Ptrp promoters are linked in tandem, a tac promoter, a lacT7 promoter, or a let I promoter.

Examples of the host cell include *E. coli* XL-1 Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, *E. coli* DH5a, and the like.

As a method for introducing a recombinant vector into a host cell, any method can be used as long as it is a method for introducing a DNA into a host cell to be used, and examples thereof include a method using calcium ions [Proc. Natl. Acad. Sci. USA, 69, 2110 (1972), Gene, 17, 107 (1982), Molecular& General Genetics, 168, 111 (1979)].

When an animal cell is used as a host, as the expression vector, any vector can be used as long as it can exhibits its function in an animal cell, and examples thereof include pcDNA I, pcDM8 (manufactured by Funakoshi Co., Ltd.), pAGE107 [JP-A-H3-22979; Cytotechnology, 3, 133 (1990)], pAS3-3 (JP-A-H2-227075), pcDM8 [Nature, 329, 840 (1987)], pcDNA I/Amp (manufactured by Invitrogen, Inc.), pcDNA3.1 (manufactured by Invitrogen, Inc.), pREP4 (manufactured by Invitrogen, Inc.), pAGE103 [J. Biochemistry, 101, 1307 (1987)], pAGE210, pME18SFL3, N5KG4PE R409K (WO 2006/033386), pKANTEX93 (WO 97/10354), and the like.

As the promoter, any promoter can be used as long as it can exhibit its functions in an animal cell, and examples thereof include a cytomegalovirus (CMV) immediate early (IE) gene promoter, an SV40 early promoter, a retrovirus promoter, a metallothionein promoter, a heat-shock promoter, an SRα promoter, or a Moloney murine leukemia virus promoter or enhancer. In addition, a human CMV IE gene enhancer may be used together with the promoter.

Examples of the host cell include a human leukemia cell Namalwa cell, a monkey cell COS cell, a Chinese hamster ovary cell CHO cell (Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci. USA, 60, 1275 (1968); Cell, 6, 121 (1975); Molecular Cellgenetics, Appendix I, II (pp. 883-900), CHO/DG44, CHO-K1 (ATCC No. CCL-61), DUkXB11 (ATCC No. CCL-9096), Pro-5 (ATCC No. CCL-1781), CHO-S(Life Technologies, Cat #11619), Pro-3, a rat myeloma cell YB2/3HL.P2.G11.16Ag.20 (or also referred to as YB2/0), a mouse myeloma cell NS0, a mouse myeloma cell SP2/0-Ag14, a Syrian hamster cell BHK, HBT5637 (JP-A-S63-000299), and the like.

As a method for introducing a recombinant vector into a host cell, any method can be used as long as it is a method for introducing a DNA into an animal cell. Examples thereof include an electroporation method [Cytotechnology, 3, 133 (1990)], a calcium phosphate method (JP-A-H2-227075), a lipofection method [Proc. Natl. Acad. Sci. USA, 84, 7413 (1987)], and the like.

BMP10 can be produced by culturing a microorganism having a recombinant vector incorporating a DNA encoding BMP10, or a transformant derived from an animal cell or the like obtained as described above in a culture medium, producing and accumulating the BMP10 in a culture, and then collecting it from the culture. A method for culturing the transformant in a culture medium can be carried out according to a usual method used for culturing a host.

In the case where expression is carried out in a cell derived from a eukaryote, it is possible to obtain BMP10 to which a sugar or a sugar chain is added.

When culturing a microorganism transformed with a recombinant vector using an inducible promoter, an inducer may be added to a culture medium as needed. For example, when a microorganism transformed with a recombinant vector using a lac promoter is cultured, isopropyl-β-D-thiogalactopyranoside or the like may be added to a culture medium, and when a microorganism transformed with a recombinant vector using a trp promoter is cultured, indoleacrylic acid or the like may be added to a culture medium.

Examples of the culture medium in which the transformant obtained using an animal cell as a host is cultured include RPMI 1640 medium [The Journal of the American Medical Association, 199, 519 (1967)], Eagle's MEM medium [Science, 122, 501 (1952)], Dulbecco's modified MEM medium [Virology, 8, 396 (1959)], Medium 199 [Proc. Soc. Exp. Biol. Med., 73, 1 (1950)], Iscove's modified Dulbecco's medium (IMDM), which are generally used, or a culture medium in which fetal bovine serum (FBS) or the like is added to any of these culture media, and the like. The culture is usually carried out for 1 to 7 days under the conditions of pH 6 to 8 and 30 to 40° C. in the presence of 5% $CO_2$. In addition, during the culture, an antibiotic such as kanamycin or penicillin may be added to the culture medium as needed.

As a method for expressing a gene encoding BMP10, a method of secretory production, fused protein expression, or the like [Molecular Cloning, A Laboratory Manual, Second Edition, Cold Spring Harbor Laboratory Press (1989)] can be used in addition to direct expression.

Examples of a method for producing BMP10 include a method for producing it in a host cell, a method for secreting it out of a host cell, and a method for producing it on an outer membrane of a host cell, and an appropriate method can be selected by changing a host cell to be used or the structure of BMP10 to be produced.

When BMP10 is produced in a host cell or on an outer membrane of a host cell, BMP10 can be actively secreted out of the host cell using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)], or a method described in JP-A-H05-336963, WO 94/23021, or the like.

In addition, the production amount of BMP10 can also be increased by utilizing a gene amplification system using a dihydrofolate reductase gene or the like (JP-A-H2-227075).

The obtained BMP10 can be isolated and purified, for example, as follows.

When BMP10 is expressed in cells in a dissolved state, the cells are collected by centrifugation after completion of the culture, suspended in an aqueous buffer solution, followed by homogenization of the cells using an ultrasonic homogenizer, a French press, a Manton Gaulin homogenizer, a Dyno mill, or the like, whereby a cell-free extract solution is obtained.

It is possible to obtain a purified preparation from a supernatant obtained by centrifugation of the cell-free extract solution using methods such as usual protein isolation and purification methods, that is, a solvent extraction method, a salting-out method using ammonium sulfate or the like, a desalting method, a precipitation method using an organic solvent, anion exchange chromatography using a resin such as diethylaminoethyl (DEAE)-Sepharose or DIAION HPA-75 (manufactured by Mitsubishi Chemical Corporation), cation exchange chromatography using a resin such as S-Sepharose FF (manufactured by Pharmacia Corporation), hydrophobic chromatography using a resin such as Butyl Sepharose or Phenyl Sepharose, a gel filtration method using a molecular sieve, affinity chromatography, a chromatofocusing method, electrophoresis such isoelectric focusing electrophoresis, and the like alone or in combination.

When BMP10 is expressed in cells by forming an insoluble body, the cells are collected and then homogenized in the same manner as described above, followed by centrifugation, whereby the insoluble body of the BMP10 is collected as a precipitated fraction. The collected insoluble body of the BMP10 is solubilized with a protein denaturing agent. The BMP10 is returned to a normal conformation by diluting or dialyzing the solubilized solution, and thereafter, a purified preparation of a polypeptide can be obtained by the same isolation and purification methods as described above.

When BMP10, or a derivative such as a sugar-modified body thereof is extracellularly secreted, the BMP10, or the derivative such as a sugar-modified body thereof can be collected in a culture supernatant. The culture is subjected to a treatment using a method such as centrifugation in the same manner as described above, thereby obtaining a soluble fraction, and then by using the same isolation and purification methods as described above, a purified preparation can be obtained from the soluble fraction.

In addition, BMP10 used in the present invention can also be produced using a chemical synthesis method such an Fmoc method or a tBoc method. Further, chemical synthesis can also be carried out using a peptide synthesizer manufactured by Advanced Chemtech, Inc., PerkinElmer, Inc., Pharmacia Corporation, Protein Technology Instrument, Inc., Synthecell-Vega Biomolecules Corporation, Perceptive, Inc., Shimadzu Corporation, or the like.

(2) Immunization of Animal and Preparation of Antibody-Producing Cells for Fusion An animal such as a mouse, a rat, or a hamster at 3 to 20 weeks of age is immunized with the antigen obtained in (1), and antibody-producing cells in the spleen, the lymph node, or the peripheral blood of the animal are collected. In addition, when a sufficient increase in the antibody titer is not observed in the above-mentioned animal due to low immunogenicity, a BMP9 knockout mouse can also be used as an animal to be immunized.

The immunization is carried out by subcutaneously, intradermally, intravenously, or intraperitoneally administering an antigen to an animal, for example, together with an appropriate adjuvant such as a Freund's complete adjuvant, an aluminum hydroxide gel, *Bordetella pertussis* vaccine, or the like. When the antigen is a partial peptide, a conjugate of the antigen with a carrier protein such as BSA (bovine serum albumin) or KLH (Keyhole Limpet hemocyanin) is produced and used as an immunogen.

The administration of the antigen is carried out 2 to 10 times every 1 to 2 weeks after the first administration. On day 3 to 7 after each administration, the blood is collected from a venous plexus of the fundus, and the antibody titer of the serum thereof is measured using an enzyme immunoassay method [Antibodies—A Laboratory Manual, Cold Spring Harbor Laboratory (1988)] or the like. An animal whose serum shows a sufficient antibody titer against the antigen used for the immunization is used as a supply source for the antibody-producing cells for fusion.

On day 3 to 7 after the final administration of the antigen, a tissue containing the antibody-producing cells such as the spleen is extracted from the immunized animal, and the antibody-producing cells are collected. When spleen cells are used, the spleen is shredded and loosened, followed by centrifugation, and then red blood cells are removed, whereby the antibody-producing cells for fusion are obtained.

(3) Preparation of Myeloma Cells

As myeloma cells, an established cell line obtained from a mouse is used, for example, an 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)], or the like is used.

The myeloma cells are subcultured in a normal culture medium [RPMI-1640 medium supplemented with glutamine, 2-mercaptoethanol, gentamicin, FBS, and 8-azaguanine], and subcultured in a normal culture medium 3 to 4 days before cell fusion, and $2 \times 10^7$ or more cells are ensured on the day of performing the fusion.

(4) Cell Fusion and Preparation of Monoclonal Antibody-Producing Hybridoma The antibody-producing cells for fusion obtained in (2) and the myeloma cells obtained in (3) are washed well with Minimum Essential Medium (MEM) or PBS (1.83 g of disodium phosphate, 0.21 g of monopotassium phosphate, 7.65 g of sodium chloride, 1 L of distilled water, pH 7.2), and mixed so that the cell count becomes as follows: the antibody-producing cells for fusion: the myeloma cells=5:1 to 10:1, followed by centrifugation, and then, the supernatant is removed.

After the precipitated cell aggregate is well loosened, a mixed solution of polyethylene glycol 1000 (PEG-1000), MEM medium, and dimethylsulfoxide is added thereto while stirring at 37° C. Further, 1 to 2 mL of MEM medium is added thereto several times every 1 to 2 minutes, and then MEM medium is added thereto so that the total amount becomes 50 mL. After centrifugation, the supernatant is removed. The precipitated cell aggregate is gently loosened, and then the cells are gently suspended in HAT medium [a normal culture medium supplemented with hypoxanthine, thymidine, and aminopterin] as the antibody-producing cells for fusion. The resulting suspension is cultured in a 5% $CO_2$ incubator at 37° C. for 7 to 14 days.

After the culture, a portion of the culture supernatant is withdrawn, and a cell aggregate that reacts with an antigen including BMP10, but does not react with an antigen not including BMP10 is selected by a hybridoma selection method such as the below-mentioned binding assay. Subsequently, cloning is repeated twice by a limiting dilution method [HT medium (a medium obtained by removing aminopterin from HAT medium) is used in the first cloning, and the normal culture medium is used in the second cloning], and a cell in which a high antibody titer is stably observed is selected as a monoclonal antibody-producing hybridoma.

(5) Preparation of Purified Monoclonal Antibody

The monoclonal antibody-producing hybridoma obtained in (4) is intraperitoneally injected into a mouse or a nude mouse at 8 to 10 weeks of age having been subjected to a pristane treatment [0.5 mL of 2,6,10,14-tetramethylpentadecane (pristane) is intraperitoneally administered, followed by rearing the mouse for 2 weeks]. In 10 to 21 days, the hybridoma is converted into an ascites tumor. The ascites is collected from this mouse, followed by centrifugation to remove solids, and then salting out is carried out with 40% to 50% ammonium sulfate. Thereafter, purification is carried out by a caprylic acid precipitation method, a DEAE-Sepharose column, a protein A column, or a gel filtration column, and then an IgG or IgM fraction is collected and a purified monoclonal antibody is prepared.

Further, after culturing the monoclonal antibody-producing hybridoma obtained in (4) in RPMI 1640 medium supplemented with 10% FBS, or the like, the supernatant is removed by centrifugation, and the residue is suspended in Hybridoma-SFM medium, and then cultured for 3 to 7 days. The obtained cell suspension is centrifuged, and purification is carried out from the obtained supernatant by a protein A column or a protein G column, and then an IgG fraction is collected, whereby a purified monoclonal antibody can also be obtained. Note that it is also possible to add 5% Daigo's GF21 to the Hybridoma-SFM medium.

The determination of the subclass of the antibody is carried out by an enzyme immunoassay method using a subclass typing kit. The quantitative determination of a protein content can be carried out by a Lowry method or by calculation from an absorbance at 280 nm.

(6) Selection of Monoclonal Antibody

The selection of a monoclonal antibody is carried out by a binding assay using an enzyme immunoassay method and a kinetics analysis using Biacore described below.

(6-a) Binding Assay

As an antigen, a transgenic cell obtained by introducing the expression vector containing a cDNA encoding BMP10 obtained in (1) into *E. coli*, yeast, an insect cell, an animal cell, or the like, a recombinant protein, or a purified polypeptide or a partial peptide obtained from a human tissue, or the like is used. When the antigen is a partial peptide, a conjugate thereof with a carrier protein such as BSA or KLH is produced and may be used.

The antigen is dispensed in a plate such as a 96-well plate and immobilized thereon, and thereafter, a test substance such as serum, a culture supernatant of a hybridoma, or a purified monoclonal antibody is dispensed therein as a first antibody and reacted therewith. After well washing with PBS or PBS containing 0.05 to 0.1% Tween 20 (hereinafter also referred to as PBST), or the like, an anti-immunoglobulin antibody labeled with biotin, an enzyme, a chemiluminescent substance, a radioactive compound, or the like is dispensed therein as a second antibody and reacted therewith. After well washing with PBST, a reaction corresponding to the labeling substance of the second antibody is carried out, and a monoclonal antibody that specifically reacts with the immunogen is selected.

Further, the monoclonal antibody of the present invention can be obtained by adding a test antibody to the above-mentioned binding assay system to cause a reaction. That is, by screening an antibody with which the binding of the monoclonal antibody is inhibited when a test antibody is added, it is possible to obtain a monoclonal antibody that competes with the obtained monoclonal antibody for binding to the amino acid sequence of BMP10 or the conformation thereof.

Further, an antibody that binds to the same epitope as an epitope which the monoclonal antibody of the present invention recognizes can be obtained by identifying an epitope of an antibody obtained in the above-mentioned binding assay system, producing a partial synthetic peptide of the identified epitope, a synthetic peptide mimicking the conformation of the epitope, or the like, and then performing immunization therewith.

(6-b) Kinetics Analysis by Biacore

By using Biacore T100, the kinetics of binding between an antigen and a test substance are measured, and the result is analyzed with an analysis software attached to an instrument. After fixing an anti-mouse IgG antibody to a sensor chip CM5 by an amine coupling method, a test substance such as a hybridoma culture supernatant or a purified monoclonal antibody is allowed to flow to bind an appropriate amount, further the antigen at a plurality of known concentrations is allowed to flow, and then binding and dissociation are measured.

A kinetics analysis by a 1:1 binding model is carried out with respect to the obtained data using the software attached to the instrument to obtain various parameters. Alternatively, after fixing human BMP10 onto the sensor chip by, for example, an amine coupling method, a purified monoclonal antibody at a plurality of known concentrations is allowed to flow, and then binding and dissociation are measured. A kinetics analysis by a bivalent binding model is carried out with respect to the obtained data using the software attached to the instrument to obtain various parameters.

2. Production of Genetically Recombinant Antibody

As production examples of genetically recombinant antibodies, methods for producing a human chimeric antibody and a humanized antibody will be described below.

(1) Construction of Expression Vector for Genetically Recombinant Antibody

An expression vector for a genetically recombinant antibody is an expression vector for an animal cell into which DNAs encoding CH and CL of a human antibody are incorporated, and can be constructed by cloning each of the DNAs encoding CH and CL of a human antibody into an expression vector for an animal cell.

As a C region of a human antibody, CH and CL of an arbitrary human antibody can be used. For example, CH of γ1 subclass and CL of a class of a human antibody, or the like are used. As the DNA encoding CH or CL of a human antibody, a cDNA is used, but it is also possible to use a chromosomal DNA composed of an exon and an intron.

As the expression vector for an animal cell, any vector can be used as long as it can incorporate a gene encoding a C region of a human antibody and express the gene, and for example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)], or the like is used. Further, when an IgG4PE R409K antibody is expressed, for example, N5KG4PE R409K (WO 2006/033386), or the like can be used.

As a promoter or an enhancer of the expression vector for an animal cell, an SV40 early promoter [J. Biochem., 101, 1307 (1987)], Moloney murine leukemia virus LTR [Biochem. Biophys. Res. Commun., 149, 960 (1987)], or an immunoglobulin H chain promoter [Cell, 41, 479 (1985)] or enhancer [Cell, 33, 717 (1983)], or the like is used.

As the expression vector for a genetically recombinant antibody, an expression vector for a genetically recombinant antibody of a type (tandem-type) in which the antibody H chain and L chain are present on the same vector [J. Immunol. Methods, 167, 271 (1994)] can be used from the viewpoints of ease of construction of the expression vector for a genetically recombinant antibody, ease of introduction into an animal cell, balancing of the expression levels of the antibody H chain and L chain in the animal cell, and the like. In addition, a type in which the antibody H chain and L chain are present on separate vectors can also be used. As the tandem-type expression vector for a genetically recombinant antibody, pKANTEX93 (WO 97/10354), pEE18 [Hybridoma, 17, 559 (1998)], N5KG4PE R409K (WO 2006/033386), or the like is used.

(2) Acquisition of cDNA Encoding V Region of Antibody Derived from Animal Other than Human and Analysis of Amino Acid Sequence Acquisition of cDNAs encoding VH and VL of a non-human antibody and an analysis of an amino acid sequence can be carried out as follows.

mRNA is extracted from hybridoma cells that produce a non-human antibody, and cDNAs are synthesized. The synthesized cDNAs are each cloned into a vector such as a phage or a plasmid, thereby producing a cDNA library.

A recombinant phage or a recombinant plasmid comprising a cDNA encoding VH or VL is isolated from the library using a DNA encoding a C region part or a V region part of a mouse antibody as a probe, respectively. The entire nucleotide sequence of the target VH or VL of the mouse antibody in the recombinant phage or the recombinant plasmid is determined, respectively, and the entire amino acid sequence of VH or VL is deduced from the nucleotide sequence respectively.

As an animal other than a human for preparing hybridoma cells that produce a non-human antibody, a mouse, a rat, a hamster, a rabbit, or the like is used, but any animal can be used as long as it can prepare hybridoma cells.

For the preparation of the total RNA from hybridoma cells, a guanidine thiocyanate-cesium trifluoroacetate method [Methods in Enzymol., 154, 3 (1987)], or a kit such as RNA easy Kit (manufactured by QIAGEN, Inc.), or the like is used.

In the preparation of mRNA from the total RNA, an oligo (dT)-immobilized cellulose column method [Molecular Cloning, A Laboratory Manual, Second Edition, Cold Spring Harbor Laboratory Press (1989)], or a kit such as Oligo-dT30<Super> mRNA Purification Kit (manufactured by Takara Bio Inc.), or the like is used. Further, it is also possible to prepare mRNA from hybridoma cells using a kit such as Fast Track mRNA Isolation Kit (manufactured by Invitrogen, Inc.), or QuickPrep mRNA Purification Kit (manufactured by Pharmacia Corporation).

In the synthesis of cDNAs and the production of a cDNA library, a known method [Molecular Cloning, A Laboratory Manual, Second Edition, Cold Spring Harbor Laboratory Press (1989), Current Protocols in Molecular Biology, Supplement 1, John Wiley & Sons (1987-1997)], or a kit such as SuperScript Plasmid System for cDNA Synthesis and Plasmid Cloning (manufactured by Invitrogen, Inc.) or ZAP-cDNA Synthesis Kit (manufactured by Stratagene Corporation), or the like is used.

When the cDNA library is produced, as the vector into which a cDNA synthesized using mRNA extracted from hybridoma cells as a template is incorporated, any vector can be used as long as it is a vector capable of incorporating the cDNA. For example, ZAP ExPress [Strategies, 5, 58 (1992)], pBluescript II SK(+) [Nucleic Acids Research, 17, 9494 (1989)], XZAPII (manufactured by Stratagene Corporation), λgt 10, λgt 11 [DNA Cloning: A Practical Approach, I, 49 (1985)], Lambda BlueMid (manufactured by Clontech Laboratories, Inc.), λEx Cell, pT7T3-18U (manufactured by Pharmacia Corporation), pcD2 [Mol. Cell. Biol., 3, 280 (1983)], pUC18 [Gene, 33, 103 (1985)], or the like is used.

As E. coli into which a cDNA library constructed by a phage or a plasmid vector is introduced, any E. coli can be used as long as it can introduce, express, and maintain the cDNA library. For example, XL-1Blue MRF [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)], or the like is used.

In the selection of a cDNA clone encoding VH or VL of a non-human antibody from the cDNA library, a colony hybridization method using an isotope or a fluorescently labeled probe, or a plaque hybridization method [Molecular Cloning, A Laboratory Manual, Second Edition, Cold Spring Harbor Laboratory Press (1989)], or the like is used.

In addition, it is possible to prepare a cDNA encoding VH or VL by preparing a primer and performing a polymerase chain reaction method [hereinafter referred to as a PCR method, Molecular Cloning, A Laboratory Manual, Second Edition, Cold Spring Harbor Laboratory Press (1989), Current Protocols in Molecular Biology, Supplement 1, John Wiley & Sons (1987-1997)] using a cDNA or a cDNA library synthesized from mRNA as a template.

The selected cDNA is cleaved with an appropriate restriction enzyme or the like, and then cloned into a plasmid such as pBluescript SK(-) (manufactured by Stratagene Corporation), and the nucleotide sequence of the cDNA is determined by a commonly used nucleotide sequence analysis method or the like. In the nucleotide sequence analysis method, for example, after performing a reaction such as a dideoxy method [Proc. Natl. Acad. Sci. USA, 74, 5463 (1977)], an automatic nucleotide sequence analyzer such as ABI Prism 3700 (manufactured by PE Biosystems, Inc.) or A. L. F. DNA sequencer (manufactured by Pharmacia Corporation) is used.

By deducing the entire amino acid sequence of each of VH and VL from the determined nucleotide sequence and comparing it with the entire amino acid sequence of each of VH and VL of a known antibody [A. L. F. DNA, US Dept. Health and Human Services (1991)], it is confirmed whether the obtained cDNA encodes the complete amino acid sequence of each of VH and VL of the antibody including a secretion signal sequence.

With respect to the complete amino acid sequence of each of VH and VL of the antibody including a secretion signal sequence, by comparison with the entire amino acid sequence of each of VH and VL of a known antibody [A. L. F. DNA, US Dept. Health and Human Services (1991)], the length of the secretion signal sequence and the N-terminal amino acid sequence can be deduced, and further the subgroup to which these belong can be identified. In addition, the amino acid sequence of each CDR of VH and VL can also be found out by comparison with the amino acid sequence of each of VH and VL of a known antibody [A. L. F. DNA, US Dept. Health and Human Services (1991)].

Further, by using the obtained complete amino acid sequence of each of VH and VL, it is possible to confirm whether the complete amino acid sequence of each of VH and VL is new by, for example, carrying out a homology search by a BLAST method [J. Mol. Biol., 215, 403 (1990)] or the like with respect to an arbitrary database such as SWISS-PROT or PIR-Protein.

(3) Construction of Human Chimeric Antibody Expression Vector

By cloning each cDNA encoding VH or VL of a non-human antibody upstream of each gene encoding CH or CL of a human antibody in the expression vector for a genetically recombinant antibody obtained in (1), a human chimeric antibody expression vector can be constructed.

In order to ligate the cDNA encoding VH or VL of a non-human antibody at the 3' end side with CH or CL of a human antibody at the 5' end side, cDNAs of VH and VL designed so that the nucleotide sequence of a ligation region encodes an appropriate amino acid and to become an appropriate restriction enzyme recognition sequence are produced.

The produced cDNAs of VH and VL are each cloned upstream of each gene encoding CH or CL of a human antibody in the expression vector for a human CDR-grafted antibody obtained in (1) so that they are expressed in an appropriate form, whereby a human chimeric antibody expression vector is constructed.

In addition, each cDNA encoding VH or VL of a non-human antibody is amplified by a PCR method using a synthetic DNA containing an appropriate restriction enzyme recognition sequence at both ends, and can be cloned into the expression vector for a genetically recombinant antibody obtained in (1).

(4) Construction of cDNA Encoding V Region of Human CDR-Grafted Antibody

A cDNA encoding VH or VL of a human CDR-grafted antibody can be constructed as follows.

Each amino acid sequence of FR of VH or VL of a human antibody, to which the amino acid sequence of a CDR of VH or VL of a non-human antibody is to be grafted is selected. As the amino acid sequence of FR to be selected, any amino acid sequence can be used as long as it is derived from a human antibody.

For example, an amino acid sequence of FR of a human antibody registered in a database such as Protein Data Bank, or a common amino acid sequence in each subgroup of FR of a human antibody [A. L. F. DNA, US Dept. Health and Human Services (1991)], or the like is used. In order to suppress a decrease in the binding activity of an antibody, an amino acid sequence of FR having a homology as high as possible (at least 60% or more) with the amino acid sequence of FR of VH or VL of the original antibody is selected.

Subsequently, each of the amino acid sequences of the CDRs of the original antibody is grafted to the selected amino acid sequence of FR of VH or VL of a human antibody, and each amino acid sequence of VH or VL of a human CDR-grafted antibody is designed. By converting the designed amino acid sequence into a DNA sequence in consideration of the usage frequency of codons found in the nucleotide sequence of the antibody gene [A. L. F. DNA, US Dept. Health and Human Services (1991)], each DNA sequence encoding the amino acid sequence of VH or VL of a human CDR-grafted antibody is designed.

Based on the designed DNA sequences, several synthetic DNAs having a length of around 100 nucleotides are synthesized and a PCR reaction is carried out using them. In this case, from the viewpoint of the reaction efficiency in the PCR reaction and the length of a synthesizable DNA, preferably 6 synthetic DNAs are designed for each of the H chain and the L chain.

Further, by introducing an appropriate restriction enzyme recognition sequence at the 5' end of the synthetic DNA located at both ends, a cDNA encoding VH or VL of a human CDR-grafted antibody can be easily cloned into the expression vector for a human CDR-grafted antibody obtained in (1).

Alternatively, the cloning can be carried out by using a full-length synthetic DNA of each of the H chain and the L chain synthesized as a single DNA based on the designed DNA sequences.

After the PCR reaction, each amplification product is cloned into a plasmid such as pBluescript SK(−) (manufactured by Stratagene Corporation), the nucleotide sequence is determined by the same method as the method described in (2), and a plasmid having a DNA sequence encoding the amino acid sequence of VH or VL of a desired human CDR-grafted antibody is obtained.

(5) Alteration of Amino Acid Sequence of V Region of Human CDR-Grafted Antibody

The antigen-binding activity of a human CDR-grafted antibody prepared merely by grafting only CDRs of VH and VL of a non-human antibody to FRs of VH and VL of a human antibody is decreased as compared with that of the original non-human antibody [BIO/TECHNOLOGY, 9,266 (1991)].

In the human CDR-grafted antibody, the lowered antigen-binding activity can be increased by identifying an amino acid residue directly involved in the binding to an antigen, an amino acid residue interacting with an amino acid residue of a CDR, and an amino acid residue maintaining the conformation of the antibody and indirectly involved in the binding to an antigen in the amino acid sequences of FRs of VH and VL of a human antibody, and substituting such an amino acid residue with an amino acid residue of the original non-human antibody.

In order to identify an amino acid residue of FR involved in the antigen-binding activity, it is possible to construct and analyze the conformation of the antibody using X-ray crystallography [J. Mol. Biol., 112, 535 (1977)], or computer modeling [Protein Engineering, 7, 1501 (1994)], or the like. Further, it is possible to obtain an altered human CDR-grafted antibody having a necessary antigen-binding activity by producing several types of variants for each antibody, and repeatedly examining the correlation with the antigen-binding activity thereof through trial and error.

The amino acid residues of FRs of VH and VL of a human antibody can be altered by carrying out a PCR reaction described in (4) using a synthetic DNA for alteration. With respect to the amplification product after the PCR reaction, the nucleotide sequence is determined to confirm that the desired alteration has been carried out by the method described in (2).

(6) Construction of cDNA Encoding V Region of Humanized Antibody by Surface Reconstruction Method A cDNA encoding VH or VL of a humanized antibody by a surface reconstruction method can be constructed as follows.

In the amino acid sequence of FR of VH or VL of a non-human antibody, an amino acid residue considered to have a low effect on the antigen-binding activity is selected, respectively, and the amino acid residue is substituted with an amino acid residue considered to have lower antigenicity than the amino acid residue.

The thus designed amino acid sequence of VH or VL is converted into a DNA sequence in consideration of the usage frequency of codons found in the nucleotide sequence of the antibody gene [A. L. F. DNA, US Dept. Health and Human Services (1991)], and each DNA sequence encoding the amino acid sequence of VH or VL of a humanized antibody by a surface reconstruction method is designed, respectively.

Based on the designed DNA sequences, several synthetic DNAs having a length of around 100 nucleotides are synthesized and a PCR reaction is carried out using them. In this case, from the viewpoint of the reaction efficiency in the PCR reaction and the length of a synthesizable DNA, preferably 6 synthetic DNAs are designed for each of the H chain and the L chain.

Further, by introducing an appropriate restriction enzyme recognition sequence at the 5' end of the synthetic DNA located at both ends, a cDNA encoding VH or VL of a humanized antibody by a surface reconstruction method can be easily cloned into the expression vector for a humanized antibody obtained in (1).

Alternatively, the cloning can be carried out by using a full-length synthetic DNA of each of the H chain and the L chain synthesized as a single DNA based on the designed DNA sequences.

After the PCR reaction, each amplification product is cloned into a plasmid such as pBluescript SK(−) (manufactured by Stratagene Corporation), the nucleotide sequence is determined by the same method as the method described in (2), and a plasmid having a DNA sequence encoding the amino acid sequence of VH or VL of a desired human antibody is obtained.

(7) Construction of Humanized Antibody Expression Vector

A humanized antibody expression vector can be constructed by cloning each cDNA encoding VH or VL of a constructed genetically recombinant antibody upstream of each gene encoding CH or CL of a human antibody of the expression vector for a genetically recombinant antibody obtained in (1).

For example, the cloning is carried out upstream of each gene encoding CH or CL of a human antibody in the expression vector for a humanized antibody obtained in (1) by introducing an appropriate restriction enzyme recognition sequence at the 5' end of the synthetic DNA located at both ends among the synthetic DNAs used when constructing VH or VL of the humanized antibody obtained in (4), (5), or (6) so that they are expressed in an appropriate form.

(8) Transient Expression of Genetically Recombinant Antibody

By transiently expressing a genetically recombinant antibody using the genetically recombinant antibody expression vector obtained in (3) and (7), or an expression vector obtained by alteration thereof, the antigen-binding activities of many types of humanized antibodies produced can be efficiently evaluated.

As a host cell into which the expression vector is introduced, any cell can be used as long as it is a host cell capable of expressing a genetically recombinant antibody. For example, a COS-7 cell (ATCC No: CRL 1651) is used [Methods in Nucleic Acids Res., CRC Press, 283 (1991)].

In the introduction of the expression vector into a COS-7 cell, a DEAE-dextran method [Methods in Nucleic Acids Res., CRC Press (1991)], a lipofection method [Proc. Natl. Acad. Sci. USA, 84, 7413 (1987)], or the like is used.

After the introduction of the expression vector, the expression level and the antigen-binding activity of the genetically recombinant antibody in a culture supernatant are measured using an enzyme immunoassay method [Monoclonal Antibodies-Principles and practice, Third Edition, Academic Press (1996), Antibodies-A Laboratory Manual, Cold Spring Harbor Laboratory (1988), Monoclonal Antibody Experimental Manual, Kodansha scientific books (1987)], or the like.

(9) Acquisition of Transformant Stably Expressing Genetically Recombinant Antibody and Preparation of Genetically Recombinant Antibody A transformant that stably expresses a genetically recombinant antibody can be obtained by introducing the genetically recombinant antibody expression vector obtained in (3) and (7) into an appropriate host cell.

In the introduction of the expression vector into a host cell, an electroporation method [JP-A-H2-257891, Cytotechnology, 3, 133 (1990)], or the like is used.

As a host cell into which the genetically recombinant antibody expression vector is introduced, any cell can be used as long as it is a host cell capable of expressing a genetically recombinant antibody.

For example, CHO-K1 (ATCC No. CCL-61), DUkXB11 (ATCC No. CCL-9096), Pro-5 (ATCC No. CCL-1781), CHO-S(Life Technologies, Cat #11619), rat myeloma cells YB2/3HL.P2.G11.16Ag.20 (or also referred to as YB2/0), mouse myeloma cells NS0, mouse myeloma cells SP2/0-Ag14 (ATCC No. CRL 1581), mouse P3-X63-Ag8653 cells (ATCC No. CRL 1580), dihydrofolate reductase gene-deficient CHO cells [Proc. Natl. Acad. Sci. USA, 77, 4216 (1980)], Lec13 having acquired lectin resistance [Somatic Cell and Molecular Genetics, 12, 55 (1986)], α1,6-fucosyltransferase gene-deficient CHO cells (WO 2005/035586, WO 02/31140), Rat YB2/3HL.P2.G11.16Ag.20 cells (ATCC No: CRL 1662), or the like is used.

After introduction of the expression vector, a transformant that stably expresses a genetically recombinant antibody is selected by culturing the transformant in a culture medium for animal cell culture containing an agent such as G418 sulfate (JP-A-H2-257891).

As the culture medium for animal cell culture, RPMI 1640 medium (manufactured by Invitrogen, Inc.), GIT medium (manufactured by Nippon Pharmaceutical Co., Ltd.), EX-CELL 301 medium (manufactured by JRH Biosciences, Inc.), IMDM medium (manufactured by Invitrogen, Inc.), Hybridoma-SFM medium (manufactured by Invitrogen, Inc.), or a medium in which any of various additives such as FBS is added to any of these media, or the like is used.

By culturing the obtained transformant in a culture medium, a genetically recombinant antibody is expressed and accumulated in the culture supernatant. The expression level and the antigen-binding activity of the genetically recombinant antibody in the culture supernatant can be measured by an ELISA method or the like. In addition, the transformant can increase the expression level of the genetically recombinant antibody utilizing a DHFR amplification system (JP-A-H2-257891) or the like.

The genetically recombinant antibody is purified from the culture supernatant of the transformant using a protein A column [Monoclonal Antibodies—Principles and Practice, Third Edition, Academic Press (1996), Antibodies—A Laboratory Manual, Cold Spring Harbor Laboratory (1988)]. In addition, it is also possible to combine methods used for purifying a protein such as gel filtration, ion exchange chromatography, and ultrafiltration.

The molecular weights of an H chain, an L chain, or the entire antibody molecule of a purified genetically recombinant antibody can be measured using polyacrylamide gel electrophoresis [Nature, 227, 680 (1970)], or a Western blotting method [Monoclonal Antibodies—Principles and Practice, Third Edition, Academic Press (1996), Antibodies—A Laboratory Manual, Cold Spring Harbor Laboratory (1988)], or the like.

3. Evaluation of Activity of Purified Monoclonal Antibody or Antibody Fragment Thereof The evaluation of the activity of the purified monoclonal antibody or the antibody fragment thereof of the present invention can be carried out as follows.

The binding activity to BMP10 and BMP10 expressing tissue is measured using a binding assay described in the above 1-(6-a) and a surface plasmon resonance method using a Biacore system or the like described in the above (6-b). Further, it can be measured using a fluorescent antibody method [Cancer Immunol. Immunother., 36, 373 (1993)] or the like.

The production of a bispecific antibody can be carried out by, for example, a known method such as a method described in WO 2009/131239.

4. Therapeutic Method for Disease Using Anti-BMP10 Monoclonal Antibody or Antibody Fragment Thereof of the Present Invention The monoclonal antibody or the antibody fragment thereof of the present invention can be used for a treatment of hypertension and a hypertensive disease.

A therapeutic agent comprising the monoclonal antibody or the antibody fragment thereof of the present invention or a derivative thereof may contain only the antibody or the antibody fragment thereof, or a derivative thereof as an active ingredient, however, in general, it is provided as a pharmaceutical preparation produced by mixing it together with one or more pharmacologically acceptable carriers using a method known in the technical field of pharmaceutics.

Examples of a route of administration include oral administration or parenteral administration such as intraoral, intraairway, intrarectal, subcutaneous, intramuscular, or intravenous administration. Examples of a dosage form include a spray, a capsule, a tablet, a powder, a granule, a syrup, an emulsion, a suppository, an injection, an ointment, a tape, and the like.

Examples of the pharmaceutical preparation suitable for oral administration include an emulsion, a syrup, a capsule, a tablet, a powder, a granule, and the like.

A liquid preparation such as an emulsion or a syrup is produced using water, a saccharide such as sucrose, sorbitol, or fructose, a glycol such as polyethylene glycol or propylene glycol, an oil such as sesame oil, olive oil, or soybean oil, a preservative such as a p-hydroxybenzoic acid ester, a flavor such as strawberry flavor or peppermint, or the like, as an additive.

A capsule, a tablet, a powder, a granule, or the like can be produced using an excipient such as lactose, glucose, sucrose, or mannitol, a disintegrating agent such as starch or sodium alginate, a lubricant such as magnesium stearate or talc, a binder such as polyvinyl alcohol, hydroxypropyl cellulose, or gelatin, a surfactant such as a fatty acid ester, a plasticizer such as glycerin, or the like as an additive.

Examples of the pharmaceutical preparation suitable for parenteral administration include an injection, a suppository, a spray, and the like.

An injection is produced using a carrier composed of a salt solution, a glucose solution, or a mixture of both, or the like.

A suppository is produced using a carrier such as cacao butter, a hydrogenated fat, or carboxylic acid.

A spray is produced using a carrier which does not stimulate the buccal and airway mucous membranes of a recipient and disperses the monoclonal antibody or the antibody fragment thereof of the present invention as fine particles so as to facilitate absorption thereof, or the like. As the carrier, for example, lactose, glycerin, or the like is used. In addition, it can also be produced as an aerosol or a dry powder.

Further, a component exemplified as the additive for the pharmaceutical preparation suitable for oral administration can also be added to the above-mentioned parenteral preparation.

Hereinafter, the present invention will be more specifically described by way of Examples, however, the present invention is not limited to the following Examples. Reagents to be used shall be used according to the package insert unless otherwise particularly stated.

EXAMPLES

[Example 1] Preparation of Anti-Human BMP10 Monoclonal Antibody 1-1) Preparation of Immunogen As an immunogen, a human BMP10 recombinant protein or a human BMP10 mature dimer (manufactured by R & D Systems, Inc., Cat #2926-BP) was used. The human BMP10 recombinant protein was prepared according to the method described in Example 20 in WO 2014/007198. The human BMP10 recombinant protein prepared by this method includes a mature protein, an N-terminal propeptide protein, and a full-length protein.

1-2) Immunization of Animal and Preparation of Antibody-Producing Cells

An antigen suspension containing the human BMP10 prepared in Example 1, 1-1) as an antigen was prepared according to the package insert using Sigma Adjuvant System (registered trademark) (manufactured by Sigma-Aldrich Co. LLC) or Alum+pertussis vaccine adjuvant (manufactured by Nacalai Tesque, Inc.) as an adjuvant, and thereafter, a WKY/NcrlCrlj rat or an SD rat was immunized therewith through intraperitoneal and subcutaneous or intramuscular routes. The amount of the antigen used for the immunization was set to 20 μg/head in the case of the human BMP10 recombinant protein, and 10 μg/head in the case of the human BMP10 mature dimer. The immunization was carried out twice or four times in total including the final boosting. The spleen was excised 3 to 4 days after the final administration.

The excised spleen was shredded in Minimum Essential Media (manufactured by Nacalai Tesque, Inc.) (hereinafter referred to as MEM medium), and spleen cells were collected by centrifugation (1200 rpm, 5 minutes). Since the obtained spleen cell fraction contains red blood cells, the red blood cells were removed by adding RED Blood Cell Lysing Buffer (manufactured by Sigma-Aldrich Co. LLC) and treated on ice. Alternatively, the iliac lymph node was collected and cells were loosened in MEM medium to obtain lymphocytes. The obtained spleen cells or lymphocytes were washed twice with MEM medium, and then provided for cell fusion.

1-3) Preparation of Mouse Myeloma Cells

An 8-azaguanine resistant mouse myeloma cell line P3-U1 [P3X63Ag8U.1, ATCC: CRL-1597 European Journal of Immunology, 6, 511 (1976)] was subjected to conditioned culture in a medium obtained by adding gentamycin (10 μg/mL) to S-Clone Cloning Medium CM-B (manufactured by Sanko Junyaku Co., Ltd.) (hereinafter referred to as a serum-free culture medium) so as to ensure a necessary cell count ($4\times10^7$ cells or more) at the time of cell fusion, and provided for cell fusion.

1-4) Production of Hybridoma

The mouse spleen cells or the lymphocytes obtained in Example 1, 1-2) and the myeloma cells obtained in Example 1, 1-3) were mixed at 8:1, followed by centrifugation (1200 rpm, 5 min). To the obtained precipitated fraction (cell aggregate), 500 μL of a mixed liquid of polyethylene glycol 1000 (manufactured by Junsei Chemical Co., Ltd., Cat #69257-1210), MEM medium, and dimethyl sulfoxide (DMSO, manufactured by Sigma-Aldrich Co. LLC, Cat # D2650) was gradually added while gently shaking. Subsequently, 5 mL of MEM medium was added to the cell liquid while gently shaking, and further 45 mL of MEM medium was added thereto. Then, a tube containing the cell liquid was centrifuged (900 rpm, 5 min).

The obtained precipitated fraction (cell aggregate) was seeded into a 96-well plate using a serum-free culture medium containing HAT at 200 μL/well excluding the row A. At that time, the spleen cell count or the lymphocyte count was adjusted to $1.5\times10^7$ cells/18 mL per plate, and the cells were cultured under the condition of 37° C. and 5% $CO_2$. Medium exchange was appropriately carried out using a serum-free culture medium containing HAT until the cells in the well reached a cell count suitable for screening.

1-5) Screening of Anti-BMP10 Antibody-Producing Hybridoma by Solid-Phase Antigen ELISA In the screening of an anti-BMP 10 antibody-producing hybridoma, a solid-phase antigen ELISA system in which human BMP10 was immobilized on an ELISA plate was used. Specifically, a solution in which the human BMP10 recombinant prepared in Example 1, 1-1) or a human BMP10 mature dimer (manufactured by R & D Systems, Inc., Cat #2926-BP) was prepared at 0.5 μg/mL with a phosphate buffer solution (manufactured by Nacalai Tesque, Inc.) was dispensed in a 96-well ELISA plate (F96 MAX-ISORP NUNC-IMMNO PLATE, manufactured by Thermo Fisher Scientific, Inc., Cat #442404) at 50 μL/well, and adsorption was carried out by leaving the plate to stand overnight at 4° C.

After the immobilization solution was removed, washing was carried out 3 to 5 times with PBS, and 1% BSA-PBS (manufactured by Nacalai Tesque, Inc., Cat #099968-35) was added at 200 μL/well, and blocking was carried out by leaving the plate to stand at room temperature for 1 hour.

Subsequently, the hybridoma supernatant was dispensed at 50 μL/well, and the plate was left to stand at room temperature for 1 hour. After this plate was washed 3 to 5 times with PBST, Goat F(ab')$_2$ Anti-Rat IgG-Fc (HRP), pre-adsorbed (manufactured by Abcam PLC, Cat # ab6257) diluted 1000 times with 1% BSA-PBS was dispensed at 50 μL/well, and the plate was left to stand at room temperature for 1 hour.

This plate was washed 3 to 5 times with PBST, an ABTS (2,2'-Azino-bis(3-ethylbenzothiazoline-6-sulfonic Acid, manufactured by Wako, Cat #016-08521) substrate solution or a TMB substrate solution was added at 50 μL/well so as to develop a color. When appropriate color development was obtained, a 5% SDS solution or a 1 mol/L hydrochloric acid was added at 50 μL/well, and an absorbance (415 nm to 490 nm) at a sample wavelength of 415 nm and a reference wavelength of 490 nm, or an absorbance (450 nm to 570 nm) at a sample wavelength of 450 nm and a reference wavelength of 570 nm was measured using a plate reader (Spectra Max, manufactured by Molecular Devices, LLC).

1-6) Preparation of Cell Capable of Detecting BMP Signal

In the screening of a hybridoma that produces an anti-BMP10 antibody, cells capable of detecting a signal of various types of BMP proteins (hereinafter, BMP signal detection cells) were used. As the BMP signal detection cells, Id1-Luc/CHO cells described in Example 5 of JP-A-2017-25011 were used.

1-7) Screening of Anti-BMP10 Neutralizing Antibody-Producing Hybridoma Using Id1-Luc/CHO To a 96-well fluorescence and luminescence plate (manufactured by Corning, Inc., Cat #3916), a human BMP10 mature dimer was added at a final concentration of 3 ng/mL. Subsequently, a hybridoma culture supernatant was added at a final concentration of 50%. Thereafter, an Id1-Luc/CHO cell liquid in which the cells were suspended in Excell 325 medium [Excell 325 PF CHO (manufactured by SAFC, Inc., Cat #14340C-1000 mL), 4 mM L-glutamine, 1×Penicillin, 1×Streptomycin (manufactured by Nacalai, Inc., Cat #09367-34), 0.5 µg/mL hygromycin] was added at $5\times10^4$ cells/well.

Note that all samples were diluted with Excell 325 medium so as to achieve 100 µL/well when the samples were added. Thereafter, the liquid in the well was made uniform with a plate mixer, and the cells were cultured at 37° C. for 20 hours. After 20 hours, an assay solution of Nano-Glo Luciferase Assay (manufactured by Promega Corporation, Cat #N1120) prepared according to the package insert was added at 40 µL/well, followed by stirring, and then, a luciferase activity was measured using Glomax (manufactured by Promega Corporation).

The neutralizing activity (%) of the antibody in the hybridoma culture supernatant was calculated by setting the value of the well in which only the BMP10 mature dimer was added without adding the hybridoma culture supernatant to be 0%, and the value of the well in which only Excell 325 medium was added without adding an antibody to be 100%.

1-8) Isolation of Anti-BMP10 Neutralizing Antibody-Producing Hybridoma

A hybridoma that exhibits a neutralizing activity of 50% or more in the above-mentioned screening was determined to be positive. The hybridoma determined to be positive was monocloned by limiting dilution with a serum-free culture medium, and seeding into a 96-well plate. The monocloning was carried out once to twice in total with respect to the hybridoma derived from the well determined to be positive at the first time. By the above operation, hybridomas that produce 18C1 antibody, 12H3 antibody, and 11H10 antibody, respectively, were isolated.

1-9) Large-Scale Acquisition of Antibody from Hybridoma

Each of the hybridomas isolated in Example 1, 1-8) was seeded into two large flask bottles. A serum-free culture medium was used as the culture medium. After culturing at 37° C. for 6 to 8 days, the culture medium containing the cells was collected. The collected culture medium was centrifuged, and the obtained culture supernatant was filtered through a 0.22 µm filter.

The anti-human BMP10 antibody was purified from the culture supernatant filtered through the filter using an open column packed with Protein G Sepharose 4 Fast Flow (manufactured by GE Healthcare, Inc.) or Ab-Capchure Extra (manufactured by Protenova Co., Ltd.).

[Example 2] Comparison of BMP10 Neutralizing Activity Between Obtained Antibody and Known Antibody Using Id1-Luc/CHO Cells Comparison of the BMP10 neutralizing activity with respect to the obtained anti-BMP10 antibodies and a known antibody was carried out using the Id1-Luc/CHO cells produced in Example 1, 1-6). To a 96-well fluorescence and luminescence plate (manufactured by Corning, Inc., Cat #3916), a human BMP10 mature dimer (manufactured by R & D Systems, Inc., Cat #2926-BP) was added at a final concentration of 3 ng/mL. Subsequently, a known antibody MAB2926 (the known antibody refers to MAB2926), and the 18C1 antibody, the 12H3 antibody, and the 11H10 antibody, each of which is an anti-BMP10 antibody purified in Example 1, 1-9), or a control antibody (Purified Rat IgG1 λ Isotype control, manufactured by BD, Inc., Cat #553993) were prepared at 6 concentrations by 3-fold serial dilution from the final concentration of 3000 ng/mL, and then added.

Thereafter, an Id1-Luc/CHO cell liquid in which the cells were suspended in Excell 325 medium [Excell 325 PF CHO (manufactured by SAFC, Inc., Cat #14340C-1000 mL), 4 mM L-glutamine, 1×Penicillin, 1×Streptomycin (manufactured by Nacalai, Inc., Cat #09367-34), 0.5 mg/mL hygromycin] was added at $5\times10^4$ cells/well. After all samples were added, the liquid in each well was made uniform with a plate mixer, and the cells were cultured at 37° C. for 20 hours.

After 20 hours, an assay solution of Nano-Glo Luciferase Assay (manufactured by Promega Corporation, Cat # N1120) prepared according to the package insert was added at 40 µL/well, followed by stirring, and then, a luciferase activity was measured using Glomax (manufactured by Promega Corporation). The neutralizing activity (%) of the antibody was calculated by setting the value of the well in which only the BMP10 mature dimer was added without adding an antibody to be 0%, and the value of the well in which only Excell 325 medium was added without adding an antibody to be 100%. The results are shown in FIG. 1.

Figure 1:
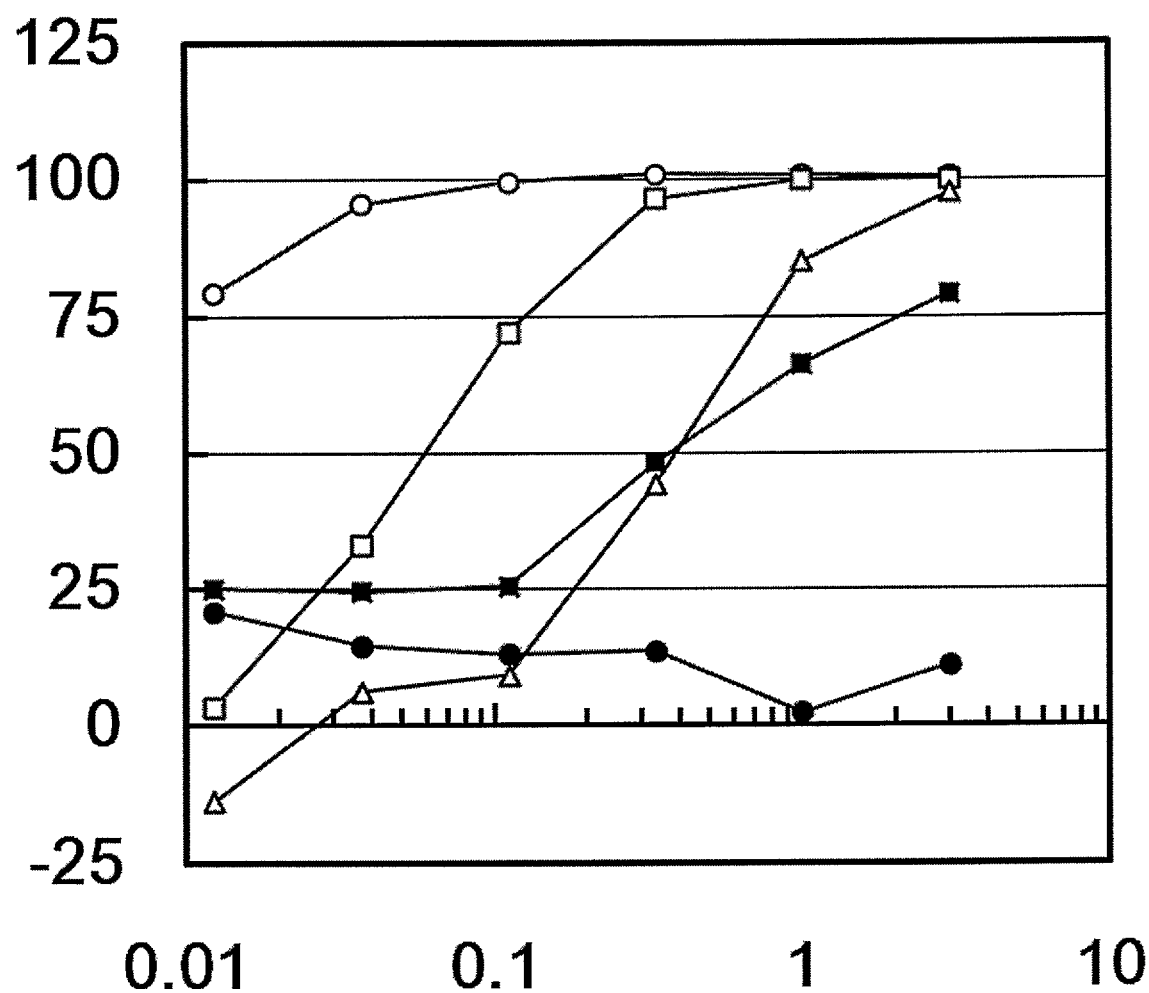
FIG. 1 is a graph comparing the BMP10 neutralizing activity of obtained anti-BMP10 monoclonal antibodies with that of a known antibody using Id1-Luc/CHO cells. The horizontal axis represents the added concentration of the antibodies (μg/mL), and the vertical axis represents the neutralizing activity (%). Black circles indicate a control antibody, black squares indicate MAB2926, white circles indicate 18C1 antibody, white squares indicate 12H3 antibody, and white triangles indicate 11H10 antibody.

As shown in FIG. 1, any antibody exhibited a neutralizing activity against BMP10 except for the control antibody. It was found that the known antibody MAB2926 cannot completely neutralize 3 ng/mL of mature BMP10 at 3 µg/mL. On the other hand, the obtained antibodies: the 11H10 antibody, the 12H3 antibody, and the 18C1 antibody could completely neutralize 3 ng/mL of mature BMP10 at 3 µg/mL. Further, the 18C1 antibody and the 12H3 antibody exhibited a BMP10 neutralizing activity at a lower concentration than MAB2926.

From the above results, it was revealed that all the obtained three antibodies are antibodies having a significantly improved BMP10 neutralizing activity as compared with the known antibody.

[Example 3] Comparison of BMP10 Neutralizing Activity Between Obtained Antibody and Known Antibody Using Human ALK1 Expressing Reporter Cells The neutralizing activities against BMP10 of the obtained anti-BMP10 antibodies and a known antibody were compared using human ALK1 expressing reporter cells made to highly express human ALK1. As the known antibody, MAB2926 (R & D Systems, Inc.) was used.

3-1) Production of Human ALK1 Expressing Reporter Cells

As the human ALK1 expressing reporter cells, ALK1/Id1-Luc/CHO cells described in Example 6 in JP-A-2017-25011 were used.

3-2) Comparison of BMP10 Neutralizing Activity Between Newly Obtained Antibody and Known Antibody To a 96-well fluorescence and luminescence plate (manufactured by Corning, Inc., Cat #3916), human BMP10 mature dimer (manufactured by R & D Systems, Inc., Cat #2926-BP) was added at a final concentration of 0.3 ng/mL.

Subsequently, the 18C1 antibody, the 12H3 antibody, the 11H10 antibody or MAB2926, each of which is an anti-BMP10 antibody, or a control antibody (Purified Rat IgG1 λ Isotype control, manufactured by BD, Inc., Cat #553993) was prepared at 6 concentrations by 3-fold serial dilution from the final concentration of 3000 ng/mL, and then added.

Thereafter, an ALK1/Id1-Luc/CHO cell suspension prepared with Excell 325 medium was added at $5\times10^4$ cells/well. All samples were diluted with Excell 325 medium so as to achieve 100 µL/well when combining human BMP10, the antibody dilution solution, and the cell suspension. Thereafter, the liquid in the well was made uniform with a plate mixer, and the cells were cultured at 37° C. for 20 hours.

After 20 hours, an assay solution of Nano-Glo Luciferase Assay prepared according to the package insert was added at 40 µL/well, followed by stirring, and then, a luciferase activity was measured using Glomax (manufactured by Promega Corporation). The neutralizing activity (%) of the antibody was calculated by setting the value of the well in which only the BMP10 mature dimer was added without adding an antibody to be 0%, and the value of the well in which only Excell 325 medium was added without adding an antibody to be 100%. The results are shown in FIG. 2.

Figure 2:
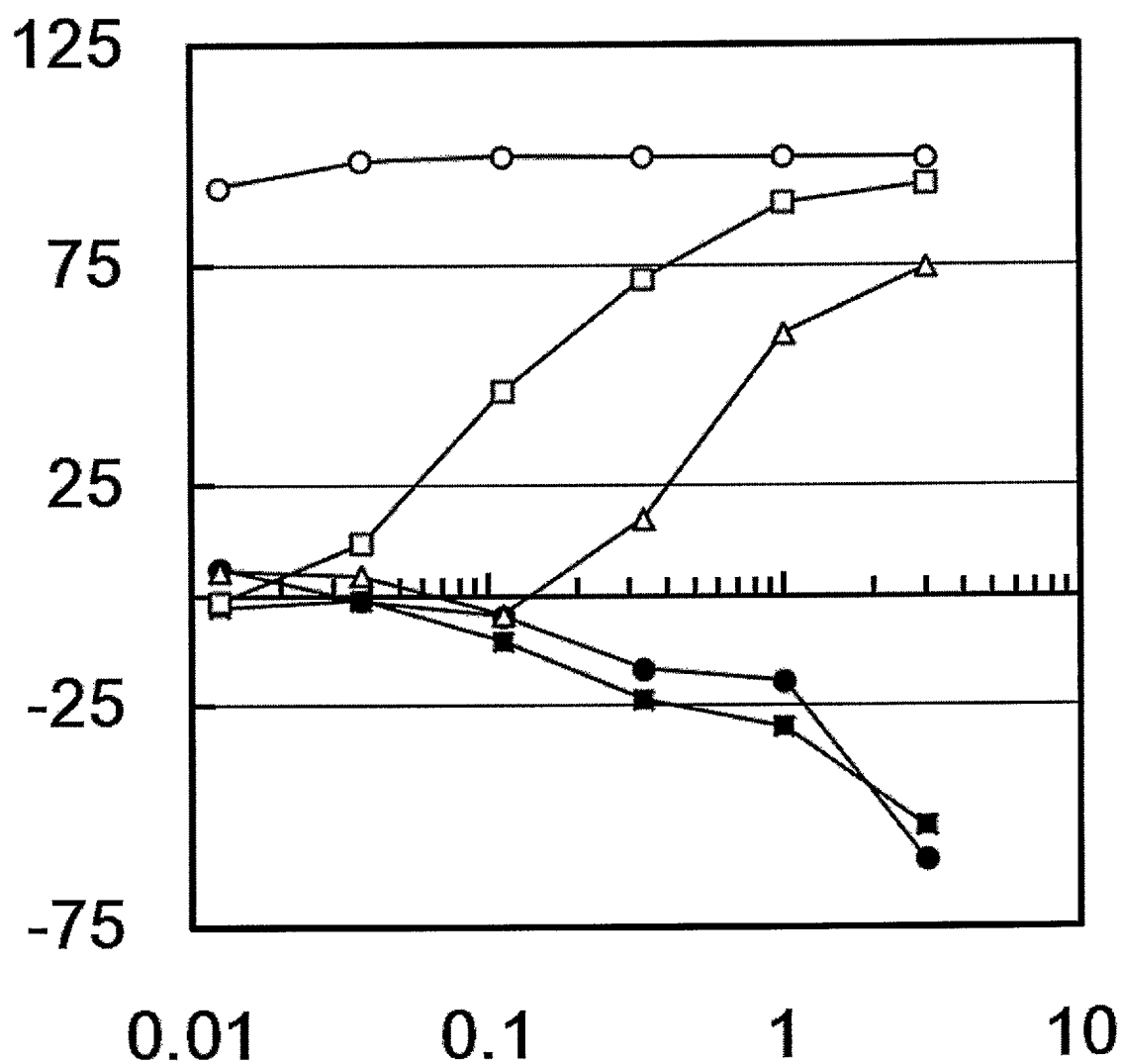
FIG. 2 is a figure comparing the BMP10 neutralizing activity of obtained anti-BMP10 monoclonal antibodies with that of a known antibody using ALK1/Id1-Luc/CHO cells. The horizontal axis represents the added concentration of the antibodies (μg/mL), and the vertical axis represents the neutralizing activity (%). Black circles indicate a control antibody, black squares indicate MAB2926, white circles indicate 18C1 antibody, white squares indicate 12H3 antibody, and white triangles indicate 11H10 antibody.

As shown in FIG. 2, the control antibody and the known antibody MAB2926 did not exhibit a neutralizing activity in the ALK1/Id1-Luc/CHO cells. On the other hand, the obtained antibodies: the 18C1 antibody, the 12H3 antibody, and the 11H10 antibody exhibited a distinct BMP10 neutralizing activity also in the ALK1/Id1-Luc/CHO cells. Further, the strength of the neutralizing activity was higher in the order of the 18C1 antibody, the 12H3 antibody, and the 11H10 antibody.

From the above results, it was revealed that the obtained antibodies are novel antibodies exhibiting a neutralizing activity in ALK1 highly expressing cells.

[Example 4] Inhibitory Effect of Obtained Antibody on Various Types of BMP Family Molecules In order to confirm that the 18C1 antibody specifically neutralizes BMP10, an inhibitory effect of the 18C1 antibody on various types of BMP signals was examined using the Id1-Luc/CHO cells produced in Example 1, 1-6).

To a 96-well fluorescence and luminescence plate (manufactured by Corning, Inc., Cat #3916), each of various types of human BMP mature dimers was added at a final concentration of 3 ng/mL, and subsequently, a dilution solution of the 18C1 antibody was added at a final concentration of 1.0 µg/mL. As the various types of human BMP10 mature dimers, human BMP2, human BMP4, human BMP6, human BMP7, human BMP9, human BMP10, human BMP15, human GDF5, and human GDF7 (all manufactured by R & D Systems, Inc.) were used. Thereafter, an Id1-Luc/CHO cell liquid in which the cells were suspended in Excell 325 medium [Excell 325 PF CHO (manufactured by SAFC, Inc., Cat #14340C-1000 mL), 4 mM L-glutamine, 1×Penicillin, 1×Streptomycin (manufactured by Nacalai, Inc., Cat #09367-34), 0.5 µg/mL hygromycin] was added at $5\times10^4$ cells/well.

All samples were diluted with Excell 325 medium so as to achieve 100 L/well in the end. Thereafter, the liquid in the well was made uniform with a plate mixer, and the cells were cultured at 37° C. for 20 hours.

After 20 hours, an assay solution of Nano-Glo Luciferase Assay (manufactured by Promega Corporation, Cat # N1120) prepared according to the package insert was added at 40 µL/well, followed by stirring, and then, a luciferase activity was measured using Glomax (manufactured by Promega Corporation).

The neutralizing activity (%) of the antibody was calculated by setting the value of the well in which only the BMP mature dimer was added without adding an antibody to be 0%, and the value of the well in which only Excell 325 medium was added without adding an antibody to be 100%. The results are shown in FIG. 3.

Figure 3:
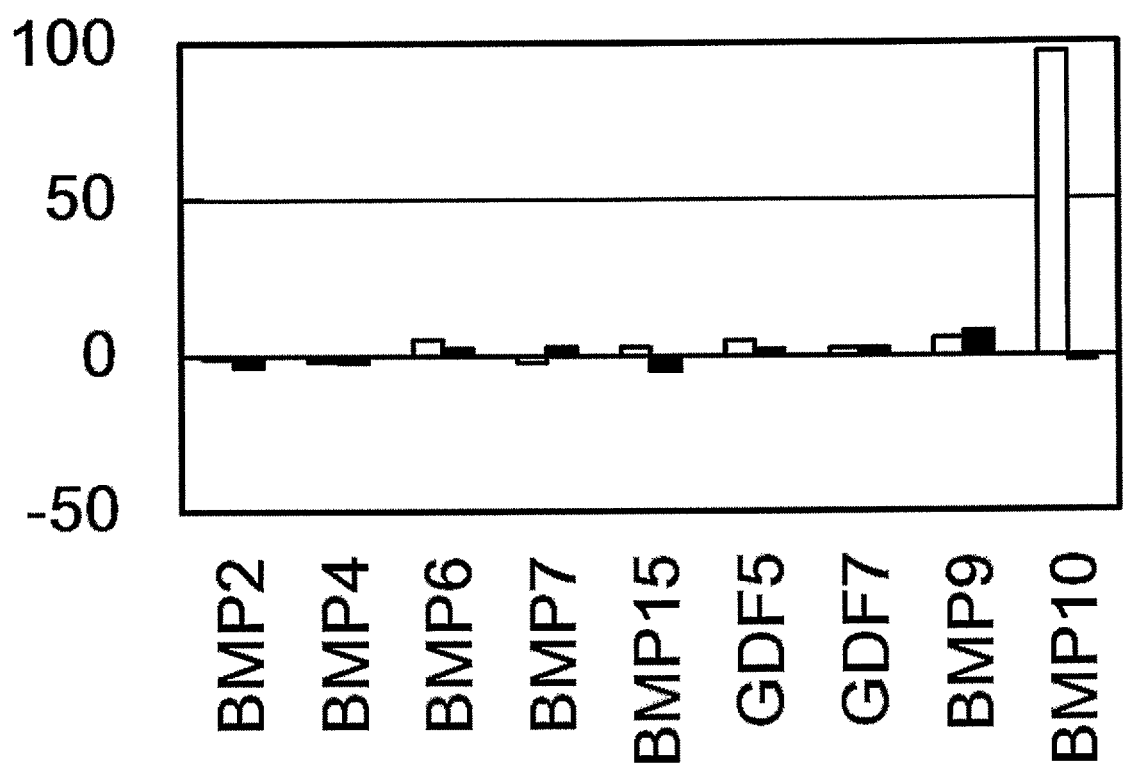
FIG. 3 is a figure evaluating the neutralizing activity of obtained 18C1 antibody against various types of BMP molecules. The vertical axis represents the neutralizing activity (%). White bar graphs indicate the 18C1 antibody, and black bar graphs indicate a control antibody.

As shown in FIG. 3, the 18C1 antibody did not inhibit at all any signals by human BMP2, human BMP4, human BMP6, human BMP7, human BMP9, human BMP15, human GDF5, and human GDF7, and therefore was found to be an antibody that specifically inhibits only a signal by human BMP10.

[Example 5] Isolation of Gene Sequences Encoding VH and VL of Anti-BMP10 Monoclonal Antibody 5-1) Preparation of Total RNA from Anti-BMP10 Monoclonal Antibody-Producing Hybridoma Cells The total RNA of each of the hybridomas was prepared from $1\times10^6$ cells of the hybridomas that produce the 18C1 antibody, the 12H3 antibody, and the 11H10 antibody described in Example 1 using Maxwell 16 LEV simplyRNA Tissue kit (manufactured by Promega Corporation, # AS1280).

5-2) Cloning of Genes of VH and VL of Anti-BMP10 Monoclonal Antibody

From 1 µg of the total RNA of each of the hybridomas obtained in Example 5-1, cDNAs were prepared using SMARTer RACE cDNA Amplification Kit (manufactured by Clontech Laboratories, Inc., Cat #634924). By using the obtained cDNA as a template, sequence determination of the cDNA of VH was carried out by combining Universal Primer A Mix (containing a forward primer) attached to the kit and a reverse primer encoding a rat IgG1 or IgG2a heavy chain constant region.

Specifically, a PCR reaction was carried out using a primer specific to rat IgG1 (SEQ ID NO: 1) or a primer specific to rat IgG2a (SEQ ID NO: 2) by combining each with Universal Primer A, whereby a cDNA fragment of VH of each antibody was amplified.

Further, PCR was carried out using a primer specific to rat Ig(κ) (SEQ ID NO: 3) or a primer specific to rat Ig(λ) (SEQ ID NO: 4) in the same manner by combining each with Universal Primer A, whereby a cDNA fragment of VL of each antibody was amplified.

In the PCR, a reaction cycle composed of 94° C. for 30 seconds and 72° C. for 3 minutes was carried out 5 times, a reaction cycle composed of 94° C. for 30 seconds, 70° C. for 30 seconds, and 72° C. for 3 minutes was carried out 5 times, and a reaction cycle composed of 94° C. for 30 seconds, 68° C. for 30 seconds, and 72° C. for 3 minutes was carried out 25 times.

As a result of carrying out agarose gel electrophoresis, in the case of the cDNA derived from the 18C1 antibody hybridoma, a PCR amplification product was obtained when a specific primer encoding the IgG1 heavy chain constant region was used. In the case of the cDNAs derived from the 12H3 antibody-producing and 11H10 antibody hybridomas, PCR amplification products were obtained when a specific primer encoding the IgG2a heavy chain constant region was used.

Further, in the case of the cDNAs derived from the 12H3 antibody-producing hybridoma and 11H10 antibody-producing hybridoma, PCR amplification products were obtained also when the primer specific to rat Ig(κ) was used. In the case of the cDNA derived from the 18C1 antibody-producing hybridoma, a PCR amplification product was obtained also when the primer specific to rat Ig(λ) was used. Each of the PCR amplification products was purified using Gel Extraction Kit (QIAEX 11, manufactured by QIAGEN, Inc., Cat #20021).

The obtained gene fragment was inserted into a pCR4 vector (manufactured by Invitrogen, Inc.) using Zero Blunt TOPO PCR Cloning Kit for Sequencing (manufactured by Invitrogen, Inc., Cat # K287540SP).

The obtained plasmid was introduced into an *E. coli* DH5a strain. The plasmid was extracted from the obtained transformant using an automatic plasmid extractor (manufactured by Kurabo Industries, Ltd.), and the nucleotide sequence was analyzed. As a result, it was confirmed that full-length VH cDNA and VL cDNA, in which an ATG sequence presumed to be a start codon is present at the 5' end of the cDNA, were obtained.

5-3) Analysis of Gene Sequence of Anti-Human BMP10 Monoclonal Antibody V Region

The entire nucleotide sequences of VHs of the 18C1 antibody, the 12H3 antibody, and the 11H10 antibody obtained in Example 5-2 are represented by SEQ ID NOs: 5, 6, and 7, respectively, the entire amino acid sequences of VHs including a signal sequence deduced from the sequences are represented by SEQ ID NOs: 8, 9, and 10, respectively, the entire nucleotide sequences of VLs thereof are represented by SEQ ID NOs: 11, 12, and 13, respectively, and the entire amino acid sequences of VLs including a signal sequence deduced from the sequences are represented by SEQ ID NOs: 14, 15, and 16, respectively.

Further, the nucleotide sequences excluding the signal sequence from SEQ ID NOs: 5, 6, and 7 are represented by SEQ ID NOs: 17, 18, and 19, respectively, the nucleotide sequences excluding the signal sequence from SEQ ID NOs: 11, 12, and 13 are represented by SEQ ID NOs: 20, 21, and 22, respectively, the amino acid sequences excluding the signal sequence from SEQ ID NOs: 8, 9, and 10 are represented by SEQ ID NOs: 23, 24, and 25, respectively, and the amino acid sequences excluding the signal sequence from SEQ ID NOs: 14, 15, and 16 are represented by SEQ ID NOs: 26, 27, and 28, respectively.

By the comparison with the sequence data of known rat antibodies [SEQUENCES of Proteins of Immunological Interest, US Dept. Health and Human Services (1991)], it could be confirmed that the respective isolated cDNAs are full-length cDNAs encoding the 18C1 antibody, the 12H3 antibody, and the 11H10 antibody including a secretory signal sequence.

The CDRs of VH and VL of the 18C1 antibody, the 12H3 antibody, and the 11H10 antibody were identified by comparison with the amino acid sequences of known antibodies. The amino acid sequences of CDR1, CDR2, and CDR3 of VH of the 18C1 antibody are represented by SEQ ID NOs: 29, 30, and 31, respectively, and the amino acid sequences of CDR1, CDR2, and CDR3 of VL thereof are represented by SEQ ID NOs: 32, 33, and 34, respectively. The amino acid sequences of CDR1, CDR2, and CDR3 of VH of the 12H3 antibody are represented by SEQ ID NOs: 35, 36, and 37, respectively, and the amino acid sequences of CDR1, CDR2, and CDR3 of VL thereof are represented by SEQ ID NOs: 38, 39, and 40, respectively. The amino acid sequences of CDR1, CDR2, and CDR3 of VH of the 11H10 antibody are represented by SEQ ID NOs: 41, 42, and 43, respectively, and the amino acid sequences of CDR1, CDR2, and CDR3 of VL thereof are represented by SEQ ID NOs: 44, 45, and 46, respectively.

5-4) Production of Anti-BMP10 Chimeric Antibody

In the recombinant expression of 18C1 chimeric antibody, an N5LG4PE(R409K) vector having a human k-type light chain constant region and a human IgG4 modified-type heavy chain constant region was used, and in the recombinant expression of 12H3 and 11H10 chimeric antibodies, an N5KG4PE(R409K) vector having a human κ-type light chain constant region and a human IgG4 modified-type heavy chain constant region was used. A vector in which a modification of substituting Arg at position 409 according to the EU-index of the human IgG4 heavy chain constant region with Lys was introduced in the N5KG4PE vector backbone used in WO 2006033386 was produced and named N5KG4PE(R409K) vector. In addition, a vector in which a human K chain constant region part was substituted with a human X constant region in this vector was named N5LG4PE(R409K) vector. The cDNAs encoding VH and VL were inserted into each of the above-mentioned antibody expression vectors. VH was inserted between the SalI and NheI sites, and VL was inserted between the BgIII and BlpI (λ-type) sites or the BgIII and BsiWI (κ-type) sites.

The nucleotide sequence of VH and the nucleotide sequence of VL of the 18C1 antibody inserted are represented by SEQ ID NOs: 5 and 11, respectively, and the amino acid sequence of VH and the amino acid sequence of VL expressed thereby are represented by SEQ ID NOs: 8 and 14, respectively. The nucleotide sequence of VH and the nucleotide sequence of VL of the 12H3 antibody inserted are represented by SEQ ID NOs: 6 and 12, respectively, and the amino acid sequence of VH and the amino acid sequence of VL expressed thereby are represented by SEQ ID NOs: 9 and 15, respectively. The nucleotide sequence of VH and the nucleotide sequence of VL of the 11H10 antibody inserted are represented by SEQ ID NOs: 7 and 13, respectively, and the amino acid sequence of VH and the amino acid sequence of VL expressed thereby are represented by SEQ ID NOs: 10 and 16, respectively.

PCR was carried out using primers composed of nucleotide sequences represented by SEQ ID NOs: 53 to 56, respectively, in the amplification of the nucleotide sequences of VL and VH of the 18C1 antibody, primers composed of nucleotide sequences represented by SEQ ID NOs: 57 to 60, respectively, in the amplification of the nucleotide sequences of VL and VH of the 12H3 antibody, and primers composed of nucleotide sequences represented by SEQ ID NOs: 61 to 64, respectively, in the amplification of the nucleotide sequences of VL and VH of the 11H10 antibody.

A recombinant chimeric antibody was expressed using the produced expression vector and Expi293F Expression System Kit (manufactured by Life Technologies Corporation). The antibody was purified from the culture supernatant using Mab Select SuRe (manufactured by GE Healthcare, Inc.). After replacing the buffer with D-PBS(−) (manufactured by Nacalai Tesque, Inc., Cat #14249-24) using a NAP-25 column (manufactured by GE Healthcare, Inc.), the concentration of the antibody was determined by measuring the absorbance at 280 nm. As the molecular extinction coefficient, 1.50 mL/(mg·cm) was used.

5-5) Evaluation of Binding Activity of Anti-BMP10 Chimeric Antibody to Human BMP10 Protein by Biacore For the purpose of comparing the binding activity to human BMP10 between the anti-BMP10 chimeric antibody obtained in Example 5-4 and MAB2926 (R & D Systems, Inc.) that is a known antibody, the binding activity to a human BMP10 mature dimer (manufactured by R & D Systems, Cat #2926-BP) was measured by a surface plasmon resonance method (SPR method) using Biacore T100 (manufactured by GE Healthcare Bio-Sciences Corporation).

The binding activity of the chimeric antibody was measured as follows. An anti-human IgG antibody was immobilized on a CM5 sensor chip (manufactured by GE Healthcare Bio-Sciences, Inc., BR100530) using Human Antibody Capture Kit (manufactured by GE Healthcare Bio-Sciences Corporation, Cat # BR-1008-39) according to the attached protocol. To a flow cell in which the anti-human IgG antibody was immobilized, the 18C1 chimeric antibody (hereinafter referred to as ch18C1 antibody) or the 12H3 chimeric antibody (hereinafter referred to as ch12H3 antibody) or the 11H10 chimeric antibody (hereinafter referred to as ch11H10 antibody) prepared at 5 µg/mL was added at a flow rate of 10 µL/min for 10 seconds.

Further, subsequently, human mature BMP10 prepared at 5 concentrations by 3-fold serial dilution from 300 ng/mL was added thereto at a flow rate of 30 µL/min, and a binding reaction was monitored for 1 minute and a dissociation reaction was monitored for 30 minutes. The obtained sensorgram was analyzed using Bia Evaluation Software (manufactured by GE Healthcare Bio-Sciences Corporation), and the kinetic constant of each antibody was calculated.

The binding activity of MAB2926 was measured as follows. An anti-mouse IgG antibody was immobilized on a CM5 sensor chip (manufactured by GE Healthcare Bio-Sciences, Inc., BR100530) using Mouse Antibody Capture Kit (manufactured by GE Healthcare Bio-Sciences Corporation, Cat # BR-1008-38) according to the attached protocol. To a flow cell in which an anti-mouse IgG antibody was immobilized, MAB2926 prepared at 5 µg/mL was added at a flow rate of 10 µL/min for 10 seconds.

Further, subsequently, human mature BMP10 protein prepared at 5 concentrations by 3-fold serial dilution from 300 ng/mL was added thereto at a flow rate of 30 µL/min, and a binding reaction was monitored for 1 minute and a dissociation reaction was monitored for 30 minutes. The obtained sensorgram was analyzed using Bia Evaluation Software (manufactured by GE Healthcare Bio-Sciences Corporation), and the kinetic constant of MAB2926 was calculated. The calculated association rate constant (ka), dissociation rate constant (kd), and dissociation constant $[kd/ka=K_D]$ of each antibody are shown in Table 1.

TABLE 1

| Antibody name | ka | kd | KD |
|---|---|---|---|
| MAB2926 | 4.06E+07 | 0.001343 | 3.31E-11 |
| ch11H10 antibody | 3.22E+07 | 2.02E-04 | 6.26E-12 |
| ch12H3 antibody | 1.31E+07 | 1.54E-04 | 1.18E-11 |
| ch18C1 antibody | 3.88E+07 | 1.02E-04 | 2.62E-12 |

* ka exceeds the detection limit of the apparatus, and therefore, the value is shown for reference only.

As shown in Table 1, it was revealed that the obtained ch18C1 antibody, ch12H3 antibody, and ch11H10 antibody exhibit stronger binding than the known antibody MAB2926.

[Example 6] Analysis of Receptor with which Obtained Antibody Competes 6-1) Preparation of ALK1-Fc
ALK1-Fc was prepared according to the method described in Example 1 of WO 2010/126169.
6-2) Analysis of Competing Receptor by Biacore
BMP10 transmits a signal by binding to two receptors: type I and type II. In order to analyze which receptor the obtained anti-BMP10 antibody competes with, measurement was carried out by a surface plasmon resonance method (SPR method) using Biacore T100 (manufactured by GE Healthcare Bio-Sciences Corporation).

An anti-human IgG antibody was immobilized on a CM5 sensor chip (manufactured by GE Healthcare Bio-Sciences, Inc., BR100530) using Human Antibody Capture Kit (manufactured by GE Healthcare Bio-Sciences Corporation, Cat # BR-1008-39) according to the attached protocol.

To a flow cell in which the anti-human IgG antibody was immobilized, any of ALK1-Fc, BMPR2-Fc (manufactured by R & D Systems, Inc., Cat #811-BR-100), and Endoglin-Fc (manufactured by R & D Systems, Inc., Cat. #6578-EN-025) prepared at 10 µg/mL was added at a flow rate of 10 µL/min for 10 seconds.

Further, subsequently, a mixture of human mature BMP10 (manufactured by R & D Systems, Inc., Cat #2926-BP) prepared at 100 ng/mL and 1 µg/mL of an anti-BMP10 antibody was added thereto at a flow rate of 10 µL/min for 30 seconds.

The results are shown in Table 2. In Table 2, a case where the mixture of the antibody with the mature BMP10 binds to the captured ALK1-Fc, BMPR2-Fc, or Endoglin-Fc is denoted by "+", and a case where it does not bind thereto is denoted by "−".

TABLE 2

| Antibody name | ALK1-Fc | BMPR2-Fc | Endoglin-Fc |
|---|---|---|---|
| MAB2926 | − | + | + |
| 11H10 antibody | + | − | − |
| 12H3 antibody | + | − | − |
| 18C1 antibody | + | − | − |

As shown in Table 2, it can be said that in the case where the mixture of the mature BMP10 and the antibody does not bind to the captured receptor, the antibody and the receptor compete with each other. As a result, it was found that MAB2926 inhibits the binding of BMP10 to ALK1-Fc.

On the other hand, MAB2926 did not inhibit the binding of BMP10 to BMPR2-Fc and Endoglin-Fc. The 18C1 antibody, the 12H3 antibody, and the 11H10 antibody all did not inhibit the binding of BMP10 to ALK1-Fc. On the other hand, the 18C1 antibody, the 12H3 antibody, and the 11H10 antibody all inhibited the binding of BMP10 to BMPR2-Fc and Endoglin-Fc.

From the above results, it was revealed that the 18C1 antibody, the 12H3 antibody, and the 11H10 antibody are antibodies having a novel inhibitory mode of inhibiting a different receptor from the known antibody.

[Example 7] Evaluation of Effect of Obtained Antibody on Blood Pressure of Normal Animal The effect of the 18C1 antibody on blood pressure was evaluated using SD rats. Male SD rats (manufactured by Charles River Laboratories Japan, Inc.) at 6 weeks of age were purchased and used for an experiment. The rats were given sterile tap water as drinking water and chow FR-2 (manufactured by Funabashi Farm Co., Ltd.) as feed ad libitum. After acclimation, the rats underwent surgery for implantation of a telemetry transmitter at 7 weeks of age.

Specifically, the rats were anesthetized by administering 50 mg/kg of pentobarbital sodium (manufactured by Tokyo Chemical Industry Co., Ltd.) to the abdominal cavity of each rat. A blood pressure sensor of a telemetry transmitter (TA11PA-C40, Data Sciences International) was inserted into the abdominal aorta, and the transmitter body was implanted into the abdominal cavity. By observation of general conditions and hemodynamic monitoring, it was confirmed that the rats were recovered satisfactorily from the effect of the surgery. The animals implanted with the telemetry transmitter were grouped using the average value of the systolic blood pressure as an index. Administration of an antibody was carried out at 12 weeks of age.

Specifically, a solution in which the 18C1 antibody was prepared at 1 mg/mL with PBS was administered at a dose of 1 mL/kg. Further, a solution in which the 12H3 antibody or the 11H10 antibody was prepared at 5 mg/mL with PBS was administered at a dose of 1 mL/kg. The administration was carried out through a subcutaneous route. The signal of the blood pressure waveform sent from the transmitter was received by a receiving board (RPC-1, Data Sciences International) installed under the cage. The signal was incorporated into a data acquisition/analysis system (DATAQUEST ART Gold ver. 2.30, Data Sciences International) via Data Exchange Matrix (Data Sciences International), and the measurement data of the systolic blood pressure for 10 seconds was obtained every 5 minutes. The results are shown in FIG. 4A to FIG. 4C.

Figure 4:
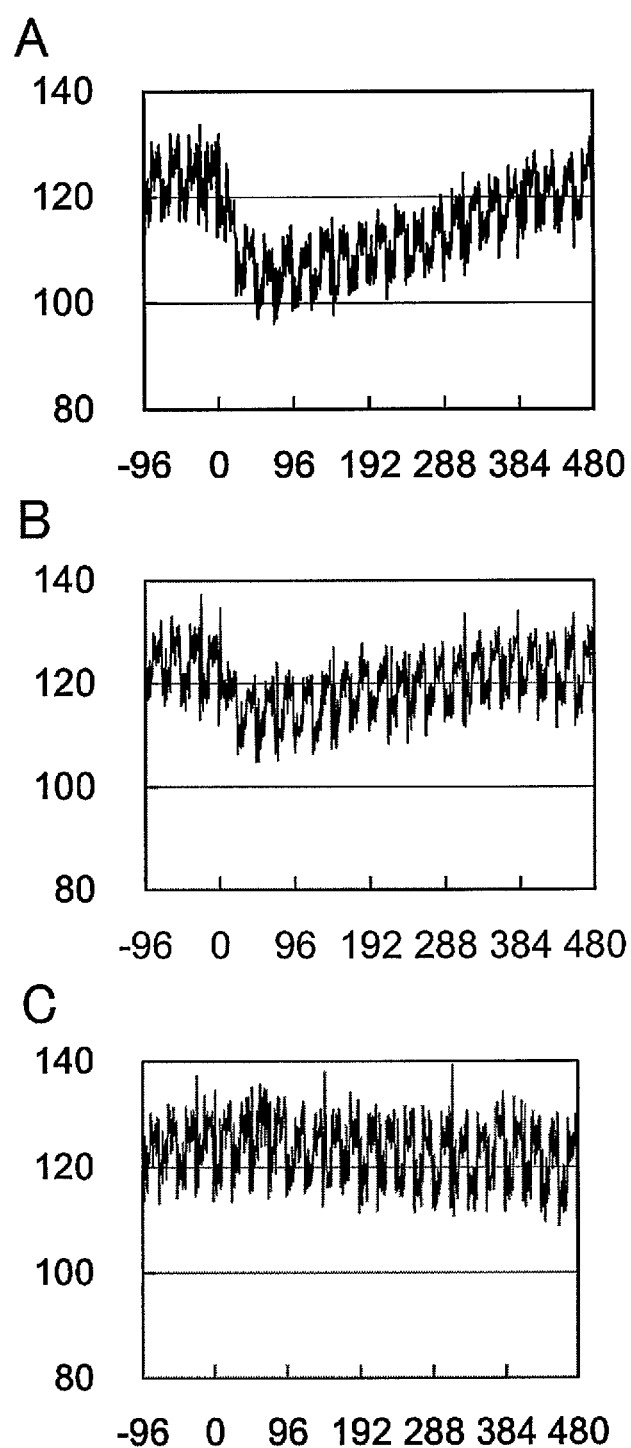
FIG. 4A to FIG. 4C are figures showing the effect on the systemic blood pressure of normal rats by single administration of obtained anti-BMP10 antibodies. The graph of FIG. 4A shows a change in systolic blood pressure by single administration of 18C1 antibody. The graph of FIG. 4B shows a change in systolic blood pressure by single administration of 12H3 antibody. The graph of FIG. 4C shows a change in systolic blood pressure by single administration of 11H10 antibody. The horizontal axis of the graph represents the elapsed time when the time at which the antibody was administered was set as 0 hour, and the vertical axis represents the systolic blood pressure (mmHg).

As shown in FIG. 4A and FIG. 4B, a decrease in the systolic blood pressure was observed by the administration of the 18C1 antibody or the 12H3 antibody. Further, the antihypertensive effect of the 18C1 antibody was stronger than that of the 12H3 antibody. On the other hand, as shown in FIG. 4C, in the administration of the 11H10 antibody, an effect on the systolic blood pressure was not observed. From the above results, it was newly found that the anti-BMP10 antibody has an antihypertensive effect.

In addition, it was found that the antihypertensive effect correlates with the BMP10 neutralizing activity in vitro of the antibody, and in the 11H10 antibody having a relatively weak neutralizing activity, an antihypertensive effect is not observed. Based on this, it was newly found that only an antibody having a strong BMP10 neutralizing activity has an antihypertensive effect.

[Example 8] Evaluation of Effect of 18C1 Antibody on Blood Pressure of Spontaneously Hypertensive Rat In order to examine the antihypertensive effect of the obtained antibody on a hypertensive animal, the effect of the 18C1 antibody on blood pressure was evaluated using male spontaneously hypertensive rats (SHR/Izm, Japan SLC, Inc.).

Male SHR/Izm rats (Japan SLC, Inc.) at 14 weeks of age were purchased and used for an experiment. The rats were given sterile tap water as drinking water and chow FR-2 (manufactured by Funabashi Farm Co., Ltd.) as feed ad libitum. After acclimation, the rats underwent surgery for implantation of a telemetry transmitter at 16 weeks of age. The method for the surgery for implantation of a telemetry transmitter and the acquisition of the blood pressure waveform were carried out according to Example 7. A solution in which the 18C1 antibody was prepared at 5 mg/mL with PBS was administered to the rats at 21 weeks of age at a dose of 1 mL/kg. The administration was carried out through a subcutaneous route. The results are shown in FIG. 5.

Figure 5:
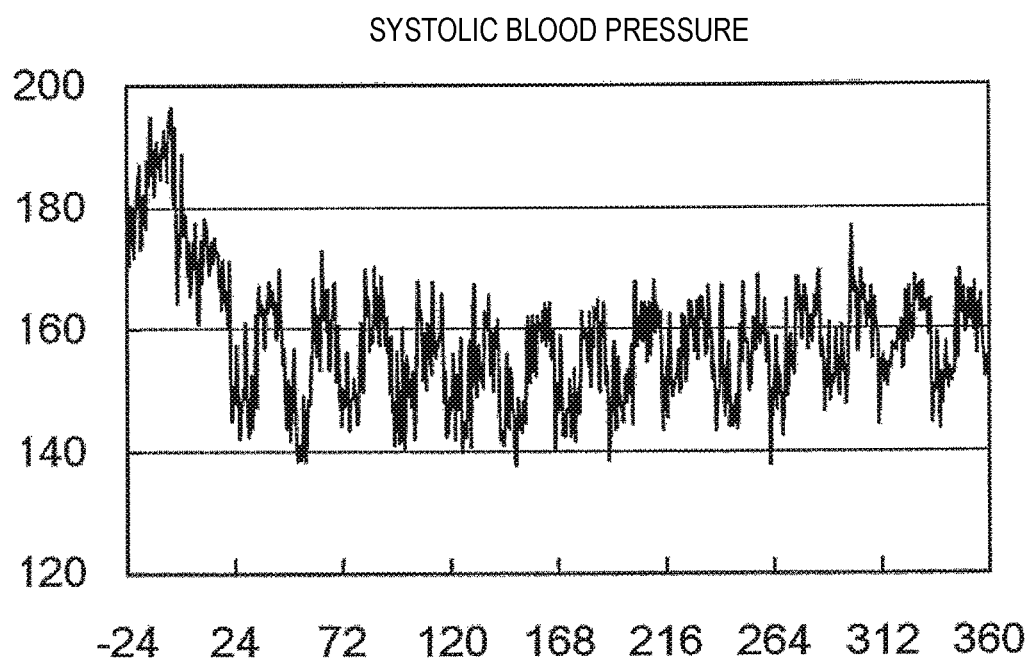
FIG. 5 is a figure showing the effect on the blood pressure of spontaneously hypertensive rats by single administration of 18C1 antibody that is an obtained anti-BMP10 antibody. The graph of FIG. 5 shows a change in systolic blood pressure. The horizontal axis of the graph represents the elapsed time when the time at which the antibody was administered was set as 0 hour, and the vertical axis represents the systolic blood pressure (mmHg).

As shown in FIG. 5, by the administration of the 18C1 antibody at 5 mg/kg, it was observed that the systolic blood pressure is persistently decreased during about one month. From the above results, it was demonstrated that neutralization of BMP10 has a therapeutic effect on hypertensive pathology.

[Example 9] Evaluation of Effect of 18C1 Antibody on Dahl Salt-Sensitive Rat

The effect of the BMP10 antibody on hypertension and a cardiac or renal disorder induced by giving high salt to Dahl salt-sensitive rats (hereinafter, Dahl-S rats) was evaluated. Male Dahl salt-sensitive rats (DIS/Eis:Slc) (manufactured by Japan SLC, Inc.) at 5 weeks of age were purchased and used for an experiment.

The rats were given FR-2 feed (manufactured by Funabashi Farm Co., Ltd.) until 6 weeks of age, and thereafter given a high salt feed (8% NaCl-containing FR-2 feed, manufactured by Oriental Yeast Co., Ltd.). As a normal control group, Dahl-S rats given a normal diet (FR-2 feed) also after 6 weeks of age were used. As drinking water, drinking water for animals was given ad libitum.

The blood pressure and heart rate were measured at 8 weeks of age. The measurement of the blood pressure and heart rate was carried out after each acclimation for measurement twice using a mouse-rat non-invasive sphygmomanometer (BP-98E, manufactured by Softron Co., Ltd.). The high salt feed group was divided into two groups each consisting of 12 rats using the body weight, blood pressure, and heart rate at 8 weeks of age as indices, and the vehicle (PBS 1 mL/kg) or the 18C1 antibody at a dose of 5 mg/kg was subcutaneously administered at a frequency of once a week.

At 16 weeks of age, measurement of the blood pressure, echocardiography, and measurement of urine parameters were carried out. Further, the blood was collected from the abdominal aorta under isoflurane inhalation anesthesia, and autopsy was carried out after the rats were sacrificed by bleeding. The heart, lung, and bilateral kidneys were excised, and the tissue weight was measured.

The echocardiography was carried out using an ultrasound high-resolution imaging system for small animals (Vevo 2100, manufactured by VisualSonics, Inc.) and a high frequency high frame rate probe (MS-200, manufactured by VisualSonics, Inc.) with ultrasonic waves at a central frequency of 15.0 MHz after shaving the anterior thorax of each rat under isoflurane inhalation anesthesia. The left ventricular posterior wall thickness (LVPW; s, LVPW; d) was measured at the papillary muscle level by the M-mode method. The mitral annulus velocity (e') was measured by a tissue Doppler method in which a sample volume was placed on the mitral annulus.

Urine collection was carried out for 24 hours in a metabolic cage (T-480, manufactured by Tokiwa Kagaku Kikai Co., Ltd.) with feeding and drinking ad libitum. A urine sample was centrifuged at 1870×g and 4° C. for 15 minutes after the urine volume was measured, and the supernatant was used for measurement. The urine parameters were measured using an automatic analyzer Hitachi 7170S (manufactured by Hitachi, Ltd.) or a fully automatic electrolyte analyzer [PVA-EXII manufactured by A& T Co., Ltd.].

The collected heart, aorta, and kidney were subjected to a histopathological analysis. Specifically, the collected heart, aorta, and kidney were fixed with a 10 vol % neutral buffered formalin solution. A section was prepared from a paraffin-embedded block according to a usual method and subjected to Masson trichrome (MT) staining or Hematoxylin-Eosin (HE) staining.

As for the renal glomerular damage pathology score, HE-stained specimens were observed under a light microscope, and the area ratio of lesion per glomerulus (mesangial expansion, glomerular sclerosis, and/or glomerular capillary collapse) with respect to 100 or more glomeruli as test subjects for each individual was graded into the following five levels (0: normal, 1: 1 to 25%, 2: 26 to 50%, 3: 51 to 75%, and 4: 76 to 100%). Thereafter, a glomerular lesion score (the sum of "the score points of each grade"×"the ratio of glomeruli for each grade") for each individual was calculated. In a statistical analysis, the number of glomeruli with a score of 1 or more was compared.

As for a renal tubulointerstitial damage pathology score, HE-stained specimens were observed under a light microscope, and the ratio of renal tubular and interstitial lesions (basophilic tubule, hyaline cast, interstitial inflammation and/or tubular dilatation) in each section to the area of each section was graded into the following five levels (0: normal, 1: 1 to 25%, 2: 26 to 50%, 3: 51 to 75%, and 4: 76 to 100) for each individual.

The results are shown in FIGS. 6 to 13.

Figure 6:
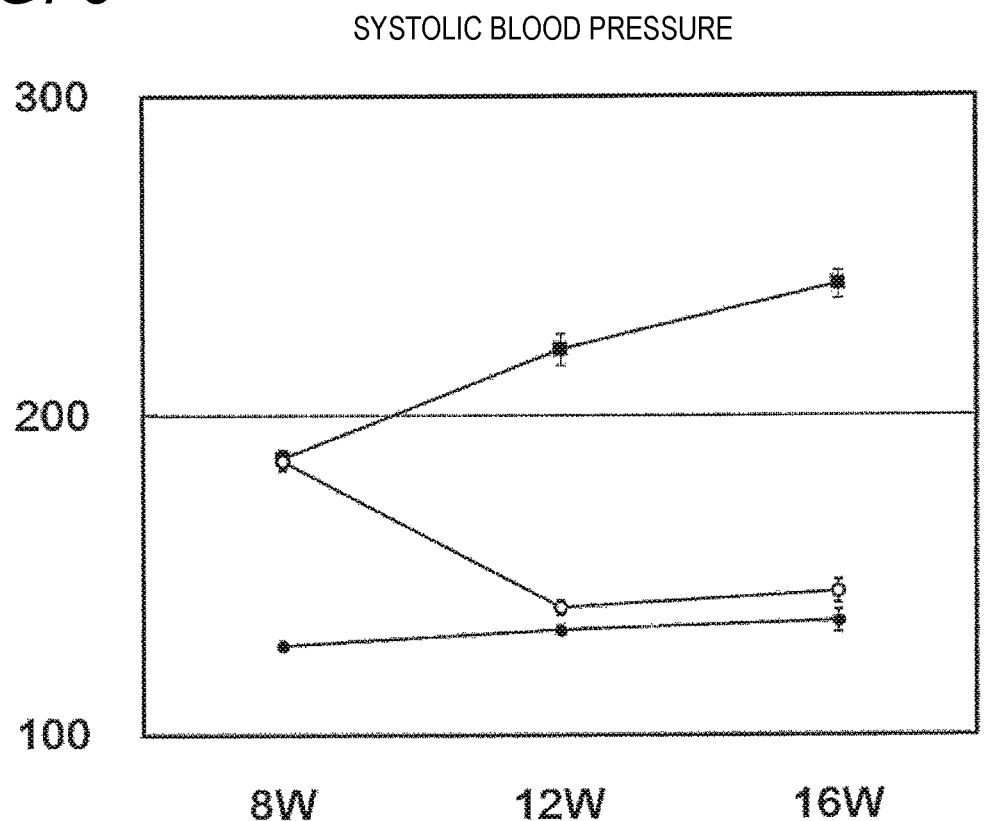
FIG. 6 is a figure showing the effect of 18C1 antibody that is an obtained anti-BMP10 antibody on the systolic blood pressure of Dahl salt-sensitive hypertensive rats. The graph of FIG. 6 shows a change in systolic blood pressure. The horizontal axis of the graph represents the weeks of age (w) of the rats, and the vertical axis represents the systolic blood pressure (mmHg). Black circles indicate a normal diet group (n=6), black squares indicate a high salt group (n=12), and white circles indicate a high salt diet+18C1 antibody group (n=12). Error bars in the figure indicate the standard error (SE).

As shown in FIG. 6, the blood pressure of the Dahl-S rats was remarkably increased by the high salt diet. By administration of the 18C1 antibody, the high blood pressure of the Dahl-S rats induced by the high salt diet was reduced to a level equivalent to that of the normal diet group.

Further, as shown in FIG. 7A and FIG. 7B, both the blood sodium level and the urine sodium excretion of the Dahl-S rats were increased by the high salt diet. By administration of the 18C1 antibody, the urine sodium excretion was further increased. In addition, by administration of the 18C1 antibody, the blood sodium level was normalized to a level equivalent to that of the normal diet group. From the above results, it was revealed that the anti-BMP10 antibody exhibits a remarkable effect on sodium retention and high blood pressure caused by the high salt diet in the Dahl-S rats.

Figure 8:
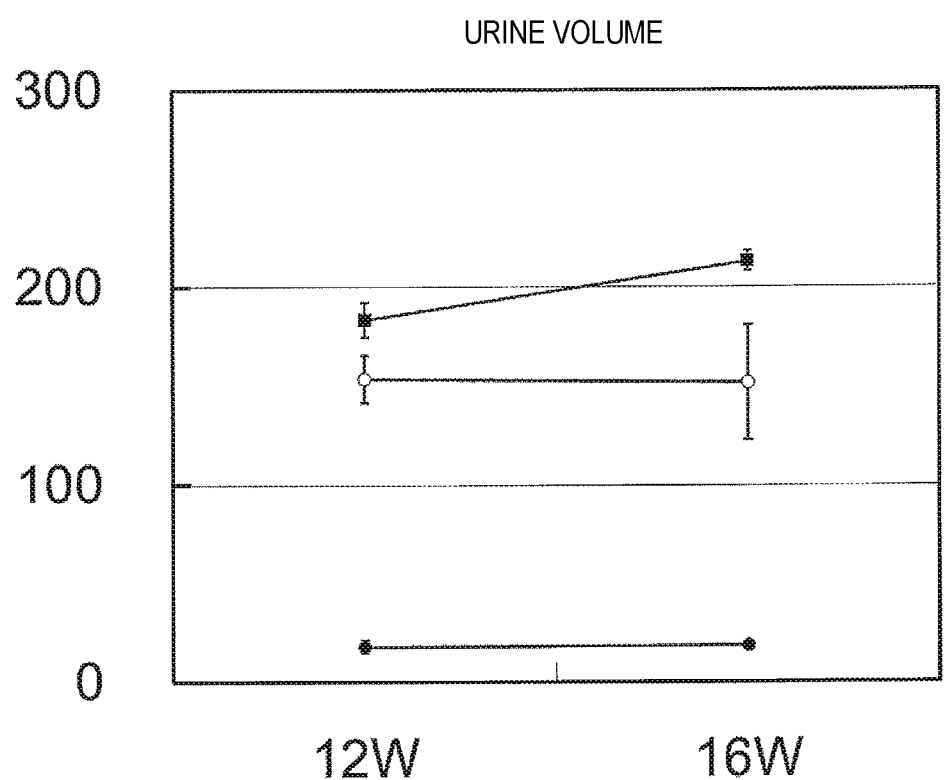
FIG. 8 shows a change in urine volume per day in Dahl salt-sensitive hypertensive rats by 18C1 antibody that is an obtained anti-BMP10 antibody. The horizontal axis of the graph represents the weeks of age (w) of the rats, and the vertical axis represents the urine volume per body weight per day (mL/Kg/day). Black circles indicate a normal diet group (n=6), black squares indicate a high salt group (n=12), and white circles indicate a high salt diet+18C1 antibody group (n=12). Error bars in the figure indicate the standard error (SE).

On the other hand, as shown in FIG. 8, the urine volume of the Dahl-S rats was increased by the high salt diet and decreased by the anti-BMP10 antibody. That is, it was demonstrated that the anti-BMP10 antibody has an effect of normalizing the renal sodium excretion disorder in the salt-sensitive pathological conditions, and it was suggested that the antibody has a mode of action different from a diuretic agent which increases the urine volume.

Figure 9:
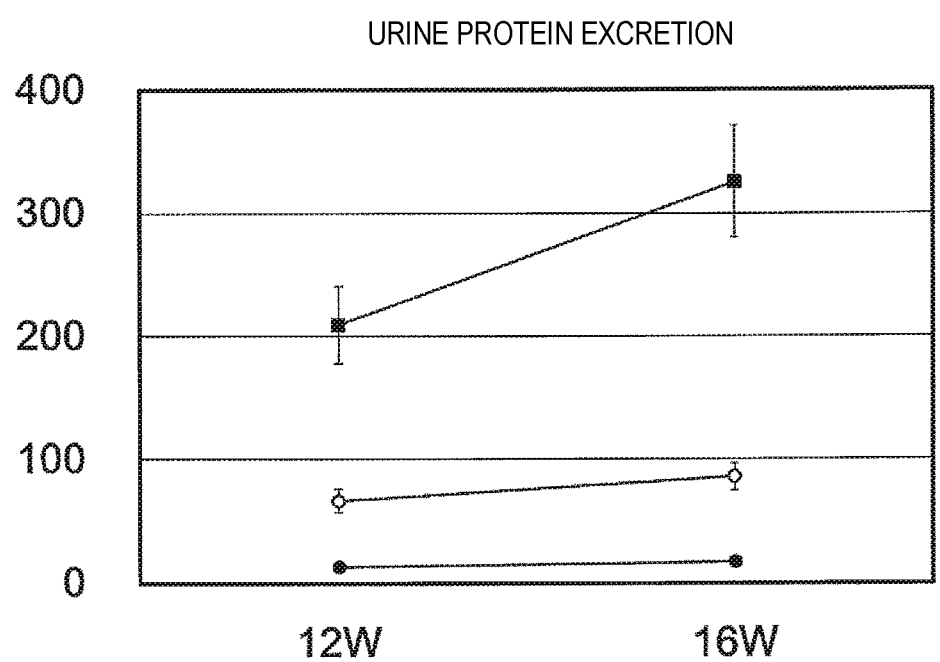
FIG. 9 is a figure showing the effect of 18C1 antibody that is an obtained anti-BMP10 antibody on a renal function in Dahl salt-sensitive hypertensive rats.
Figure 10:
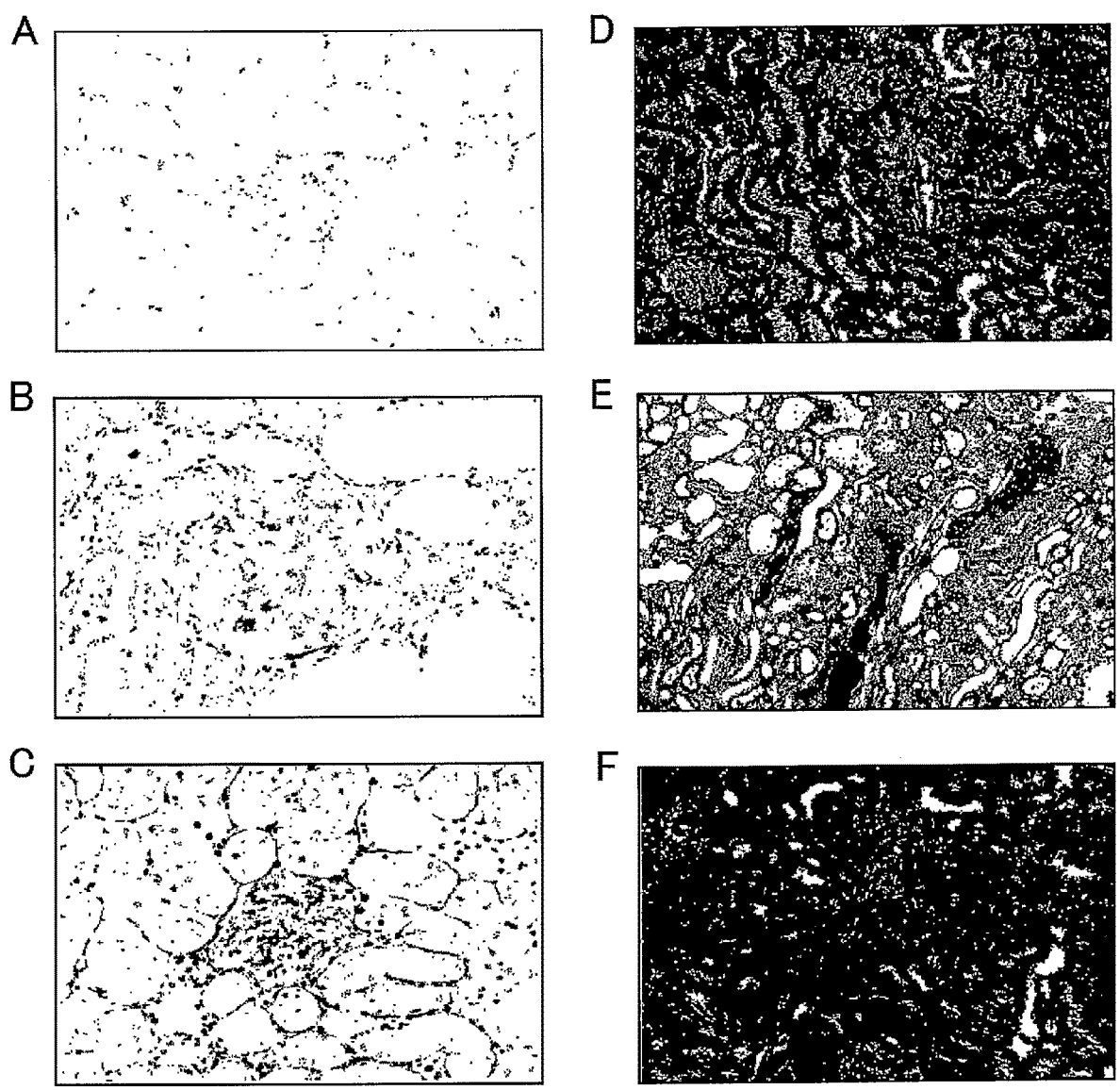
FIG. 10A to FIG. 10F are figures showing the effect of 18C1 antibody that is an obtained anti-BMP10 antibody on a renal function in Dahl salt-sensitive hypertensive rats.

As shown in FIG. 9, an increase in urine protein excretion was observed in the high salt diet group as compared with the normal diet group. In addition, as shown in FIG. 10A, FIG. 10B, and FIG. 11B, hyaline casts, basophilic tubules, and tubular dilation were observed in the kidney in the high salt diet group, and it was confirmed that the renal tubulointerstitium is remarkably impaired. Further, as shown in FIG. 10D, FIG. 10E, and FIG. 11A, a glomerular hyaline deposit was observed in the high salt diet group, and it was confirmed that the renal glomerulus was remarkably impaired. On the other hand, as shown in FIG. 9, FIG. 10C, and FIG. 10F, in the high salt diet+18C1 antibody administration group, the increase in urine protein excretion, the renal glomerular disorder, and the renal tubulointerstitial disorder were dramatically suppressed.

From the above results, it was suggested that the anti-BMP10 antibody has a therapeutic effect on a glomerular disorder and a tubulointerstitial disorder caused by high blood pressure.

As shown in FIG. 12A, thickening of the left ventricular posterior wall was observed in the high salt diet group as compared with the normal diet group. Further, as shown in FIG. 12B, in the high salt diet group, a decrease in the index e' of the left ventricular diastolic function was observed as compared with the normal diet group, and it was demonstrated that cardiac diastolic dysfunction has occurred.

Figure 13:
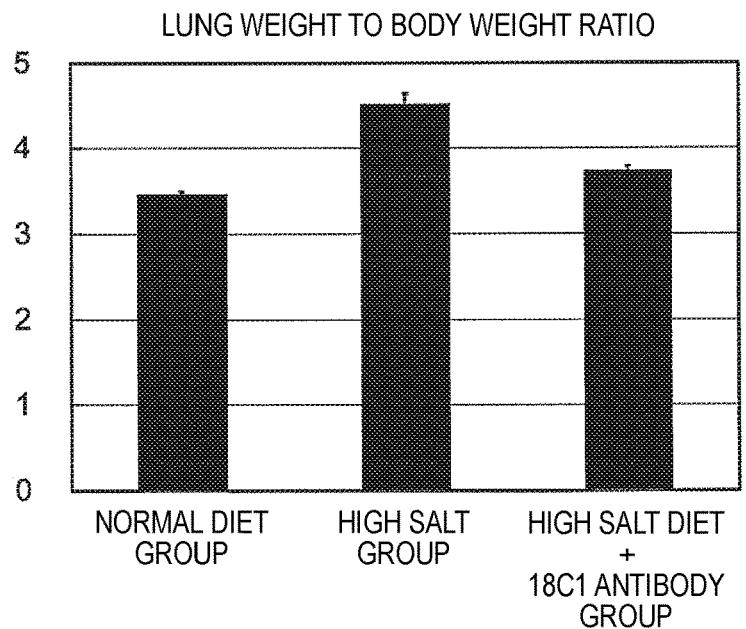
FIG. 13 is a figure showing the effect of 18C1 antibody that is an obtained anti-BMP10 antibody on a cardiac function in Dahl salt-sensitive hypertensive rats.

As shown in FIG. 13, an increase in the lung weight was observed in the high salt diet group, and it was suggested that pulmonary congestion due to left ventricular diastolic dysfunction has occurred. On the other hand, as shown in FIG. 12A, FIG. 12B, and FIG. 13, in the high salt diet+18C1 antibody administration group, the left ventricular posterior wall thickness, e', and lung weight were maintained at a level equivalent to that of the normal diet group.

From the above results, it was suggested that the anti-BMP10 antibody has a therapeutic effect on diastolic heart failure caused by high blood pressure.

[Example 10] Evaluation of Neutralizing Activity of Anti-BMP10 Antibody Against Human Serum As a ligand for ALK1, BMP9 is also known other than BMP10. For the purpose of evaluating the neutralizing activity against BMP9 and BMP10 in blood, the neutralizing activity against human ALK1 expressing reporter cells when stimulating with human serum was compared.

10-1) Acquisition of 10D5 Antibody that is Anti-BMP9 Antibody

An anti-BMP9 antibody 10D5 was prepared according to the method described in Example 7 of WO 2014/007198.

10-2) Comparison of BMP10 Neutralizing Activity Between Obtained Antibody and Known Antibody To a 96-well fluorescence and luminescence plate (manufactured by Corning, Inc., Cat #3916), human serum (Human True A serum, pool of donors, manufactured by Biopredic International, Cat # SER019) was added at a final concentration of 5%.

Subsequently, the 18C1 antibody, the 12H3 antibody, or the 1H10 antibody, each of which is an anti-BMP10 antibody, the 10D5 antibody, which is an anti-BMP9 antibody, or a control antibody (Purified Rat IgG1 λ Isotype control, manufactured by BD, Inc., Cat #553993), or a mixture of an anti-BMP9 antibody and an anti-BMP10 antibody was added thereto. As the mixture of an anti-BMP9 antibody and an anti-BMP10 antibody, a mixture of the 12H3 antibody and the 10D5 antibody or a mixture of the 11H10 antibody and the 10D5 antibody was used.

As for the antibody, each antibody was prepared at 5 serial concentrations by 3-fold dilution from the final concentration of 10000 ng/mL regardless of whether it is mixed or not, and added. Thereafter, an ALK1/Id1-Luc/CHO cell suspension was added at $5 \times 10^4$ cells/well. All samples were diluted with Excell 325 medium so as to achieve 100 μL/well in the end when combining the human serum, the antibody dilution solution, and the cell suspension. The liquid in the well was made uniform with a plate mixer, and the cells were cultured at 37° C. for 20 hours.

After 20 hours, an assay solution of Nano-Glo Luciferase Assay prepared according to the package insert was added at 40 μL/well, followed by stirring, and then, a luciferase activity was measured using Glomax (manufactured by Promega Corporation). The neutralizing activity (%) of the antibody was calculated by setting the value of the well in which only the serum was added without adding an antibody to be 0%, and the value of the well in which only Excell 325 medium was added without adding an antibody to be 100%.

Figure 14:
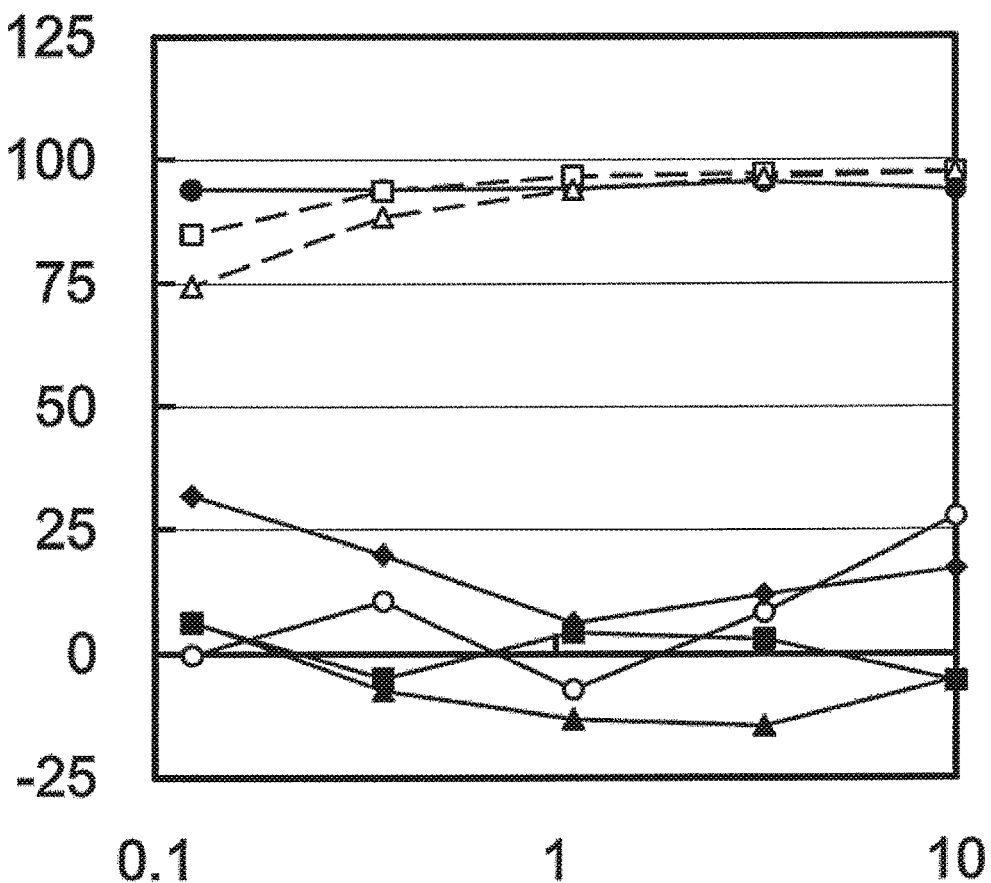
FIG. 14 is a figure showing that a BMP9/BMP10 heterodimer is present in human blood, and 18C1 antibody that is an obtained anti-BMP10 antibody has a neutralizing activity against the BMP9/BMP10 heterodimer.

As a result, as shown in FIG. 14, the control antibody, the 12H3 antibody and the 11H10 antibody, each of which is an anti-BMP10 antibody, and the 10D5 antibody, which is an anti-BMP9 antibody all did not exhibit a neutralizing activity against human serum. On the other hand, the mixture of the 12H3 antibody and the 10D5 antibody and the mixture of the 11H10 antibody and the 10D5 antibody exhibited a distinct neutralizing activity against human serum.

From the above results, it was suggested that a human BMP9/BMP10 heterodimer is present in human serum. Further, the 18C1 antibody which is an anti-BMP10 antibody exhibited a neutralizing activity against human serum alone. This result suggested that the 18C1 antibody is a novel antibody having a strong neutralizing activity against a human BMP9/BMP10 heterodimer present in human serum.

[Example 11] Detection of BMP9/BMP10 Heterodimer in Human Blood

In order to detect the BMP9/BMP10 heterodimer suggested in Example 10, sandwich ELISA was carried out using an anti-BMP9 antibody and an anti-BMP10 antibody.
11-1) Biotinylation of 12H3 Antibody The 12H3 antibody which is an anti-BMP10 antibody was biotinylated for being used as a detection antibody in sandwich ELISA. The biotinylation was carried out using Biotin Labeling Kit-NH2 kit (Cat # LK03) manufactured by Dojindo Laboratories. The method was carried out in accordance with the attached document described on the product.
11-2) Sandwich ELISA Using Anti-BMP9 Antibody and Anti-BMP10 Antibody A solution in which the 10D5 antibody which is an anti-BMP9 antibody, the 11H10 antibody which is an anti-BMP10 antibody, or a control antibody (Purified Mouse IgG1 κ Isotype control, manufactured by BD, Inc., Cat #554121) was diluted to 3 μg/mL with a carbonate-bicarbonate buffer (50 mM NaHCO₃pH 9.6, Sigma-Aldrich Co. LLC, Cat #C3041) was added as an immobilizing solution to a 96-well ELISA plate (F96 MAXISORP NUNC-IM-MNO PLATE, manufactured by Thermo Fisher Scientific, Inc., Cat #442404) at 100 μL/well, and adsorption was carried out by leaving the plate to stand overnight at 4° C.

After the antibody solution was removed, 1% BSA-PBS was added at 300 μL/well, and blocking was carried out by leaving the plate to stand at room temperature for 1 hour, followed by washing 5 times with PBST. Subsequently, a solution obtained by diluting human serum (Human True A serum, pool of donors, manufactured by Biopredic International, Cat # SER019) to a final concentration of 1%, 2%, 4%, 8%, or 16% with 0.1% BSA-PBST was added at 100 VL/well, and the plate was left to stand at room temperature for 1 hour to cause a reaction, followed by washing 5 times with PBST.

Subsequently, a solution in which the biotinylated 12H3 antibody produced in Example 11, 11-1) was prepared at 50 ng/mL with 0.1% BSA-PBST was dispensed at 100 μL/well, and the plate was left to stand at room temperature for 1 hour. After this plate was washed 5 times with PBST, Streptavidin-PolyHRP80, Pre-diluted in Stabilizer (1/20) (manufactured by Stereospecific Detection Technologies GmbH, Cat # SP80D50) diluted 500 times with 0.1% BSA-PBST was added at 100 μL/well, and the plate was left to stand at room temperature for 1 hour.

The plate was washed 5 times with PBST, a TMB substrate solution (TMB+Substrate-Chromogen, manufactured by Dako, Inc., Cat # S1599) was added at 50 μL/well so as to develop a color. When appropriate color development was obtained, a 1 N sulfuric acid solution (manufactured by Wako, Cat #192-04755) was added at 50 μL/well, and an absorbance at 450 and 570 nm was measured using Multiskan Spectrum (manufactured by Thermo Labsystems, Inc.). The results are sown in FIG. 15.

Figure 15:
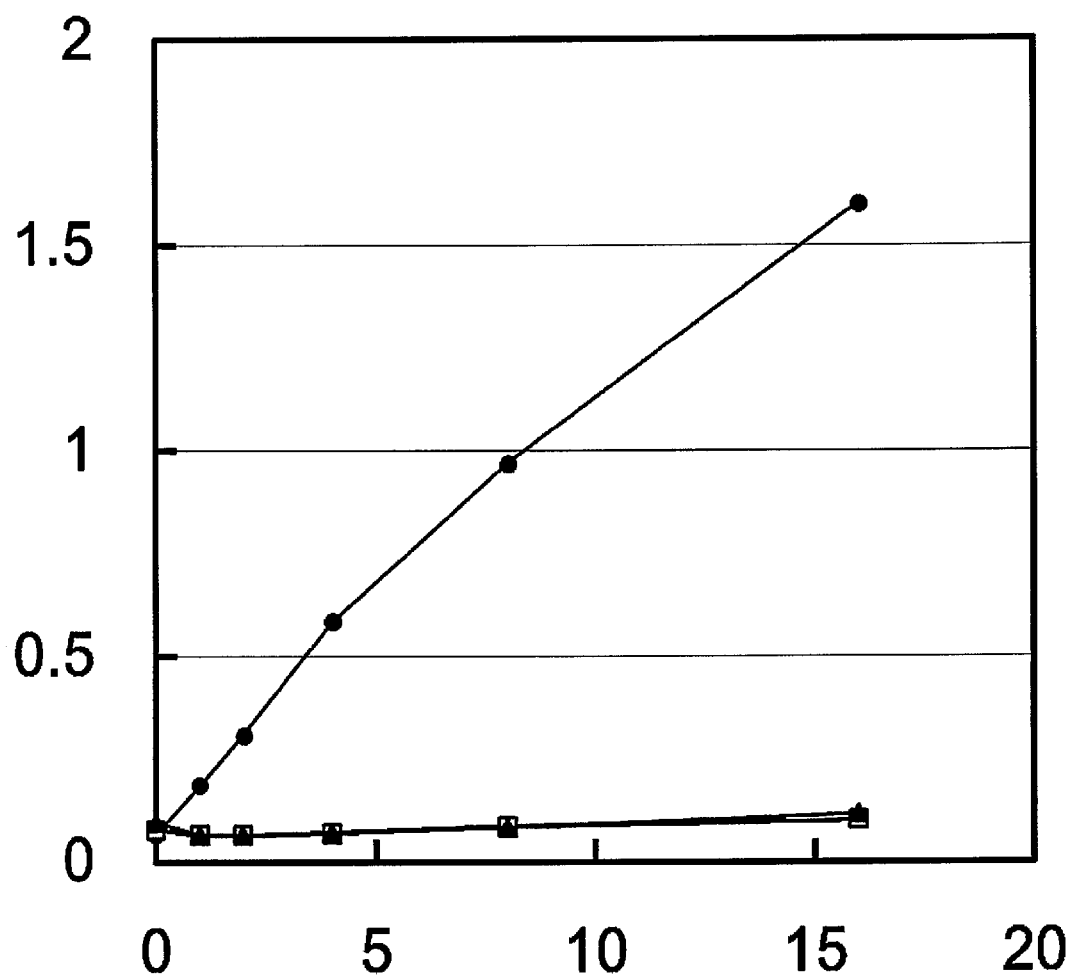
FIG. 15 is a figure showing that a BMP9/BMP10 heterodimer is present in blood.

As shown in FIG. 15, when the control antibody and the 11H10 antibody which is an anti-BMP10 antibody were immobilized, a reaction for the serum was not observed. On the other hand, when the 10D5 antibody which is an anti-BMP9 antibody was immobilized, a distinct reaction was observed in a serum concentration dependent manner. From the above results, it was suggested that a BMP9/BMP10 heterodimer that is simultaneously recognized by the anti-BMP9 antibody and the anti-BMP10 antibody is present in human serum.

[Example 12] Production of Humanized Antibody of 18C1 Antibody (1) Designing of Amino Acid Sequences of VH and VL of 18C1 Humanized Antibody By the method described below, the amino acid sequences of various VH and VL of 18C1 humanized antibodies were designed. In the following description, the 18C1 humanized antibodies having amino acid sequences of various VH and VL are collectively referred to as hz18C1 antibody. As the amino acid sequence of a framework (hereinafter referred to as FR) of a known human antibody suitable for grafting the amino acid sequence of a CDR of the 18C1 antibody, hSGHII and V1-22 were selected from human FR consensus sequences and human antibody germline sequences reported by Kabat et al. [Sequences of Proteins of Immunological Interest, US Dept. Health and Human Services (1991)], and the CDR was to be grafted into FR thereof.

The amino acid sequences of CDRs 1 to 3 of 18C1 VH represented by SEQ ID NOs: 29, 30, and 31, respectively, were grafted into appropriate positions of the amino acid sequence of FR of hSGHII, whereby hz18C1 HV0 (SEQ ID NO: 70) was designed. In addition, the amino acid sequences of CDRs 1 to 3 of 18C1 VL represented by SEQ ID NOs: 32, 33, and 34, respectively, were grafted into appropriate positions of the amino acid sequence of FR of V1-22 (as FR4, the FR4 of the 18C1 chimeric antibody was used as it is), whereby hz18C1 LV0 (SEQ ID NO: 71) was designed.

By computer modeling of hz18C1 HV0 and hz18C1 LV0 designed as described above, amino acid residues of FR considered to affect the binding activity of the antibody were identified. As a result, among the amino acid residues of FR of the variable region of the hz18C1 LV0HV0 antibody, as the amino acid residues considered to change the three-dimensional structure of an antigen-binding site so as to affect the binding activity of the antibody, in VH, Pro at position 14, Leu at position 20, Gly at position 27, Val at position 29, Ser at position 30, Ile at position 37, Ile at position 48, Val at position 67, Val at position 71, Asn at position 76, Phe at position 78, Leu at position 82, Val at position 85, Val at position 92, Tyr at position 94, and Thr at position 109 of the amino acid sequence represented by SEQ ID NO: 70, and in VL, Pro at position 7, Val at position 10, Glu at position 12, Pro at position 14, Lys at position 16, Thr at position 19, Ile at position 20, Pro at position 41, Val at position 48, Ser at position 75, Leu at position 81, Lys at position 82, Asp at position 88, and Tyr at position 90 of the amino acid sequence represented by SEQ ID NO: 71 were selected, respectively. Among the selected amino acid residues, at least one or more amino acid residues were substituted with amino acid residues present at the same site of the 18C1 antibody, thereby designing VH and VL of humanized antibodies having various alterations.

In addition to the designing of standard CDR grafting as described above, in some VH or VL, an alteration of VH CDR was also carried out. In the VH of the hz18C1 antibody in which the alteration of VH CDR was carried out, at least one alteration of an alteration of substituting Val at position 4 in the amino acid sequence of CDR1 of VH represented by SEQ ID NO: 29 is substituted with Ala, and an alteration of substituting Ser at position 16 in CDR2 of VH represented by SEQ ID NO: 30 with Asp was introduced.

Specific amino acid sequences as the amino acid sequence designed according to the above process are shown in FIG. 16 for VH and in FIG. 18A for VL.

Further, other than the above-mentioned CDR grafting method, by a surface reconstruction method (Proc. Natl. Acad. Sci. USA, 1994, 91(3): 969-73, and Protein Engineering, 1996, 10, 895-90), VL and VH of humanized antibodies having various alterations were designed by substituting an amino acid residue in FR considered not to affect the binding activity of an antibody with an amino acid residue considered to lower the antigenicity from a model structure of the variable region of the 18C1 antibody constructed above. In some VL or VH, an alteration of VH CDR as mentioned with respect to the case of the CDR grafting method was also carried out.

Specifically, at least one alteration of amino acid alterations of substituting Val at position 3 with Ala, Asn at position 8 with Asp, Leu at position 14 with Ala, Lys at position 19 with Thr, Phe at position 75 with Ser, Asn at position 80 with Asp, Ile at position 83 with Val, and Ile at position 88 with Val was introduced in the amino acid sequence represented by SEQ ID NO: 26. By doing this, hz18C1 VLres01 to 16 composed of the amino acid sequences represented by SEQ ID NOS: 72 to 87, respectively, were designed as the VL of the hz18C1 antibody and are shown in FIG. 18B.

Further, with respect to VH, at least one alteration of amino acid alterations of substituting Leu at position 11 with Ala, Leu at position 14 with Pro, Ser at position 19 with Asp, Phe at position 27 with Ala, Val at position 34 with Ala, Ser at position 65 with Asp, Ser at position 68 with Ala, Arg at position 71 with Lys, Gln at position 77 with Glu, Phe at position 79 with Ala, Asn at position 83 with Asp, Leu at position 85 with Asp, and His at position 107 with Gln was introduced in the amino acid sequence represented by SEQ ID NO: 23. As the VH of the hz18C1 antibody designed in this manner, hz18C1 VHres01 to 32 are shown in FIG. 17. With respect to hz18C1 VHres16, the amino acid sequence thereof is represented by SEQ ID NO: 98.

In addition, as the amino acid sequence of VH of a humanized antibody, an amino acid sequence of VH was designed using a CDR grafting method and a surface reconstruction method in combination. Specifically, at least one alteration of amino acid alterations of substituting Gly at position 10 with Asp, Lys at position 13 with Gln, Ser at position 19 with Asp, Leu at position 20 with Ile, Gly at position 27 with Phe, Val at position 29 with Leu, Ser at position 30 with Thr, Ile at position 37 with Val, Ile at position 48 with Met, Ser at position 65 with Asp, Val at position 67 with Leu, Thr at position 68 with Ala, Val at position 71 with Arg, Asn at position 76 with Ser, Gln at position 77 with Glu, Phe at position 78 with Val, Ser at position 79 with Phe, Leu at position 82 with Met, Ser at position 83 with Asp, Val at position 85 with Leu, Thr at position 86 with Gln, Ala at position 87 with Thr, Ala at position 88 with Asp, Val at position 92 with Lys, Tyr at position 94 with Phe, Thr at position 109 with Ile, and Leu at position 110 with Met was introduced in the amino acid sequence represented by SEQ ID NO: 70. By doing this, hz18C1 HVmut01 to 10 (SEQ ID NOs: 88 to 97) were designed as the VH of the hz18C1 antibody, and the amino acid sequences thereof are shown in FIG. 19. Among these, CDRs 1 to 3 of the hz18C1 HVmut01 to 04 all contain the same amino acid sequences (amino acid sequences represented by SEQ ID NOs: 29 to 31) as those of the 18C1 antibody. On the other hand, the hz18C1 HVmut05 to 10 contain a mutation in CDR2. That is, CDRs 1 and 3 of the hz18C1 HVmut05 to 10 contain amino acid sequences represented by SEQ ID NOs: 29 and 31, respectively, and CDR2 thereof contains an amino acid sequence (SEQ ID NO: 99) in which Ser at position 16 of the amino acid sequence represented by SEQ ID NO: 30 is substituted with Asp.

(2) Designing of Gene of Variable Region of Humanized Antibody

Nucleotide sequences encoding amino acid sequences of the variable region of humanized antibodies shown in Table 3 were designed using a codon used highly frequently in animal cells.

TABLE 3

| Antibody name | VH | VL | SEQ ID NO of VH | SEQ ID NO of VL |
|---|---|---|---|---|
| VLres02HVmut07 | HVmut07 | VLres02 | SEQ ID NO: 94 | SEQ ID NO: 73 |
| VLres02HVmut08 | HVmut08 | VLres02 | SEQ ID NO: 95 | SEQ ID NO: 73 |
| VLres04HVmut04 | HVmut04 | VLres04 | SEQ ID NO: 91 | SEQ ID NO: 75 |
| VLres04VHres16 | VHres16 | VLres04 | SEQ ID NO: 98 | SEQ ID NO: 75 |
| VLres06HVmut02 | HVmut02 | VLres06 | SEQ ID NO: 89 | SEQ ID NO: 77 |
| VLres06HVmut10 | HVmut10 | VLres06 | SEQ ID NO: 97 | SEQ ID NO: 77 |
| VLres07HVmut10 | HVmut10 | VLres07 | SEQ ID NO. 97 | SEQ ID NO: 78 |
| VLres07VHres16 | VHres16 | VLres07 | SEQ ID NO: 98 | SEQ ID NO: 78 |
| VLres08HVmut04 | HVmut04 | VLres08 | SEQ ID NO: 91 | SEQ ID NO: 79 |
| VLres08HVmut08 | HVmut08 | VLres08 | SEQ ID NO: 95 | SEQ ID NO: 79 |
| VLres08VHres16 | VHres16 | VLres08 | SEQ ID NO: 98 | SEQ ID NO: 79 |
| VLres10HVmut02 | HVmut02 | VLres10 | SEQ ID NO: 89 | SEQ ID NO: 81 |
| VLres10HVmut04 | HVmut04 | VLres10 | SEQ ID NO: 91 | SEQ ID NO: 81 |
| VLres10HVmut08 | HVmut08 | VLres10 | SEQ ID NO: 95 | SEQ ID NO: 81 |
| VLres10HVmut10 | HVmut10 | VLres10 | SEQ ID NO: 97 | SEQ ID NO: 81 |
| VLres10VHres16 | VHres16 | VLres10 | SEQ ID NO: 98 | SEQ ID NO: 81 |

TABLE 3-continued

| Antibody name | VH | VL | SEQ ID NO of VH | SEQ ID NO of VL |
|---|---|---|---|---|
| VLres14HVmut07 | HVmut07 | VLres14 | SEQ ID NO: 94 | SEQ ID NO: 85 |
| VLres14HVmut08 | HVmut08 | VLres14 | SEQ ID NO: 95 | SEQ ID NO: 85 |
| VLres14HVmut10 | HVmut10 | VLres14 | SEQ ID NO: 97 | SEQ ID NO: 85 |
| VLres14VHres16 | VHres16 | VLres14 | SEQ ID NO: 98 | SEQ ID NO: 85 |
| VLres16HVmut07 | HVmut07 | VLres16 | SEQ ID NO: 94 | SEQ ID NO: 87 |
| VLres16HVmut10 | HVmut10 | VLres16 | SEQ ID NO: 97 | SEQ ID NO: 87 |
| VLres16VHres16 | VHres16 | VLres16 | SEQ ID NO: 98 | SEQ ID NO: 87 |

(3) Production of Humanized Antibody

A necessary plasmid was produced by introducing a gene fragment corresponding to the nucleotide sequence designed in (2) into an expression vector using a seamless cloning method. However, as a VL expression vector, a pCI-OtCMV_hL vector having a signal sequence and a human λ chain constant region sequence was used, and as a VH expression vector, a pCI-OtCAG_hG4PE(R409K) vector having a signal sequence and a human γ chain constant region sequence was used. The constant region sequence included in the pCI-OtCAG_hG4PE(R409K) vector is a heavy chain constant region of an IgG4 mutant obtained by substituting a Ser residue at position 228 according to the EU-index in the heavy chain constant region of human IgG4 with Pro, a Leu residue at position 235 therein with Glu, and an Arg residue at position 409 therein with Lys (hereinafter denoted by IgG4PE R409K (WO 2006/033386)). Note that these vectors are vectors produced through total synthesis by introducing restriction enzyme sites necessary for expressing a human antibody gene using a pCI vector of Promega Corporation as a common main backbone. The completed plasmid was prepared in a large amount using NucleoBond Xtra Midi EF Kit (Takara Bio, Inc.). Subsequently, a target humanized antibody was transiently expressed using Expi293 Expression System Kit (Life Technologies, Inc.). The method for introducing the plasmid was carried out according to the package insert.

The light chain expression vector and the heavy chain expression vector were mixed at a ratio of 1:2 and introduced. The cells after the introduction of the plasmid were cultured for 3 days under conditions of 37° C., 5% $CO_2$, and 125 rpm. Thereafter, the cell culture suspension was centrifuged, and the culture supernatant was collected through a 0.2 µm filter (Thermo Scientific, Inc.). A purified antibody was obtained from the culture supernatant by affinity purification using MabSelect SuRe (GE Healthcare, Inc.).

Specifically, after a resin packed in the column was equilibrated with PBS, the culture supernatant was added to the column, washed twice with PBS, and then washed once with Wash buffer 1 (PBS with 1 M NaCl) and once with Wash buffer 2 (20 mM citric acid and 50 mM NaCl, pH 5.0), and thereafter, the antibody was eluted using an elution buffer (20 mM citric acid and 50 mM NaCl, pH 3.4). The obtained antibody solution was neutralized by adding a 1/10 amount of a neutralization buffer (1 M phosphoric acid-NaOH, pH 7.0), and the solvent of the antibody solution was replaced with PBS using NAP 25 (GE Healthcare, Inc.). The antibody solution after buffer replacement was concentrated by ultrafiltration using Amicon Ultra-4 Centrifugal Filter Units (Millipore, Inc.), and an absorbance $A_{280}$ was measured using Nanodrop (Thermo Scientific, Inc.), and the concentration of the antibody solution was measured and adjusted. The extinction coefficient was calculated based on the amino acid sequence of each humanized antibody according to the method of C. N. Pace et al. (1995, Prot. Sci. 4: 2411-2423). The purified antibody was confirmed for its quality by analytical gel filtration chromatography (using an apparatus manufactured by Shimadzu Corporation, and a column TSKgel SuperSW3000 manufactured by Tosoh Corporation) and SDS-PAGE.

[Example 13] Evaluation of Binding Activity of Anti-BMP10 Humanized Antibody

For the purpose of comparing the binding activity to human BMP10 between the ch18C1 antibody obtained in Example 5-3 and the anti-BMP10 humanized antibody obtained in Example 12, the binding activity to a human BMP10 mature dimer (manufactured by R & D Systems, Cat #2926-BP) was measured by a surface plasmon resonance method (SPR method) using Biacore T100 (manufactured by GE Healthcare Bio-Sciences Corporation).

The binding activity of the anti-BMP10 antibody was measured as follows. An anti-human IgG antibody was immobilized on a CM5 sensor chip (manufactured by GE Healthcare Bio-Sciences, Inc., BR100530) using Human Antibody Capture Kit (manufactured by GE Healthcare Bio-Sciences Corporation, Cat # BR-1008-39) according to the attached protocol. To a flow cell in which the anti-human IgG antibody was immobilized, the antibody prepared at 5 µg/mL was added at a flow rate of 10 µL/min for 10 seconds.

Subsequently, human mature BMP10 prepared at 5 concentrations by 3-fold serial dilution from the 100 ng/mL was added thereto at a flow rate of 30 µL/min, and a binding reaction was monitored for 1 minute and a dissociation reaction was monitored for 10 minutes. The obtained sensorgram was analyzed using Bia Evaluation Software (manufactured by GE Healthcare Bio-Sciences Corporation), and the kinetic constant of each antibody was calculated. The calculated association rate constant (ka), dissociation rate constant (kd), and dissociation constant [kd/ka=$K_D$] of each antibody are shown in Table 4.

TABLE 4

| Antibody name | ka | kd | KD |
|---|---|---|---|
| VLres02HVmut07 | 4.48E+07 | 1.33E−04 | 2.97E−12 |
| VLres02HVmut08 | 3.68E+07 | 1.13E−04 | 3.05E−12 |
| VLres04HVmut04 | 4.09E+07 | 1.30E−04 | 3.19E−12 |
| VLres04VHres16 | 4.45E+07 | 1.43E−04 | 3.21E−12 |
| VLres06HVmut02 | 4.06E+07 | 1.37E−04 | 3.37E−12 |
| VLres06HVmut10 | 4.30E+07 | 1.26E−04 | 2.94E−12 |
| VLres07HVmut10 | 4.51E+07 | 1.21E−04 | 2.69E−12 |
| VLres07VHres16 | 4.59E+07 | 1.43E−04 | 3.11E−12 |
| VLres08HVmut04 | 4.72E+07 | 1.36E−04 | 2.88E−12 |
| VLres08HVmut08 | 4.82E+07 | 1.44E−04 | 2.99E−12 |
| VLres08VHres16 | 4.61E+07 | 1.50E−04 | 3.25E−12 |
| VLres10HVmut02 | 3.58E+07 | 1.22E−04 | 3.41E−12 |
| VLres10HVmut04 | 4.01E+07 | 1.28E−04 | 3.20E−12 |
| VLres10HVmut08 | 4.73E+07 | 1.45E−04 | 3.06E−12 |
| VLres10HVmut10 | 5.87E+07 | 1.29E−04 | 2.19E−12 |
| VLres10VHres16 | 4.23E+07 | 1.51E−04 | 3.57E−12 |

TABLE 4-continued

| Antibody name | ka | kd | KD |
| --- | --- | --- | --- |
| VLres14HVmut07 | 4.18E+07 | 1.25E−04 | 2.99E−12 |
| VLres14HVmut08 | 4.37E+07 | 1.18E−04 | 2.71E−12 |
| VLres14HVmut10 | 4.35E+07 | 1.24E−04 | 2.84E−12 |
| VLres14VHres16 | 4.03E+07 | 1.33E−04 | 3.30E−12 |
| VLres16HVmut07 | 3.93E+07 | 1.25E−04 | 3.19E−12 |
| VLres16HVmut10 | 4.17E+07 | 1.20E−04 | 2.88E−12 |
| VLres16VHres16 | 3.77E+07 | 1.39E−04 | 3.69E−12 |
| Ch18C1 | 3.88E+07 | 1.02E−04 | 2.62E−12 |

From the above results, it was revealed that the produced anti-BMP10 humanized antibodies have a binding activity equivalent to that of the ch18C1 antibody.

[Example 14] Comparison of Neutralizing Activity Between Anti-BMP10 Humanized Antibody and ch18C1 Antibody 14-1) Evaluation of Neutralizing Activity of Anti-BMP10 Humanized Antibody Against BMP10 Homodimer With respect to the obtained anti-BMP10 humanized antibodies and the ch18C1 antibody, the neutralizing activities against BMP10 were compared using the human ALK1 expressing reporter cells produced in Example 3, 3-1).

To a 96-well fluorescence and luminescence plate (manufactured by Corning, Inc., Cat #3916), a human BMP10 mature dimer (manufactured by R & D Systems, Inc., Cat #2926-BP) was added at a final concentration of 0.3 ng/mL, and subsequently, the anti-BMP10 humanized antibody obtained in Example 12 or the ch18C1 antibody was prepared at 7 concentrations by 3-fold serial dilution from the final concentration of 3000 ng/mL, and then added.

Thereafter, an ALK1/Id1-Luc/CHO cell liquid in which the cells were suspended in Excell 325 medium [Excell 325 PF CHO (manufactured by SAFC, Inc., Cat #14340C-1000 mL), 4 mM L-glutamine, 1×Penicillin, 1×Streptomycin (manufactured by Nacalai, Inc., Cat #09367-34), 0.5 mg/mL hygromycin] was added at 5×10⁴ cells/well. After all samples were added, the liquid in the well was made uniform with a plate mixer, and the cells were cultured at 37° C. for 20 hours.

After 20 hours, an assay solution of Nano-Glo Luciferase Assay (manufactured by Promega Corporation, Cat # N1120) prepared according to the package insert was added at 40 µL/well, followed by stirring, and then, a luciferase activity was measured using Glomax (manufactured by Promega Corporation). The neutralizing activity (%) of the antibody was calculated by setting the value of the well in which only the BMP10 mature dimer was added without adding an antibody to be 0%, and the value of the well in which only Excell 325 medium was added without adding an antibody to be 100%. The results are shown in FIGS. 20 to 25.

As shown in FIGS. 20 to 25, all the produced anti-BMP10 humanized antibodies exhibited a neutralizing activity equivalent to that of the ch18C1 antibody.

14-2) Evaluation of Neutralizing Activity of Anti-BMP10 Humanized Antibody Against BMP9/BMP10 Heterodimer in Human Blood With respect to the obtained anti-BMP10 humanized antibodies and the ch18C1 antibody, the neutralizing activities against a BMP9/BMP 10 heterodimer in human blood were compared using human ALK1 expressing reporter cells. As the human ALK1 expressing reporter cells, the cells produced in Example 3, 3-1) were used.

To a 96-well fluorescence and luminescence plate (manufactured by Corning, Inc., Cat #3916), human serum (Human True A serum, pool of donors, manufactured by Biopredic International, Cat # SER019) was added at a final concentration of 10%.

Subsequently, the anti-BMP10 humanized antibody or the ch18C1 antibody was added at a final concentration of 1000 ng/mL. Thereafter, an ALK1/Id1-Luc/CHO cell suspension was added at 5×10⁴ cells/well. In all wells, Excell 325 medium was added so that the liquid amount became 100 VL/well. After the liquid in the well was made uniform with a plate mixer, the cells were cultured at 37° C. for 20 hours.

After 20 hours, an assay solution of Nano-Glo Luciferase Assay prepared according to the package insert was added at 40 µL/well, followed by stirring, and then, a luciferase activity was measured using Glomax (manufactured by Promega Corporation).

As shown in FIG. 26, all the produced anti-BMP10 humanized antibodies exhibited a neutralizing activity equivalent to that of the ch18C1 antibody against the BMP9/BMP10 heterodimer in human blood.

[Example 15] Evaluation of BMP9/BMP10 Heterodimer Neutralizing Activity on Blood Pressure of Normal Animal An effect on blood pressure when neutralizing a BMP9/BMP10 heterodimer was evaluated using SD rats. Male SD rats (manufactured by Charles River Laboratories Japan, Inc.) at 6 weeks of age were purchased and used for an experiment. The rats were given sterile tap water as drinking water and chow FR-2 (manufactured by Funabashi Farm Co., Ltd.) as feed ad libitum. After acclimation, the rats underwent surgery for implantation of a telemetry transmitter at 7 weeks of age. The method for the surgery for implantation of a telemetry transmitter and the acquisition of the blood pressure waveform were carried out according to Example 7.

In a BMP9 antibody administration group, a solution in which the BMP9 antibody 10D5 was prepared at 10 mg/mL with PBS was administered at a dose of 1 mL/kg. In a BMP9/BMP10 heterodimer neutralization group, a solution in which the BMP9 antibody 10D5 and the BMP10 antibody 11H10 were mixed and prepared at a final concentration of 10 mg/mL and 5 mg/mL, respectively, with PBS was administered at a dose of 1 mL/kg. The administration was carried out through a subcutaneous route.

As shown in FIG. 27A, as compared with the case when the vehicle was administered, a change in the systolic blood pressure by the administration of the 10D5 antibody was not observed. On the other hand, as shown in FIG. 27B, as compared with the case when the vehicle was administered, in the BMP9/BMP10 heterodimer neutralization group in which the 10D5 antibody and the 11H10 antibody were mixed and administered, a decrease in the systolic blood pressure was observed.

A change in the systolic blood pressure is not caused by either of the 10D5 antibody and the 11H10 antibody alone. However, it was newly found that when the 10D5 antibody and the 11H10 antibody are used in combination, by the neutralization of the BMP9/BMP10 heterodimer, an antihypertensive action is exhibited.

[Example 16] Evaluation of Effect of Human BMP10 Homodimer on Blood Pressure of Normal Animal 16-1) Preparation of Human BMP10 Recombinant Protein In order to evaluate the effect of a human BMP10 homodimer on blood pressure, a human BMP10 recombinant protein was prepared. A human BMP10 expression vector was prepared according to the method described in Example 20 in WO 2014/007198. Further, a human Furin expression plasmid was prepared by incorporating a human Furin full-length cDNA into a pEAK8 vector (Edge Biosystems, Inc.) using In-Fusion HD Cloning Kit (manufactured by Takara Bio, Inc.).

Transient expression was carried out for human BMP10 and human Furin using EXPI 293 Expression system (manufactured by Thermo Fisher Scientific, Inc.), whereby a human BMP10 recombinant protein was expressed. The culture supernatant was obtained from the culture solution by centrifugation and filtration using a 0.22 μm filter.

Subsequently, each protein was purified using Ni-NTA Agarose (manufactured by QIAGEN, Inc.). As a binding buffer, 20 mM HEPES-NaOH (pH 7.4) containing 500 mM NaCl and 40 mM imidazole was used, and as an elution buffer, 20 mM HEPES-NaOH (pH 7.4) containing 500 mM NaCl and 200 mM imidazole was used.

The buffer was replaced with PBS using a NAP-25 column (manufactured by GE Healthcare, Inc., 17-0852-02). An absorbance at 280 nm was measured to determine the concentration of each protein solution. As a molecular extinction coefficient, 0.96 mL/(mg·cm) was used. The thus obtained BMP10 recombinant protein does not contain a full-length protein, but contains only a mature protein and an N-terminal propeptide protein, however, it forms a homodimer in the same manner as the BMP10 recombinant protein containing a full-length protein produced by the method of Example 1-1 and has a function as BMP10.

16-2) Evaluation of Effect of BMP10 Recombinant Protein on Blood Pressure

An effect on blood pressure when administering the human BMP10 recombinant protein was evaluated using SD rats. Male SD rats (manufactured by Charles River Laboratories Japan, Inc.) at 6 weeks of age were purchased and used for an experiment. The rats were given sterile tap water as drinking water and chow FR-2 (manufactured by Funabashi Farm Co., Ltd.) as feed ad libitum. After acclimation, the rats underwent surgery for implantation of a telemetry transmitter at 7 weeks of age.

The method for the surgery for implantation of a telemetry transmitter and the acquisition of the blood pressure waveform were carried out according to Example 7. A solution in which the human BMP10 recombinant protein obtained in Example 16-1 was prepared at 0.5 mg/mL with PBS was administered at a dose of 1 mL/kg. The administration was carried out through an intravenous route.

As shown in FIG. 28, as compared with the case when the vehicle was administered, an increase in the systolic blood pressure by the administration of the human BMP10 recombinant protein was observed.

From the above results, it was newly found that the human BMP10 homodimer has a vasopressor effect.

While the present invention has been described in detail with reference to specific embodiments, it will be apparent to those skilled in the art that various changes and modifications can be made without departing from the spirit and scope of the present invention. Note that the present application is based on Japanese Patent Application (Japanese Patent Application No. 2017-238106) filed on Dec. 12, 2017, which is incorporated by reference in its entirety.

The invention claimed is:

1. A monoclonal antibody or an antibody fragment thereof which binds to BMP10,
wherein the monoclonal antibody and the antibody fragment thereof comprises:
a heavy chain comprising heavy chain complementarity determining regions (CDRs) 1 to 3,
wherein heavy chain CDR 1 comprises the amino acid sequence of SEQ ID NO: 29,
wherein heavy chain CDR 2 comprises the amino acid sequence of SEQ ID NO: 30 or an amino acid sequence in which serine at position 16 of the amino acid sequence of SEQ ID NO: 30 is substituted with aspartic acid, and
wherein heavy chain CDR3 comprises the amino acid sequence of SEQ ID NO: 31; and
a light chain comprising light chain CDRs 1 to 3, wherein light chain CDRs 1 to 3 comprise the amino acid sequences of SEQ ID NO: 32 to 34, respectively.

2. The monoclonal antibody or the antibody fragment thereof according to claim 1, wherein the monoclonal antibody comprises:

a light chain variable region (VL) comprising any one amino acid sequence selected from SEQ ID NO: 71 to 87 and/or
a heavy chain variable region (VH) comprising any one amino acid sequence selected from SEQ ID NO: 70 and 88 to 98.

3. The monoclonal antibody or the antibody fragment thereof according to claim 1 selected from the following (a) to (w):
(a) a monoclonal antibody comprising a VH comprising an amino acid sequence of SEQ ID NO: 94 and a VL comprising an amino acid sequence of SEQ ID NO: 73, or an antibody fragment thereof,
(b) a monoclonal antibody including a VH comprising an amino acid sequence of SEQ ID NO: 95 and a VL comprising an amino acid sequence of SEQ ID NO: 73, or an antibody fragment thereof,
(c) a monoclonal antibody including a VH comprising an amino acid sequence of SEQ ID NO: 91 and a VL comprising an amino acid sequence of SEQ ID NO: 75, or an antibody fragment thereof,
(d) a monoclonal antibody comprising a VH comprising an amino acid sequence of SEQ ID NO: 98 and a VL comprising an amino acid sequence of SEQ ID NO: 75, or an antibody fragment thereof,
(e) a monoclonal antibody comprising a VH comprising an amino acid sequence of SEQ ID NO: 89 and a VL comprising an amino acid sequence of SEQ ID NO: 77, or an antibody fragment thereof,
(f) a monoclonal antibody comprising a VH comprising an amino acid sequence of SEQ ID NO: 97 and a VL comprising an amino acid sequence of SEQ ID NO: 77, or an antibody fragment thereof,
(g) a monoclonal antibody comprising a VH comprising an amino acid sequence of SEQ ID NO: 97 and a VL comprising an amino acid sequence of SEQ ID NO: 78, or an antibody fragment thereof,
(h) a monoclonal antibody comprising a VH comprising an amino acid sequence of SEQ ID NO: 98 and a VL comprising an amino acid sequence of SEQ ID NO: 78, or an antibody fragment thereof,
(i) a monoclonal antibody comprising a VH comprising an amino acid sequence of SEQ ID NO: 91 and a VL comprising an amino acid sequence of SEQ ID NO: 79, or an antibody fragment thereof,
(j) a monoclonal antibody comprising a VH comprising an amino acid sequence of SEQ ID NO: 95 and a VL comprising an amino acid sequence of SEQ ID NO: 79, or an antibody fragment thereof,
(k) a monoclonal antibody comprising a VH comprising an amino acid sequence of SEQ ID NO: 98 and a VL comprising an amino acid sequence of SEQ ID NO: 79, or an antibody fragment thereof,
(l) a monoclonal antibody comprising a VH comprising an amino acid sequence of SEQ ID NO: 89 and a VL comprising an amino acid sequence of SEQ ID NO: 81, or an antibody fragment thereof,
(m) a monoclonal antibody comprising a VH comprising an amino acid sequence of SEQ ID NO: 91 and a VL comprising an amino acid sequence of SEQ ID NO: 81, or an antibody fragment thereof,
(n) a monoclonal antibody comprising a VH comprising an amino acid sequence of SEQ ID NO: 95 and a VL comprising an amino acid sequence of SEQ ID NO: 81, or an antibody fragment thereof,
(o) a monoclonal antibody comprising a VH comprising an amino acid sequence of SEQ ID NO: 97 and a VL comprising an amino acid sequence of SEQ ID NO: 81, or an antibody fragment thereof,
(p) a monoclonal antibody comprising a VH comprising an amino acid sequence of SEQ ID NO: 98 and a VL comprising an amino acid sequence of SEQ ID NO: 81, or an antibody fragment thereof,
(q) a monoclonal antibody comprising a VH comprising an amino acid sequence of SEQ ID NO: 94 and a VL comprising an amino acid sequence of SEQ ID NO: 85, or an antibody fragment thereof,
(r) a monoclonal antibody comprising a VH comprising an amino acid sequence of SEQ ID NO: 95 and a VL comprising an amino acid sequence of SEQ ID NO: 85, or an antibody fragment thereof,
(s) a monoclonal antibody comprising a VH comprising an amino acid sequence of SEQ ID NO: 97 and a VL comprising an amino acid sequence of SEQ ID NO: 85, or an antibody fragment thereof,
(t) a monoclonal antibody comprising a VH comprising an amino acid sequence of SEQ ID NO: 98 and a VL comprising an amino acid sequence of SEQ ID NO: 85, or an antibody fragment thereof,
(u) a monoclonal antibody comprising a VH comprising an amino acid sequence of SEQ ID NO: 94 and a VL comprising an amino acid sequence of SEQ ID NO: 87, or an antibody fragment thereof,
(v) a monoclonal antibody comprising a VH comprising an amino acid sequence of SEQ ID NO: 97 and a VL comprising an amino acid sequence of SEQ ID NO: 87, or an antibody fragment thereof, and
(w) a monoclonal antibody comprising a VH comprising an amino acid sequence of SEQ ID NO: 98 and a VL comprising an amino acid sequence of SEQ ID NO: 87, or an antibody fragment thereof.

4. The monoclonal antibody or the antibody fragment thereof according to claim 1, having a neutralizing activity against BMP10.

5. The monoclonal antibody or the antibody fragment thereof according to claim 1, having a neutralizing activity against a BMP9/BMP10 heterodimer.

6. The monoclonal antibody or the antibody fragment thereof according to claim 1, wherein the monoclonal antibody is a recombinantly-produced antibody.

7. The monoclonal antibody or the antibody fragment thereof according to claim 1 which is selected from a Fab, a Fab', a (Fab')$_2$, a single chain antibody (scFv), a dimerized V region (diabody), and a disulfide stabilized V region (dsFv).

* * * * *